US012304968B2

(12) United States Patent
Terrett et al.

(10) Patent No.: US 12,304,968 B2
(45) Date of Patent: May 20, 2025

(54) T-CELLS EXPRESSING ANTI-LIV1 CHIMERIC ANTIGEN RECEPTOR

(71) Applicant: CRISPR THERAPEUTICS AG, Zug (CH)

(72) Inventors: Jonathan Alexander Terrett, Cambridge, MA (US); Jason Sagert, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 932 days.

(21) Appl. No.: 16/677,267

(22) Filed: Nov. 7, 2019

(65) Prior Publication Data

US 2020/0231699 A1 Jul. 23, 2020

Related U.S. Application Data

(60) Provisional application No. 62/756,723, filed on Nov. 7, 2018.

(51) Int. Cl.

| | |
|---|---|
| ***C07K 16/30*** | (2006.01) |
| ***A61K 39/395*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 14/47*** | (2006.01) |
| ***C07K 14/705*** | (2006.01) |
| ***C07K 14/725*** | (2006.01) |
| ***C07K 16/28*** | (2006.01) |
| ***C07K 19/00*** | (2006.01) |
| ***C12N 5/0783*** | (2010.01) |
| ***C12N 9/22*** | (2006.01) |
| ***C12N 15/11*** | (2006.01) |
| ***C12N 15/85*** | (2006.01) |
| ***C12N 15/86*** | (2006.01) |
| *A61K 38/00* | (2006.01) |

(52) U.S. Cl.

CPC ...... *C07K 16/3015* (2013.01); *A61K 39/3955* (2013.01); *A61K 40/11* (2025.01); *A61K 40/31* (2025.01); *A61K 40/32* (2025.01); *A61K 40/4202* (2025.01); *A61K 40/421* (2025.01); *A61P 35/00* (2018.01); *C07K 14/4717* (2013.01); *C07K 14/705* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 19/00* (2013.01); *C12N 5/0636* (2013.01); *C12N 9/22* (2013.01); *C12N 15/11* (2013.01); *C12N 15/85* (2013.01); *C12N 15/86* (2013.01); *A61K 38/00* (2013.01); *A61K 2239/49* (2023.05); *A61K 2239/56* (2023.05); *C07K 2317/565* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2310/20* (2017.05); *C12N 2502/30* (2013.01); *C12N 2502/99* (2013.01); *C12N 2510/00* (2013.01); *C12N 2750/14143* (2013.01); *C12N 2800/80* (2013.01)

(58) Field of Classification Search

CPC .... C07K 16/28; C07K 19/00; C07K 2319/33; C07K 14/70521; C07K 14/70578; A61K 39/3955

See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 6,140,081 | A | 10/2000 | Barbas |
| 6,352,694 | B1 | 3/2002 | June et al. |
| 6,453,242 | B1 | 9/2002 | Eisenberg et al. |
| 6,534,055 | B1 | 3/2003 | June et al. |
| 6,534,261 | B1 | 3/2003 | Cox et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |

(Continued)

FOREIGN PATENT DOCUMENTS

| | | |
|---|---|---|
| CA | 3041039 A1 | 4/2018 |
| EP | 3156420 A1 | 4/2017 |

(Continued)

OTHER PUBLICATIONS

Kim et al, 2021. Frontiers in Immunology 12: 1-12.*

(Continued)

*Primary Examiner* — Zachary C Howard

(74) *Attorney, Agent, or Firm* — Casimir Jones, S.C.; J. Mitchell Jones

(57) ABSTRACT

Provided herein, in some embodiments, are methods and compositions (e.g., cell compositions) for the treatment of cancer, such as LIV1$^+$ malignancies.

12 Claims, 9 Drawing Sheets

Specification includes a Sequence Listing.

(56) References Cited

U.S. PATENT DOCUMENTS

| | | | |
|---|---|---|---|
| 7,888,121 | B2 | 2/2011 | Urnov et al. |
| 7,972,854 | B2 | 7/2011 | Miller et al. |
| 9,228,026 | B2 | 1/2016 | Smith et al. |
| 2011/0145940 | A1 | 6/2011 | Voytas et al. |

FOREIGN PATENT DOCUMENTS

| | | | | |
|---|---|---|---|---|
| WO | 98/53058 | A1 | 11/1998 | |
| WO | 98/53059 | A1 | 11/1998 | |
| WO | 98/53060 | A1 | 11/1998 | |
| WO | 02/16536 | A1 | 2/2002 | |
| WO | 03/16496 | A2 | 2/2003 | |
| WO | 2016/069282 | A1 | 5/2016 | |
| WO | 2017/161007 | | 9/2017 | |
| WO | 2018/027036 | A1 | 2/2018 | |
| WO | 2018/073393 | | 4/2018 | |
| WO | WO-2018102795 | A2 * | 6/2018 | ............ A61K 35/17 |

OTHER PUBLICATIONS

Benjamini et al, 1991. Immunology: A Short Course, 2nd edition, p. 40 only.*

Ferrara et al (2015. mAbs. 7(1): 32-41).*

Al-Lazikani et al., Standard conformations for the canonical structures of immunoglobulins, J. Mol. Biol., 273:927-948 (1997).

Almagro, Identification of differences in the specificity-determining residues of antibodies that recognize antigens of different size: implications for the rational design of antibody repertoires, J. Mol. Recognit., 17:132-143 (2004).

Bauer et al., Generation of genomic deletions in mammalian cell lines via CRISPR/Cas9, Vis. Exp., 95:e52118 (2015).

Chang et al., Modification of DNA ends can decrease end joining relative to homologous recombination in mammalian cells, Proc. Natl. Acad. Sci. USA., 84:4959-4963 (1987).

Chothia et al., Canonical structures for the hypervariable regions of immunoglobulins, J. Mol. Biol., 196:901-917 (1987).

Chothia et al., Conformations of immunoglobulin hypervariable regions, Nature, 342:877-883 (1989).

Deltcheva et al., CRISPR RNA maturation by trans-encoded small RNA and host factor RNase III, Nature, 471:602-607 (2011).

Enblad et al., CAR T-Cell Therapy: The Role of Physical Barriers and Immunosuppression in Lymphoma, Hum. Gen. Ther., 26:498-505 (2015).

Eyquem et al., Targeting a CAR to the TRAC locus with CRISPR/Cas9 enhances tumour rejection, Nature, 543:113-117 (2017).

International Application No. PCT/IB2019/059586, International Search Report and Written Opinion, mailed Feb. 7, 2020.

Jinek et al., A programmable dual-RNA-guided DNA endonuclease in adaptive bacterial immunity, Science, 337:816-821 (2012).

Kakarla et al., CAR T cells for solid tumors: armed and ready to go?, Cancer J., 20:151-155 (2014).

Liu et al., CRISPR-Cas9-mediated multiplex gene editing in CAR-T cells, Cell Res., 27(1):154-157 (2017).

Maude et al., CD19-targeted chimeric antigen receptor T-cell therapy for acute lymphoblastic leukemia, Blood, 125:4017-4023 (2015).

Nehls et al., Two genetically separable steps in the differentiation of thymic epithelium, Science, 272:886-889 (1996).

Ren et al., A versatile system for rapid multiplex genome-edited CAR T cell generation, Oncot., 8(10):17002-17011 (2017).

Ren et al., Multiplex Genome Editing to Generate Universal CAR T Cells Resistant to PD1 Inhibition, Clin. Cancer Res., 23(9):2255-2266 (2016).

* cited by examiner

CTX-974

CTX-975

FIG. 4

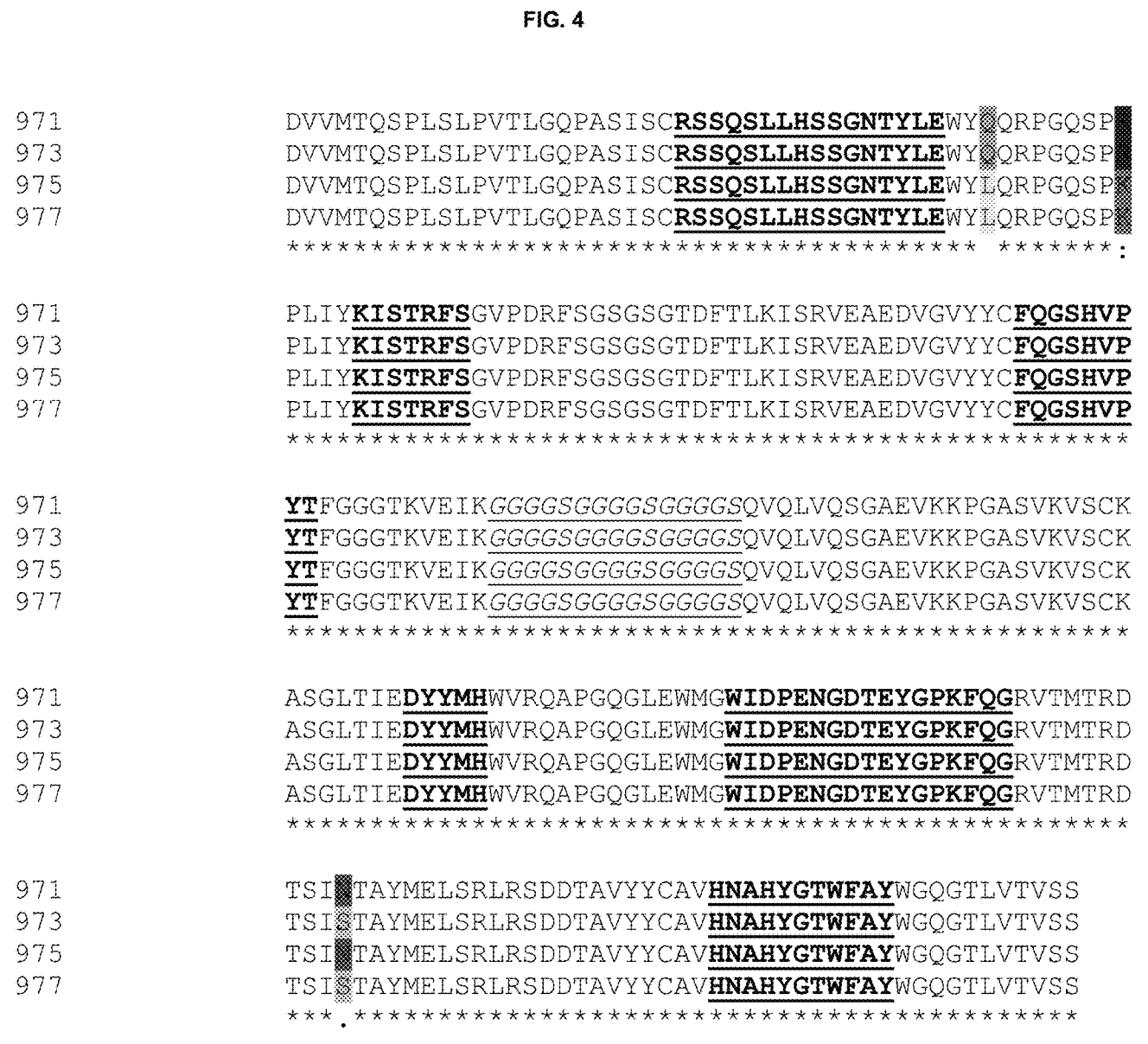

971 DVVMTQSPLSLPVTLGQPASISCRSSQSLLHSSGNTYLEWYQQRPGQSP[illegible]
973 DVVMTQSPLSLPVTLGQPASISCRSSQSLLHSSGNTYLEWYQQRPGQSP[illegible]
975 DVVMTQSPLSLPVTLGQPASISCRSSQSLLHSSGNTYLEWYLQRPGQSP[illegible]
977 DVVMTQSPLSLPVTLGQPASISCRSSQSLLHSSGNTYLEWYLQRPGQSP[illegible]
**************************************  *****:

971 PLIYKISTRFSGVPDRFSGSGSGTDFTLKISRVEAEDVGVYYCFQGSHVP
973 PLIYKISTRFSGVPDRFSGSGSGTDFTLKISRVEAEDVGVYYCFQGSHVP
975 PLIYKISTRFSGVPDRFSGSGSGTDFTLKISRVEAEDVGVYYCFQGSHVP
977 PLIYKISTRFSGVPDRFSGSGSGTDFTLKISRVEAEDVGVYYCFQGSHVP
**************************************************

971 YTFGGGTKVEIK*GGGGSGGGGSGGGGS*QVQLVQSGAEVKKPGASVKVSCK
973 YTFGGGTKVEIK*GGGGSGGGGSGGGGS*QVQLVQSGAEVKKPGASVKVSCK
975 YTFGGGTKVEIK*GGGGSGGGGSGGGGS*QVQLVQSGAEVKKPGASVKVSCK
977 YTFGGGTKVEIK*GGGGSGGGGSGGGGS*QVQLVQSGAEVKKPGASVKVSCK
**************************************************

971 ASGLTIEDYYMHWVRQAPGQGLEWMGWIDPENGDTEYGPKFQGRVTMTRD
973 ASGLTIEDYYMHWVRQAPGQGLEWMGWIDPENGDTEYGPKFQGRVTMTRD
975 ASGLTIEDYYMHWVRQAPGQGLEWMGWIDPENGDTEYGPKFQGRVTMTRD
977 ASGLTIEDYYMHWVRQAPGQGLEWMGWIDPENGDTEYGPKFQGRVTMTRD
**************************************************

971 TSI[illegible]TAYMELSRLRSDDTAVYYCAVHNAHYGTWFAYWGQGTLVTVSS
973 TSISTAYMELSRLRSDDTAVYYCAVHNAHYGTWFAYWGQGTLVTVSS
975 TSI[illegible]TAYMELSRLRSDDTAVYYCAVHNAHYGTWFAYWGQGTLVTVSS
977 TSISTAYMELSRLRSDDTAVYYCAVHNAHYGTWFAYWGQGTLVTVSS
*.***************************************

FIG. 5

```
979   QVQLVQSGAEVKKPGASVKVSCKASGLTIEDYYMHWVRQAPGQGLEWMGW
974   QVQLVQSGAEVKKPGASVKVSCKASGLTIEDYYMHWVRQAPGQGLEWMGW
976   QVQLVQSGAEVKKPGASVKVSCKASGLTIEDYYMHWVRQAPGQGLEWMGW
978   QVQLVQSGAEVKKPGASVKVSCKASGLTIEDYYMHWVRQAPGQGLEWMGW
972   QVQLVQSGAEVKKPGASVKVSCKASGLTIEDYYMHWVRQAPGQGLEWMGW
      **************************************************

979   IDPENGDTEYGPKFQGRVTMTRDTSISTAYMELSRLRSDDTAVYYCAVHN
974   IDPENGDTEYGPKFQGRVTMTRDTSISTAYMELSRLRSDDTAVYYCAVHN
976   IDPENGDTEYGPKFQGRVTMTRDTSISTAYMELSRLRSDDTAVYYCAVHN
978   IDPENGDTEYGPKFQGRVTMTRDTSISTAYMELSRLRSDDTAVYYCAVHN
972   IDPENGDTEYGPKFQGRVTMTRDTSISTAYMELSRLRSDDTAVYYCAVHN
      ***************************.**********************

979   AHYGTWFAYWGQGTLVTVSSGGGGSGGGGSGGGGSDVVMTQSPLSLPVTL
974   AHYGTWFAYWGQGTLVTVSSGGGGSGGGGSGGGGSDVVMTQSPLSLPVTL
976   AHYGTWFAYWGQGTLVTVSSGGGGSGGGGSGGGGSDVVMTQSPLSLPVTL
978   AHYGTWFAYWGQGTLVTVSSGGGGSGGGGSGGGGSDVVMTQSPLSLPVTL
972   AHYGTWFAYWGQGTLVTVSSGGGGSGGGGSGGGGSDVVMTQSPLSLPVTL
      **************************************************

979   GQPASISCRSSQSLLHSSGNTYLEWYQQRPGQSPRPLIYKISTRFSGVPD
974   GQPASISCRSSQSLLHSSGNTYLEWYQQRPGQSPRPLIYKISTRFSGVPD
976   GQPASISCRSSQSLLHSSGNTYLEWYLQRPGQSPKPLIYKISTRFSGVPD
978   GQPASISCRSSQSLLHSSGNTYLEWYLQRPGQSPKPLIYKISTRFSGVPD
972   GQPASISCRSSQSLLHSSGNTYLEWYQQRPGQSPRPLIYKISTRFSGVPD
      ************************** ********:***************

979   RFSGSGSGTDFTLKISRVEAEDVGVYYCFQGSHVPYTEGGGTKVEIK
974   RFSGSGSGTDFTLKISRVEAEDVGVYYCFQGSHVPYTEGGGTKVEIK
976   RFSGSGSGTDFTLKISRVEAEDVGVYYCFQGSHVPYTEGGGTKVEIK
978   RFSGSGSGTDFTLKISRVEAEDVGVYYCFQGSHVPYTEGGGTKVEIK
972   RFSGSGSGTDFTLKISRVEAEDVGVYYCFQGSHVPYT-GGGTKVEIK
      *************************************.*********
```

T-CELLS EXPRESSING ANTI-LIV1 CHIMERIC ANTIGEN RECEPTOR

RELATED APPLICATIONS

This application claims the benefit of U.S. Provisional Application No. 62/756,723, filed Nov. 7, 2018, the disclosure of which is hereby incorporated by reference in its entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "CT113_Seqlisting.txt", which was created on Nov. 7, 2019 and is 191,166 bytes in size. The subject matter of the Sequence Listing is incorporated herein in its entirety by reference.

BACKGROUND

Chimeric antigen receptor (CAR) T-cell therapy uses genetically-modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

SUMMARY

LIV1, a member of the ZIP family of highly conserved transmembrane zinc transporter proteins, is expressed at elevated levels in estrogen receptor-positive breast cancer and tumors of the lymph nodes. Further aberrant expression of zinc transporters such as LIV1 is known to lead to deregulated Zn intake or deficiency, leading to uncontrolled growth such that occur in cancer. Thus, LIV1 is a desirable transmembrane protein for targeting cancer. In fact, the LIV-1 protein has been implicated in breast cancer, prostate cancer, squamous tumors, and neuronal tumors.

Some aspects of the present disclosure provide an engineered T cell comprising a nucleic acid encoding a chimeric antigen receptor (CAR), wherein the CAR comprise an ectodomain that binds specifically to LIV1. In some embodiments, the engineered T cell further comprises a disrupted T cell receptor alpha chain constant region (TRAC) gene. For example, the TRAC gene may be disrupted by insertion of the nucleic acid encoding a CAR. In some embodiments, the engineered T cell further comprises a disrupted beta-2-microglobulin (β2M) gene.

The ectodomain of the CAR, in some embodiments, comprises an anti-LIV1 antibody. In some embodiments, the anti-LIV1 antibody is an anti-LIV1 single-chain variable fragment (scFv). The anti-LIV1 scFv, in some embodiments, comprises an amino acid sequence of any one of SEQ ID NO: 54, 70, 83 or 86. In some embodiments, the anti-LIV1 scFv comprises a heavy chain variable region (VH) comprising an amino acid sequence of any one of SEQ ID NO: 55 or 90 and/or a light chain variable region (VL) comprising an amino acid sequence of any one of SEQ ID NO: 56 or 88. In some embodiments, the anti-LIV1 scFv comprises a VH comprising CDR amino acid sequences of SEQ ID NO: 57, SEQ ID NO: 58, and/or SEQ ID NO: 59; and/or the anti-LIV1 scFv comprises a VL sequence comprising CDR amino acid sequences of SEQ ID NO: 60, SEQ ID NO: 61, and/or SEQ ID NO: 62.

The CAR, in some embodiments, comprises a CD3ζ cytoplasmic signaling domain. In some embodiments, the CAR comprises a CD28 co-stimulatory domain or a 41BB co-stimulatory domain.

In some embodiments, the TRAC gene comprises the nucleotide sequence of any one of SEQ ID NOs: 63, 64, 107, or 111, and/or wherein the CAR comprises the nucleotide sequence of any one of SEQ ID NOs: 49, 51, 104, or 108. In some embodiments, the disrupted β2M gene comprises at least one nucleotide sequence selected from any one of SEQ ID NOs: 9-14.

Also provided herein, in some aspects, is a population of engineered T cells (e.g., comprising a nucleic acid encoding an anti-LIV1 CAR), wherein at least 25% or at least 50% of engineered T cells of the population express the CAR. In some aspects, at least 15% or at least 50% of engineered T cells of the population express the CAR. For example, at least 70% of engineered T cells of the population express the CAR. In another example, at least 30% of engineered T cells of the population express the CAR.

In some embodiments, at least 25% of engineered T cells of the population express the CAR following at least 7 or at least 14 days of in vitro proliferation.

In some embodiments, at least 50% of engineered T cells of the population do not express a detectable level of T cell receptor (TCR) protein. For example, at least 90% of engineered T cells of the population may not express a detectable level of TCR protein.

In some embodiments, at least 50% of engineered T cells of the population do not express a detectable level of β2M protein. For example, at least 70% of engineered T cells of the population may not express a detectable level of β2M protein.

In some embodiments, engineered T cells of the population, when co-cultured in vitro with a population of cancer cells that express LIV1, induce cell lysis of at least 50% of the cancer cells of the population. For example, engineered T cells of the population may induce cell lysis of at least 70%, at least 80%, or at least 90% of the cancer cells of the population. In some embodiments, engineered T cells of the population, when co-cultured in vitro with a population of cancer cells, secrete IFNγ. In some embodiments, the ratio of engineered T cells to cancer cells is 1:1 to 2:1. The cancer cells may be, for example, sarcoma cells or breast cancer cells. Other cancer cells may be targeted.

In some embodiments, proliferative capacity of engineered T cells of the population is within 10% of proliferative capacity of control cells.

Other aspects of the present disclosure provide a method that comprises administering the population of engineered T cells as described herein. In some embodiments, percent body weight of the subject, following 5-10 days of administration, is within 10% of initial body weight of the subject, wherein initial body weight of the subject is body weight of the subject at the time of administration. In some embodiments, the subject is a human subject. In some embodiments, the subject has a cancer. The cancer may express LIV1, for example.

Further aspects of the present disclosure provide a method for producing an engineered T cell, the method comprising (a) delivering to a T cell a RNA-guided nuclease, a gRNA targeting a TRAC gene, and a vector comprising a donor template that comprises a nucleic acid encoding a CAR that comprise an ectodomain that binds specifically to LIV1, wherein the nucleic acid encoding the CAR is flanked by left and right homology arms to the TRAC gene, and (b) producing an engineered T cell. In some embodiments, the gRNA targeting the TRAC gene comprises the nucleotide sequence of SEQ ID NO: 18 or 19, or targets the nucleotide sequence of SEQ ID NO: 40.

In some embodiments, the method further comprises delivering to the T cell a gRNA targeting the β2M gene. In some embodiments, the gRNA targeting the β2M gene comprises the nucleotide sequence of SEQ ID NO: 20 or 21, or targets the nucleotide sequence of SEQ ID NO: 41.

In some embodiments, the RNA-guided nuclease is a Cas9 nuclease, optionally a *S. pyogenes* Cas9 nuclease.

In some embodiments, the donor template comprises the nucleotide sequence of any one of SEQ ID NOs: 63, 64, 107, or 111.

In some embodiments, the CAR comprises the nucleotide sequence of any one of SEQ ID NOs: 49, 51, 104, or 108.

BRIEF DESCRIPTION OF THE DRAWINGS

FIGS. 3A and 3B show secretion of the effector cytokine interferon-γ (IFN-γ) in A498 (FIG. 3A) and ZR-75-1 (FIG. 3B) cell lines. FIGS. 3C and 3D show secretion of the effector cytokine interleukin-2 (IL-2) in A498 (FIG. 3C) and ZR-75-1 (FIG. 3D) cell lines.

FIG. 4 shows an alignment of scFV constructs (VL and VH)—971 (SEQ ID NO: 54); 973 (SEQ ID NO: 82); 975 (SEQ ID NO: 83); 977 (SEQ ID NO: 84)

FIG. 5 shows an alignment of scFV constructs (VH and VL)—979 (SEQ ID NO: 70); 974 (SEQ ID NO: 85); 976 (SEQ ID NO: 86); 978 (SEQ ID NO: 87), 972 (SEQ ID NO: 127)

DETAILED DESCRIPTION

LIV1 Cancer Antigen

Figure 1A:
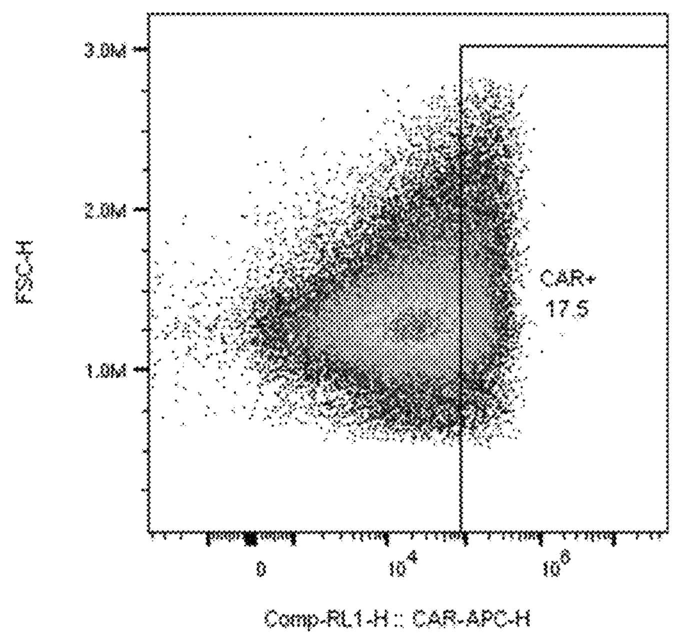
FIGS. 1A-1E show flow cytometry results to assess TRAC, β2M, and anti-Liv1a CAR expression levels at the cell surface of the edited cell population.
Figure 1A:
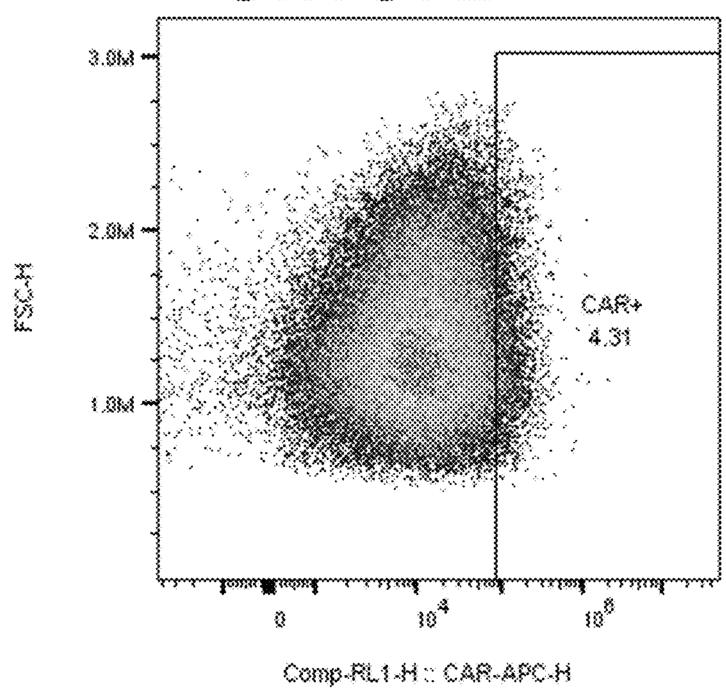
Figure 1B:
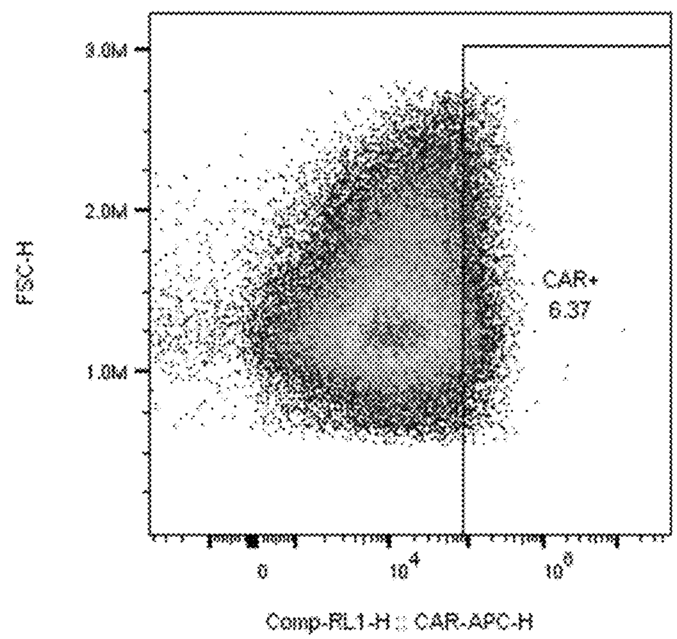
Figure 1B:
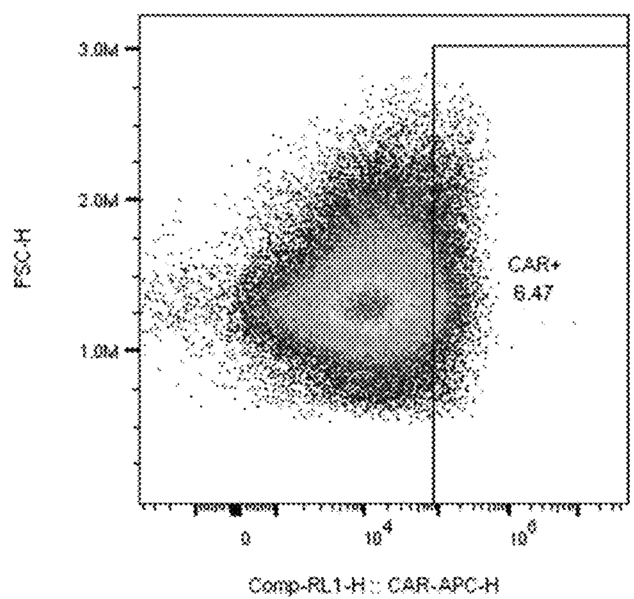
Figure 1C:
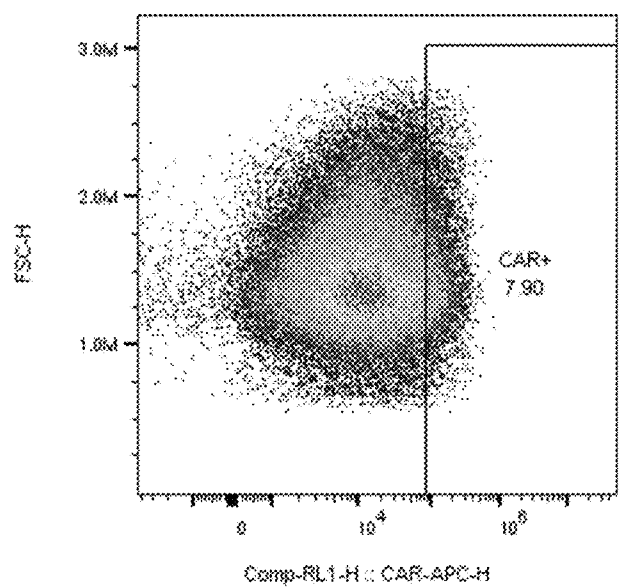
Figure 1C:
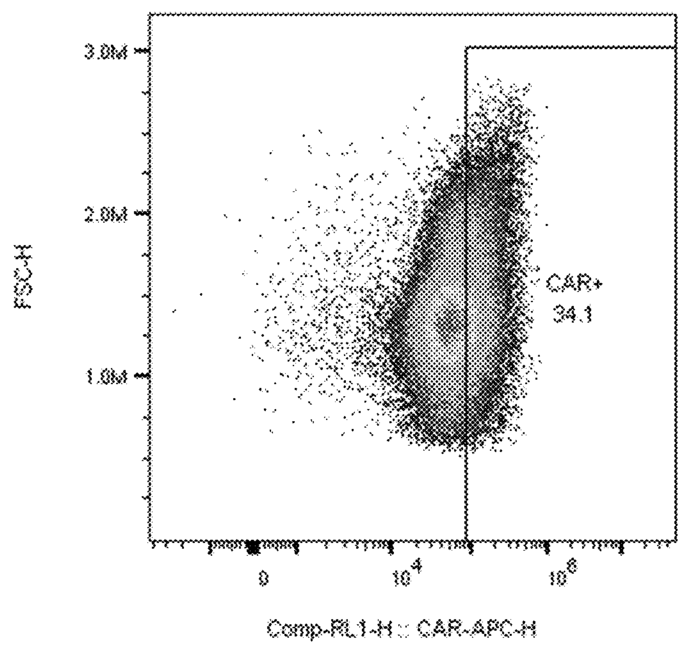
Figure 1D:
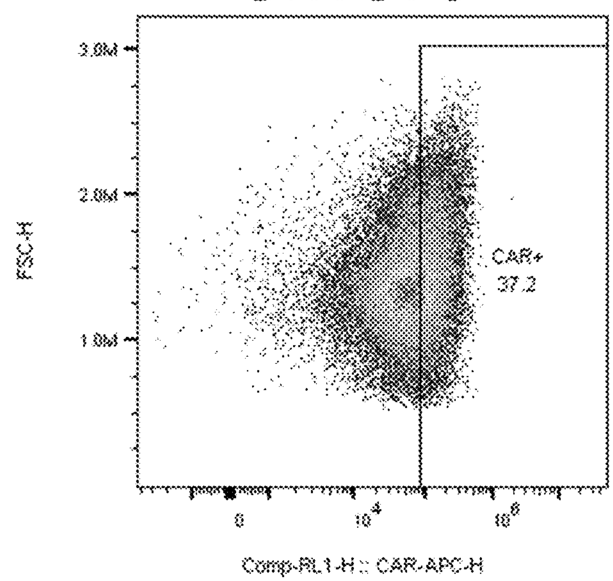
Figure 1D:
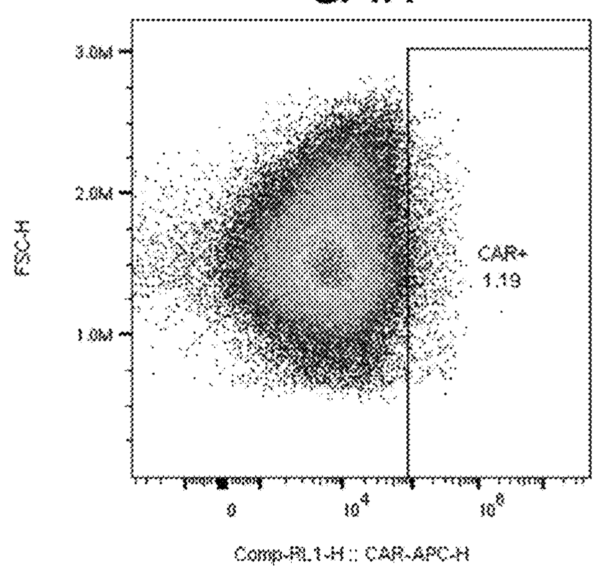
Figure 1E:
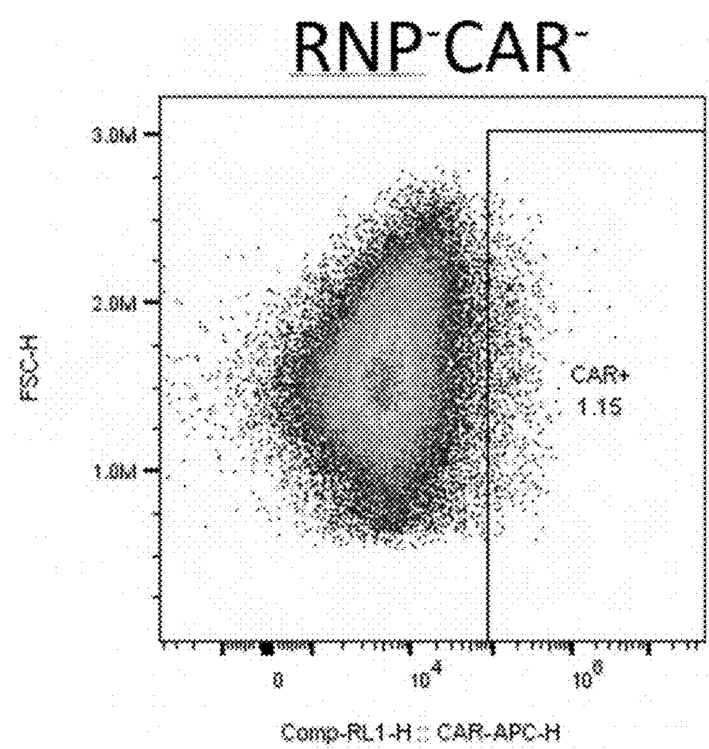

In some embodiments, the T cells of the present disclosure are engineered with a chimeric antigen receptor (CAR) designed to target LIV1. LIV1, also known as Solute Carrier Family 39 Member 6, SLC39A6, ZIP6, and LIV-1, is a member of the ZIP family of highly conserved transmembrane zinc transporter proteins. LIV1 is expressed at elevated levels in breast cancer, e.g., estrogen receptor-positive breast cancer, prostate cancer, squamous tumors, e.g., of the skin, bladder, lung, cervix, endometrium, head neck, and biliary tract, and neuronal tumors. Notably, LIV1 has a restricted expression in normal tissues, e.g., non-cancerous breast, prostate, and testis. Thus, LIV1 is a desirable transmembrane protein for targeting cancer. In fact, the LIV-1 protein has been implicated in breast cancer, prostate cancer, squamous tumors, and neuronal tumors.

Thus, in some embodiments, T cells of the present disclosure are engineered to express a CAR comprising an anti-LIV1 antibody (e.g., anti-LIV1 scFv). In some embodiments, the anti-LIV1 antibody is an anti-LIV1 scFv encoded by the sequence of any one of SEQ ID NOs: 53, 69, 97, 102, 106, 110, 114, or 118. In some embodiments, the anti-LIV1 antibody is an anti-LIV1 scFv comprising the sequence of any one of SEQ ID NOs: 54, 70, 82, 83, 84, 85, 86, or 87. In some embodiments, the anti-LIV1 antibody is an anti-LIV1 scFv comprising a VH comprising an amino acid sequence of any one of SEQ ID NO: 55, 90 or 98. In some embodiments, the anti-LIV1 antibody is an anti-LIV1 scFv comprising a VL comprising an amino acid sequence of any one of SEQ ID NO: 56, 88 or 128. In some embodiments, a CAR comprising an anti-LIV1 antibody is encoded by the sequence of any one of SEQ ID NOs: 49, 51, 65, 67, 95, 100, 104, 108, 112, or 116. In some embodiments, a CAR comprising an anti-LIV7 antibody is encoded by a sequence comprising a nucleic acid that is at least 90% identical to SEQ ID NOs: 49, 51, 65, 67, 95, 100, 104, 108, 112, or 116. In some embodiments, a CAR comprising an anti-LIV1 antibody comprises the sequence of any one of SEQ ID NOs: 49, 51, 65, 67, 95, 100, 104, 108, 112, or 116. In some embodiments, a CAR comprising an anti-LIV1 antibody comprises an anti-LIV1 antibody as described in U.S. Pat. No. 9,228,026.

Multi-Gene Editing

The engineered T cells of the present disclosure, in some embodiments, include more than one gene edit, for example, in more than one gene. For example, an engineered T cell may comprise a disrupted T cell receptor alpha chain constant region (TRAC) gene, a disrupted beta-2-microglobulin (β2M) gene, a disrupted programmed cell death-1 (PD-1 or PDCD1) gene, a disrupted CD70 gene, or any combination of two or more of the foregoing disrupted genes. In some embodiments, an engineered T cell comprises a disrupted TRAC gene, a disrupted β2M gene, and a disrupted CD70 gene. In some embodiments, an engineered T cell comprises a disrupted TRAC gene, a disrupted β2M gene, and a disrupted PD-1 gene. In some embodiments, an engineered T cell comprises a disrupted TRAC gene, a disrupted β2M gene, a disrupted CD70 gene and a disrupted PD-1 gene.

It should be understood that gene disruption encompasses gene modification through gene editing (e.g., using CRISPR/Cas gene editing to insert or delete one or more nucleotides). In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having β2M gene edit may be considered β2M knockout cell β2M protein cannot be detected at the cell surface using an antibody that specifically binds β2M protein.

Provided herein, in some embodiments, are populations of cells in which a certain percentage of the cells has been edited (e.g., β2M gene edited), resulting in a certain percentage of cells not expressing a particular gene and/or protein. In some embodiments, at least 50% (e.g., 50%, 55%, 60%, 65%, 70%, 75%, 80%, 85%, 90%, or 85%) of the cells of a gene-edited population of cells are β2M knockout cells. In some embodiments, at least 50% of the cells (e.g. T cells) of the population do not express detectable levels of β2M protein. In some embodiments, at least 55%, at least 60%, at least 65%, at least 70%, at least 75%, at least 80%, at least 85%, at least 90%, or at least 95% of the cells of a gene-edited population of cells may be β2M knockout cells.

Methods of using CRISPR-Cas gene editing technology to create a genomic deletion in a cell (e.g., to knock out a gene in a cell) are known (Bauer D E et al. Vis. Exp. 2015; 95; e52118).

TRAC Gene Edit

In some embodiments, an engineered T cell comprises a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. In some embodiments, a disruption in the TRAC gene expression is created by knocking a chimeric antigen receptor (CAR) into the TRAC gene (e.g., using an adeno-associated viral (AAV) vector and donor template). In some embodiments, a disruption in the TRAC gene expression is created by gRNAs targeting the TRAC genomic region. In some embodiments, a genomic deletion in the TRAC gene is created by knocking a chimeric antigen receptor (CAR) into the TRAC gene (e.g., using an AAV vector and donor template). In some embodiments, a disruption in the TRAC gene expression is created by gRNAs targeting the TRAC genomic region and knocking a chimeric antigen receptor (CAR) into the TRAC gene.

Non-limiting examples of modified and unmodified TRAC gRNA sequences that may be used as provided herein to create a genomic disruption in the TRAC gene are listed in Table 4 (e.g., SEQ ID NOs: 18 and 19). See also International Application No. PCT/US2018/032334, filed May 11, 2018, incorporated herein by reference. Other gRNA sequences may be designed using the TRAC gene sequence located on chromosome 14 (GRCh38: chromosome 14: 22,547,506-22,552,154; . Ensembl; ENSG00000277734). In some embodiments, gRNAs targeting the TRAC genomic region create Indels in the TRAC gene disrupting expression of the mRNA or protein.

In some embodiments, at least 50% of a population of engineered T cells do not express a detectable level of T cell receptor (TCR) surface protein. For example, at least 55%, at least 60%, at least 70%, at least 75%, at least 80%, at least 85%, at least 90%, or at least 95% of a population may not express a detectable level of TCR surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the population of engineered T cells do not express a detectable level of TCR surface protein.

In some embodiments, gRNAs targeting the TRAC genomic region create Indels in the TRAC gene comprising at least one nucleotide sequence selected from the following sequences in Table 1:

TABLE 1

| Sequence | SEQ ID NO: |
|---|---|
| AAGAGCAACAAATCTGACT | 1 |
| AAGAGCAACAGTGCTGTGCCTGGAGCAACAAATCTGACT AAGAGCAACAAATCTGACT | 2 |
| AAGAGCAACAGTGCTGGAGCAACAAATCTGACT AAGAGCAACAAATCTGACT | 3 |
| AAGAGCAACAGTGCCTGGAGCAACAAATCTGACT AAGAGCAACAAATCTGACT | 4 |
| AAGAGCAACAGTGCTGACTAAGAGCAACAAATCTGACT | 5 |
| AAGAGCAACAGTGCTGTGGGCCTGGAGCAACAAATCTGACT AAGAGCAACAAATCTGACT | 6 |

TABLE 1-continued

| Sequence | SEQ ID NO: |
|---|---|
| AAGAGCAACAGTGCTGGCCTGGAGCAACAAATCTGACT AAGAGCAACAAATCTGACT | 7 |
| AAGAGCAACAGTGCTGTGTGCCTGGAGCAACAAATCTGACT AAGAGCAACAAATCTGACT | 8 |

In some embodiments, an engineered T cell comprises a deletion in the TRAC gene relative to unmodified T cells. In some embodiments, an engineered T cell comprises a deletion of 15-30 base pairs in the TRAC gene relative to unmodified T cells. In some embodiments, an engineered T cell comprises a deletion of 15, 16, 17, 18, 19, 20, 21, 22, 23, 24, 25, 26, 27, 28, 29 or 30 base pairs in the TRAC gene relative to unmodified T cells. In some embodiments, an engineered T cell comprises a deletion of more than 30 base pairs in the TRAC gene relative to unmodified T cells. In some embodiments, an engineered T cell comprises a deletion of 20 base pairs in the TRAC gene relative to unmodified T cells. In some embodiments, an engineered T cell comprises a deletion of SEQ ID NO: 92 (AGAGCAACAGTGCTGTGGCC) in the TRAC gene relative to unmodified T cells. In some embodiments, an engineered T cell comprises a deletion comprising SEQ ID NO: 92 (AGAGCAACAGTGCTGTGGCC) in the TRAC gene relative to unmodified T cells. In some embodiments, an engineered T cell comprises a deletion of SEQ ID NO: 40 in the TRAC gene relative to unmodified T cells. In some embodiments, an engineered T cell comprises a deletion comprising SEQ ID NO: 40 in the TRAC gene relative to unmodified T cells.

β2M Gene Edit

In some embodiments, an engineered T cell comprises a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

Non-limiting examples of modified and unmodified β2M gRNA sequences that may Non-limiting examples of modified and unmodified β2M gRNA sequences that may be used as provided herein to create a genomic disruption in the β2M gene are listed in Table 4 (e.g., SEQ ID NOs: 20 and 21). See also International Application No. PCT/US2018/032334, filed May 11, 2018, incorporated herein by reference. Other gRNA sequences may be designed using the β2M gene sequence located on Chromosome 15 (GRCh38 coordinates: Chromosome 15: 44,711,477-44,718,877; Ensembl: ENSG00000166710).

In some embodiments, gRNAs targeting the β2M genomic region create Indels in the β2M gene disrupting expression of the mRNA or protein.

In some embodiments, at least 50% of the engineered T cells of a population of engineered T cells does not express a detectable level of β2M surface protein. For example, at least 55%, at least 60%, at least 70%, at least 75%, at least 80%, at least 85%, at least 90%, or at least 95% of the engineered T cells of a population may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

In some embodiments, an edited β2M gene comprises at least one nucleotide sequence selected from the following sequences in Table 2.

TABLE 2

| Sequences | SEQ ID NO: |
|---|---|
| CGTGGCCTTAGCTGTGCTCGCGCTACTCTCTCTTTCTGCCTGGAGGCTATCCAGCGTGAGTCTCTCCTACCCTCCCGCT | 9 |
| CGTGGCCTTAGCTGTGCTCGCGCTACTCTCTCTTTCGCCTGGAGGCTATCCAGCGTGAGTCTCTCCTACCCTCCCGCT | 10 |
| CGTGGCCTTAGCTGTGCTCGCGCTACTCTCTCTTTCTGGAGGCTATCCAGCGTGAGTCTCTCCTACCCTCCCGCT | 11 |
| CGTGGCCTTAGCTGTGCTCGCGCTACTCTCTCTTTCTGGATAGCCTGGAGGCTATCCAGCGTGAGTCTCTCCTACCCTCCCGCT | 12 |
| CGTGGCCTTAGCTGTGCTCGCGCTATCCAGCGTGAGTCTCTCCTACCCTCCCGCT | 13 |
| CGTGGCCTTAGCTGTGCTCGCGCTACTCTCTCTTTCTGTGGCCTGGAGGCTATCCAGCGTGAGTCTCTCCTACCCTCCCGCT | 14 |

PD-1 Gene Edit

PD-1 is an immune checkpoint molecule that is upregulated in activated T cells and serves to dampen or stop T cell responses. Disrupting PD-1 by gene editing could lead to more persistent and/or potent therapeutic T cell responses and/or reduce immune suppression in a subject. In some embodiments, an engineered T cell comprises a disrupted PD-1 gene. In some embodiments, expression of the endogenous PD-1 gene is eliminated to enhance anti-tumor efficacy of the CAR T cells of the present disclosure.

Non-limiting examples of modified and unmodified PD-1 gRNA sequences that may be used as provided herein to create a genomic deletion in the PD-1 gene are listed in Table 4 (e.g., SEQ ID NOs: 22 and 23). See also International Application No. PCT/US2018/032334, filed May 11, 2018, incorporated herein by reference. Other gRNA sequences may be designed using the PD-1 gene sequence located on Chromosome 2 (GRCh38 coordinates: Chromosome 2: 241,849,881-241,858,908; Ensembl: ENS G00000188389).

In some embodiments, gRNAs targeting the PD-1 genomic region create Indels in the PD-1 gene disrupting expression of the PD-1 mRNA or protein.

In some embodiments, an engineered T cell comprises a disrupted PD-1 gene. In some embodiments, at least 50% of the engineered T cells of a population of engineered T cells does not express a detectable level of PD-1 surface protein. For example, at least 55%, at least 60%, at least 70%, at least 75%, at least 80%, at least 85%, at least 90%, or at least 95% of the engineered T cells of a population may not express a detectable level of PD-1 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of PD-1 surface protein.

CD70 Gene Edit

Cluster of Differentiation 70 (CD70) is a member of the tumor necrosis factor superfamily and its expression is restricted to activated T and B lymphocytes and mature dendritic cells. CD70 has also been detected on hematological tumors and on carcinomas. CD70 is implicated in tumor cell and regulatory T cell survival through interaction with its ligand, CD27. Disrupting CD70 by gene editing increases cell expansion and reduces cell exhaustion. In some embodiments, an engineered T cell comprises a disrupted CD70 gene. In some embodiments, expression of the endogenous CD70 gene is eliminated to enhance anti-tumor efficacy of the CAR T cells of the present disclosure. In some embodiments, gRNAs targeting the CD70 genomic region create Indels in, or around, the CD70 gene disrupting expression of the CD70 mRNA and/or protein.

Non-limiting examples of modified and unmodified CD70 gRNA sequences that may be used as provided herein to create a genomic disruption in the CD70 gene are listed in Table 4 (e.g., SEQ ID NOs: 24-27). Other gRNA sequences may be designed using the CD70 gene sequence located on Chromosome 19 (GRCh38 coordinates: Chromosome 19: 6,583,183-6,604,103; Ensembl: ENSG00000125726).

In some embodiments, an engineered T cell comprises a disrupted CD70 gene. In some embodiments, at least 50% of the engineered T cells of a population of engineered T cells does not express a detectable level of CD70 surface protein. For example, at least 55%, at least 60%, at least 70%, at least 75%, at least 80%, at least 85%, at least 90%, or at least 95% of the engineered T cells of a population may not express a detectable level of CD70 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of CD70 surface protein.

Cellular Phenotypes

In some embodiments, one or more gene edits within a population of cells results in a phenotype associated with changes in cellular proliferative capacity, cellular exhaustion, cellular viability, cellular lysis capability (e.g., increase cytokine production and/or release), or any combination thereof.

In some embodiments, engineered T cells of the present disclosure exhibit at least 20% greater cellular proliferative capacity, relative to control T cells. For example, engineered T cells may exhibit at least 25%, at least 30%, at least 35%, at least 40%, at least 45%, at least 50%, at least 55%, at least 60%, at least 65%, at least 70%, at least 75%, at least 80%, or at least 90% greater cellular proliferative capacity, relative to control T cells. In some embodiments, engineered T cells of the present disclosure exhibit 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% greater cellular proliferative capacity, relative to control T cells.

In some embodiments, engineered T cells of the present disclosure exhibit an at least 20% increase in cellular viability, relative to control cells. For example, engineered T cells of the present disclosure may exhibit at least 25%, at least 30%, at least 35%, at least 40%, at least 45%, at least 50%, at least 55%, at least 60%, at least 65%, at least 70%, at least 75%, at least 80%, or at least 90% increase in cellular viability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-

70%, 40%-60%, 40%-50%, 50%-100%, 50%-90%, 50%-80%, 50%-70%, or 50%-60% increase in cellular viability, relative to control cells.

In some embodiments, engineered T cells of the present disclosure exhibit an at least 20% increase in cellular lysis capability (kill at least 20% more target cells), relative to control cells. For example, engineered T cells of the present disclosure may exhibit an at least at least 25%, at least 30%, at least 35%, at least 40%, at least 45%, at least 50%, at least 55%, at least 60%, at least 65%, at least 70%, at least 75%, at least 80%, or at least 90% increase in cellular lysis capability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular lysis capability, relative to control cells. For example, the level of cytokines (e.g., IL-2 and/or IFN-gamma) secreted by the engineered T cells may at least 2-fold (e.g., at least 3-fold, at least 4-fold, or at least 5-fold) greater than the level of cytokines secreted by control T cells.

Control T cells, in some embodiments, are engineered T cells (e.g., gene edited T cells). In some embodiments, control T cells are engineered T cells that comprise a disrupted TRAC gene, a nucleic acid encoding a CAR (e.g., an anti-LIV1 CAR) inserted into the TRAC gene, and/or a disrupted β2M gene. In some embodiments, control T cells are unedited T cells.

Gene Editing Methods

Gene editing (including genomic editing) is a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When an sequence of an endogenous gene is edited, for example by deletion, insertion or substitution of nucleotide(s)/nucleic acid(s), the endogenous gene comprising the affected sequence may be knocked-out or knocked-down due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

Available endonucleases capable of introducing specific and targeted DSBs include, but not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the Fokl nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the Fokl nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination.

Other non-limiting examples of targeted nucleases include naturally-occurring and recombinant nucleases, e.g., CRISPR/Cas9, restriction endonucleases, meganucleases homing endonucleases, and the like.

CRISPR-Cas9 Gene Editing

The CRISPR-Cas9 system is a naturally-occurring defense mechanism in prokaryotes that has been repurposed as a RNA-guided DNA-targeting platform used for gene editing. It relies on the DNA nuclease Cas9, and two noncoding RNAs-crisprRNA (crRNA) and trans-activating RNA (tracrRNA)—to target the cleavage of DNA.

crRNA drives sequence recognition and specificity of the CRISPR-Cas9 complex through Watson-Crick base pairing typically with a 20 nucleotide (nt) sequence in the target DNA. Changing the sequence of the 5' 20nt in the crRNA allows targeting of the CRISPR-Cas9 complex to specific loci. The CRISPR-Cas9 complex only binds DNA sequences that contain a sequence match to the first 20 nt of the crRNA, single-guide RNA (sgRNA), if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

In some embodiments, the Cas9 (CRISPR associated protein 9) endonuclease is from *Streptococcus pyogenes*, although other Cas9 homologs may be used. It should be understood, that wild-type Cas9 may be used or modified versions of Cas9 may be used (e.g., evolved versions of Cas9, or Cas9 orthologues or variants), as provided herein. In some embodiments, Cas9 may be substituted with another RNA-guided endonuclease, such as Cpf1 (of a class II CRISPR/Cas system).

Guide RNAs

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA comprises at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid is a double-molecule guide RNA. In some embodiments, the genome-targeting nucleic acid is a single-molecule guide RNA.

A double-molecule guide RNA comprises two strands of RNA. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (sgRNA) in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

A single-molecule guide RNA (referred to as a "sgRNA" or "gRNA") in a Type V system comprises, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence (see Table 3).

The sgRNA can comprise no uracil at the 3' end of the sgRNA sequence. The sgRNA can comprise one or more uracil at the 3' end of the sgRNA sequence. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 3

| SEQ ID NO. | sgRNA sequence |
|---|---|
| 15 | nnnnnnnnnnnnnnnnnnnnguuuuagagcua-gaaauagcaa guuaaaauaaggcuaguccguuaucaac-uugaaaaaguggca ccgagucggugcuuuu |
| 16 | nnnnnnnnnnnnnnnnnnnnguuuuagagcua-gaaauagcaa guuaaaauaaggcuaguccguuaucaac-uugaaaaaguggca ccgagucggugc |
| 17 | $n_{(17-30)}$ guuuuagagcua-gaaauagcaaguuaaaauaaggcu aguccguuaucaacuugaaaaaguggcaccgagucggugc $u_{(1-8)}$ |

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Sequence

A gRNA comprises a spacer sequence. A spacer sequence is a sequence (e.g., a 20 nucleotide sequence) that defines the target sequence (e.g., a DNA target sequences, such as a genomic target sequence) of a target nucleic acid of interest. In some embodiments, the spacer sequence is 15 to 30 nucleotides. In some embodiments, the spacer sequence is 15, 16, 17, 18, 19, 29, 21, 22, 23, 24, 25, 26, 27, 28, 29, or 30 nucleotides. In some embodiments, a spacer sequence is 20 nucleotides.

The "target sequence" is adjacent to a PAM sequence and is the sequence modified by an RNA-guided nuclease (e.g., Cas9). The "target nucleic acid" is a double-stranded molecule: one strand comprises the target sequence and is referred to as the "PAM strand," and the other complementary strand is referred to as the "non-PAM strand." One of skill in the art recognizes that the gRNA spacer sequence hybridizes to the reverse complement of the target sequence, which is located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 92), then the gRNA spacer sequence is 5'-AGAGCAACAGUGCUGUGGCC-3' (SEQ ID NO: 93). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence comprises 20 nucleotides. In some embodiments, the target nucleic acid comprises less than 20 nucleotides. In some embodiments, the target nucleic acid comprises more than 20 nucleotides. In some embodiments, the target nucleic acid comprises at least: 5, 10, 15, 16, 17, 18, 19, 20, 21, 22, 23, 24, 25, 30 or more nucleotides. In some embodiments, the target nucleic acid comprises at most: 5, 10, 15, 16, 17, 18, 19, 20, 21, 22, 23, 24, 25, 30 or more nucleotides. In some embodiments, the target nucleic acid sequence comprises 20 bases immediately 5' of the first nucleotide of the PAM. For example, in a sequence comprising 5'-NNNNNNNNNNNNNNNNNNNNNRG-3' (SEQ ID NO: 130), the target nucleic acid comprises the sequence that corresponds to the Ns, wherein N is any nucleotide, and the underlined NRG sequence is the *S. pyogenes* PAM.

Non-limiting examples of gRNAs that may be used as provided herein are provided in Table 4 and PCT/US2018/032334, filed May 11, 2018.

TABLE 4

| gRNA Sequences/Target Sequences | | |
|---|---|---|
| gRNA Sequences | | |
| Name | Unmodified Sequence | Modified Sequence |
| TRAC sgRNA | AGAGCAACAGUGCUGUGGC Cguuuuagagcuagaaauagcaaguuaaa auaaggcuaguccguuaucaacuugaaaa aguggcaccgagucggugcUUUU (SEQ ID NO: 18) | A*G*A*GCAACAGUGCUGUG GCCguuuuagagcuagaaauagcaaguu aaaauaaggcuaguccguuaucaacuuga aaaaguggcaccgagucggugcU*U*U *U (SEQ ID NO: 28) |
| TRAC sgRNA spacer | AGAGCAACAGUGCUGUGGC C (SEQ ID NO: 19) | A*G*A*GCAACAGUGCUGUG GCC (SEQ ID NO: 29) |

TABLE 4-continued

| gRNA Sequences/Target Sequences | | |
|---|---|---|
| β2M sgRNA | GCUACUCUCUCUUUCUGGC Cguuuuagagcuagaaauagcaaguuaaa auaaggcuaguccguuaucaacuugaaaa aguggcaccgagucggugcUUUU (SEQ ID NO: 20) | G*C*U*ACUCUCUCUUUCUG GCCguuuuagagcuagaaauagcaaguu aaaauaaggcuaguccguuaucaacuuga aaaaguggcaccgagucggugcU*U*U *U (SEQ ID NO: 30) |
| β2M sgRNA spacer | GCUACUCUCUCUUUCUGGC C (SEQ ID NO: 21) | G*C*U*ACUCUCUCUUUCUG GCC (SEQ ID NO: 31) |
| PD-1 sgRNA | CUGCAGCUUCUCCAACACA Uguuuuagagcuagaaauagcaaguuaaa auaaggcuaguccguuaucaacuugaaaa aguggcaccgagucggugcUUUU (SEQ ID NO: 22) | C*U*G*CAGCUUCUCCAACA CAUguuuuagagcuagaaauagcaagu uaaaauaaggcuaguccguuaucaacuug aaaaaguggcaccgagucggugcU*U* U*U (SEQ ID NO: 32) |
| PD-1 sgRNA spacer | CUGCAGCUUCUCCAACACA U (SEQ ID NO: 23) | C*U*G*CAGCUUCUCCAACA CAU (SEQ ID NO: 33) |
| CD70 sgRNA (E1_T7) | GCUUUGGUCCCAUUGGUCG Cguuuuagagcuagaaauagcaaguuaaa auaaggcuaguccguuaucaacuugaaaa aguggcaccgagucggugcUUUU (SEQ ID NO: 24) | G*C*U*UUGGUCCCAUUGGU CGCguuuuagagcuagaaauagcaaguu aaaauaaggcuaguccguuaucaacuuga aaaaguggcaccgagucggugcU*U*U *U (SEQ ID NO: 34), T7 |
| CD70 sgRNA (E1_T7) spacer | GCUUUGGUCCCAUUGGUCG C (SEQ ID NO: 25) | G*C*U*UUGGUCCCAUUGGU CGC (SEQ ID NO: 35) |
| CD70 sgRNA (E1_T8) | GCCCGCAGGACGCACCCAUA guuuuagagcuagaaauagcaaguuaaaa uaaggcuaguccguuaucaacuugaaaaa guggcaccgagucggugcUUUU (SEQ ID NO: 26) | G*C*C*CGCAGGACGCACCC AUAguuuuagagcuagaaauagcaagu uaaaauaaggcuaguccguuaucaacuug aaaaaguggcaccgagucggugcU*U* U*U (SEQ ID NO: 36), T8 |
| CD70 sgRNA (E1_T8) spacer | GCCCGCAGGACGCACCCAUA (SEQ ID NO: 27) | G*C*C*CGCAGGACGCACCC AUA (SEQ ID NO: 37) |

| Target Sequences Guide Name | Target Sequence (PAM) |
|---|---|
| CD70 sgRNA (E1_T7) | GCTTTGGTCCCATTGGTCGC (GGG) (SEQ ID NO: 38) |
| CD70 sgRNA (E1_T8) | GCCCGCAGGACGCACCCATA (GGG) (SEQ ID NO: 39) |
| TRAC sgRNA | AGAGCAACAGTGCTGTGGCC (TGG) (SEQ ID NO: 40) |
| β2M sgRNA | GCTACTCTCTCTTTCTGGCC (TGG) (SEQ ID NO: 41) |
| PD-1 sgRNA | CTGCAGCTTCTCCAACACAT (CGG) (SEQ ID NO: 42) |

*: 2'-O-methyl phosphorothioate residue

Chimeric Antigen Receptor (CAR) T Cells

A chimeric antigen receptor refers to an artificial immune cell receptor that is engineered to recognize and bind to an antigen expressed by tumor cells. Generally, a CAR is designed for a T cell and is a chimera of a signaling domain of the T-cell receptor (TCR) complex and an antigen-recognizing domain (e.g., a single chain fragment (scFv) of an antibody or other antibody fragment) (Enblad et al., Human Gene Therapy. 2015; 26(8):498-505). A T cell that expresses a CAR is referred to as a CAR T cell. CARs have the ability to redirect T-cell specificity and reactivity toward a selected target in a non-MHC-restricted manner. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

There are four generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TCR CD3ζ chain. Third-generation costimulatory domains may include, e.g., a combination of CD3ζ, CD27, CD28, 4-1BB, ICOS, or OX40. CARs, in some embodiments, contain an ectodomain (e.g., CD3ζ), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., *Blood.* 2015; 125(26):4017-4023; Kakarla and Gottschalk, *Cancer J.* 2014; 20(2):151-155).

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency.

In some embodiments, a chimeric antigen receptor is a first generation CAR. In other embodiments, a chimeric antigen receptor is a second generation CAR. In yet other embodiments, a chimeric antigen receptor is a third generation CAR.

A CAR, in some embodiments, comprises an extracellular (ecto) domain comprising an antigen binding domain (e.g., an antibody, such as an scFv), a transmembrane domain, and a cytoplasmic (endo) domain.

Ectodomain. The ectodomain is the region of the CAR that is exposed to the extracellular fluid and, in some embodiments, includes an antigen binding domain, and optionally a signal peptide, a spacer domain, and/or a hinge domain. In some embodiments, the antigen binding domain is a single-chain variable fragment (scFv) that include the light and heavy chains of immunoglobulins connected with a short linker peptide. The linker, in some embodiments, includes hydrophilic residues with stretches of glycine and serine for flexibility as well as stretches of glutamate and lysine for added solubility. A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. Non-limiting examples of VH and VL protein sequences that may be used to create an anti-LIV1 scFv may include the amino acid sequence of SEQ ID NOs: 55, 90 or 98 (VH) and SEQ ID NOs: 56, 88 or 128 (VL). In some embodiments, the scFv of the present disclosure is humanized. In other embodiments, the scFv is fully human. In yet other embodiments, the scFv is a chimera (e.g., of mouse and human sequence). In some embodiments, the scFv is an anti-LIV1 scFv (binds specifically to LIV1). Non-limiting examples of anti-LIV1 scFv proteins that may be used as provided herein may include the amino acid sequence of any one of SEQ ID NOs: 54, 70, 82, 83, 84, 85, 86, or 87. Other scFv proteins may be used.

The signal peptide can enhance the antigen specificity of CAR binding. Signal peptides can be derived from antibodies, such as, but not limited to, CD8, as well as epitope tags such as, but not limited to, GST or FLAG. Examples of signal peptides include MLLLVTSLLLCELPHPAFLLIP (SEQ ID NO: 94) and MALPVTALLLPLALLLHAARP (SEQ ID NO: 73). Other signal peptides may be used.

In some embodiments, a spacer domain or hinge domain is located between an extracellular domain (comprising the antigen binding domain) and a transmembrane domain of a CAR, or between a cytoplasmic domain and a transmembrane domain of the CAR. A spacer domain is any oligopeptide or polypeptide that functions to link the transmembrane domain to the extracellular domain and/or the cytoplasmic domain in the polypeptide chain. A hinge domain is any oligopeptide or polypeptide that functions to provide flexibility to the CAR, or domains thereof, or to prevent steric hindrance of the CAR, or domains thereof. In some embodiments, a spacer domain or a hinge domain may comprise up to 300 amino acids (e.g., 10 to 100 amino acids, or 5 to 20 amino acids). In some embodiments, one or more spacer domain(s) may be included in other regions of a CAR. In some embodiments, the hinge domain is a CD8 hinge domain. Other hinge domains may be used.

Transmembrane Domain. The transmembrane domain is a hydrophobic alpha helix that spans the membrane. The transmembrane domain provides stability of the CAR. In some embodiments, the transmembrane domain of a CAR as provided herein is a CD8 transmembrane domain. In other embodiments, the transmembrane domain is a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain: FVPVFLPAKPTTTPAPRPPTPAPTIASQPLSLRPEACRPAAGG AVHTRGLDFACDIYIWAPLAGTCGVLLLSLVITLYCNHRNR (SEQ ID NO: 129). Other transmembrane domains may be used.

Endodomain. The endodomain is the functional end of the receptor. Following antigen recognition, receptors cluster and a signal is transmitted to the cell. The most commonly used endodomain component is CD3-zeta, which contains three (3) immunoreceptor tyrosine-based activation motif (ITAM)s. This transmits an activation signal to the T cell after the antigen is bound. In many cases, CD3-zeta may not provide a fully competent activation signal and, thus, a co-stimulatory signaling is used. For example, CD28 and/or 4-1BB may be used with CD3-zeta (CD3ζ) to transmit a proliferative/survival signal. Thus, in some embodiments, the co-stimulatory molecule of a CAR as provided herein is a CD28 co-stimulatory molecule. In other embodiments, the co-stimulatory molecule is a 4-1BB co-stimulatory molecule. In some embodiments, a CAR includes CD3ζ and CD28. In other embodiments, a CAR includes CD3-zeta and 4-1BB. In still other embodiments, a CAR includes CD3ζ, CD28, and 4-1BB. Table 5 provides examples of signaling molecules that may be used as provided herein.

TABLE 5

| Name | Sequence | SEQ ID NO: |
|---|---|---|
| 4-1BB | AAACGGGGCAGAAAGAAACTCCTGTATATATTCAAACAACCATTT<br>ATGAGACCAGTACAAACTACTCAAGAGGAAGATGGCTGTAGCTGC<br>CGATTTCCAGAAGAAGAAGAAGGAGGATGTGAACTG | 43 |

TABLE 5-continued

| Name | Sequence | SEQ ID NO: |
|---|---|---|
| | KRGRKKLLYIFKQPFMRPVQTTQEEDGCSCRFPEEEEGGCEL | 44 |
| CD28 | TCAAAGCGGAGTAGGTTGTTGCATTCCGATTACATGAATATGACTC CTCGCCGGCCTGGGCCGACAAGAAAACATTACCAACCCTATGCCC CCCCACGAGACTTCGCTGCGTACAGGTCC | 45 |
| | SKRSRLLHSDYMNMTPRRPGPTRKHYQPYAPPRDFAAYRS | 46 |
| CD3-zeta | CGAGTGAAGTTTTCCCGAAGCGCAGACGCTCCGGCATATCAGCAA GGACAGAATCAGCTGTATAACGAACTGAATTTGGGACGCCGCGAG GAGTATGACGTGCTTGATAAACGCCGGGGGAGAGACCCGGAAATG GGGGGTAAACCCCGAAGAAAGAATCCCCAAGAAGGACTCTACAA TGAACTCCAGAAGGATAAGATGGCGGAGGCCTACTCAGAAATAGG TATGAAGGGCGAACGACGACGGGGAAAAGGTCACGATGGCCTCT ACCAAGGGTTGAGTACGGCAACCAAAGATACGTACGATGCACTGC ATATGCAGGCCCTGCCTCCCAGA | 47 |
| | RVKFSRSADAPAYQQGQNQLYNELNLGRREEYDVLDKRRGRDPEMG GKPRRKNPQEGLYNELQKDKMAEAYSEIGMKGERRRGKGHDGLYQ GLSTATKDTYDALHMQALPPR | 48 |

Antibodies

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) monoclonal antibodies, but also antigen-binding fragments (such as Fab, Fab', F(ab')2, Fv), single chain variable fragment (scFv), mutants thereof, fusion proteins comprising an antibody portion, humanized antibodies, chimeric antibodies, diabodies, linear antibodies, single chain antibodies, single domain antibodies (e.g., camel or llama VHH antibodies), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies.

A typical antibody molecule comprises a heavy chain variable region (VH) and a light chain variable region (VL), which are usually involved in antigen binding. These regions/residues that are responsible for antigen-binding can be identified from amino acid sequences of the VH/VL sequences of a reference antibody (e.g., an anti-LIV1 antibody as described herein) by methods known in the art. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. As used herein, a CDR may refer to the CDR defined by any method known in the art. Two antibodies having the same CDR means that the two antibodies have the same amino acid sequence of that CDR as determined by the same method. See, e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

In some embodiments, an antibody is an scFv, such as an anti-LIV1 scFv. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used as provided herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC).

In some embodiments, an antibody of the present disclosure is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody optimally also will comprise at least a portion of an immunoglobulin constant region or domain (Fc), typically that of a human immunoglobulin. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In some embodiments, an antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, an antibody of the present disclosure specifically binds a target antigen, such as human LIV1. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a LIV1 epitope is an antibody that binds this LIV1 epitope with greater affinity, avidity, more readily, and/or with greater duration than it binds to other LIV1 epitopes or non-LIV1 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, the equilibrium dissociation constant ($K_D$) between the antibody and LIV1 is 100 μM to 1 μM. In some embodiments, the $K_D$ between the antibody and LIV1 is 1 nM to 100 nM.

Also within the scope of the present disclosure are functional variants of any of the exemplary antibodies as disclosed herein. A functional variant may contain one or more amino acid residue variations in the VH and/or VL, or in one or more of the VH CDRs and/or one or more of the VL CDRs as relative to a reference antibody, while retaining substantially similar binding and biological activities (e.g., substantially similar binding affinity, binding specificity, inhibitory activity, anti-tumor activity, or a combination thereof) as the reference antibody.

In some examples, an antibody disclosed herein comprises a VH CDR1, a VH CDR2, and a VH CDR3, which collectively contains no more than 10 amino acid variations (e.g., no more than 9, 8, 7, 6, 5, 4, 3, 2, or 1 amino acid variation) as compared with the VH CDR1, VH CDR2, and VH CDR3 of a reference antibody such as in VH: SEQ ID NO: 55 or 90 or 98; VL: SEQ ID NO: 56 or 88 or 128. "Collectively" means that the total number of amino acid variations in all of the three VH CDRs is within the defined range. Alternatively or in addition, antibody may comprise a VL CDR1, a VL CDR2, and a VL CDR3, which collectively contains no more than 10 amino acid variations (e.g., no more than 9, 8, 7, 6, 5, 4, 3, 2 or 1 amino acid variation) as compared with the VL CDR1, VL CDR2, and VL CDR3 of the reference antibody.

In some examples, an antibody disclosed herein may comprise a VH CDR1, a VH CDR2, and a VH CDR3, at least one of which contains no more than 5 amino acid variations (e.g., no more than 4, 3, 2, or 1 amino acid variation) as the counterpart VH CDR of a reference antibody such as in VH: SEQ ID NO: 55 or 90 or 98; VL: SEQ ID NO: 56 or 88 or 128. In specific examples, the antibody comprises a VH CDR3, which contains no more than 5 amino acid variations (e.g., no more than 4, 3, 2, or 1 amino acid variation) as the VH CDR3 of a reference antibody such as in VH: SEQ ID NO: 55 or 90 or 98; VL: SEQ ID NO: 56 or 88 or 128. Alternatively or in addition, an antibody may comprise a VL CDR1, a VL CDR2, and a VL CDR3, at least one of which contains no more than 5 amino acid variations (e.g., no more than 4, 3, 2, or 1 amino acid variation) as the counterpart VL CDR of the reference antibody. In specific examples, the antibody comprises a VL CDR3, which contains no more than 5 amino acid variations (e.g., no more than 4, 3, 2, or 1 amino acid variation) as the LC CDR3 of the reference antibody.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) A→G, S; (b)→R→K, H; (c) N→Q, H; (d) D→E, N; (e) C→S, A; (f) Q→N; (g) E→D, Q; (h) G→A; (i) H→N, Q; (j) I→L, V; (k) L→I, V; (1) K→R, H; (m) M→L, I, Y; (n) F→Y, M, L; (o) P→A; (p) S→T; (q) T→S; (r) W→Y, F; (s) Y→W, F; and (t) V→I, L.

In some embodiments, an antibody disclosed herein may comprise VH CDRs that collectively are at least 80% (e.g., 85%, 90%, 95%, or 98%) identical to the VH CDRs of a reference antibody such as Antibody A (VH: SEQ ID NO: 55; VL: SEQ ID NO: 56) or Antibody B (VH: SEQ ID NO: 90; VL: SEQ ID NO: 88). Alternatively or in addition, the antibody may comprise VL CDRs that collectively are at least 80% (e.g., 85%, 90%, 95%, or 98%) identical to the VL CDRs of the reference antibody. In some embodiments, an antibody may comprise a VH that is at least 80% (e.g., 85%, 90%, 95%, or 98%) identical to the VH of a reference antibody such as in VH: SEQ ID NO: 55 or 90 or 98; VL: SEQ ID NO: 56 or 88 or 128 and/or a VL variable region that is at least 80% (e.g., 85%, 90%, 95%, or 98%) identical to the VL variable region of the reference antibody.

Donor Template

The nucleic acid encoding a CAR may be delivered to a T cell that comprises what is referred to herein as a donor template (also referred to as a donor polynucleotide). A donor template can contain a non-homologous sequence, such as the nucleic acid encoding a CAR, flanked by two regions of homology to allow for efficient HDR at a genomic location of interest. Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, is inserted so that its expression is driven by the endogenous promoter at the integration site, namely the promoter that drives expression of the endogenous gene into which the donor is inserted. However, in some embodiments, the donor template comprises an exogenous promoter and/or enhancer, for example a constitutive promoter, an inducible promoter, or tissue-specific promoter. In some embodiments, the exogenous promoter is an EFla promoter comprising a sequence of SEQ ID NO: 79. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

Delivery Methods and Constructs

Nucleases and/or donor templates may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Adeno-Associated Viral Delivery

The donor nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

Homology-Directed Repair (HDR)

The donor nucleic acid encoding a CAR is inserted by homology directed repair (HDR) into the target gene locus. Both strands of the DNA at the target locus are cut by a CRISPR Cas9 enzyme. HDR then occurs to repair the double-strand break (DSB) and insert the donor DNA. For this to occur correctly, the donor sequence is designed with flanking residues which are complementary to the sequence surrounding the DSB site in the target gene (hereinafter "homology arms"). These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

The target gene can be associated with an immune response in a subject, wherein permanently deleting at least a portion of the target gene will modulate the immune response. For example, to generate a CAR T cell, the target gene can be the TCRα constant region (TRAC). Disruption of TRAC leads to loss of function of the endogenous TCR.

In some embodiments, the target gene is in a safe harbor locus.

Engineered T Cells

Engineered (gene edited) CAR T cells of the present disclosure may be autologous ("self") or non-autologous ("non-self," e.g., allogeneic, syngeneic or xenogeneic). "Autologous" refers to cells from the same subject. "Allogeneic" refers to cells of the same species as a subject, but that differ genetically to the cells in the subject. In some embodiments, the T cells are obtained from a mammalian subject. In some embodiments, the T cells are obtained from a human subject.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some embodiments, an isolated population of T cells is used. In some embodiments, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, the engineered T cell populations do not express or do not substantially express one or more of the following markers: CD70, CD57, CD244, CD160, PD-1, CTLA4, HM3, and LAGS. In some embodiments, subpopulations of T cells may be isolated by positive or negative selection prior to genetic engineering and/or post genetic engineering.

In some embodiments, an isolated population of T cells expresses one or more of the markers including, but not limited to a CD3+, CD4+, CD8+, or a combination thereof. In some embodiments, the T cells are isolated from a subject and first activated and stimulated to proliferate in vitro prior to undergoing gene editing.

To achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells.

In some embodiments, T cells are activated at the same time that genome editing compositions are introduced into the T cells.

Treatment Methods and Compositions

Provided herein, in some embodiments, are methods for treating cancer (e.g.: breast cancer). Non-limiting examples of cancers that may be treated as provided herein include: breast cancer, e.g., estrogen receptor-positive breast cancer, prostate cancer, squamous tumors, e.g., of the skin, bladder, lung, cervix, endometrium, head neck, and biliary tract, and neuronal tumors. In some embodiments, the methods comprise delivering the CAR T cells (e.g., anti-LIV1 CAR T cells) of the present disclosure to a subject having cancer, including, breast cancer, e.g., estrogen receptor-positive breast cancer, prostate cancer, squamous tumors, e.g., of the skin, bladder, lung, cervix, endometrium, head neck, and biliary tract, and/or neuronal tumors.

The step of administering may include the placement (e.g., transplantation) of cells, e.g., engineered T cells, into a subject, by a method or route that results in at least partial localization of the introduced cells at a desired site, such as tumor, such that a desired effect(s) is produced. Engineered T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of engineered T cells is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient. For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

In some embodiments, an engineered T cell population being administered according to the methods described herein does not induce toxicity in the subject, e.g., the engineered T cells do not induce toxicity in non-cancer cells. In some embodiments, an engineered T cell population being administered does not trigger complement mediated lysis, or does not stimulate antibody-dependent cell mediated cytotoxicity (ADCC).

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various aspects described herein, an effective amount of cells (e.g., engineered T cells) comprises at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The cells are derived from one or more donors, or are obtained from an autologous source. In some examples described herein, the cells are expanded in culture prior to administration to a subject in need thereof.

Modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

In some embodiments, engineered T cells are administered systemically, which refers to the administration of a population of cells other than directly into a target site, tissue, or organ, such that it enters, instead, the subject's circulatory system and, thus, is subject to metabolism and other like processes.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

The present disclosure is exemplified by the following embodiments:

Embodiment 1. An engineered T cell comprising a nucleic acid encoding a chimeric antigen receptor (CAR), wherein the CAR comprise an ectodomain that binds specifically to LIV1.

Embodiment 2. The engineered T cell of embodiment 1 further comprising a disrupted T cell receptor alpha chain constant region (TRAC) gene.

Embodiment 3. The engineered T cell of embodiment 2, wherein the nucleic acid encoding the CAR is inserted into the TRAC gene.

Embodiment 4. The engineered T cell of any one of embodiments 1-3 further comprising a disrupted beta-2-microglobulin (β2M) gene.

Embodiment 5. The engineered T cell of any one of embodiments 1-4, wherein the ectodomain of the CAR comprises an anti-LIV1 antibody.

Embodiment 6. The engineered T cell of embodiment 5, wherein the anti-LIV1 antibody is an anti-LIV1 single-chain variable fragment (scFv).

Embodiment 7. The engineered T cell of embodiment 6, wherein the anti-LIV1 scFv comprises the same heavy chain variable region (VH) complementarity determining regions (CDRs) and the same light chain variable region (VL) CDRs as a reference antibody, wherein the reference antibody comprises (i) a VH set forth as SEQ ID NO: 55 and a VL set forth as SEQ ID NO: 56, (ii) a VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84.

Embodiment 8. The engineered T cell of embodiment 7, wherein the anti-LIV1 scFv comprises the same VH and VL chains as the reference antibody.

Embodiment 8.1. The engineered T cell of embodiment 7, wherein the anti-LIV1 scFv comprises the amino acid sequence of any one of SEQ ID NOs: 54 or 70.

Embodiment 9. The engineered T cell of any one of embodiments 1-8.1, wherein the CAR comprises a CD28 co-stimulatory domain or a 41BB co-stimulatory domain.

Embodiment 10. The engineered T cell of embodiment 9, wherein the CAR further comprises a CD3z cytoplasmic signaling domain.

Embodiment 11. The engineered T cell of any one of embodiments 3-10, wherein the TRAC gene comprises the nucleotide sequence of any one of SEQ ID NOS: 63, 64, 71, or 72, and/or wherein the CAR is encoded by the nucleotide sequence of any one of SEQ ID NOS: 49, 51, 65, or 67.

Embodiment 12. The engineered T cell of any one of embodiments 4-11, wherein the disrupted β2M gene comprises at least one nucleotide sequence selected from any one of SEQ ID NOS: 9-14.

Embodiment 13. A population of the engineered T cell of any one of embodiments 1-12, wherein at least 25% or at least 50% of engineered T cells of the population express the CAR.

Embodiment 14. The population of embodiment 14, wherein at least 70% of engineered T cells of the population express the CAR.

Embodiment 15. The population of embodiment 13, wherein at least 25% of engineered T cells of the population express the CAR following at least 7 or at least 14 days of in vitro proliferation.

Embodiment 16. The population of any one of embodiments 13-15, wherein at least 50% of engineered T cells of the population do not express a detectable level of T cell receptor (TCR) protein.

Embodiment 17. The population of embodiment 16, wherein at least 90% of engineered T cells of the population do not express a detectable level of TCR protein.

Embodiment 18. The population of any one of embodiments 13-17, wherein at least 50% of engineered T cells of the population do not express a detectable level of β2M protein.

Embodiment 19. The population of embodiment 18, wherein at least 70% of engineered T cells of the population do not express a detectable level of β2M protein.

Embodiment 20. The population of any one of embodiments 13-19, wherein engineered T cells of the population, when co-cultured in vitro with a population of cancer cells that express LIV1, induce cell lysis of at least 10%, at least 25%, or at least 50% of the cancer cells of the population.

Embodiment 21. The population of embodiment 20, wherein engineered T cells of the population, when co-cultured in vitro with a population of cancer cells that express LIV1, induce cell lysis of at least 70%, at least 80%, or at least 90% of the population of cancer cells.

Embodiment 22. The population of embodiments 20 or 21, wherein engineered T cells of the population, when co-cultured in vitro with a population of cancer cells, secrete IFNγ.

Embodiment 23. The population of any one of embodiments 20-22, wherein the ratio of engineered T cells to cancer cells is 1:1 to 2:1.

Embodiment 24. The population of any one of embodiments 20-23, wherein the cancer cells comprise sarcoma cells.

Embodiment 25. The population of any one of embodiments 20-23, wherein the cancer cells comprise breast cancer cells.

Embodiment 27. The population of any one of embodiments 13-26, when administered in vivo to a subject, does not induce toxicity in the subject.

Embodiment 26. A method comprising administering the population of engineered T cells any one of embodiments 13-27 to a subject.

Embodiment 27. The method of embodiment 26, wherein the subject is a human subject.

Embodiment 28. The method of embodiment 27, wherein the subject has a cancer.

Embodiment 29. The method of embodiment 28, wherein the cancer is selected from the group consisting of: breast cancer, e.g., estrogen receptor-positive breast cancer, prostate cancer, squamous tumors, e.g., of the skin, bladder, lung, cervix, endometrium, head neck, and biliary tract, and/or neuronal tumors.

Embodiment 30. The method of embodiments 28 or 31, wherein the cancer comprises cancer cells expressing LIV1.

Embodiment 31. A method for producing an engineered T cell, the method comprising (a) delivering to a T cell, a RNA-guided nuclease, a gRNA targeting a TRAC gene, and a vector comprising a donor template that comprises a nucleic acid encoding a CAR that comprise an ectodomain that binds specifically to LIV1; and (b) producing an engineered T cell having a disrupted TRAC gene and expressing the CAR.

Embodiment 32. The method of embodiment 31, wherein the gRNA targeting the TRAC gene comprises the nucleotide sequence of SEQ ID NO: 18 or 19, or targets the nucleotide sequence of SEQ ID NO: 40.

Embodiment 33. The method of embodiments 31 or 32, wherein the nucleic acid encoding the CAR is flanked by left and right homology arms to the TRAC gene.

Embodiment 34. The method of any one of embodiments 31-33 further comprising delivering to the T cell a gRNA targeting the β2M gene.

Embodiment 35. The method of embodiment 34, wherein the gRNA targeting the β2M gene comprises the nucleotide sequence of SEQ ID NO: 20 or 21, or targets the nucleotide sequence of SEQ ID NO: 41.

Embodiment 36. The method of any one of embodiments 31-35, wherein the RNA-guided nuclease is a Cas9 nuclease, optionally a *S. pyogenes* Cas9 nuclease.

Embodiment 37. The method of any one of embodiments 31-38, wherein the ectodomain of the CAR is an anti-LIV1 antibody.

Embodiment 38. The method of embodiment 37, wherein the anti-LIV1 antibody is an anti-LIV1 single-chain variable fragment (scFv).

Embodiment 39. The method of embodiment 38, wherein the anti-LIV1 scFv comprises the same VH complementarity determining regions (CDRs) and the same VL CDRs as a reference antibody, wherein the reference antibody comprises (i) a VH set forth as SEQ ID NO: 55 and a VL set forth as SEQ ID NO: 56.

Embodiment 40. The method of embodiment 39, wherein the anti-LIV1 scFv comprises the same VH and VL chains as the reference antibody.

Embodiment 41. The method of embodiment 39, wherein the anti-LIV1 scFv comprises the amino acid sequence of any one of SEQ ID NOs: 54 or 70.

Embodiment 42. The method of any one of embodiments 31-41, wherein the CAR comprises a CD28 co-stimulatory domain or a 41BB co-stimulatory domain.

Embodiment 43. The method of embodiment 42, wherein the CAR further comprises a CD3z cytoplasmic signaling domain.

Embodiment 44. The method of any one of embodiments 31-43, wherein the donor template comprises the nucleotide sequence of any one of SEQ ID NOS: 63, 64, 71, or 72.

Embodiment 45. The method of any one of embodiments 31-44, wherein the CAR is encoded by a nucleotide sequence of any one of SEQ ID NOS: 49, 51, 65, or 67.

The present disclosure is further exemplified by the following embodiments:

Embodiment A1. An engineered T cell comprising a nucleic acid encoding a chimeric antigen receptor (CAR), wherein the CAR comprises an ectodomain that binds specifically to LIV1.

Embodiment A2. The engineered T cell of embodiment A1 further comprising a disrupted T cell receptor alpha chain constant region (TRAC) gene.

Embodiment A3. The engineered T cell of embodiment A1 or A2 further comprising a disrupted beta-2-microglobulin (β2M) gene.

Embodiment A4. The engineered T cell of any one of embodiments A1-3, wherein the ectodomain of the CAR comprises an anti-LIV1 antibody.

Embodiment A5. The engineered T cell of embodiment A4, wherein the anti-LIV1 antibody is an anti-LIV1 single-chain variable fragment (scFv).

Embodiment A6. The engineered T cell of embodiment A5, wherein the anti-LIV1 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and a VL set forth as SEQ ID NO: 56 or (ii) a VH set forth as SEQ ID NO: 90 and a VL set forth as SEQ ID NO: 88.

Embodiment A7. The engineered T cell of embodiment A6, wherein the anti-LIV1 scFv comprises the same VH and VL chains as the reference antibody.

Embodiment A8. The engineered T cell of embodiment A6, wherein the anti-LIV1 scFv comprises the amino acid sequence of any one of SEQ ID NOs: 54, 70, 83, or 86.

Embodiment A9. The engineered T cell of any one of embodiments A1-A8, wherein the CAR further comprises a CD28 co-stimulatory domain or a 41BB co-stimulatory domain.

Embodiment A10. The engineered T cell of embodiment A9, wherein the CAR further comprises a CD3 cytoplasmic signaling domain.

Embodiment A11. The engineered T cell of any one of embodiments A1-A10, wherein the CAR is encoded by the nucleotide sequence of any one of SEQ ID NOs: 49, 51, 104, or 108 or a nucleotide sequence comprising a nucleic acid sequence that is at least 90% identical to SEQ ID NOs: 49, 51, 104, or 108.

Embodiment A12. The engineered T cell of any one of embodiments A1-A11, wherein the nucleic acid encoding the CAR is inserted into the disrupted TRAC gene.

Embodiment A13. The engineered T cell of any one of embodiments A2-A12, wherein the disrupted TRAC gene comprises the nucleotide sequence of any one of SEQ ID NOs: 63, 64, 107, or 111, and/or the nucleotide sequence of any one of SEQ ID NOs: 49, 51, 104, or 108.

Embodiment A14. The engineered T cell of any one of embodiments A4-A13, wherein the disrupted β2M gene comprises at least one nucleotide sequence selected from any one of SEQ ID NOs: 9-14.

Embodiment A15. An engineered T cell comprising: (i) a disrupted TRAC gene; (ii) a disrupted β2M gene; and (iii) a nucleic acid encoding a CAR comprising an anti-LIV1 antigen-binding fragment.

Embodiment A16. The engineered T cell of embodiment A15, wherein the CAR comprises (a) an ectodomain that comprises an anti-LIV1 antigen-binding fragment, (b) a CD8 transmembrane domain, and (c) an endodomain that comprises a 41BB co-stimulatory domain and a CD3ζ cytoplasmic signaling domain.

Embodiment A17. The engineered T cell of embodiments A15 or A16, wherein the disrupted TRAC gene comprises the nucleic acid encoding the CAR.

Embodiment A18. An engineered T cell comprising: (i) a disrupted TRAC gene, wherein the disrupted TRAC gene comprises a nucleic acid encoding a CAR comprising (a) an ectodomain that comprises an anti-LIV1 antigen-binding fragment, (b) a CD8 transmembrane domain, and (c) an endodomain that comprises a 41BB co-stimulatory domain and a CD3ζ cytoplasmic signaling domain; and (ii) a disrupted β2M gene.

Embodiment A19. An engineered T cell comprising: (i) a disrupted TRAC gene, wherein the disrupted TRAC gene comprises a nucleic acid encoding a CAR comprising an amino acid sequence of any one of SEQ ID NOs: 50, 52, 105, 109, 68 or 66; and (ii) a disrupted β2M gene.

Embodiment A20. An engineered T cell comprising: (i) a disrupted TRAC gene, wherein the disrupted TRAC gene comprises a nucleic acid encoding a CAR, wherein the nucleic acid sequence is at least 90% identical to SEQ ID NOs: 49, 51, 104, or 108 and/or encodes a CAR comprising an amino acid sequence of any one of SEQ ID NOs: 50, 52, 105, 109, 68 or 66; and (ii) a disrupted β2M gene.

Embodiment A21. The engineered T cell of any one of embodiments A1-A20, wherein the T cell is a human T cell.

Embodiment A22. A population of cells comprising the engineered T cell of any one of embodiments A1-A21, wherein at least 15% or at least 50% of engineered T cells of the population express the CAR.

Embodiment A23. The population of embodiment A22, wherein at least 30% of engineered T cells of the population express the CAR.

Embodiment A24. The population of embodiment A22, wherein at least 70% of engineered T cells of the population express the CAR.

Embodiment A25. The population of embodiment A22, wherein at least 25% of engineered T cells of the population express the CAR following at least 7 days or at least 14 days of in vitro proliferation.

Embodiment A26. The population of any one of embodiments A22-A25, wherein at least 50% of engineered T cells of the population do not express a detectable level of T cell receptor (TCR) protein.

Embodiment A27. The population of embodiments A26, wherein at least 90% of engineered T cells of the population do not express a detectable level of TCR protein.

Embodiment A28. The population of any one of embodiments A22-A27, wherein at least 50% of engineered T cells of the population do not express a detectable level of β2M protein.

Embodiment A29. The population of embodiment A28, wherein at least 70% of engineered T cells of the population do not express a detectable level of β2M protein.

Embodiment A30. The population of any one of embodiments A22-A29, wherein engineered T cells of the population, when co-cultured in vitro with a population of cancer cells that express LIV1, induce cell lysis of at least 10%, at least 25%, or at least 50% of the cancer cells of the population.

Embodiment A31. The population of embodiment A30, wherein engineered T cells of the population, when co-cultured in vitro with a population of cancer cells that express LIV1, induce cell lysis of at least 70%, at least 80%, or at least 90% of the population of cancer cells.

Embodiment A32. The population of embodiments A30 or A31, wherein engineered T cells of the population, when co-cultured in vitro with a population of cancer cells, secrete IFNγ.

Embodiment A33. The population of any one of embodiments A30-A32, wherein the ratio of engineered T cells to cancer cells is 1:1 to 2:1.

Embodiment A34. The population of any one of embodiments A30-A33, wherein the cancer cells comprise sarcoma cells.

Embodiment A35. The population of any one of embodiments A30-A33, wherein the cancer cells comprise breast cancer cells.

Embodiment A36. The population of any one of embodiments A22-A35, when administered in vivo to a subject, does not induce toxicity in the subject.

Embodiment A37. A population of cells comprising engineered T cells, wherein the engineered T cells comprise: (i) a disrupted TRAC gene; (ii) a disrupted β2M gene; and (iii) a nucleic acid encoding a CAR comprising an anti-LIV1 antigen-binding fragment.

Embodiment A38. The population of cells of embodiment A37, wherein the CAR comprises (a) an ectodomain that comprises an anti-LIV1 antigen-binding fragment, (b) a CD8 transmembrane domain, and (c) an endodomain that comprises a 41BB co-stimulatory domain and a CD3ζ cytoplasmic signaling domain.

Embodiment A39. The population of cells of embodiments A37 or A38, wherein the disrupted TRAC gene comprises the nucleic acid encoding the CAR.

Embodiment A40. A population of cells comprising engineered T cells, wherein the engineered T cells comprise: (i) a disrupted TRAC gene, wherein the disrupted TRAC gene comprises a nucleic acid encoding a CAR comprising (a) an ectodomain that comprises an anti-LIV1 antigen-binding fragment, (b) a CD8 transmembrane domain, and (c) an endodomain that comprises a 41BB co-stimulatory domain and a CD3ζ cytoplasmic signaling domain; and (ii) a disrupted β2M gene.

Embodiment A41. A population of cells comprising engineered T cells, wherein the engineered T cells comprise: (i) a disrupted TRAC gene, wherein the disrupted TRAC gene comprises a nucleic acid encoding a CAR, wherein the nucleic acid sequence is at least 90% identical to SEQ ID NOs: 49, 51, 104, or 108 and/or encodes the CAR of SEQ ID NOs: 50, 52, 105, 109, 68 or 66; and (ii) a disrupted β2M gene.

Embodiment A42. A method comprising administering the population of engineered T cells any one of embodiments A22-A41 to a subject.

Embodiment A43. The method of embodiment A42, wherein the subject is a human subject.

Embodiment A44. The method of embodiment A43, wherein the subject has a cancer.

Embodiment A45. The method of embodiment A44, wherein the cancer is selected from the group consisting of: breast cancer, e.g., estrogen receptor-positive breast cancer, prostate cancer, squamous tumors, e.g., of the skin, bladder, lung, cervix, endometrium, head neck, and biliary tract, and/or neuronal tumors.

Embodiment A46. The method of embodiments A44 or A45, wherein the cancer comprises cancer cells expressing LIV1.

Embodiment A47. A method for producing an engineered T cell, the method comprising (a) delivering to a T cell (i) a RNA-guided nuclease, (ii) a gRNA targeting a TRAC gene, and (iii) a vector comprising a donor template that comprises a nucleic acid encoding a CAR that comprise an ectodomain that binds specifically to LIV1; and (b) producing an engineered T cell having a disrupted TRAC gene and expressing the CAR.

Embodiment A48. The method of embodiments A47, wherein the gRNA targeting the TRAC gene comprises the nucleotide sequence of SEQ ID NO: 18 or 19, or targets the nucleotide sequence of SEQ ID NO: 40.

Embodiment A49. The method of embodiments A47 or A48 further comprising delivering to the T cell a gRNA targeting the β2M gene.

Embodiment A50. The method of embodiments A49, wherein the gRNA targeting the β2M gene comprises the nucleotide sequence of SEQ ID NO: 20 or 21, or targets the nucleotide sequence of SEQ ID NO: 41.

Embodiment A51. The method of any one of embodiments A47-A50, wherein the ectodomain of the CAR comprises an anti-LIV1 antibody.

Embodiment A52. The method of embodiment A51, wherein the anti-LIV1 antibody is an anti-LIV1 single-chain variable fragment (scFv).

Embodiment A53. The method of embodiment A52, wherein the anti-LIV1 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and a VL set forth as SEQ ID NO: 56, or (ii) a VH set forth as SEQ ID NO: 90 and a VL set forth as SEQ ID NO: 88.

Embodiment A54. The method of embodiment A53, wherein the anti-LIV1 scFv comprises the same VH and VL chains as the reference antibody.

Embodiment A55. The method of embodiment A53, wherein the anti-LIV1 scFv comprises the amino acid sequence of any one of SEQ ID NOs: 54, 83, 86 or 70.

Embodiment A56. The method of any one of embodiments A47-A56, wherein the CAR further comprises a CD28 co-stimulatory domain or a 41BB co-stimulatory domain.

Embodiment A57. The method of embodiment A56, wherein the CAR further comprises a CD3ζ cytoplasmic signaling domain.

Embodiment A58. The method of any one of embodiments A47-A57, wherein the CAR is encoded by a nucleotide sequence of any one of SEQ ID NOs: 49, 51, 104, or 108 or a nucleotide sequence comprising a nucleic acid sequence that is at least 90% identical to SEQ ID NOs: 49, 51, 104, or 108.

Embodiment A59. The method of any one of embodiments A47-A58, wherein the nucleic acid encoding the CAR is flanked by left and right homology arms to the TRAC gene.

Embodiment A60. The method of any one of embodiments A47-A59, wherein the donor template comprises the nucleotide sequence of any one of SEQ ID NOs: 63, 64, 107, or 111.

Embodiment A61. The method of any one of embodiments A47-A60, wherein the RNA-guided nuclease is a Cas9 nuclease, optionally a *S. pyogenes* Cas9 nuclease.

Embodiment A62. An engineered T cell produced by the method of any one of embodiments A47-A61.

Embodiment A63. A population of cells comprising the engineered T cell of embodiment A62.

Embodiment A64. A method of treating cancer in a subject, comprising administering to the subject the population of cells of any one of embodiments A22-A41 or A63.

Embodiment A65. The method of embodiment A64, wherein the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer.

Embodiment A66. The method of embodiments A64 or A65, wherein the cancer comprises cancer cells expressing LIV1.

EXAMPLES

Example 1. CAR T Cell Generation and CAR Expression

Activated primary human T cells were electroporated with Cas9: gRNA RNP complexes and adeno-associated adenoviral vectors (AAVs) to generate TRAC⁻/anti-Liv1a CARP T cells. Recombinant AAV serotype 6 (AAV6) comprising one of the nucleotide sequences encoding an anti-Liv1a CAR (971 (SEQ ID NO:49), 972 (SEQ ID NO: 65), 972b (SEQ ID NO: 67), 973 (SEQ ID NO: 95), 974 (SEQ ID NO: 100), 975 (SEQ ID NO: 104), and 976 (SEQ ID NO: 108), were delivered with Cas9: sgRNA RNPs (1 μM Cas9, 5 μM gRNA) to activated allogeneic human T cells. The following sgRNAs were used: TRAC (SEQ ID NO: 28) and β2M (SEQ ID NO: 30). The unmodified versions (or other modified versions) of the gRNAs may also be used (e.g., SEQ ID NO: 18 or 20).

About one (1) week post electroporation, cells were processed for flow cytometry to assess TRAC, β2M, and anti-Liv1a CAR expression levels at the cell surface of the edited cell population (FIG. 1). For all anti-Liv1a CAR T cells and $TRAC^-$/$\beta 2M^-$ control cells, >90% of viable cells lacked expression of TCR and >60% lacked expression of β2M. The cells treated with the construct encoding the 975 and 976 Liv1a CAR had the highest percentage of viable cells expressing an anti-Liv1a CARP (>30%).

Example 2. Cytotoxicity

Figure 2A:
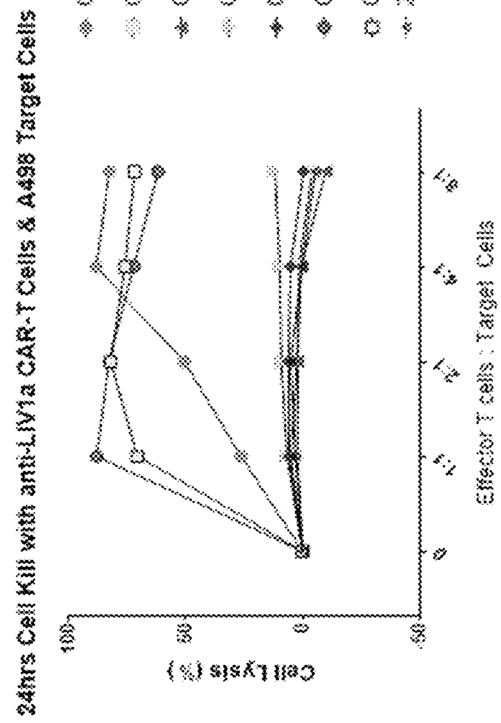
FIGS. 2A-2B show that anti-Liv1a CAR T cells, particularly those expressing the CTX971, CTX975 and CTX976 constructs, exhibited potent cytotoxicity towards the A498 (FIG. 2A) and ZR-75-1 (FIG. 2B) cell lines.
Figure 2B:
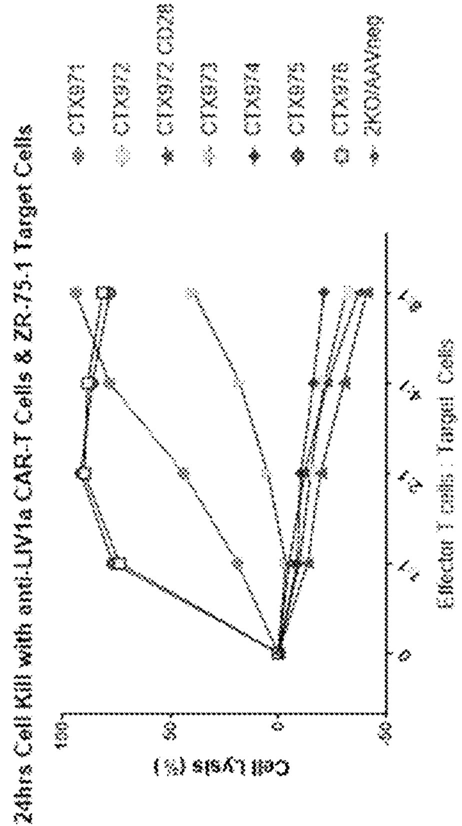
Figure 3A:
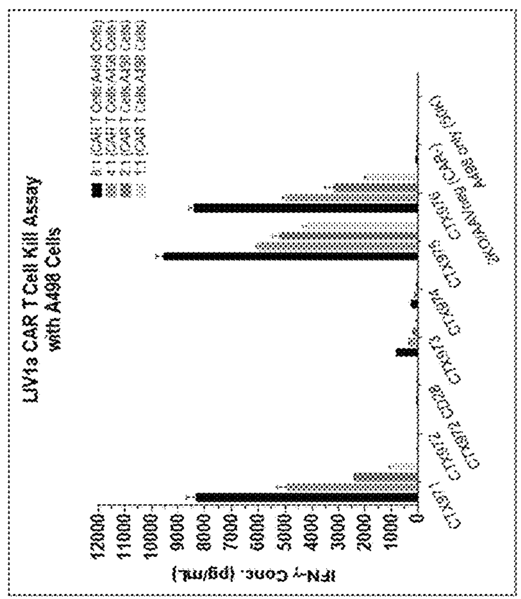
FIGS. 3A-3D show cytokine secretion of anti-Liv1a CAR T cells when co-cultured with target cell lines A498 and ZR-75-1.
Figure 3B:
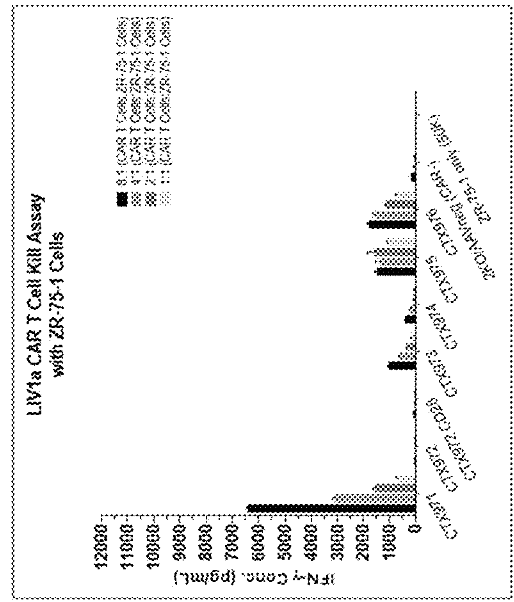
Figure 3C:
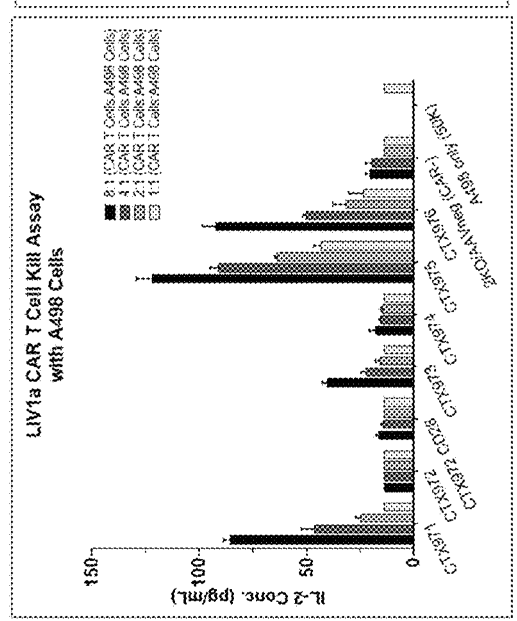
Figure 3D:
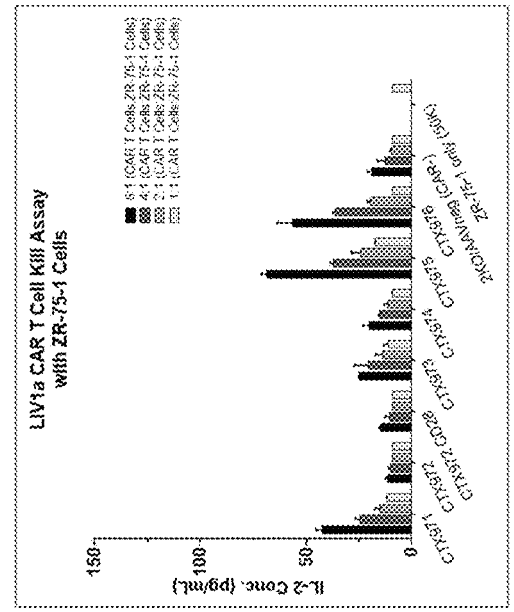

Cell Kill Assay. A cell killing (cytotoxicity) assay was used to assess the ability of the TRAC-/β2M-/anti-Liv1a CAR+ T cells to cause cellular lysis in adherent kidney carcinoma and breast cancer cell lines (A498 and ZR-75-1, respectively). Adherent cells were seeded in 96-well plates at 50,000 cells per well and left overnight at 37° C. During the following day, T cells were added to the wells containing target cells at ratios of 8:1, 4:1, 2:1 or 1:1 T cell:target cell. TRAC-/β2M-T cells were used as a negative control. After approximately 24 hours, 100 μLs of supernatant was removed for cytokine quantification (see below) and T cells were removed from the culture by aspiration and 100 μL CellTiter-Glo® (Promega) was added to each well of the plate to assess the number of remaining viable cells. The amount of light emitted from each well was then quantified using a plate reader. The anti-Liv1a CAR T cells, particularly those expressing the CTX971, CTX975 and CTX976 constructs, exhibited potent cytotoxicity towards the A498 (FIG. 2A) and ZR-75-1 (FIG. 2B) cell lines.

Example 3. Effector Cytokine Secretion

The MILLIPLEX MAP Human Cytokine/Chemokine Magnetic Bead Panel—Immunology Multiplex Assay kit (Millipore, catalog #HCYTOMAG-60K) using magnetic microspheres, anti-human IFNγ bead (Millipore, catalog #HCYIFNG-MAG) and anti-human IL-2 bead (Millipore, catalog #HIL2-MAG), respectively, was used to quantify IFN-γ and IL-2 secretion in samples from the cytotoxicity assay. The assay was conducted following manufacturer's protocol. MILLIPLEX® standard and quality control (QC) samples were reconstituted, and serial dilutions of the working standards from 10,000 pg/mL to 3.2 pg/mL were prepared. MILLIPLEX® standards, QCs and cell supernatants were added to each plate, and assay media was used to dilute the supernatants. All samples were incubated with anti-human IFNγ and anti-human IL-2 beads for 2 hours. After incubation, the plate was washed using an automated magnetic plate washer. Human cytokine/chemokine detection antibody solution was added to each well and incubated for 1 hour followed by incubation with Streptavidin-Phycoerythrin for 30 minutes. The plate was subsequently washed, samples were resuspended with 150 μL Sheath Fluid, and agitated on a plate shaker for 5 minutes. The samples were read using the Luminex® 100/200™ instrument with xPONENT® software and data acquisition and analysis was completed using MILLIPLEX® Analyst software. The Median Fluorescent Intensity (MFI) data was automatically analyzed using a 5-parameter logistic curve-fitting method for calculating the cytokine concentration measured in the unknown samples.

As shown in FIGS. 3A-3D, allogeneic T cells containing the CTX971, 975, or 976 CARs secreted the effector cytokines interferon-γ (3A, B) and interleukin-2 (3C, D) when co-cultured with the target cells lines A498 and ZR-75-1 at levels significantly above background (2KO/AAV neg T cells co-cultured with the target cell lines).

TABLE 6

| CAR | CAR structure | SEQ ID NO: |
|---|---|---|
| CTX-971 CAR | CD8[signal peptide]-VL-linker-VH-CD8[tm]-CD28[co-stimulatory domain]-CD3ζ | 49, 50 |
| CTX-971b CAR | CD8[signal peptide]-VL-linker-VH-CD8[tm]-41BB[co-stimulatory domain]-CD3ζ | 51, 52 |
| CTX-972 CAR | CD8[signal peptide]-VH-linker-VL-CD8[tm]-CD28[co-stimulatory domain]-CD3ζ | 65, 125 |
| CTX-972b CAR | CD8[signal peptide]-VH-linker-VL-CD8[tm]-41BB[co-stimulatory domain]-CD3ζ | 67, 126 |

TABLE 7

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| CTX-971 CAR CD28 co-stim | CCACCATGGCGCTTCCGGTGACAGCACTGCTCCTCCCCTTGGCGCTG TTGCTCCACGCAGCAAGGCCGGACGTGGTCATGACTCAAAGCCCAC TTTCCTTGCCCGTGACTCTCGGACAACCGGCTTCAATATCTTGCCGC TCATCACAGTCCCTGCTGCATAGCAGTGGTAACACTTATCTTGAGTG GTACCAACAGCGGCCCGGCCAATCTCCTAGGCCCCTGATATATAAG ATAAGTACTCGCTTTTCCGGGGTCCCGGACCGGTTCAGCGGGTCTGG GAGTGGTACAGACTTCACATTGAAGATTTCACGAGTAGAAGCCGAA GACGTGGGTGTTTATTACTGCTTCCAAGGATCTCACGTGCCATATAC GTTTGGTGGGGGCACAAAAGTCGAGATTAAGGGAGGCGGAGGATC AGGAGGTGGGGGAAGTGGAGGTGGTGGGTCACAAGTACAGCTCGT GCAATCAGGGGCGGAGGTGAAGAAACCAGGGGCGTCTGTGAAGGT AAGCTGTAAGGCATCCGGATTGACAATCGAGGATTATTACATGCAT TGGGTCCGCCAGGCACCAGGGCAGGGATTGGAGTGGATGGGGTGGA TAGATCCTGAAAATGGGGATACAGAGTATGGCCCTAAGTTCCAGGG CAGAGTTACGATGACTCGAGATACTAGCATTAATACGGCCTACATG GAGCTTAGCCGCCTGCGGTCCGATGACACGGCCGTTTATTATTGCGC CGTACACAATGCGCACTACGGGACATGGTTCGCGTATTGGGGTCAA GGAACGCTCGTTACTGTCTCAAGTAGTGCTGCTGCCTTTGTCCCGGT ATTTCTCCCAGCCAAACCGACCACGACTCCCGCCCCGCGCCCTCCGA CACCCGCTCCCACCATCGCCTCTCAACCTCTTAGTCTTCGCCCCGAG | 49 |

TABLE 7-continued

| CAR Components<br>CAR Structure:<br>CD8 [signal peptide]-anti-LIV1[scFV]-CD8[tm]-CD28[co-stimulatory domain]-CD3ζ; or<br>CD8 [signal peptide]-anti-LIV1[scFV]-CD8[tm]-41BB[co-stimulatory domain]-CD3ζ | | |
|---|---|---|
| Name | Sequence | SEQ ID NO: |
| | GCATGCCGACCCGCCGCCGGGGGTGCTGTTCATACGAGGGGCTTGG ACTTCGCTTGTGATATTTACATTTGGGCTCCGTTGGCGGGTACGTGC GGCGTCCTTTTGTTGTCACTCGTTATTACTTTGTATTGTAATCACAGG AATCGCTCAAAGCGGAGTAGGTTGTTGCATTCCGATTACATGAATAT GACTCCTCGCCGGCCTGGGCCGACAAGAAAACATTACCAACCCTAT GCCCCCCCACGAGACTTCGCTGCGTACAGGTCCCGAGTGAAGTTTTC CCGAAGCGCAGACGCTCCGGCATATCAGCAAGGACAGAATCAGCTG TATAACGAACTGAATTTGGGACGCCGCGAGGAGTATGACGTGCTTG ATAAACGCCGGGGGAGAGACCCGGAAATGGGGGGTAAACCCCGAA GAAAGAATCCCCAAGAAGGACTCTACAATGAACTCCAGAAGGATAA GATGGCGGAGGCCTACTCAGAAATAGGTATGAAGGGCGAACGACG ACGGGGAAAAGGTCACGATGGCCTCTACCAAGGGTTGAGTACGGCA ACCAAAGATACGTACGATGCACTGCATATGCAGGCCCTGCCTCCCA GATAAT | |
| CTX-971<br>CAR<br>CD28 co-stim | MALPVTALLLPLALLLHAARPDVVMTQSPLSLPVTLGQPASISCRSSQS LLHSSGNTYLEWYQQRPGQSPRPLIYKISTRFSGVPDRFSGSGSGTDFTL KISRVEAEDVGVYYCFQGSHVPYTFGGGTKVEIKGGGGSGGGGSGGG GSQVQLVQSGAEVKKPGASVKVSCKASGLTIEDYYMHWVRQAPGQGL EWMGWIDPENGDTEYGPKFQGRVTMTRDTSINTAYMELSRLRSDDTA VYYCAVHNAHYGTWFAYWGQGTLVTVSSSAAAFVPVFLPAKPTTTPA PRPPTPAPTIASQPLSLRPEACRPAAGGAVHTRGLDFACDIYIWAPLAGT CGVLLLSLVITLYCNHRNRSKRSRLLHSDYMNMTPRRPGPTRKHYQPY APPRDFAAYRSRVKFSRSADAPAYQQGQNQLYNELNLGRREEYDVLD KRRGRDPEMGGKPRRKNPQEGLYNELQKDKMAEAYSEIGMKGERRR GKGHDGLYQGLSTATKDTYDALHMQALPPR | 50 |
| CTX-971b<br>CAR<br>41BB co-stim | CCACCATGGCGCTTCCGGTGACAGCACTGCTCCTCCCCTTGGCGCTG TTGCTCCACGCAGCAAGGCCGGACGTGGTCATGACTCAAAGCCCAC TTTCCTTGCCCGTGACTCTCGGACAACCGGCTTCAATATCTTGCCGC TCATCACAGTCCCTGCTGCATAGCAGTGGTAACACTTATCTTGAGTG GTACCAACAGCGGCCCGGCCAATCTCCTAGGCCCCTGATATATAAG ATAAGTACTCGCTTTTCCGGGGTCCCGGACCGGTTCAGCGGGTCTGG GAGTGGTACAGACTTCACATTGAAGATTTCACGAGTAGAAGCCGAA GACGTGGGTGTTTATTACTGCTTCCAAGGATCTCACGTGCCATATAC GTTTGGTGGGGGCACAAAAGTCGAGATTAAGGGAGGCGGAGGATC AGGAGGTGGGGGAAGTGGAGGTGGTGGGTCACAAGTACAGCTCGT GCAATCAGGGGCGGAGGTGAAGAAACCAGGGGCGTCTGTGAAGGT AAGCTGTAAGGCATCCGGATTGACAATCGAGGATTATTACATGCAT TGGGTCCGCCAGGCACCAGGGCAGGGATTGGAGTGGATGGGGTGGA TAGATCCTGAAAATGGGGATACAGAGTATGGCCCTAAGTTCCAGGG CAGAGTTACGATGACTCGAGATACTAGCATTAATACGGCCTACATG GAGCTTAGCCGCCTGCGGTCCGATGACACGGCCGTTTATTATTGCGC CGTACACAATGCGCACTACGGGACATGGTTCGCGTATTGGGGTCAA GGAACGCTCGTTACTGTCTCAAGTAGTGCTGCTGCCTTTGTCCCGGT ATTTCTCCCAGCCAAACCGACCACGACTCCCGCCCCGCGCCCTCCGA CACCCGCTCCCACCATCGCCTCTCAACCTCTTAGTCTTCGCCCCGAG GCATGCCGACCCGCCGCCGGGGGTGCTGTTCATACGAGGGGCTTGG ACTTCGCTTGTGATATTTACATTTGGGCTCCGTTGGCGGGTACGTGC GGCGTCCTTTTGTTGTCACTCGTTATTACTTTGTATTGTAATCACAGG AATCGCAAACGGGGCAGAAAGAAACTCCTGTATATATTCAAACAAC CATTTATGAGACCAGTACAAACTACTCAAGAGGAAGATGGCTGTAG CTGCCGATTTCCAGAAGAAGAAGAAGGAGGATGTGAACTGCGAGTG AAGTTTTCCCGAAGCGCAGACGCTCCGGCATATCAGCAAGGACAGA ATCAGCTGTATAACGAACTGAATTTGGGACGCCGCGAGGAGTATGA CGTGCTTGATAAACGCCGGGGGAGAGACCCGGAAATGGGGGGTAA ACCCCGAAGAAAGAATCCCCAAGAAGGACTCTACAATGAACTCCAG AAGGATAAGATGGCGGAGGCCTACTCAGAAATAGGTATGAAGGGC GAACGACGACGGGGAAAAGGTCACGATGGCCTCTACCAAGGGTTGA GTACGGCAACCAAAGATACGTACGATGCACTGCATATGCAGGCCCT GCCTCCCAGATAAT | 51 |
| CTX-971b<br>CAR<br>co-stim 41BB | MALPVTALLLPLALLLHAARPDVVMTQSPLSLPVTLGQPASISCRSSQS LLHSSGNTYLEWYQQRPGQSPRPLIYKISTRFSGVPDRFSGSGSGTDFTL KISRVEAEDVGVYYCFQGSHVPYTFGGGTKVEIKGGGGSGGGGSGGG GSQVQLVQSGAEVKKPGASVKVSCKASGLTIEDYYMHWVRQAPGQGL EWMGWIDPENGDTEYGPKFQGRVTMTRDTSINTAYMELSRLRSDDTA VYYCAVHNAHYGTWFAYWGQGTLVTVSSSAAAFVPVFLPAKPTTTPA PRPPTPAPTIASQPLSLRPEACRPAAGGAVHTRGLDFACDIYIWAPLAGT CGVLLLSLVITLYCNHRNRKRGRKKLLYIFKQPFMRPVQTTQEEDGCSC | 52 |

TABLE 7-continued

| CAR Components<br>CAR Structure:<br>CD8 [signal peptide]-anti-LIV1[scFV]-CD8[tm]-CD28[co-stimulatory domain]-CD3ζ; or<br>CD8 [signal peptide]-anti-LIV1[scFV]-CD8[tm]-41BB[co-stimulatory domain]-CD3ζ | | |
|---|---|---|
| Name | Sequence | SEQ ID NO: |
| | RFPEEEEGGCELRVKFSRSADAPAYQQGQNQLYNELNLGRREEYDVLD KRRGRDPEMGGKPRRKNPQEGLYNELQKDKMAEAYSEIGMKGERRR GKGHDGLYQGLSTATKDTYDALHMQALPPR | |
| CTX-971 and CTX-971b scFv | GACGTGGTCATGACTCAAAGCCCACTTTCCTTGCCCGTGACTCTCGG ACAACCGGCTTCAATATCTTGCCGCTCATCACAGTCCCTGCTGCATA GCAGTGGTAACACTTATCTTGAGTGGTACCAACAGCGGCCCGGCCA ATCTCCTAGGCCCCTGATATATAAGATAAGTACTCGCTTTTCCGGGG TCCCGGACCGGTTCAGCGGGTCTGGGAGTGGTACAGACTTCACATT GAAGATTTCACGAGTAGAAGCCGAAGACGTGGGTGTTTATTACTGC TTCCAAGGATCTCACGTGCCATATACGTTTGGTGGGGGCACAAAAG TCGAGATTAAGGGAGGCGGAGGATCAGGAGGTGGGGGAAGTGGAG GTGGTGGGTCACAAGTACAGCTCGTGCAATCAGGGGCGGAGGTGAA GAAACCAGGGGCGTCTGTGAAGGTAAGCTGTAAGGCATCCGGATTG ACAATCGAGGATTATTACATGCATTGGGTCCGCCAGGCACCAGGGC AGGGATTGGAGTGGATGGGGTGGATAGATCCTGAAAATGGGGATAC AGAGTATGGCCCTAAGTTCCAGGGCAGAGTTACGATGACTCGAGAT ACTAGCATTAATACGGCCTACATGGAGCTTAGCCGCCTGCGGTCCG ATGACACGGCCGTTTATTATTGCGCCGTACACAATGCGCACTACGGG ACATGGTTCGCGTATTGGGGTCAAGGAACGCTCGTTACTGTCTCAAG T | 53 |
| CTX-971 and CTX-971b scFv (linker underlined) | DVVMTQSPLSLPVTLGQPASISCRSSQSLLHSSGNTYLEWYQQRPGQSP RPLIYKISTRFSGVPDRFSGSGSGTDFTLKISRVEAEDVGVYYCFQGSHV PYTFGGGTKVEIK**GGGGSGGGGSGGGGS**QVQLVQSGAEVKKPGASV KVSCKASGLTIEDYYMHWVRQAPGQGLEWMGWIDPENGDTEYGPKF QGRVTMTRDTSINTAYMELSRLRSDDTAVYYCAVHNAHYGTWFAYW GQGTLVTVSS | 54 |
| CTX-971 and CTX-971b scFv VH CDRs-in bold | QVQLVQSGAEVKKPGASVKVSCKASGLTIE**DYYMH**WVRQAPGQGLE WMG**WIDPENGDTEYGPKFQG**RVTMTRDTSINTAYMELSRLRSDDTA VYYCAV**HNAHYGTWFAY**WGQGTLVTVSS | 55 |
| CTX-971 and CTX-97 lb scFv VL CDRs-in bold | DVVMTQSPLSLPVTLGQPASISC**RSSQSLLHSSGNTYLE**WYQQRPGQS PRPLIY**KISTRFS**GVPDRFSGSGSGTDFTLKISRVEAEDVGVYYC**FQGS HVPYT**FGGGTKVEIK | 56 |
| CTX-971 and CTX-971b VH CDR1 | DYYMH | 57 |
| CTX-971 and CTX-971b VH CDR2 | WIDPENGDTEYGPKFQG | 58 |
| CTX-971 and CTX-971b VH CDR3 | HNAHYGTWFAY | 59 |
| CTX-971 and CTX-971b VL CDR1 | RSSQSLLHSSGNTYLE | 60 |
| CTX-971 and CTX-971b VL CDR2 | KISTRFS | 61 |
| CTX-971 and CTX-971b VL CDR3 | FQGSHVPYT | 62 |
| CTX-971 Donor to LHA RHA | GAGATGTAAGGAGCTGCTGTGACTTGCTCAAGGCCTTATATCGAGT AAACGGTAGTGCTGGGGCTTAGACGCAGGTGTTCTGATTTATAGTTC AAAACCTCTATCAATGAGAGAGCAATCTCCTGGTAATGTGATAGAT TTCCCAACTTAATGCCAACATACCATAAACCTCCCATTCTGCTAATG CCCAGCCTAAGTTGGGGAGACCACTCCAGATTCCAAGATGTACAGT TTGCTTTGCTGGGCCTTTTTCCCATGCCTGCCTTTACTCTGCCAGAGT TATATTGCTGGGGTTTTGAAGAAGATCCTATTAAATAAAAGAATAA GCAGTATTATTAAGTAGCCCTGCATTTCAGGTTTCCTTGAGTGGCAG GCCAGGCCTGGCCGTGAACGTTCACTGAAATCATGGCCTCTTGGCCA | 63 |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| | AGATTGATAGCTTGTGCCTGTCCCTGAGTCCCAGTCCATCACGAGCA<br>GCTGGTTTCTAAGATGCTATTTCCCGTATAAAGCATGAGACCGTGAC<br>TTGCCAGCCCCACAGAGCCCCGCCCTTGTCCATCACTGGCATCTGGA<br>CTCCAGCCTGGGTTGGGGCAAAGAGGGAAATGAGATCATGTCCTAA<br>CCCTGATCCTCTTGTCCCACAGATATCCAGAACCCTGACCCTGCCGT<br>GTACCAGCTGAGAGACTCTAAATCCAGTGACAAGTCTGTCTGCCTAT<br>TCACCGATTTTGATTCTCAAACAAATGTGTCACAAAGTAAGGATTCT<br>GATGTGTATATCACAGACAAAACTGTGCTAGACATGAGGTCTATGG<br>ACTTCAggctccggtgcccgtcagtgggcagagcgcacatcgcccacagtccccgagaagttggggga<br>ggggtcggcaattgaaccggtgcctagagaaggtggcgcggggtaaactgggaaagtgatgtcgtgtactggc<br>tccgcctttttcccgagggtgggggagaaccgtatataagtgcagtagtcgccgtgaacgttctttttcgcaacgg<br>gtttgccgccagaacacaggtaagtgccgtgtgtggttcccgcgggcctggcctctttacgggttatggcccttgc<br>gtgccttgaattacttccactggctgcagtacgtgattcttgatcccgagcttcgggttggaagtgggtgggagagt<br>tcgaggccttgcgcttaaggagccccttcgcctcgtgcttgagttgaggcctggcctgggcgctggggccgccg<br>cgtgcgaatctggtggcaccttcgcgcctgtctcgctgctttcgataagtctctagccatttaaaatttttgatgacct<br>gctgcgacgctttttttctggcaagatagtcttgtaaatgcgggccaagatctgcacactggtatttcggtttttgggg<br>ccgcgggcggcgacggggcccgtgcgtcccagcgcacatgttcggcgaggcggggcctgcgagcgcggcc<br>accgagaatcggacgggggtagtctcaagctggccggcctgctctggtgcctggcctcgcgccgccgtgtatc<br>gccccgccctgggcggcaaggctggcccggtcggcaccagttgcgtgagcggaaagatggccgcttcccgg<br>ccctgctgcagggagctcaaaatggaggacgcggcgctcgggagagcgggcgggtgagtcacccacacaaa<br>ggaaaagggcctttccgtcctcagccgtcgcttcatgtgactccacggagtaccgggcgccgtccaggcacctc<br>gattagttctcgagcttttggagtacgtcgtctttaggttgggggggaggggttttatgcgatggagtttccccacact<br>gagtgggtggagactgaagttaggccagcttggcacttgatgtaattctccttggaatttgccctttttgagtttggat<br>cttggttcattctcaagcctcagacagtggttcaaagtttttttcttccatttcaggtgtcgtgaCCACCATGG<br>CGCTTCCGGTGACAGCACTGCTCCTCCCCTTGGCGCTGTTGCTCCAC<br>GCAGCAAGGCCGGACGTGGTCATGACTCAAAGCCCACTTTCCTTGC<br>CCGTGACTCTCGGACAACCGGCTTCAATATCTTGCCGCTCATCACAG<br>TCCCTGCTGCATAGCAGTGGTAACACTTATCTTGAGTGGTACCAACA<br>GCGGCCCGGCCAATCTCCTAGGCCCCTGATATATAAGATAAGTACTC<br>GCTTTTCCGGGGTCCCGGACCGGTTCAGCGGGTCTGGGAGTGGTAC<br>AGACTTCACATTGAAGATTTCACGAGTAGAAGCCGAAGACGTGGGT<br>GTTTATTACTGCTTCCAAGGATCTCACGTGCCATATACGTTTGGTGG<br>GGGCACAAAAGTCGAGATTAAGGGAGGCGGAGGATCAGGAGGTGG<br>GGGAAGTGGAGGTGGTGGGTCACAAGTACAGCTCGTGCAATCAGGG<br>GCGGAGGTGAAGAAACCAGGGGCGTCTGTGAAGGTAAGCTGTAAG<br>GCATCCGGATTGACAATCGAGGATTATTACATGCATTGGGTCCGCCA<br>GGCACCAGGGCAGGGATTGGAGTGGATGGGGTGGATAGATCCTGAA<br>AATGGGGATACAGAGTATGGCCCTAAGTTCCAGGGCAGAGTTACGA<br>TGACTCGAGATACTAGCATTAATACGGCCTACATGGAGCTTAGCCG<br>CCTGCGGTCCGATGACACGGCCGTTTATTATTGCGCCGTACACAATG<br>CGCACTACGGGACATGGTTCGCGTATTGGGGTCAAGGAACGCTCGT<br>TACTGTCTCAAGTAGTGCTGCTGCCTTTGTCCCGGTATTTCTCCCAGC<br>CAAACCGACCACGACTCCCGCCCCGCGCCCTCCGACACCCGCTCCC<br>ACCATCGCCTCTCAACCTCTTAGTCTTCGCCCCGAGGCATGCCGACC<br>CGCCGCCGGGGGTGCTGTTCATACGAGGGGCTTGGACTTCGCTTGTG<br>ATATTTACATTTGGGCTCCGTTGGCGGGTACGTGCGGCGTCCTTTTG<br>TTGTCACTCGTTATTACTTTGTATTGTAATCACAGGAATCGCTCAAA<br>GCGGAGTAGGTTGTTGCATTCCGATTACATGAATATGACTCCTCGCC<br>GGCCTGGGCCGACAAGAAAACATTACCAACCCTATGCCCCCCCACG<br>AGACTTCGCTGCGTACAGGTCCCGAGTGAAGTTTTCCCGAAGCGCA<br>GACGCTCCGGCATATCAGCAAGGACAGAATCAGCTGTATAACGAAC<br>TGAATTTGGGACGCCGCGAGGAGTATGACGTGCTTGATAAACGCCG<br>GGGGAGAGACCCGGAAATGGGGGGTAAACCCCGAAGAAAGAATCC<br>CCAAGAAGGACTCTACAATGAACTCCAGAAGGATAAGATGGCGGA<br>GGCCTACTCAGAAATAGGTATGAAGGGCGAACGACGACGGGGAAA<br>AGGTCACGATGGCCTCTACCAAGGGTTGAGTACGGCAACCAAAGAT<br>ACGTACGATGCACTGCATATGCAGGCCCTGCCTCCCAGATAATAAT<br>AAAATCGCTATCCATCGAAGATGGATGTGTGTTGGTTTTTTGTGTGT<br>GGAGCAACAAATCTGACTTTGCATGTGCAAACGCCTTCAACAACAG<br>CATTATTCCAGAAGACACCTTCTTCCCCAGCCCAGGTAAGGGCAGCT<br>TTGGTGCCTTCGCAGGCTGTTTCCTTGCTTCAGGAATGGCCAGGTTC<br>TGCCCAGAGCTCTGGTCAATGATGTCTAAAACTCCTCTGATTGGTGG<br>TCTCGGCCTTATCCATTGCCACCAAAACCCTCTTTTTACTAAGAAAC<br>AGTGAGCCTTGTTCTGGCAGTCCAGAGAATGACACGGGAAAAAAGC<br>AGATGAAGAGAAGGTGGCAGGAGAGGGCACGTGGCCCAGCCTCAG<br>TCTCTCCAACTGAGTTCCTGCCTGCCTGCCTTTGCTCAGACTGTTTGC<br>CCCTTACTGCTCTTCTAGGCCTCATTCTAAGCCCCTTCTCCAAGTTGC<br>CTCTCCTTATTTCTCCCTGTCTGCCAAAAAATCTTTCCCAGCTCACTA<br>AGTCAGTCTCACGCAGTCACTCATTAACCCACCAATCACTGATTGTG<br>CCGGCACATGAATGCACCAGGTGTTGAAGTGGAGGAATTAAAAAGT<br>CAGATGAGGGGTGTGCCCAGAGGAAGCACCATTCTAGTTGGGGGAG<br>CCCATCTGTCAGCTGGGAAAAGTCCAAATAACTTCAGATTGGAATG | |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| | TGTTTTAACTCAGGGTTGAGAAAACAGCTACCTTCAGGACAAAAGT<br>CAGGGAAGGGCTCTCTGAAGAAATGCTACTTGAAGATACCAGCCCT<br>ACCAAGGGCAGGGAGAGGACCCTATAGAGGCCTGGGACAGGAGCT<br>CAATGAGAAAGG | |
| CTX-971b<br>Donor<br>LHA to RHA | GAGATGTAAGGAGCTGCTGTGACTTGCTCAAGGCCTTATATCGAGT<br>AAACGGTAGTGCTGGGGCTTAGACGCAGGTGTTCTGATTTATAGTTC<br>AAAACCTCTATCAATGAGAGAGCAATCTCCTGGTAATGTGATAGAT<br>TTCCCAACTTAATGCCAACATACCATAAACCTCCCATTCTGCTAATG<br>CCCAGCCTAAGTTGGGGAGACCACTCCAGATTCCAAGATGTACAGT<br>TTGCTTTGCTGGGCCTTTTTCCCATGCCTGCCTTTACTCTGCCAGAGT<br>TATATTGCTGGGGTTTTGAAGAAGATCCTATTAAATAAAAGAATAA<br>GCAGTATTATTAAGTAGCCCTGCATTTCAGGTTTCCTTGAGTGGCAG<br>GCCAGGCCTGGCCGTGAACGTTCACTGAAATCATGGCCTCTTGGCCA<br>AGATTGATAGCTTGTGCCTGTCCCTGAGTCCCAGTCCATCACGAGCA<br>GCTGGTTTCTAAGATGCTATTTCCCGTATAAAGCATGAGACCGTGAC<br>TTGCCAGCCCCACAGAGCCCCGCCCTTGTCCATCACTGGCATCTGGA<br>CTCCAGCCTGGGTTGGGGCAAAGAGGGAAATGAGATCATGTCCTAA<br>CCCTGATCCTCTTGTCCCACAGATATCCAGAACCCTGACCCTGCCGT<br>GTACCAGCTGAGAGACTCTAAATCCAGTGACAAGTCTGTCTGCCTAT<br>TCACCGATTTTGATTCTCAAACAAATGTGTCACAAAGTAAGGATTCT<br>GATGTGTATATCACAGACAAAACTGTGCTAGACATGAGGTCTATGG<br>ACTTCAggctccggtgcccgtcagtgggcagagcgcacatcgcccacagtccccgagaagttggggga<br>ggggtcggcaattgaaccggtgcctagagaaggtggcgcggggtaaactgggaaagtgatgtcgtgtactggc<br>tccgcctttttcccgagggtgggggagaaccgtatataagtgcagtagtcgccgtgaacgttctttttcgcaacgg<br>gtttgccgccagaacacaggtaagtgccgtgtgtggttcccgcgggcctggcctctttacgggttatggcccttgc<br>gtgccttgaattacttccactggctgcagtacgtgattcttgatcccgagcttcgggttggaagtgggtgggagagt<br>tcgaggccttgcgcttaaggagccccttcgcctcgtgcttgagttgaggcctggcctgggcgctggggccgccg<br>cgtgcgaatctggtggcaccttcgcgcctgtctcgctgctttcgataagtctctagccatttaaaatttttgatgacct<br>gctgcgacgctttttttctggcaagatagtcttgtaaatgcgggccaagatctgcacactggtatttcggtttttgggg<br>ccgcgggcggcgacggggcccgtgcgtcccagcgcacatgttcggcgaggcggggcctgcgagcgcggcc<br>accgagaatcggacgggggtagtctcaagctggccggcctgctctggtgcctggcctcgcgccgccgtgtatc<br>gccccgccctgggcggcaaggctggcccggtcggcaccagttgcgtgagcggaaagatggccgcttcccgg<br>ccctgctgcagggagctcaaaatggaggacgcggcgctcgggagagcgggcgggtgagtcacccacacaaa<br>ggaaaagggcctttccgtcctcagccgtcgcttcatgtgactccacggagtaccgggcgccgtccaggcacctc<br>gattagttctcgagcttttggagtacgtcgtctttaggttggggggaggggttttatgcgatggagtttccccacact<br>gagtgggtggagactgaagttaggccagcttggcacttgatgtaattctccttggaatttgccctttttgagtttggat<br>cttggttcattctcaagcctcagacagtggttcaaagtttttttcttccatttcaggtgtcgtgaCCACCATGG<br>CGCTTCCGGTGACAGCACTGCTCCTCCCCTTGGCGCTGTTGCTCCAC<br>GCAGCAAGGCCGGACGTGGTCATGACTCAAAGCCCACTTTCCTTGC<br>CCGTGACTCTCGGACAACCGGCTTCAATATCTTGCCGCTCATCACAG<br>TCCCTGCTGCATAGCAGTGGTAACACTTATCTTGAGTGGTACCAACA<br>GCGGCCCGGCCAATCTCCTAGGCCCCTGATATATAAGATAAGTACTC<br>GCTTTTCCGGGGTCCCGGACCGGTTCAGCGGGTCTGGGAGTGGTAC<br>AGACTTCACATTGAAGATTTCACGAGTAGAAGCCGAAGACGTGGGT<br>GTTTATTACTGCTTCCAAGGATCTCACGTGCCATATACGTTTGGTGG<br>GGGCACAAAAGTCGAGATTAAGGGAGGCGGAGGATCAGGAGGTGG<br>GGGAAGTGGAGGTGGTGGGTCACAAGTACAGCTCGTGCAATCAGGG<br>GCGGAGGTGAAGAAACCAGGGGCGTCTGTGAAGGTAAGCTGTAAG<br>GCATCCGGATTGACAATCGAGGATTATTACATGCATTGGGTCCGCCA<br>GGCACCAGGGCAGGGATTGGAGTGGATGGGGTGGATAGATCCTGAA<br>AATGGGGATACAGAGTATGGCCCTAAGTTCCAGGGCAGAGTTACGA<br>TGACTCGAGATACTAGCATTAATACGGCCTACATGGAGCTTAGCCG<br>CCTGCGGTCCGATGACACGGCCGTTTATTATTGCGCCGTACACAATG<br>CGCACTACGGGACATGGTTCGCGTATTGGGGTCAAGGAACGCTCGT<br>TACTGTCTCAAGTAGTGCTGCTGCCTTTGTCCCGGTATTTCTCCCAGC<br>CAAACCGACCACGACTCCCGCCCCGCGCCCTCCGACACCCGCTCCC<br>ACCATCGCCTCTCAACCTCTTAGTCTTCGCCCCGAGGCATGCCGACC<br>CGCCGCCGGGGGTGCTGTTCATACGAGGGGCTTGGACTTCGCTTGTG<br>ATATTTACATTTGGGCTCCGTTGGCGGGTACGTGCGGCGTCCTTTTG<br>TTGTCACTCGTTATTACTTTGTATTGTAATCACAGGAATCGCAAACG<br>GGGCAGAAAGAAACTCCTGTATATATTCAAACAACCATTTATGAGA<br>CCAGTACAAACTACTCAAGAGGAAGATGGCTGTAGCTGCCGATTTC<br>CAGAAGAAGAAGAAGGAGGATGTGAACTGCGAGTGAAGTTTTCCCG<br>AAGCGCAGACGCTCCGGCATATCAGCAAGGACAGAATCAGCTGTAT<br>AACGAACTGAATTTGGGACGCCGCGAGGAGTATGACGTGCTTGATA<br>AACGCCGGGGGAGAGACCCGGAAATGGGGGGTAAACCCCGAAGAA<br>AGAATCCCCAAGAAGGACTCTACAATGAACTCCAGAAGGATAAGAT<br>GGCGGAGGCCTACTCAGAAATAGGTATGAAGGGCGAACGACGACG<br>GGGAAAAGGTCACGATGGCCTCTACCAAGGGTTGAGTACGGCAACC<br>AAAGATACGTACGATGCACTGCATATGCAGGCCCTGCCTCCCAGAT<br>AATAATAAAATCGCTATCCATCGAAGATGGATGTGTGTTGGTTTTTT | 64 |

TABLE 7-continued

| CAR Components<br>CAR Structure:<br>CD8 [signal peptide]-anti-LIV1[scFV]-CD8[tm]-CD28[co-stimulatory domain]-CD3ζ; or<br>CD8 [signal peptide]-anti-LIV1[scFV]-CD8[tm]-41BB[co-stimulatory domain]-CD3ζ | | |
|---|---|---|
| Name | Sequence | SEQ ID NO: |
| | GTGTGTGGAGCAACAAATCTGACTTTGCATGTGCAAACGCCTTCAAC<br>AACAGCATTATTCCAGAAGACACCTTCTTCCCCAGCCCAGGTAAGG<br>GCAGCTTTGGTGCCTTCGCAGGCTGTTTCCTTGCTTCAGGAATGGCC<br>AGGTTCTGCCCAGAGCTCTGGTCAATGATGTCTAAAACTCCTCTGAT<br>TGGTGGTCTCGGCCTTATCCATTGCCACCAAAACCCTCTTTTTACTA<br>AGAAACAGTGAGCCTTGTTCTGGCAGTCCAGAGAATGACACGGGAA<br>AAAAGCAGATGAAGAGAAGGTGGCAGGAGAGGGCACGTGGCCCAG<br>CCTCAGTCTCTCCAACTGAGTTCCTGCCTGCCTGCCTTTGCTCAGACT<br>GTTTGCCCCTTACTGCTCTTCTAGGCCTCATTCTAAGCCCCTTCTCCA<br>AGTTGCCTCTCCTTATTTCTCCCTGTCTGCCAAAAAATCTTTCCCAGC<br>TCACTAAGTCAGTCTCACGCAGTCACTCATTAACCCACCAATCACTG<br>ATTGTGCCGGCACATGAATGCACCAGGTGTTGAAGTGGAGGAATTA<br>AAAAGTCAGATGAGGGGTGTGCCCAGAGGAAGCACCATTCTAGTTG<br>GGGGAGCCCATCTGTCAGCTGGGAAAAGTCCAAATAACTTCAGATT<br>GGAATGTGTTTTAACTCAGGGTTGAGAAAACAGCTACCTTCAGGAC<br>AAAAGTCAGGGAAGGGCTCTCTGAAGAAATGCTACTTGAAGATACC<br>AGCCCTACCAAGGGCAGGGAGAGGACCCTATAGAGGCCTGGGACA<br>GGAGCTCAATGAGAAAGG | |
| CTX-972<br>CAR<br>CD28 co-stim | CCACCATGGCGCTTCCGGTGACAGCACTGCTCCTCCCCTTGGCGCTG<br>TTGCTCCACGCAGCAAGGCCGCAAGTTCAACTGGTCCAGTCAGGCG<br>CTGAGGTCAAAAAGCCCGGCGCGAGCGTAAAAGTCTCCTGCAAGGC<br>GTCAGGGTTGACGATAGAAGATTATTACATGCATTGGGTCAGACAG<br>GCACCCGGACAGGGATTGGAGTGGATGGGTTGGATCGACCCGGAAA<br>ACGGTGACACGGAGTATGGGCCGAAGTTTCAGGGGAGGGTCACAAT<br>GACACGAGATACGTCCATAAATACCGCTTACATGGAACTTTCTCGGC<br>TTCGCTCTGATGATACAGCAGTTTACTACTGCGCTGTTCATAATGCC<br>CATTACGGAACCTGGTTCGCGTACTGGGGCCAAGGGACCCTGGTTA<br>CGGTTAGCTCTGGTGGGGGTGGAAGCGGGGGAGGGGGTAGCGGAG<br>GTGGCGGAAGTGATGTTGTTATGACACAGAGTCCCCTGTCATTGCCC<br>GTCACCCTCGGACAACCAGCTAGCATTTCATGCAGGTCTAGTCAAA<br>GCCTCCTTCACAGTAGCGGCAACACCTACCTCGAATGGTATCAACA<br>ACGGCCAGGGCAATCTCCTCGCCCACTCATATACAAAATCTCTACAC<br>GCTTCTCAGGTGTTCCCGACCGCTTCAGCGGTTCCGGCTCTGGGACA<br>GACTTTACCTTGAAAATAAGCAGGGTTGAAGCTGAGGACGTAGGGG<br>TATATTATTGTTTTCAGGGCAGTCACGTGCCGTACACTGGGGGCGGA<br>ACCAAAGTCGAGATAAAGAGTGCTGCTGCCTTTGTCCCGGTATTTCT<br>CCCAGCCAAACCGACCACGACTCCCGCCCCGCGCCCTCCGACACCC<br>GCTCCCACCATCGCCTCTCAACCTCTTAGTCTTCGCCCCGAGGCATG<br>CCGACCCGCCGCCGGGGGTGCTGTTCATACGAGGGGCTTGGACTTC<br>GCTTGTGATATTTACATTTGGGCTCCGTTGGCGGGTACGTGCGGCGT<br>CCTTTTGTTGTCACTCGTTATTACTTTGTATTGTAATCACAGGAATCG<br>CTCAAAGCGGAGTAGGTTGTTGCATTCCGATTACATGAATATGACTC<br>CTCGCCGGCCTGGGCCGACAAGAAAACATTACCAACCCTATGCCCC<br>CCCACGAGACTTCGCTGCGTACAGGTCCCGAGTGAAGTTTTCCCGAA<br>GCGCAGACGCTCCGGCATATCAGCAAGGACAGAATCAGCTGTATAA<br>CGAACTGAATTTGGGACGCCGCGAGGAGTATGACGTGCTTGATAAA<br>CGCCGGGGGAGAGACCCGGAAATGGGGGGTAAACCCCGAAGAAAG<br>AATCCCCAAGAAGGACTCTACAATGAACTCCAGAAGGATAAGATGG<br>CGGAGGCCTACTCAGAAATAGGTATGAAGGGCGAACGACGACGGG<br>GAAAAGGTCACGATGGCCTCTACCAAGGGTTGAGTACGGCAACCAA<br>AGATACGTACGATGCACTGCATATGCAGGCCCTGCCTCCCAGATAA<br>T | 65 |
| CTX-972<br>CAR<br>CD28 co-stim | MALPVTALLLPLALLLHAARPQVQLVQSGAEVKKPGASVKVSCKASG<br>LTIEDYYMHWVRQAPGQGLEWMGWIDPENGDTEYGPKFQGRVTMTR<br>DTSINTAYMELSRLRSDDTAVYYCAVHNAHYGTWFAYWGQGTLVTV<br>SSGGGGSGGGGSGGGGSDVVMTQSPLSLPVTLGQPASISCRSSQSLLHS<br>SGNTYLEWYQQRPGQSPRPLIYKISTRFSGVPDRFSGSGSGTDFTLKISR<br>VEAEDVGVYYCFQGSHVPYTGGGTKVEIKSAAAFVPVFLPAKPTTTPA<br>PRPPTPAPTIASQPLSLRPEACRPAAGGAVHTRGLDFACDIYIWAPLAGT<br>CGVLLLSLVITLYCNHRNRSKRSRLLHSDYMNMTPRRPGPTRKHYQPY<br>APPRDFAAYRSRVKFSRSADAPAYQQGQNQLYNELNLGRREEYDVLD<br>KRRGRDPEMGGKPRRKNPQEGLYNELQKDKMAEAYSEIGMKGERRR<br>GKGHDGLYQGLSTATKDTYDALHMQALPPR | 125 |
| CTX-972b<br>CAR<br>co-stim 41BB | CCACCATGGCGCTTCCGGTGACAGCACTGCTCCTCCCCTTGGCGCTG<br>TTGCTCCACGCAGCAAGGCCGCAAGTTCAACTGGTCCAGTCAGGCG<br>CTGAGGTCAAAAAGCCCGGCGCGAGCGTAAAAGTCTCCTGCAAGGC<br>GTCAGGGTTGACGATAGAAGATTATTACATGCATTGGGTCAGACAG<br>GCACCCGGACAGGGATTGGAGTGGATGGGTTGGATCGACCCGGAAA<br>ACGGTGACACGGAGTATGGGCCGAAGTTTCAGGGGAGGGTCACAAT | 67 |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| | GACACGAGATACGTCCATAAATACCGCTTACATGGAACTTTCTCGGC<br>TTCGCTCTGATGATACAGCAGTTTACTACTGCGCTGTTCATAATGCC<br>CATTACGGAACCTGGTTCGCGTACTGGGGCCAAGGGACCCTGGTTA<br>CGGTTAGCTCTGGTGGGGGTGGAAGCGGGGGAGGGGGTAGCGGAG<br>GTGGCGGAAGTGATGTTGTTATGACACAGAGTCCCCTGTCATTGCCC<br>GTCACCCTCGGACAACCAGCTAGCATTTCATGCAGGTCTAGTCAAA<br>GCCTCCTTCACAGTAGCGGCAACACCTACCTCGAATGGTATCAACA<br>ACGGCCAGGGCAATCTCCTCGCCCACTCATATACAAAATCTCTACAC<br>GCTTCTCAGGTGTTCCCGACCGCTTCAGCGGTTCCGGCTCTGGGACA<br>GACTTTACCTTGAAAATAAGCAGGGTTGAAGCTGAGGACGTAGGGG<br>TATATTATTGTTTTCAGGGCAGTCACGTGCCGTACACTGGGGGCGGA<br>ACCAAAGTCGAGATAAAGAGTGCTGCTGCCTTTGTCCCGGTATTTCT<br>CCCAGCCAAACCGACCACGACTCCCGCCCCGCGCCCTCCGACACCC<br>GCTCCCACCATCGCCTCTCAACCTCTTAGTCTTCGCCCCGAGGCATG<br>CCGACCCGCCGCCGGGGGTGCTGTTCATACGAGGGGCTTGGACTTC<br>GCTTGTGATATTTACATTTGGGCTCCGTTGGCGGGTACGTGCGGCGT<br>CCTTTTGTTGTCACTCGTTATTACTTTGTATTGTAATCACAGGAATCG<br>CAAACGGGGCAGAAAGAAACTCCTGTATATATTCAAACAACCATTT<br>ATGAGACCAGTACAAACTACTCAAGAGGAAGATGGCTGTAGCTGCC<br>GATTTCCAGAAGAAGAAGAAGGAGGATGTGAACTGCGAGTGAAGTT<br>TTCCCGAAGCGCAGACGCTCCGGCATATCAGCAAGGACAGAATCAG<br>CTGTATAACGAACTGAATTTGGGACGCCGCGAGGAGTATGACGTGC<br>TTGATAAACGCCGGGGGAGAGACCCGGAAATGGGGGGTAAACCCC<br>GAAGAAAGAATCCCCAAGAAGGACTCTACAATGAACTCCAGAAGG<br>ATAAGATGGCGGAGGCCTACTCAGAAATAGGTATGAAGGGCGAAC<br>GACGACGGGGAAAAGGTCACGATGGCCTCTACCAAGGGTTGAGTAC<br>GGCAACCAAAGATACGTACGATGCACTGCATATGCAGGCCCTGCCT<br>CCCAGATAAT | |
| CTX-972b<br>CAR<br>co-stim 41BB | MALPVTALLLPLALLLHAARPQVQLVQSGAEVKKPGASVKVSCKASG<br>LTIEDYYMHWVRQAPGQGLEWMGWIDPENGDTEYGPKFQGRVTMTR<br>DTSINTAYMELSRLRSDDTAVYYCAVHNAHYGTWFAYWGQGTLVTV<br>SSGGGGSGGGGSGGGGSDVVMTQSPLSLPVTLGQPASISCRSSQSLLHS<br>SGNTYLEWYQQRPGQSPRPLIYKISTRFSGVPDRFSGSGSGTDFTLKISR<br>VEAEDVGVYYCFQGSHVPYTGGGTKVEIKSAAAFVPVFLPAKPTTTPA<br>PRPPTPAPTIASQPLSLRPEACRPAAGGAVHTRGLDFACDIYIWAPLAGT<br>CGVLLLSLVITLYCNHRNRKRGRKKLLYIFKQPFMRPVQTTQEEDGCSC<br>RFPEEEEGGCELRVKFSRSADAPAYQQGQNQLYNELNLGRREEYDVLD<br>KRRGRDPEMGGKPRRKNPQEGLYNELQKDKMAEAYSEIGMKGERRR<br>GKGHDGLYQGLSTATKDTYDALHMQALPPR | 126 |
| CTX-972 and<br>CTX-972b<br>scFv | CAAGTTCAACTGGTCCAGTCAGGCGCTGAGGTCAAAAAGCCCGGCG<br>CGAGCGTAAAAGTCTCCTGCAAGGCGTCAGGGTTGACGATAGAAGA<br>TTATTACATGCATTGGGTCAGACAGGCACCCGGACAGGGATTGGAG<br>TGGATGGGTTGGATCGACCCGGAAAACGGTGACACGGAGTATGGGC<br>CGAAGTTTCAGGGGAGGGTCACAATGACACGAGATACGTCCATAAA<br>TACCGCTTACATGGAACTTTCTCGGCTTCGCTCTGATGATACAGCAG<br>TTTACTACTGCGCTGTTCATAATGCCCATTACGGAACCTGGTTCGCG<br>TACTGGGGCCAAGGGACCCTGGTTACGGTTAGCTCTGGTGGGGGTG<br>GAAGCGGGGGAGGGGGTAGCGGAGGTGGCGGAAGTGATGTTGTTA<br>TGACACAGAGTCCCCTGTCATTGCCCGTCACCCTCGGACAACCAGCT<br>AGCATTTCATGCAGGTCTAGTCAAAGCCTCCTTCACAGTAGCGGCAA<br>CACCTACCTCGAATGGTATCAACAACGGCCAGGGCAATCTCCTCGC<br>CCACTCATATACAAAATCTCTACACGCTTCTCAGGTGTTCCCGACCG<br>CTTCAGCGGTTCCGGCTCTGGGACAGACTTTACCTTGAAAATAAGCA<br>GGGTTGAAGCTGAGGACGTAGGGGTATATTATTGTTTTCAGGGCAG<br>TCACGTGCCGTACACTGGGGGCGGAACCAAAGTCGAGATAAAG | 69 |
| CTX-972 and<br>CTX-972b<br>scFv<br>(linker<br>underlined) | QVQLVQSGAEVKKPGASVKVSCKASGLTIEDYYMHWVRQAPGQGLE<br>WMGWIDPENGDTEYGPKFQGRVTMTRDTSINTAYMELSRLRSDDTAV<br>YYCAVHNAHYGTWFAYWGQGTLVTVSS**GGGGSGGGGSGGGGS**DVV<br>MTQSPLSLPVTLGQPASISCRSSQSLLHSSGNTYLEWYQQRPGQSPRPLI<br>YKISTRFSGVPDRFSGSGSGTDFTLKISRVEAEDVGVYYCFQGSHVPYT<br>GGGTKVEIK | 127 |
| CTX-972 and<br>CTX-972b<br>scFv VH<br>CDRs-in bold | QVQLVQSGAEVKKPGASVKVSCKASGLTIE**DYYMH**WVRQAPGQGLE<br>WMG**WIDPENGDTEYGPKFQG**RVTMTRDTSINTAYMELSRLRSDDTA<br>VYYCAV**HNAHYGTWFAY**WGQGTLVTVSS | 55 |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| CTX-972 and CTX-972b scFv VL CDRs-in bold | DVVMTQSPLSLPVTLGQPASISC**RSSQSLLHSSGNTYLE**WYQQRPGQS<br>PRPLIY**KISTRFS**GVPDRFSGSGSGTDFTLKISRVEAEDVGVYYC**FQGS**<br>**HVPYT**GGGTKVEIK | 128 |
| CTX-972 and CTX-972b VH CDR1 | DYYMH | 57 |
| CTX-972 and CTX-972b VH CDR2 | WIDPENGDTEYGPKFQG | 58 |
| CTX-972 and CTX-972b VH CDR3 | HNAHYGTWFAY | 59 |
| CTX-972 and CTX-972b VL CDR1 | RSSQSLLHSSGNTYLE | 60 |
| CTX-972 and CTX-972b VL CDR2 | KISTRFS | 61 |
| CTX-972 and CTX-972b VL CDR3 | FQGSHVPYT | 62 |
| CTX-972 Donor LHA to RHA | GAGATGTAAGGAGCTGCTGTGACTTGCTCAAGGCCTTATATCGAGT<br>AAACGGTAGTGCTGGGGCTTAGACGCAGGTGTTCTGATTTATAGTTC<br>AAAACCTCTATCAATGAGAGAGCAATCTCCTGGTAATGTGATAGAT<br>TTCCCAACTTAATGCCAACATACCATAAACCTCCCATTCTGCTAATG<br>CCCAGCCTAAGTTGGGGAGACCACTCCAGATTCCAAGATGTACAGT<br>TTGCTTTGCTGGGCCTTTTTCCCATGCCTGCCTTTACTCTGCCAGAGT<br>TATATTGCTGGGGTTTTGAAGAAGATCCTATTAAATAAAAGAATAA<br>GCAGTATTATTAAGTAGCCCTGCATTTCAGGTTTCCTTGAGTGGCAG<br>GCCAGGCCTGGCCGTGAACGTTCACTGAAATCATGGCCTCTTGGCCA<br>AGATTGATAGCTTGTGCCTGTCCCTGAGTCCCAGTCCATCACGAGCA<br>GCTGGTTTCTAAGATGCTATTTCCCGTATAAAGCATGAGACCGTGAC<br>TTGCCAGCCCCACAGAGCCCCGCCCTTGTCCATCACTGGCATCTGGA<br>CTCCAGCCTGGGTTGGGGCAAAGAGGGAAATGAGATCATGTCCTAA<br>CCCTGATCCTCTTGTCCCACAGATATCCAGAACCCTGACCCTGCCGT<br>GTACCAGCTGAGAGACTCTAAATCCAGTGACAAGTCTGTCTGCCTAT<br>TCACCGATTTTGATTCTCAAACAAATGTGTCACAAAGTAAGGATTCT<br>GATGTGTATATCACAGACAAAACTGTGCTAGACATGAGGTCTATGG<br>ACTTCAggctccggtgcccgtcagtgggcagagcgcacatcgcccacagtccccgagaagttggggga<br>ggggtcggcaattgaaccggtgcctagagaaggtggcgcggggtaaactgggaaagtgatgtcgtgtactggc<br>tccgcctttttcccgagggtgggggagaaccgtatataagtgcagtagtcgccgtgaacgttctttttcgcaacgg<br>gtttgccgccagaacacaggtaagtgccgtgtgtggttcccgcgggcctggcctctttacgggttatggcccttgc<br>gtgccttgaattacttccactggctgcagtacgtgattcttgatcccgagcttcgggttggaagtgggtgggagagt<br>tcgaggccttgcgcttaaggagccccttcgcctcgtgcttgagttgaggcctggcctgggcgctggggccgccg<br>cgtgcgaatctggtggcaccttcgcgcctgtctcgctgctttcgataagtctctagccatttaaaatttttgatgacct<br>gctgcgacgctttttttctggcaagatagtcttgtaaatgcgggccaagatctgcacactggtatttcggtttttgggg<br>ccgcgggcggcgacggggcccgtgcgtcccagcgcacatgttcggcgaggcggggcctgcgagcgcggcc<br>accgagaatcggacgggggtagtctcaagctggccggcctgctctggtgcctggcctcgcgccgccgtgtatc<br>gccccgccctgggcggcaaggctggcccggtcggcaccagttgcgtgagcggaaagatggccgcttcccgg<br>ccctgctgcagggagctcaaaatggaggacgcggcgctcgggagagcgggcgggtgagtcacccacacaaa<br>ggaaaagggcctttccgtcctcagccgtcgcttcatgtgactccacggagtaccgggcgccgtccaggcacctc<br>gattagttctcgagcttttggagtacgtcgtctttaggttggggggaggggttttatgcgatggagtttccccacact<br>gagtgggtggagactgaagttaggccagcttggcacttgatgtaattctccttggaatttgccctttttgagtttggat<br>cttggttcattctcaagcctcagacagtggttcaaagtttttttcttccatttcaggtgtcgtgaCCACCATGG<br>CGCTTCCGGTGACAGCACTGCTCCTCCCCTTGGCGCTGTTGCTCCAC<br>GCAGCAAGGCCGCAAGTTCAACTGGTCCAGTCAGGCGCTGAGGTCA<br>AAAAGCCCGGCGCGAGCGTAAAAGTCTCCTGCAAGGCGTCAGGGTT<br>GACGATAGAAGATTATTACATGCATTGGGTCAGACAGGCACCCGGA<br>CAGGGATTGGAGTGGATGGGTTGGATCGACCCGGAAAACGGTGACA<br>CGGAGTATGGGCCGAAGTTTCAGGGGAGGGTCACAATGACACGAGA<br>TACGTCCATAAATACCGCTTACATGGAACTTTCTCGGCTTCGCTCTG<br>ATGATACAGCAGTTTACTACTGCGCTGTTCATAATGCCCATTACGGA<br>ACCTGGTTCGCGTACTGGGGCCAAGGGACCCTGGTTACGGTTAGCTC | 71 |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| | TGGTGGGGGTGGAAGCGGGGGAGGGGGTAGCGGAGGTGGCGGAAG<br>TGATGTTGTTATGACACAGAGTCCCCTGTCATTGCCCGTCACCCTCG<br>GACAACCAGCTAGCATTTCATGCAGGTCTAGTCAAAGCCTCCTTCAC<br>AGTAGCGGCAACACCTACCTCGAATGGTATCAACAACGGCCAGGGC<br>AATCTCCTCGCCCACTCATATACAAAATCTCTACACGCTTCTCAGGT<br>GTTCCCGACCGCTTCAGCGGTTCCGGCTCTGGGACAGACTTTACCTT<br>GAAAATAAGCAGGGTTGAAGCTGAGGACGTAGGGGTATATTATTGT<br>TTTCAGGGCAGTCACGTGCCGTACACTGGGGGCGGAACCAAAGTCG<br>AGATAAAGAGTGCTGCTGCCTTTGTCCCGGTATTTCTCCCAGCCAAA<br>CCGACCACGACTCCCGCCCCGCGCCCTCCGACACCCGCTCCCACCAT<br>CGCCTCTCAACCTCTTAGTCTTCGCCCCGAGGCATGCCGACCCGCCG<br>CCGGGGGTGCTGTTCATACGAGGGGCTTGGACTTCGCTTGTGATATT<br>TACATTTGGGCTCCGTTGGCGGGTACGTGCGGCGTCCTTTTGTTGTC<br>ACTCGTTATTACTTTGTATTGTAATCACAGGAATCGCTCAAAGCGGA<br>GTAGGTTGTTGCATTCCGATTACATGAATATGACTCCTCGCCGGCCT<br>GGGCCGACAAGAAAACATTACCAACCCTATGCCCCCCCACGAGACT<br>TCGCTGCGTACAGGTCCCGAGTGAAGTTTTCCCGAAGCGCAGACGC<br>TCCGGCATATCAGCAAGGACAGAATCAGCTGTATAACGAACTGAAT<br>TTGGGACGCCGCGAGGAGTATGACGTGCTTGATAAACGCCGGGGGA<br>GAGACCCGGAAATGGGGGGTAAACCCCGAAGAAAGAATCCCCAAG<br>AAGGACTCTACAATGAACTCCAGAAGGATAAGATGGCGGAGGCCTA<br>CTCAGAAATAGGTATGAAGGGCGAACGACGACGGGGAAAAGGTCA<br>CGATGGCCTCTACCAAGGGTTGAGTACGGCAACCAAAGATACGTAC<br>GATGCACTGCATATGCAGGCCCTGCCTCCCAGATAATAATAAAATC<br>GCTATCCATCGAAGATGGATGTGTGTTGGTTTTTTGTGTGTGGAGCA<br>ACAAATCTGACTTTGCATGTGCAAACGCCTTCAACAACAGCATTATT<br>CCAGAAGACACCTTCTTCCCCAGCCCAGGTAAGGGCAGCTTTGGTG<br>CCTTCGCAGGCTGTTTCCTTGCTTCAGGAATGGCCAGGTTCTGCCCA<br>GAGCTCTGGTCAATGATGTCTAAAACTCCTCTGATTGGTGGTCTCGG<br>CCTTATCCATTGCCACCAAAACCCTCTTTTTACTAAGAAACAGTGAG<br>CCTTGTTCTGGCAGTCCAGAGAATGACACGGGAAAAAAGCAGATGA<br>AGAGAAGGTGGCAGGAGAGGGCACGTGGCCCAGCCTCAGTCTCTCC<br>AACTGAGTTCCTGCCTGCCTGCCTTTGCTCAGACTGTTTGCCCCTTAC<br>TGCTCTTCTAGGCCTCATTCTAAGCCCCTTCTCCAAGTTGCCTCTCCT<br>TATTTCTCCCTGTCTGCCAAAAAATCTTTCCCAGCTCACTAAGTCAG<br>TCTCACGCAGTCACTCATTAACCCACCAATCACTGATTGTGCCGGCA<br>CATGAATGCACCAGGTGTTGAAGTGGAGGAATTAAAAAGTCAGATG<br>AGGGGTGTGCCCAGAGGAAGCACCATTCTAGTTGGGGGAGCCCATC<br>TGTCAGCTGGGAAAAGTCCAAATAACTTCAGATTGGAATGTGTTTTA<br>ACTCAGGGTTGAGAAAACAGCTACCTTCAGGACAAAAGTCAGGGAA<br>GGGCTCTCTGAAGAAATGCTACTTGAAGATACCAGCCCTACCAAGG<br>GCAGGGAGAGGACCCTATAGAGGCCTGGGACAGGAGCTCAATGAG<br>AAAGG | |
| CTX-972b<br>Donor<br>LHA to RHA | GAGATGTAAGGAGCTGCTGTGACTTGCTCAAGGCCTTATATCGAGT<br>AAACGGTAGTGCTGGGGCTTAGACGCAGGTGTTCTGATTTATAGTTC<br>AAAACCTCTATCAATGAGAGAGCAATCTCCTGGTAATGTGATAGAT<br>TTCCCAACTTAATGCCAACATACCATAAACCTCCCATTCTGCTAATG<br>CCCAGCCTAAGTTGGGGAGACCACTCCAGATTCCAAGATGTACAGT<br>TTGCTTTGCTGGGCCTTTTTCCCATGCCTGCCTTTACTCTGCCAGAGT<br>TATATTGCTGGGGTTTTGAAGAAGATCCTATTAAATAAAAGAATAA<br>GCAGTATTATTAAGTAGCCCTGCATTTCAGGTTTCCTTGAGTGGCAG<br>GCCAGGCCTGGCCGTGAACGTTCACTGAAATCATGGCCTCTTGGCCA<br>AGATTGATAGCTTGTGCCTGTCCCTGAGTCCCAGTCCATCACGAGCA<br>GCTGGTTTCTAAGATGCTATTTCCCGTATAAAGCATGAGACCGTGAC<br>TTGCCAGCCCCACAGAGCCCCGCCCTTGTCCATCACTGGCATCTGGA<br>CTCCAGCCTGGGTTGGGGCAAAGAGGGAAATGAGATCATGTCCTAA<br>CCCTGATCCTCTTGTCCCACAGATATCCAGAACCCTGACCCTGCCGT<br>GTACCAGCTGAGAGACTCTAAATCCAGTGACAAGTCTGTCTGCCTAT<br>TCACCGATTTTGATTCTCAAACAAATGTGTCACAAAGTAAGGATTCT<br>GATGTGTATATCACAGACAAAACTGTGCTAGACATGAGGTCTATGG<br>ACTTCAggctccggtgcccgtcagtgggcagagcgcacatcgcccacagtccccgagaagttggggga<br>ggggtcggcaattgaaccggtgcctagagaaggtggcgcggggtaaactgggaaagtgatgtcgtgtactggc<br>tccgcctttttcccgagggtgggggagaaccgtatataagtgcagtagtcgccgtgaacgttctttttcgcaacgg<br>gtttgccgccagaacacaggtaagtgccgtgtgtggttcccgcgggcctggcctctttacgggttatggcccttgc<br>gtgccttgaattacttccactggctgcagtacgtgattcttgatcccgagcttcgggttggaagtgggtgggagagt<br>tcgaggccttgcgcttaaggagccccttcgcctcgtgcttgagttgaggcctggcctgggcgctggggccgccg<br>cgtgcgaatctggtggcaccttcgcgcctgtctcgctgctttcgataagtctctagccatttaaaatttttgatgacct<br>gctgcgacgctttttttctggcaagatagtcttgtaaatgcgggccaagatctgcacactggtatttcggtttttgggg<br>ccgcgggcggcgacggggcccgtgcgtcccagcgcacatgttcggcgaggcggggcctgcgagcgcggcc<br>accgagaatcggacgggggtagtctcaagctggccggcctgctctggtgcctggcctcgcgccgccgtgtatc<br>gccccgccctgggcggcaaggctggcccggtcggcaccagttgcgtgagcggaaagatggccgcttcccgg | 72 |

TABLE 7-continued

| CAR Components<br>CAR Structure:<br>CD8 [signal peptide]-anti-LIV1[scFV]-CD8[tm]-CD28[co-stimulatory domain]-CD3ζ; or<br>CD8 [signal peptide]-anti-LIV1[scFV]-CD8[tm]-41BB[co-stimulatory domain]-CD3ζ | | |
|---|---|---|
| Name | Sequence | SEQ ID NO: |
| | ccctgctgcagggagctcaaaatggaggacgcggcgctcgggagagcgggcgggtgagtcacccacacaaa<br>ggaaaagggcctttccgtcctcagccgtcgcttcatgtgactccacggagtaccgggcgccgtccaggcacctc<br>gattagttctcgagcttttggagtacgtcgtctttaggttggggggaggggttttatgcgatggagtttccccacact<br>gagtgggtggagactgaagttaggccagcttggcacttgatgtaattctccttggaatttgccctttttgagtttggat<br>cttggttcattctcaagcctcagacagtggttcaaagtttttttcttccatttcaggtgtcgtgaCCACCATGG<br>CGCTTCCGGTGACAGCACTGCTCCTCCCCTTGGCGCTGTTGCTCCAC<br>GCAGCAAGGCCGCAAGTTCAACTGGTCCAGTCAGGCGCTGAGGTCA<br>AAAAGCCCGGCGCGAGCGTAAAAGTCTCCTGCAAGGCGTCAGGGTT<br>GACGATAGAAGATTATTACATGCATTGGGTCAGACAGGCACCCGGA<br>CAGGGATTGGAGTGGATGGGTTGGATCGACCCGGAAAACGGTGACA<br>CGGAGTATGGGCCGAAGTTTCAGGGGAGGGTCACAATGACACGAGA<br>TACGTCCATAAATACCGCTTACATGGAACTTTCTCGGCTTCGCTCTG<br>ATGATACAGCAGTTTACTACTGCGCTGTTCATAATGCCCATTACGGA<br>ACCTGGTTCGCGTACTGGGGCCAAGGGACCCTGGTTACGGTTAGCTC<br>TGGTGGGGGTGGAAGCGGGGGAGGGGGTAGCGGAGGTGGCGGAAG<br>TGATGTTGTTATGACACAGAGTCCCCTGTCATTGCCCGTCACCCTCG<br>GACAACCAGCTAGCATTTCATGCAGGTCTAGTCAAAGCCTCCTTCAC<br>AGTAGCGGCAACACCTACCTCGAATGGTATCAACAACGGCCAGGGC<br>AATCTCCTCGCCCACTCATATACAAAATCTCTACACGCTTCTCAGGT<br>GTTCCCGACCGCTTCAGCGGTTCCGGCTCTGGGACAGACTTTACCTT<br>GAAAATAAGCAGGGTTGAAGCTGAGGACGTAGGGGTATATTATTGT<br>TTTCAGGGCAGTCACGTGCCGTACACTGGGGGCGGAACCAAAGTCG<br>AGATAAAGAGTGCTGCTGCCTTTGTCCCGGTATTTCTCCCAGCCAAA<br>CCGACCACGACTCCCGCCCCGCGCCCTCCGACACCCGCTCCCACCAT<br>CGCCTCTCAACCTCTTAGTCTTCGCCCCGAGGCATGCCGACCCGCCG<br>CCGGGGGTGCTGTTCATACGAGGGGCTTGGACTTCGCTTGTGATATT<br>TACATTTGGGCTCCGTTGGCGGGTACGTGCGGCGTCCTTTTGTTGTC<br>ACTCGTTATTACTTTGTATTGTAATCACAGGAATCGCAAACGGGGCA<br>GAAAGAAACTCCTGTATATATTCAAACAACCATTTATGAGACCAGT<br>ACAAACTACTCAAGAGGAAGATGGCTGTAGCTGCCGATTTCCAGAA<br>GAAGAAGAAGGAGGATGTGAACTGCGAGTGAAGTTTTCCCGAAGCG<br>CAGACGCTCCGGCATATCAGCAAGGACAGAATCAGCTGTATAACGA<br>ACTGAATTTGGGACGCCGCGAGGAGTATGACGTGCTTGATAAACGC<br>CGGGGGAGAGACCCGGAAATGGGGGGTAAACCCCGAAGAAAGAAT<br>CCCCAAGAAGGACTCTACAATGAACTCCAGAAGGATAAGATGGCGG<br>AGGCCTACTCAGAAATAGGTATGAAGGGCGAACGACGACGGGGAA<br>AAGGTCACGATGGCCTCTACCAAGGGTTGAGTACGGCAACCAAAGA<br>TACGTACGATGCACTGCATATGCAGGCCCTGCCTCCCAGATAATAAT<br>AAAATCGCTATCCATCGAAGATGGATGTGTGTTGGTTTTTTGTGTGT<br>GGAGCAACAAATCTGACTTTGCATGTGCAAACGCCTTCAACAACAG<br>CATTATTCCAGAAGACACCTTCTTCCCCAGCCCAGGTAAGGGCAGCT<br>TTGGTGCCTTCGCAGGCTGTTTCCTTGCTTCAGGAATGGCCAGGTTC<br>TGCCCAGAGCTCTGGTCAATGATGTCTAAAACTCCTCTGATTGGTGG<br>TCTCGGCCTTATCCATTGCCACCAAAACCCTCTTTTTACTAAGAAAC<br>AGTGAGCCTTGTTCTGGCAGTCCAGAGAATGACACGGGAAAAAAGC<br>AGATGAAGAGAAGGTGGCAGGAGAGGGCACGTGGCCCAGCCTCAG<br>TCTCTCCAACTGAGTTCCTGCCTGCCTGCCTTTGCTCAGACTGTTTGC<br>CCCTTACTGCTCTTCTAGGCCTCATTCTAAGCCCCTTCTCCAAGTTGC<br>CTCTCCTTATTTCTCCCTGTCTGCCAAAAAATCTTTCCCAGCTCACTA<br>AGTCAGTCTCACGCAGTCACTCATTAACCCACCAATCACTGATTGTG<br>CCGGCACATGAATGCACCAGGTGTTGAAGTGGAGGAATTAAAAAGT<br>CAGATGAGGGGTGTGCCCAGAGGAAGCACCATTCTAGTTGGGGGAG<br>CCCATCTGTCAGCTGGGAAAAGTCCAAATAACTTCAGATTGGAATG<br>TGTTTTAACTCAGGGTTGAGAAAACAGCTACCTTCAGGACAAAAGT<br>CAGGGAAGGGCTCTCTGAAGAAATGCTACTTGAAGATACCAGCCCT<br>ACCAAGGGCAGGGAGAGGACCCTATAGAGGCCTGGGACAGGAGCT<br>CAATGAGAAAGG | |
| CD8 signal peptide | MALPVTALLLPLALLLHAARP | 73 |
| CD8a trans-membrane + 5' Linker (underlined) | GCTGCTGCCTTTGTCCCGGTATTTCTCCCAGCCAAACCGACCACGAC<br>TCCCGCCCCGCGCCCTCCGACACCCGCTCCCACCATCGCCTCTCAAC<br>CTCTTAGTCTTCGCCCCGAGGCATGCCGACCCGCCGCCGGGGGTGCT<br>GTTCATACGAGGGGCTTGGACTTCGCTTGTGATATTTACATTTGGGC<br>TCCGTTGGCGGGTACGTGCGGCGTCCTTTTGTTGTCACTCGTTATTAC<br>TTTGTATTGTAATCACAGGAATCGC | 74 |

TABLE 7-continued

CAR Components
CAR Structure:
CD8 [signal peptide]-anti-LIV1[scFV]-CD8[tm]-CD28[co-stimulatory domain]-CD3ζ; or
CD8 [signal peptide]-anti-LIV1[scFV]-CD8[tm]-41BB[co-stimulatory domain]-CD3ζ

| Name | Sequence | SEQ ID NO: |
|---|---|---|
| CD8a trans-membrane + 5' Linker (underlined) | SAAAFVPVFLPAKPTTTPAPRPPTPAPTIASQPLSLRPEACRPAAGGAVH TRGLDFACDIYIWAPLAGTCGVLLLSLVITLYCNHRNR | 75 |
| CD8a transmembrane (without linker) | TTTGTCCCGGTATTTCTCCCAGCCAAACCGACCACGACTCCCGCCCC GCGCCCTCCGACACCCGCTCCCACCATCGCCTCTCAACCTCTTAGTC TTCGCCCCGAGGCATGCCGACCCGCCGCCGGGGGTGCTGTTCATAC GAGGGGCTTGGACTTCGCTTGTGATATTTACATTTGGGCTCCGTTGG CGGGTACGTGCGGCGTCCTTTTGTTGTCACTCGTTATTACTTTGTATT GTAATCACAGGAATCGC | 76 |
| CD8a transmembrane (without linker) | FVPVFLPAKPTTTPAPRPPTPAPTIASQPLSLRPEACRPAAGGAVHTRGL DFACDIYIWAPLAGTCGVLLLSLVITLYCNHRNR | 77 |
| CD28 co-stimulatory | TCAAAGCGGAGTAGGTTGTTGCATTCCGATTACATGAATATGACTCC TCGCCGGCCTGGGCCGACAAGAAAACATTACCAACCCTATGCCCCC CCACGAGACTTCGCTGCGTACAGGTCC | 45 |
| CD28 co-stimulatory | SKRSRLLHSDYMNMTPRRPGPTRKHYQPYAPPRDFAAYRS | 46 |
| 41BB co-stimulatory | AAACGGGGCAGAAAGAAACTCCTGTATATATTCAAACAACCATTTA TGAGACCAGTACAAACTACTCAAGAGGAAGATGGCTGTAGCTGCCG ATTTCCAGAAGAAGAAGAAGGAGGATGTGAACTG | 43 |
| 41BB co-stimulatory | KRGRKKLLYIFKQPFMRPVQTTQEEDGCSCRFPEEEEGGCEL | 44 |
| CD3ζ | CGAGTGAAGTTTTCCCGAAGCGCAGACGCTCCGGCATATCAGCAAG GACAGAATCAGCTGTATAACGAACTGAATTTGGGACGCCGCGAGGA GTATGACGTGCTTGATAAACGCCGGGGGAGAGACCCGGAAATGGGG GGTAAACCCCGAAGAAAGAATCCCCAAGAAGGACTCTACAATGAAC TCCAGAAGGATAAGATGGCGGAGGCCTACTCAGAAATAGGTATGAA GGGCGAACGACGACGGGGAAAAGGTCACGATGGCCTCTACCAAGG GTTGAGTACGGCAACCAAAGATACGTACGATGCACTGCATATGCAG GCCCTGCCTCCCAGA | 47 |
| CD3ζ | RVKFSRSADAPAYQQGQNQLYNELNLGRREEYDVLDKRRGRDPEMGG KPRRKNPQEGLYNELQKDKMAEAYSEIGMKGERRRGKGHDGLYQGLS TATKDTYDALHMQALPPR | 48 |

TABLE 8

Donor Components
Donor structure: TRAC [LHA]-EF1a[promoter]-CAR-polyA-TRAC[RHA]

| Name | Sequence | SEQ ID NO: |
|---|---|---|
| TRAC-LHA | GAGATGTAAGGAGCTGCTGTGACTTGCTCAAGGCCTTATATCGAGT AAACGGTAGTGCTGGGGCTTAGACGCAGGTGTTCTGATTTATAGTT CAAAACCTCTATCAATGAGAGAGCAATCTCCTGGTAATGTGATAGA TTTCCCAACTTAATGCCAACATACCATAAACCTCCCATTCTGCTAAT GCCCAGCCTAAGTTGGGGAGACCACTCCAGATTCCAAGATGTACAG TTTGCTTTGCTGGGCCTTTTTCCCATGCCTGCCTTTACTCTGCCAGA GTTATATTGCTGGGGTTTTGAAGAAGATCCTATTAAATAAAAGAAT AAGCAGTATTATTAAGTAGCCCTGCATTTCAGGTTTCCTTGAGTGG CAGGCCAGGCCTGGCCGTGAACGTTCACTGAAATCATGGCCTCTTG GCCAAGATTGATAGCTTGTGCCTGTCCCTGAGTCCCAGTCCATCAC GAGCAGCTGGTTTCTAAGATGCTATTTCCCGTATAAAGCATGAGAC | 78 |

TABLE 8-continued

| Donor Components<br>Donor structure: TRAC [LHA]-EF1a[promoter]-CAR-polyA-TRAC[RHA] | | |
|---|---|---|
| Name | Sequence | SEQ ID NO: |
| | CGTGACTTGCCAGCCCCACAGAGCCCCGCCCTTGTCCATCACTGGC<br>ATCTGGACTCCAGCCTGGGTTGGGGCAAAGAGGGAAATGAGATCA<br>TGTCCTAACCCTGATCCTCTTGTCCCACAGATATCCAGAACCCTGAC<br>CCTGCCGTGTACCAGCTGAGAGACTCTAAATCCAGTGACAAGTCTG<br>TCTGCCTATTCACCGATTTTGATTCTCAAACAAATGTGTCACAAAGT<br>AAGGATTCTGATGTGTATATCACAGACAAAACTGTGCTAGACATGA<br>GGTCTATGGACTTCA | |
| EF1α promoter | GGCTCCGGTGCCCGTCAGTGGGCAGAGCGCACATCGCCCACAGTCC<br>CCGAGAAGTTGGGGGGAGGGGTCGGCAATTGAACCGGTGCCTAGA<br>GAAGGTGGCGCGGGGTAAACTGGGAAAGTGATGTCGTGTACTGGC<br>TCCGCCTTTTTCCCGAGGGTGGGGGAGAACCGTATATAAGTGCAGT<br>AGTCGCCGTGAACGTTCTTTTTCGCAACGGGTTTGCCGCCAGAACA<br>CAGGTAAGTGCCGTGTGTGGTTCCCGCGGGCCTGGCCTCTTTACGG<br>GTTATGGCCCTTGCGTGCCTTGAATTACTTCCACTGGCTGCAGTACG<br>TGATTCTTGATCCCGAGCTTCGGGTTGGAAGTGGGTGGGAGAGTTC<br>GAGGCCTTGCGCTTAAGGAGCCCCTTCGCCTCGTGCTTGAGTTGAG<br>GCCTGGCCTGGGCGCTGGGGCCGCCGCGTGCGAATCTGGTGGCACC<br>TTCGCGCCTGTCTCGCTGCTTTCGATAAGTCTCTAGCCATTTAAAAT<br>TTTTGATGACCTGCTGCGACGCTTTTTTTCTGGCAAGATAGTCTTGT<br>AAATGCGGGCCAAGATCTGCACACTGGTATTTCGGTTTTTGGGGCC<br>GCGGGCGGCGACGGGGCCCGTGCGTCCCAGCGCACATGTTCGGCG<br>AGGCGGGGCCTGCGAGCGCGGCCACCGAGAATCGGACGGGGGTAG<br>TCTCAAGCTGGCCGGCCTGCTCTGGTGCCTGGCCTCGCGCCGCCGT<br>GTATCGCCCCGCCCTGGGCGGCAAGGCTGGCCCGGTCGGCACCAGT<br>TGCGTGAGCGGAAAGATGGCCGCTTCCCGGCCCTGCTGCAGGGAG<br>CTCAAAATGGAGGACGCGGCGCTCGGGAGAGCGGGCGGGTGAGTC<br>ACCCACACAAAGGAAAAGGGCCTTTCCGTCCTCAGCCGTCGCTTCA<br>TGTGACTCCACGGAGTACCGGGCGCCGTCCAGGCACCTCGATTAGT<br>TCTCGAGCTTTTGGAGTACGTCGTCTTTAGGTTGGGGGGAGGGGTT<br>TTATGCGATGGAGTTTCCCCACACTGAGTGGGTGGAGACTGAAGTT<br>AGGCCAGCTTGGCACTTGATGTAATTCTCCTTGGAATTTGCCCTTTT<br>TGAGTTTGGATCTTGGTTCATTCTCAAGCCTCAGACAGTGGTTCAA<br>AGTTTTTTTCTTCCATTTCAGGTGTCGTGA | 79 |
| Synthetic poly(A) signal | AATAAAATCGCTATCCATCGAAGATGGATGTGTGTTGGTTTTTTGT<br>GTG | 80 |
| TRAC-RHA | TGGAGCAACAAATCTGACTTTGCATGTGCAAACGCCTTCAACAACA<br>GCATTATTCCAGAAGACACCTTCTTCCCCAGCCCAGGTAAGGGCAG<br>CTTTGGTGCCTTCGCAGGCTGTTTCCTTGCTTCAGGAATGGCCAGGT<br>TCTGCCCAGAGCTCTGGTCAATGATGTCTAAAACTCCTCTGATTGGT<br>GGTCTCGGCCTTATCCATTGCCACCAAAACCCTCTTTTTACTAAGAA<br>ACAGTGAGCCTTGTTCTGGCAGTCCAGAGAATGACACGGGAAAAA<br>AGCAGATGAAGAGAAGGTGGCAGGAGAGGGCACGTGGCCCAGCCT<br>CAGTCTCTCCAACTGAGTTCCTGCCTGCCTGCCTTTGCTCAGACTGT<br>TTGCCCCTTACTGCTCTTCTAGGCCTCATTCTAAGCCCCTTCTCCAA<br>GTTGCCTCTCCTTATTTCTCCCTGTCTGCCAAAAAATCTTTCCCAGC<br>TCACTAAGTCAGTCTCACGCAGTCACTCATTAACCCACCAATCACT<br>GATTGTGCCGGCACATGAATGCACCAGGTGTTGAAGTGGAGGAATT<br>AAAAAGTCAGATGAGGGGTGTGCCCAGAGGAAGCACCATTCTAGT<br>TGGGGGAGCCCATCTGTCAGCTGGGAAAAGTCCAAATAACTTCAG<br>ATTGGAATGTGTTTTAACTCAGGGTTGAGAAAACAGCTACCTTCAG<br>GACAAAAGTCAGGGAAGGGCTCTCTGAAGAAATGCTACTTGAAGA<br>TACCAGCCCTACCAAGGGCAGGGAGAGGACCCTATAGAGGCCTGG<br>GACAGGAGCTCAATGAGAAAGG | 81 |

TABLE 9

| CAR | CAR structure | SEQ ID NO: |
|---|---|---|
| CTX-973 CAR | CD8[signal peptide]-VL-linker-VH-CD8[tm]-41BB[co-stimulatory domain]-CD3ζ | 95, 96 |
| CTX-974 CAR | CD8[signal peptide]-VH-linker-VL-CD8[tm]-41BB[co-stimulatory domain]-CD3ζ | 100, 101 |
| CTX-975 CAR | CD8[signal peptide]-VL-linker-VH-CD8[tm]-41BB[co-stimulatory domain]-CD3ζ | 104, 105 |
| CTX-976 CAR | CD8[signal peptide]-VH-linker-VL-CD8[tm]-41BB[co-stimulatory domain]-CD3ζ | 108, 109 |
| CTX-977 CAR | CD8[signal peptide]-VL-linker-VH-CD8[tm]-41BB[co-stimulatory domain]-CD3ζ | 112, 113 |

TABLE 9-continued

| CAR | CAR structure | SEQ ID NO: |
|---|---|---|
| CTX-978 CAR | CD8[signal peptide]-VH-linker-VL-CD8[tm]-41BB[co-stimulatory domain]-CD3ζ | 116, 117 |
| CTX-979 CAR | CD8[signal peptide]-VH-linker-VL-CD8[tm]-41BB[co-stimulatory domain]-CD3ζ | 68 |
| CTX-979b CAR | CD8[signal peptide]-VH-linker-VL-CD8[tm]-CD28[co-stimulatory domain]-CD3ζ | 66 |

TABLE 10

| CAR Components | | |
|---|---|---|
| Name | Sequence | SEQ ID NO: |
| CTX-973 CAR 41BB co-stim (nt) | CCACCATGGCGCTTCCGGTGACAGCACTGCTCCTCCCCT<br>TGGCGCTGTTGCTCCACGCAGCAAGGCCGGATGTCGTTA<br>TGACACAATCTCCCTTGAGTTTGCCGGTTACCTTGGGAC<br>AACCTGCTAGTATTTCATGTAGGAGTTCTCAAAGTCTCTT<br>GCACTCCTCAGGGAACACCTACCTCGAATGGTACCAACA<br>ACGCCCTGGCCAAAGCCCGCGGCCCTTGATATACAAAAT<br>ATCAACAAGATTTAGCGGGGTACCGGATAGATTCAGCGG<br>CTCTGGCAGCGGGACGGATTTTACCCTGAAAATTAGTCG<br>CGTAGAAGCTGAAGACGTTGGTGTGTATTACTGCTTTCA<br>AGGGAGCCATGTGCCTTACACATTTGGAGGAGGCACCA<br>AGGTCGAGATTAAGGGAGGGGGTGGATCAGGTGGGGGT<br>GGGTCCGGAGGCGGCGGCAGTCAAGTGCAGTTGGTTCA<br>ATCAGGAGCTGAAGTTAAAAAGCCAGGAGCTTCAGTCA<br>AGGTTTCATGCAAGGCGTCCGGTCTCACTATAGAGGATT<br>ACTACATGCACTGGGTGCGGCAAGCTCCAGGCCAGGGG<br>CTGGAGTGGATGGGATGGATTGATCCGGAAAACGGGGA<br>CACAGAGTATGGGCCCAAATTCCAAGGCCGGGTGACAA<br>TGACCAGAGATACTAGTATTTCAACAGCATACATGGAGC<br>TGTCACGGCTGAGGTCAGACGATACGGCAGTCTACTATT<br>GTGCAGTACATAACGCACATTATGGTACGTGGTTCGCTT<br>ATTGGGGTCAAGGTACCCTGGTCACGGTAAGTTCAAGTG<br>CTGCTGCCTTTGTCCCGGTATTTCTCCCAGCCAAACCGAC<br>CACGACTCCCGCCCCGCGCCCTCCGACACCCGCTCCCAC<br>CATCGCCTCTCAACCTCTTAGTCTTCGCCCCGAGGCATGC<br>CGACCCGCCGCCGGGGGTGCTGTTCATACGAGGGGCTTG<br>GACTTCGCTTGTGATATTTACATTTGGGCTCCGTTGGCGG<br>GTACGTGCGGCGTCCTTTTGTTGTCACTCGTTATTACTTT<br>GTATTGTAATGACAGGAATCGCAAACGGGGCAGAAAGA<br>AACTCCTGTATATATTCAAACAACCATTTATGAGACCAG<br>TACAAACTACTCAAGAGGAAGATGGCTGTAGCTGCCGAT<br>TTCCAGAAGAAGAAGAAGGAGGATGTGAACTGCGAGTG<br>AAGTTTTCCCGAAGCGCAGACGCTCCGGCATATCAGCAA<br>GGACAGAATCAGCTGTATAACGAACTGAATTTGGGACG<br>CCGCGAGGAGTATGACGTGCTTGATAAACGCGGGGGGA<br>GAGACCCGGAAATGGGGGGTAAACCCCGAAGAAAGAAT<br>CCCCAAGAAGGACTCTACAATGAACTCCAGAAGGATAA<br>GATGGCGGAGGCCTACTCAGAAATAGGTATGAAGGGCG<br>AACGACGACGGGGAAAAGGTCACGATGGCCTCTACCAA<br>GGGTTGAGTACGGCAACCAAAGATACGTACGATGCACT<br>GCATATGCAGGCCCTGCCTCCCAGATAAT | 95 |
| CTX-973 CAR 41BB co-stim (aa) | ALPVTALLLPLALLLHAARPDVVMTQSPLSLPVTLGQPASIS<br>CRSSQSLLHSSGNTYLEWYQQRPGQSPRPLIYKISTRFSGVP<br>DRFSGSGSGTDFTLKISRVEAEDVGVYYCFQGSHVPYTFGG<br>GTKVEIKGGGGSGGGGSGGGGSQVQLVQSGAEVKKPGAS<br>VKVSCKASGLTIEDYYMHWVRQAPGQGLEWMGWIDPEN<br>GDTEYGPKFQGRVTMTRDTSISTAYMELSRLRSDDTAVYY<br>CAVHNAMYGTWFAYWGQGTLVTVSSSAAAFVPVFLPAKP<br>TTTPAPRPPTPAPTIASQPLSLRPEACRPAAGGAVHTRGLDF<br>ACDIYIWAPLAGTCGVLLLSLVITLYCNHRNRKRGRKKLLY<br>IFKQPFMRPVQTTQEEDGCSCRFPEEEEGGCELRVKFSRSA<br>DAPAYQQGQNQLYNELNLGRREEYDVLDKRRGRDPEMGG<br>KPRRKNPQEGLYNELQKDKMAEAYSEIGMKGERRRGKGH<br>DGLYQGLSTATKDTYDALHMQALPPR | 96 |
| CTX-973 scFv (nt) | GATGTCGTTATGACACAATCTCCCTTGAGTTTGCCGGTTA<br>CCTTGGGACAACCTGCTAGTATTTCATGTAGGAGTTCFC<br>AAAGTCTCTTGCACTCCTCAGGGAACACCTACCTCGAAT<br>GGTACCAACAACGCCCTGGCCAAAGCCCGCGGCCCTTGA<br>TATACAAAATATCAACAAGATTTAGCGGGGTACCCGATA<br>GATTCAGCGGCTCTGGCAGCGGGACGGATTTTACCCTGA<br>AAATTAGTCGCGTAGAAGCTGAAGACGTTGGTGTGTATT<br>ACTGCTTTCAAGGGAGCCATGTGCCTTACACATTTGGAG<br>GAGGCACCAAGGTCGAGATTAAGGGAGGGGGTGGATCA<br>GGTGGGGGTGGGTCCGGAGGCGGCGGCAGTCAAGTGCA<br>GTTGGTTCAATCAGGAGCTGAAGTTAAAAAGCCAGGAG<br>CTTCAGTCAAGGTTTCATGCAAGGCGTCCGGTCTCACTA<br>TAGAGGATTACTACATGCACTGGGTGCGGCAAGCTCCAG<br>GCCAGGGGCTGGAGTGGATGGGATGGATTGATCCGGAA<br>AACGGGGACACAGAGTATGGGCCCAAATTCCAAGGCCG<br>GGTGACAATGACCAGAGATACTAGTATTTCAACAGCATA<br>CATGGAGCTGTCACGGCTGAGGTCAGACGATACGGCAG<br>TCTACTATTGTGCAGTACATAACGCACATTATGGTACGT<br>GGTTCGCTTATTGGGGTCAAGGTACCCTGGTCACGGTAA<br>GTTCA | 97 |

TABLE 10-continued

| Name | Sequence | SEQ ID NO: |
|---|---|---|
| CAR Components | | |
| CTX-973<br>scFv (aa)<br>(linker<br>underlined) | DVVMTQSPLSLPVTLGQPASISCRSSQSLLHSSGNTYLEWY<br>QQRPGQSPRPLIYKISTRFSGVPDRFSGSGSGTDFTLKISRVE<br>AEDVGVYYCFQGSHVPYTFGGGTKVEIKGGGGSGGGGSG<br>GGGSQVQLVQSGAEVKKPGASVKVSCKASGLTIEDYYMH<br>WVRQAPGQGLEWMGWIDPENGDTEYGPKFQGRVTMTRD<br>TSISTAYMELSRLRSDDTAVYYCAVHNAHYGTWFAYWGQ<br>GTLVTVSS | 82 |
| CTX-973<br>scFv VH (aa) | QVQLVQSGAEVKKPGASVKVSCKASGLTIEDYYMHWVRQ<br>APGQGLEWMGWIDPENGDTEYGPKFQGRVTMTRDTSIST<br>AYMELSRLRSDDTAVYYCAVHNAHYGTWFAYWGQGTLV<br>TVSS | 98 |
| CTX-973<br>scFv VL (aa) | DVVMTQSPLSLPVTLGQPASISCRSSQSLLHSSGNTYLEWY<br>QQRPGQSPRPLIYKISTRFSGVPDRFSGSGSGTDFTLKISRVE<br>AEDVGVYYCFQGSHVPYTFGGGTKVEIK | 56 |
| CTX-973<br>Donor (nt)<br>LHA to RHA | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCA<br>ATCTCCTGGTAATGTGATAGATTTCCCAACTTAATGCCA<br>ACATACCATAAACCTCCCATTCTGCTAATGCCCAGCCTA<br>AGTTGGGGAGACCACTCCAGATTCCAAGATGTACAGTTT<br>GCTTTGCTGGGCCTTTTTCCCATGCCTGCCTTTACTCTGC<br>CAGAGTTATATTGCTGGGGTTTTGAAGAAGATCCTATTA<br>AATAAAAGAATAAGCAGTATTATTAAGTAGCCCTGCATT<br>TCAGGTTTCCTTGAGTGGCAGGCCAGGCCTGGCCGTGAA<br>CGTTCACTGAAATCATGGCCTCTTGGCCAAGATTGATAG<br>CTTGTGCCTGTCCCTGAGTCCCAGTCCATCACGAGCAGC<br>TGGTTTCTAAGATGCTATTTCCCGTATAAAGCATGAGAC<br>CGTGACTTGCCAGCCCCACAGAGCCCCGCCCTTGTCCAT<br>CACTGGCATCTGGACTCCAGCCTGGGTTGGGGCAAAGAG<br>GGAAATGAGATCATGTCCTAACCCTGATCCTCTTGTCCC<br>ACAGATATCCAGAACCCTGACCCTGCCGTGTACCAGCTG<br>AGAGACTCTAAATCCAGTGACAAGTCTGTCTGCCTATTC<br>ACCGATTTTGATTCTCAAACAAATGTGTCACAAAGTAAG<br>GATTCTGATGTGTATATCACAGACAAAACTGTGCTAGAC<br>ATGAGGTCTATGGACTTCAggctccggtgcccgtcagtgggcagagcgca<br>catcgcccacagtccccgagaagttggggggaggggtcggcaattgaaccggtgcctaga<br>gaaggtggcgcggggtaaactgggaaagtgatgtcgtgtactggctccgcctttttcccgagg<br>gtgggggagaaccgtatataagtgcagtagtcgccgtgaacgttctttttcgcaacgggtttgc<br>cgccagaacacaggtaagtgccgtgtgtggttcccgcgggcctggcctctttacgggttatgg<br>cccttgcgtgccttgaattacttccactggctgcagtacgtgattcttgatcccgagcttcgggtt<br>ggaagtgggtgggagagttcgaggccttgcgcttaaggagccccttcgcctcgtgcttgagtt<br>gaggcctggcctgggcgctggggccgccgcgtgcgaatctggtggcaccttcgcgcctgtc<br>tcgctgctttcgataagtctctagccatttaaaatttttgatgacctgctgcgacgctttttttctggc<br>aagatagtcttgtaaatgcgggccaagatctgcacactggtatttcggtttttggggccgcggg<br>cggcgacggggcccgtgcgtcccagcgcacatgttcggcgaggcggggcctgcgagcgc<br>ggccaccgagaatcggacgggggtagtctcaagctggccggcctgctctggtgcctggcct<br>cgcgccgccgtgtatcgccccgccctgggcggcaaggctggcccggtcggcaccagttgc<br>gtgagcggaaagatggccgcttcccggccctgctgcagggagctcaaaatggaggacgcg<br>gcgctcgggagagcgggcgggtgagtcacccacacaaaggaaaagggcctttccgtcctc<br>agccgtcgcttcatgtgactccacggagtaccgggcgccgtccaggcacctcgattagttctc<br>gagcttttggagtacgtcgtctttaggttggggggaggggttttatgcgatggagtttccccaca<br>ctgagtgggtggagactgaagttaggccagcttggcacttgatgtaattctccttggaatttgcc<br>ctttttgagtttggatcttggttcattctcaagcctcagacagtggttcaaagtttttttcttccatttc<br>aggtgtcgtgaCCACCATGGCGCTTCCGGTGACAGCACTGCTC<br>CTCCCCTTGGCGCTGTTGCTCCACGCAGCAAGGCCGGAT<br>GTCGTTATGACACAATCTCCCTTGAGTTTGCCGGTTACCT<br>TGGGACAACCTGCTAGTATTTCATGTAGGAGTTCTCAAA<br>GTCTCTTGCACTCCTCAGGGAACACCTACCTCGAATGGT<br>ACCAACAACGCCCTGGCCAAAGCCCGCGGCCCTTGATAT<br>ACAAAATATCAACAAGATTTAGCGGGGTACCCGATAGA<br>TTCAGCGGCTCTGGCAGCGGGACGGATTTTACCCTGAAA<br>ATTAGTCGCGTAGAAGCTGAAGACGTTGGTGTGTATTAC<br>TGCTTTCAAGGGAGCCATGTGCCTTACACATTTGGAGGA<br>GGCACCAAGGTCGAGATTAAGGGAGGGGGTGGATCAGG<br>TGGGGGTGGGTCCGGAGGCGGCGGCAGTCAAGTGCAGT<br>TGGTTCAATCAGGAGCTGAAGTTAAAAAGCCAGGAGCTT<br>CAGTCAAGGTTTCATGCAAGGCGTCCGGTCTCACTATAG<br>AGGATTACTACATGCACTGGGTGCGGCAAGCTCCAGGCC<br>AGGGGCTGGAGTGGATGGGATGGATTGATCCGGAAAAC<br>GGGGACACAGAGTATGGGCCCAAATTCCAAGGCCGGGT<br>GACAATGACCAGAGATACTAGTATTTCAACAGCATACAT | 99 |

TABLE 10-continued

| CAR Components | | |
|---|---|---|
| Name | Sequence | SEQ ID NO: |
| | GGAGCTGTCACGGCTGAGGTCAGACGATACGGCAGTCT ACTATTGTGCAGTACATAACGCACATTATGGTACGTGGT TCGCTTATTGGGGTCAAGGTACCCTGGTCACGGTAAGTT CAAGTGCTGCTGCCTTTGTCCCGGTATTTCTCCCAGCCAA ACCGACCACGACTCCCGCCCCGCGCCCTCCGACACCCGC TCCCACCATCGCCTCTCAACCTCTTAGTCTTCGCCCCGAG GCATGCCGACCCGCCGCCGGGGGTGCTGTTCATACGAGG GGCTTGGACTTCGCTTGTGATATTTACATTTGGGCTCCGT TGGCGGGTACGTGCGGCGTCCTTTTGTTGTCACTCGTTAT TACTTTGTATTGTAATCACAGGAATCGCAAACGGGGCAG AAAGAAACTCCTGTATATATTCAAACAACCATTTATGAG ACCAGTACAAACTACTCAAGAGGAAGATGGCTGTAGCT GCCGATTTCCAGAAGAAGAAGAAGGAGGATGTCAACTG CGAGTGAAGTTTTCCCGAAGCGCAGACGCTCCGGCATAT CAGCAAGGACAGAATCAGCTGTATAACGAACTGAATTT GGGACGCCGCGAGGAGTATGACGTGCTTGATAAACGCC GGGGGAGAGACCCGGAAATGGGGGGTAAACCCCGAAGA AAGAATCCCCAAGAAGGACTCTACAATGAACTCCAGAA GGATAAGATGGCGGAGGCCTACTCAGAAATAGGTATGA AGGGCGAACGACGACGGGGAAAAGGTCACGATGGCCTC TACCAAGGGTTGAGTACGGCAACCAAAGATACGTACGA TGCACTGCATATGCAGGCCCTGCCTCCCAGATAATAATA AAATCGCTATCCATCGAAGATGGATGTGTGTTGGTTTTTT GTGTGTGGAGCAACAAATCTGACTTTGCATGTGCAAACG CCTTCAACAACAGCATTATTCCAGAAGACACCTTCTTCC CCAGCCCAGGTAAGGGCAGCTTTGGTGCCTTCGCAGGCT GTTTCCTTGCTTCAGGAATGGCCAGGTTCTGCCCAGAGC TCTGGTCAATGATGTCTAAAACTCCTCTGATTGGTGGTCT CGGCCTTATCCATTGCCACCAAAACCCTCTTTTTACTAAG AAACAGTGAGCCTTGTTCTGGCAGTCCAGAGAATGACAC GGGAAAAAAGCAGATGAAGAGAAGGTGGCAGGAGAGG GCACGTGGCCCAGCCTCAGTCTCTCCAACTGAGTTCCTG CCTGCCTGCCTTTGCTCAGACTGTTTGCCCCTTACTGCTC TTCTAGGCCTCATTCTAAGCCCCTTCTCCAAGTTGCCTCT CCTTATTTCTCCCTGTCTGCCAAAAAATCTTTCCCAGCTC ACTAAGTCAGTCTCACGCAGTCACTCATTAACCCACCAA TCACTGATTGTGCGGGCACATGAATGCACCAGGTGTTGA AGTGGAGGAATTAAAAGTCAGATGAGGGGTGTGCCCA GAGGAAGCACCATTCTAGTTGGGGGAGCCCATCTGTCAG CTGGGAAAAGTCCAAATAACTTCAGATTGGAATGTGTTT TAACTCAGGGTTGAGAAAACAGCTACCTTCAGGACAAA AGTCAGGGAAGGGCTCTCTGAAGAAATGCTACTTGAAG ATACCAGCCCTACCAAGGGCAGGGAGAGGACCCTATAG AGGCCTGGGACAGGAGCTCAATGAGAAAGG | |
| CTX-974 CAR 41BB co-stim (nt) | CCACCATGGCGCTTCCGGTGACAGCACTGCTCCTCCCCT TGGCGCTGTTGCTCCACGCAGCAAGGCCGCAGGTGCAGC TGGTCCAAAGCGGCGCCGAGGTTAAGAAACCAGGCGCA TCCGTCAAGGTTTCATGTAAAGCAAGTGGCTTGACTATA GAAGACTACTACATGCATTGGGTACGGCAAGCCCCTGGG CAGGGGCTGGAATGGATGGGGTGGATCGACCCGGAGAA TGGTGATACAGAGTACGGACCTAAGTTCCAGGGACGAG TTACCATGACGCGAGATACATCCATCTCCACGGCATACA TGGAGCTGAGTCGACTGCGGAGCGATGATACAGCTGTCT ATTATTGTGCTGTCCACAATGCGCACTACGGCACCTGGT TCGCTTATTGGGGACAAGGTACCCTGGTCACAGTCAGCT CTGGGGGTGGCGGCAGTGGAGGGGGTGGTTCTGGTGGC GGGGGTTCCGATGTTGTAATGACTCAAAGCCCTCTTTCTT TGCCAGTCACTCTCGGACAACCCGCGAGCATATCTTGCA GGTCTTCACAATCACTCCTTCACAGTAGCGGGAATACTT ACTTGGAGTGGTATCAGCAGCGGCCTGGTCAGTCCCCTA GACCGCTTATATATAAGATCTCCACTAGGTTCAGTGGAG TGCCGGACCGCTTTTCAGGCTCAGGTTCCGGGACGGACT TTACATTGAAAATATCCAGGGTGGAGGCGGAGGACGTC GGAGTCTACTATTGCTTCCAAGGCTCCCACGTCCCATAC ACTTTCGGTGGCGGTACAAAAGTGGAAATAAAAAGTGC TGCTGCCTTTGTCCCGGTATTTCTCCCAGCCAAACCGACC ACGACTCCCGCCCCGCGCCCTCCGACACCCGCTCCCACC ATCGCCTCTCAACCTCTTAGTCTTCGCCCCGAGGCATGCC GACCCGCCGCCGGGGGTGCTGTTCATACGAGGGGCTTGG ACTTCGCTTGTGATATTTACATTTGGGCTCCGTTGGCGGG TACGTGCGGCGTCCTTTTGTTGTCACTCGTTATTACTTTG TATTGTAATCACAGGAATCGCAAACGGGGCAGAAAGAA ACTCCTGTATATATTCAAACAACCATTTATGAGACCAGT ACAAACTACTCAAGAGGAAGATGGCTGTAGCTGCCGATT | 100 |

TABLE 10-continued

| CAR Components | | |
|---|---|---|
| Name | Sequence | SEQ ID NO: |
| | TCCAGAAGAAGAAGAAGGAGGATGTGAACTGCGAGTGA<br>AGTTTTCCCGAAGCGCAGACGCTCCGGCATATCAGCAAG<br>GACAGAATCAGCTGTATAACGAACTGAATTTGGGACGCC<br>GCGAGGAGTATGACGTGCTTGATAAACGCCGGGGGAGA<br>GACCCGGAAATGGGGGGTAAACCCCGAAGAAAGAATCC<br>CCAAGAAGGACTCTACAATGAACTCCAGAAGGATAAGA<br>TGGCGGAGGCCTACTCAGAAATAGGTATGAAGGGCGAA<br>CGACGACGGGGAAAAGGTCACGATGGCCTCTACCAAGG<br>GTTGAGTACGGCAACCAAAGATACGTACGATGCACTGC<br>ATATGCAGGCCCTGCCTCCCAGATAAT | |
| CTX-974 CAR 41BB co-stim (aa) | MALPVTALLLPLALLLHAARPQVQLVQSGAEVKKPGASV<br>KVSCKASGLTIEDYYMHWVRQAPGQGLEWMGWIDPENG<br>DTEYGPKFQGRVTMTRDTSISTAYMELSRLRSDDTAVYYC<br>AVHNAHYGTWFAYWGQGTLVTVSSGGGGSGGGGSGGGG<br>SDVVMTQSPLSLPVTLGQPASISCRSSQSLLHSSGNTYLEW<br>YQQRPGQSPRPLIYKISTRFSGVPDRFSGSGSGTDFTLKISRV<br>EAEDVGVYYCFQGSHVPYTFGGGTKVEIKSAAAFVPVFLP<br>AKPTTTPAPRPPTPAPTIASQPLSLRPEACRPAAGGAVHTRG<br>LDFACDIYIWAPLAGTCGVLLLSLVITLYCNHRNRKRGRK<br>KLLYIFKQPFMRPVQTTQEEDGCSCRFPEEEEGGCELRVKF<br>SRSADAPAYQQGQNQLYNELNLGRREEYDVLDKRRGRDP<br>EMGGKPRRKNPQEGLYNELQKDKMAEAYSEIGMKGERRR<br>GKGHDGLYQGLSTATKDTYDALHMQALPPR | 101 |
| CTX-974 scFv (nt) | CAGGTGCAGCTGGTCCAAAGCGGCGCCGAGGTTAAGAA<br>ACCAGGCGCATCCGTCAAGGTTTCATGTAAAGCAAGTGG<br>CTTGACTATAGAAGACTACTACATGCATTGGGTACGGCA<br>AGCCCCTGGGCAGGGGCTGGAATGGATGGGGTGGATCG<br>ACCCGGAGAATGGTGATACAGAGTACGGACCTAAGTTC<br>CAGGGACGAGTTACCATGACGCGAGATACATCCATCTCC<br>ACGGCATACATGGAGCTGAGTCGACTGCGGAGCGATGA<br>TACAGCTGTCTATTATTGTGCTGTCCACAATGCGCACTAC<br>GGCACCTGGTTCGCTTATTGGGGACAAGGTACCCTGGTC<br>ACAGTCAGCTCTGGGGGTGGCGGCAGTGGAGGGGGTGG<br>TTCTGGTGGCGGGGGTTCCGATGTTGTAATGACrCAAAG<br>CCCTCTTTCTTTGCCAGTCACTCTCGGACAACCCGCGAGC<br>ATATCTTGCAGGTCTTCACAATCACTCCTTCACAGTAGC<br>GGGAATACTTACTTGGAGTGGTATCAGCAGCGGCCTGGT<br>CAGTCCCCTAGACCGCTTATATATAAGATCTCCACTAGG<br>TTCAGTGGAGTGCCGGACCGCTTTTCAGGCTCAGGTTCC<br>GGGACGGACTTTACATTGAAAATATCCAGGGTGGAGGC<br>GGAGGACGTCGGAGTCTACTATTGCTTCCAAGGCTCCCA<br>CGTCCCATACACTTTCGGTGGCGGTACAAAAGTGGAAAT<br>AAAA | 102 |
| CTX-974 scFv (aa) (linker underlined) | QVQLVQSGAEVKKPGASVKVSCKASGLTIEDYYMHWVRQ<br>APGQGLEWMGWIDPENGDTEYGPKFQGRVTMTRDTSISTA<br>YMELSRLRSDDTAVYYCAVHNAHYGTWFAYWGQGTLVT<br>VSSGGGGSGGGGSGGGGSDVVMTQSPLSLPVTLGQPASISC<br>RSSQSLLHSSGNTYLEWYQQRPGQSPRPLIYKISTRFSGVPD<br>RFSGSGSGTDFTLKISRVEAEDVGVYYCFQGSHVPYTFGGG<br>TKVEIK | 85 |
| CTX-974 scFv VH (aa) | QVQLVQSGAEVKKPGASVKVSCKASGLTIEDYYMHWVRQ<br>APGQGLEWMGWIDPENGDTEYGPKFQGRVTMTRDTSIST<br>AYMELSRLRSDDTAVYYCAVHNAHYGTWFAYWGQGTLV<br>TVSS | 98 |
| CTX-974 scFv VL (aa) | DVVMTQSPLSLPVTLGQPASISCRSSQSLLHSSGNTYLEWY<br>QQRPGQSPRPLIYKISTRFSGVPDRFSGSGSGTDFTLKISRVE<br>AEDVGVYYCFQGSHVPYTFGGGTKVEIK | 56 |
| CTX-974 Donor (nt) LHA to RHA | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCA<br>ATCTCCTGGTAATGTGATAGATTTCCCAACTTAATGCCA<br>ACATACCATAAACCTCCCATTCTGCTAATGCCCAGCCTA<br>AGTTGGGGAGACCACTCCAGATTCCAAGATGTACAGTTT<br>GCTTTGCTGGGCCTTTTTCCCATGCCTGCCTTTACTCTGC<br>CAGAGTTATATTGCTGGGGTTTTGAAGAAGATCCTATTA<br>AATAAAAGAATAAGCAGTATTATTAAGTAGCCCTGCATT<br>TCAGGTTTCCTTGAGTGGCAGGCCAGGCCTGGCCGTGAA<br>CGTTCACTGAAATCATGGCCTCTTGGCCAAGATTGATAG<br>CTTGTGCCTGTCCCTGAGTCCCAGTCCATCACGAGCAGC | 103 |

TABLE 10-continued

| CAR Components | | |
|---|---|---|
| Name | Sequence | SEQ ID NO: |
| | TGGTTTCTAAGATGCTATTTCCCGTATAAAGCATGAGAC<br>CGTGACTTGCCAGCCCCACAGAGCCCCGCCCTTGTCCAT<br>CACTGGCATCTGGACTCCAGCCTGGGTTGGGGCAAAGAG<br>GGAAATGAGATCATGTCCTAACCCTGATCCTCTTGTCCC<br>ACAGATATCCAGAACCCTGACCCTGCCGTGTACCAGCTG<br>AGAGACTCTAAATCCAGTGACAAGTCTGTCTGCCTATTC<br>ACCGATTTTGATTCTCAAACAAATGTGTCACAAAGTAAG<br>GATTCTGATGTGTATATCACAGACAAAACTGTGCTAGAC<br>ATGAGGTCTATGGACTTCAggctccggtgcccgtcagtgggcagagcgca<br>catcgcccacagtccccgagaagttggggggaggggtcggcaattgaaccggtgcctaga<br>gaaggtggcgcggggtaaactgggaaagtgatgtcgtgtactggctccgcctttttcccgagg<br>gtgggggagaaccgtatataagtgcagtagtcgccgtgaacgttctttttcgcaacgggtttgc<br>cgccagaacacaggtaagtgccgtgtgtggttcccgcgggcctggcctctttacgggttatgg<br>cccttgcgtgccttgaattacttccactggctgcagtacgtgattcttgatcccgagcttcgggtt<br>ggaagtgggtgggagagttcgaggccttgcgcttaaggagccccttcgcctcgtgcttgagtt<br>gaggcctggcctgggcgctggggccgccgcgtgcgaatctggtggcaccttcgcgcctgtc<br>tcgctgctttcgataagtctctagccatttaaaatttttgatgacctgctgcgacgctttttttctggc<br>aagatagtcttgtaaatgcgggccaagatctgcacactggtatttcggtttttggggccgcggg<br>cggcgacggggcccgtgcgtcccagcgcacatgttcggcgaggcggggcctgcgagcgc<br>ggccaccgagaatcggacgggggtagtctcaagctggccggcctgctctggtgcctggcct<br>cgcgccgccgtgtatcgccccgccctgggcggcaaggctggcccggtcggcaccagttgc<br>gtgagcggaaagatggccgcttcccggccctgctgcagggagctcaaaatggaggacgcg<br>gcgctcgggagagcgggcgggtgagtcacccacacaaaggaaaagggcctttccgtcctc<br>agccgtcgcttcatgtgactccacggagtaccgggcgccgtccaggcacctcgattagttctc<br>gagcttttggagtacgtcgtctttaggttggggggaggggttttatgcgatggagtttccccaca<br>ctgagtgggtggagactgaagttaggccagcttggcacttgatgtaattctccttggaatttgcc<br>ctttttgagtttggatcttggttcattctcaagcctcagacagtggttcaaagtttttttcttccatttc<br>aggtgtcgtgaCCACCATGGCGCTTCCGGTGACAGCACTGCTC<br>CTCCCCTTGGCGCTGTTGCTCCACGCAGCAAGGCCGCAG<br>GTGCAGCTGGTCCAAAGCGGCGCCGAGGTTAAGAAACC<br>AGGCGCATCCGTCAAGGTTTCATGTAAAGCAAGTGGCTT<br>GACTATAGAAGACTACTACATGCATTGGGTACGGCAAGC<br>CCCTGGGCAGGGGCTGGAATGGATGGGGTGGATCGACC<br>CGGAGAATGGTGATACAGAGTACGGACCTAAGTTCCAG<br>GGACGAGTTACCATGACGCGAGATACATCCATCTCCACG<br>GCATACATGGAGCTGAGTCGACTGCGGAGCGATGATAC<br>AGCTGTCTATTATTGTGCTGTCCACAATGCGCACTACGG<br>CACCTGGTTCGCTTATTGGGGACAAGGTACCCTGGTCAC<br>AGTCAGCTCTGGGGGTGGCGGCAGTGGAGGGGGTGGTT<br>CTGGTGGCGGGGGTTCCGATGTTGTAATGACTCAAAGCC<br>CTCTTTCTTTGCCAGTCACTCTCGGACAACCCGCGAGCAT<br>ATCTTGCAGGTCTTCACAATCACTCCTTCACAGTAGCGG<br>GAATACTTACTTGGAGTGGTATCAGCAGCGGCCTGGTCA<br>GTCCCCTAGACCGCTTATATATAAGATCTCCACTAGGTT<br>CAGTGGAGTGCCGGACCGCTTTTCAGGCTCAGGTTCCGG<br>GACGGACTTTACATTGAAAATATCCAGGGTGGAGGCGG<br>AGGACGTCGGAGTCTACTATTGCTTCCAAGGCTCCCACG<br>TCCCATACACTTTCGGTGGCGGTACAAAAGTGGAAATAA<br>AAAGTGCTGCTGCCTTTGTCCCGGTATTTCTCCCAGCCAA<br>ACCGACCACGACTCCCGCCCCGCGCCCTCCGACACCCGC<br>TCCCACCATCGCCTCTCAACCTCTTAGTCTTCGCCCCGAG<br>GCATGCCGACCCGCCGCCGGGGGTGCTGTTCATACGAGG<br>GGCTTGGACTTCGCTTGTGATATTTACATTTGGGCTCCGT<br>TGGCGGGTACGTGCGGCGTCCTTTTGTTGTCACTCGTTAT<br>TACTTTGTATTGTAATCACAGGAATCGCAAACGGGGCAG<br>AAAGAAACTCCTGTATATATTCAAACAACCATTTATGAG<br>ACCAGTACAAACTACTCAAGAGGAAGATGGCTGTAGCT<br>GCCGATTTCCAGAAGAAGAAGAAGGAGGATGTGAACTG<br>CGAGTGAAGTTTTCCCGAAGCGCAGACGCTCCGGCATAT<br>CAGCAAGGACAGAATCAGCTGTATAACGAACTGAATTT<br>GGGACGCCGCGAGGAGTATGACGTGCTTGATAAACGCC<br>GGGGGAGAGACCCGGAAATGGGGGGTAAACCCCGAAGA<br>AAGAATCCCCAAGAAGGACTCTACAATGAACTCCAGAA<br>GGATAAGATGGCGGAGGCCTACTCAGAAATAGGTATGA<br>AGGGCGAACGACGACGGGGAAAAGGTCACGATGGCCTC<br>TACCAAGGGTTGAGTACGGCAACCAAAGATACGTACGA<br>TGCACTGCATATGCAGGCCCTGCCTCCCAGATAATAATA<br>AAATCGCTATCCATCGAAGATGGATGTGTGTTGGTTTTTT<br>GTGTGTGGAGCAACAAATCTGACTTTGCATGTGCAAACG<br>CCTTCAACAACAGCATTATTCCAGAAGACACCTTCTTCC<br>CCAGCCCAGGTAAGGGCAGCTTTGGTGCCTTCGCAGGCT<br>GTTTCCTTGCTTCAGGAATGGCCAGGTTCTGCCCAGAGC<br>TCTGGTCAATGATGTCTAAAACTCCTCTGATTGGTGGTCT<br>CGGCCTTATCCATTGCCACCAAAACCCTCTTTTTACTAAG<br>AAACAGTGAGCCTTGTTCTGGCAGTCCAGAGAATGACAC | |

TABLE 10-continued

| CAR Components | | |
|---|---|---|
| Name | Sequence | SEQ ID NO: |
| | GGGAAAAAAGCAGATGAAGAGAAGGTGGCAGGAGAGG<br>GCACGTGGCCCAGCCTCAGTCTCTCCAACTGAGTTCCTG<br>CCTGCCTGCCTTTGCTCAGACTGTTTGCCCCTTACTGCTC<br>TTCTAGGCCTCATTCTAAGCCCCTTCTCCAAGTTGCCTCT<br>CCTTATTTCTCCCTGTCTGCCAAAAAATCTTTCCCAGCTC<br>ACTAAGTCAGTCTCACGCAGTCACTCATTAACCCACCAA<br>TCACTGATTGTGCCGGCACATGAATGCACCAGGTGTTGA<br>AGTGGAGGAATTAAAAAGTCAGATGAGGGGTGTGCCCA<br>GAGGAAGCACCATTCTAGTTGGGGGAGCCCATCTGTCAG<br>CTGGGAAAAGTCCAAATAACTTCAGATTGGAATGTGTTT<br>TAACTCAGGGTTGAGAAAACAGCTACCTTCAGGACAAA<br>AGTCAGGGAAGGGCTCTCTGAAGAAATGCTACTTGAAG<br>ATACCAGCCCTACCAAGGGCAGGGAGAGGACCCTATAG<br>AGGCCTGGGACAGGAGCTCAATGAGAAAGG | |
| CTX-975 CAR 41BB co-stim (nt) | CCACCATGGCGCTTCCGGTGACAGCACTGCTCCTCCCCT<br>TGGCGCTGTTGCTCCACGCAGCAAGGCCGGATGTAGTTA<br>TGACCCAGAGTCCGCTCTCTTTGCCGGTGACGCTCGGCC<br>AACCGGCGTCTATTTCTTGCAGAAGTAGTCAATCACTTC<br>TGCACTCTAGCGGTAACACTTATTTGGAGTGGTATCTCC<br>AACGACCAGGGCAAAGCCCCAAGCCGTTGATTTATAAG<br>ATCTCTACAAGATTCAGCGGAGTGCCCGACAGATTTTCC<br>GGGAGTGGGTCCGGTACTGATTTCACTTTGAAAATTTCC<br>CGCGTCGAGGCTGAAGATGTTGGTGTCTACTACTGCTTT<br>CAGGGGAGCCATGTTCCATATACCTTTGGAGGTGGGACT<br>AAGGTAGAAATTAAAGGTGGGGGTGGATCAGGGGGTGG<br>CGGCAGCGGGGGAGGGGGCTCACAAGTGCAACTTGTGC<br>AAAGTGGGGCCGAGGTGAAAAAACCCGGTGCAAGTGTA<br>AAGGTCTCATGCAAAGCGTCTGGTTTGACAATTGAAGAC<br>TATTATATGCATTGGGTGAGACAGGCCCCGGGCCAAGG<br>CTTGGAATGGATGGGATGGATAGACCCCGAAAACGGTG<br>ACACGGAGTACGGACCTAAATTTCAAGGAAGAGTGACA<br>ATGACACGCGATACATCTATTAACACGGCTTATATGGAA<br>CTGAGCCGACTTCGGAGTGATGACACTGCTGTATATTAT<br>TGCGCCGTCCACAACGCACATTATGGCACCTGGTTTGCG<br>TACTGGGGACAGGGAACTTTGGTTACAGTATCAAGCAGT<br>GCTGCTGCCTTTGTCCCGGTATTTCTCCCAGCCAAACCG<br>ACCACGACTCCCGCCCCGCGCCCTCCGACACCCGCTCCC<br>ACCATCGCCTCTCAACCTCTTAGTCTTCGCCCCGAGGCA<br>TGCCGACCCGCCGCCGGGGGTGCTGTTCATACGAGGGG<br>CTTGGACTTCGCTTGTGATATTTACATTTGGGCTCCGTTG<br>GCGGGTACGTGCGGCGTCCTTTTGTTGTCACTCGTTATTA<br>CTTTGTATTGTAATCACAGGAATCGCAAACGGGGCAGA<br>AAGAAACTCCTGTATATATTCAAACAACCATTTATGAGA<br>CCAGTACAAACTACTCAAGAGGAAGATGGCTGTAGCTG<br>CCGATTTCCAGAAGAAGAAGAAGGAGGATGTGAACTGC<br>GAGTGAAGTTTTCCCGAAGCGCAGACGCTCCGGCATATC<br>AGCAAGGACAGAATCAGCTGTATAACGAACTGAATTTG<br>GGACGCCGCGAGGAGTATGACGTGCTTGATAAACGCCG<br>GGGGAGAGACCCGGAAATGGGGGGTAAACCCCGAAGA<br>AAGAATCCCCAAGAAGGACTCTACAATGAACTCCAGAA<br>GGATAAGATGGCGGAGGCCTACTCAGAAATAGGTATGA<br>AGGGCGAACGACGACGGGGAAAAGGTCACGATGGCCTC<br>TACCAAGGGTTGAGTACGGCAACCAAAGATACGTACGA<br>TGCACTGCATATGCAGGCCCTGCCTCCCAGATAAT | 104 |
| CTX-975 CAR 41BB co-stim (aa) | MALPVTALLLPLALLLHAARPDVVMTQSPLSLPVTLGQPA<br>SISCRSSQSLLHSSGNTYLEWYLQRPGQSPKPLIYKISTRFSG<br>VPDRFSGSGSGTDFTLKISRVEAEDVGVYYCFQGSHVPYTF<br>GGGTKVEIKGGGGSGGGGSGGGGSQVQLVQSGAEVKKPG<br>ASVKVSCKASGLTIEDYYMHWVRQAPGQGLEWMGWIDP<br>ENGDTEYGPKFQGRVTMTRDTSINTAYMELSRLRSDDTAV<br>YYCAVHNAHYGTWFAYWGQGTLVTVSSSAAAFVPVFLPA<br>KPTTTPAPRPPTPAPTIASQPLSLRPEACRPAAGGAVHTRGL<br>DFACDIYIWAPLAGTCGVLLLSLVITLYCNHRNRKRGRKK<br>LLYIFKQPFMRPVQTTQEEDGCSCRFPEEEEGGCELRVKFS<br>RSADAPAYQQGQNQLYNELNLGRREEYDVLDKRRGRDPE<br>MGGKPRRKNPQEGLYNELQKDKMAEAYSEIGMKGERRRG<br>KGHDGLYQGLSTATKDTYDALHMQALPPR | 105 |
| CTX-975 scFv (nt) | GATGTAGTTATGACCCAGAGTCCGCTCTCTTTGCCGGTG<br>ACGCTCGGCCAACCGGCGTCTATTTCTTGCAGAAGTAGT<br>CAATCACTTCTGACACTCTAGCGGTAACACTTATTTGGAG<br>TGGTATCTCCAACGACCAGGGCAAAGCCCCAAGCCGTTG<br>ATTTATAAGATCTCTACAAGATTCAGCGGAGTGCCCGAC | 106 |

TABLE 10-continued

CAR Components

| Name | Sequence | SEQ ID NO: |
|---|---|---|
| | AGATTTTCCGGGAGTGGGTCCGGTACTGATTTCACTFTG<br>AAAATTTCCCGCGTCGAGGCTGAAGATGTTGGTGTCTAC<br>TACTGCTTTCAGGGGAGCCATGTTCCATATACCTTTGGA<br>GGTGGGACTAAGGTAGAAATTAAAGGTGGGGGTGGATC<br>AGGGGGTGGCGGCAGCGGGGGAGGGGGCTCACAAGTGC<br>AACTTGTGCAAAGTGGGGCCGAGGTGAAAAAACCCGGT<br>GCAAGTGTAAAGGTCTCATGCAAAGCGTCTGGTTTGACA<br>ATTGAAGACTATTATATGCATTGGGTGAGACAGGCCCCG<br>GGCCAAGGCTTGGAATGGATGGGATGGATAGACCCCGA<br>AAACGGTGACACGGAGTACGGACCTAAATTTCAAGGAA<br>GAGTGACAATGACACGCGATACATCTATTAACACGGCTT<br>ATATGGAACTGAGCCGACTTCGGAGTGATGACACTGCTG<br>TATATTATTGCGCCGTCCACAACGCACATTATGGCACCT<br>GGTTTGCGTACTGGGGACAGGGAACTTTGGTTACAGTAT<br>CAAGC | |
| CTX-975 scFv (aa) (linker underlined) | DVVMTQSPLSLPVTLGQPASISCRSSQSLLHSSGNTYLEWY<br>LQRPGQSPKPLIYKISTRFSGVPDRFSGSGSGTDFTLKISRVE<br>AEDVGVYYCFQGSHVPYTFGGGTKVEIKGGGGSGGGGSG<br>GGGSQVQLVQSGAEVKKPGASVKVSCKASGLTIEDYYMH<br>WVRQAPGQGLEWMGWIDPENGDTEYGPKFQGRVTMTRD<br>TSINTAYMELSRLRSDDTAVYYCAVHNAHYGTWFAYWGQ<br>GTLVTVSS | 83 |
| CTX-975 scFv VH (aa) | QVQLVQSGAEVKKPGASVKVSCKASGLTIEDYYMHWVRQ<br>APGQGLEWMGWIDPENGDTEYGPKFQGRVTMTRDTSINT<br>AYMELSRLRSDDTAVYYCAVHNAHYGTWFAYWGQGTLV<br>TVSS | 90 |
| CTX-975 scFv VL (aa) | DVVMTQSPLSLPVTLGQPASISCRSSQSLLHSSGNTYLEWY<br>LQRPGQSPKPLIYKISTRFSGVPDRFSGSGSGTDFTLKISRVE<br>AEDVGVYYCFQGSHVPYTFGGGTKVEIK | 88 |
| CTX-975 Donor (nt) LHA to RHA | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCA<br>ATCTCCTGGTAATGTGATAGATTTCCCAACTTAATGCCA<br>ACATACCATAAACCTCCCATTCTGCTAATGCCCAGCCTA<br>AGTTGGGGAGACCACTCCAGATTCCAAGATGTACAGTTT<br>GCTTTGCTGGGCCTTTTTCCCATGCCTGCCTTTACTCTGC<br>CAGAGTTATATTGCTGGGGTTTTGAAGAAGATCCTATTA<br>AATAAAAGAATAAGCAGTATTATTAAGTAGCCCTGCATT<br>TCAGGTTTCCTTGAGTGGCAGGCCAGGCCTGGCCGTGAA<br>CGTTCACTGAAATCATGGCCTCTTGGCCAAGATTGATAG<br>CTTGTGCCTGTCCCTGAGTCCCAGTCCATCACGAGCAGC<br>TGGTTTCTAAGATGCTATTTCCCGTATAAAGCATGAGAC<br>CGTGACTTGCCAGCCCCACAGAGCCCCGCCCTTGTCCAT<br>CACTGGCATCTGGACTCCAGCCTGGGTTGGGGCAAAGAG<br>GGAAATGAGATCATGTCCTAACCCTGATCCTCTTGTCCC<br>ACAGATATCCAGAACCCTGACCCTGCCGTGTACCAGCTG<br>AGAGACTCTAAATCCAGTGACAAGTCTGTCTGCCTATTC<br>ACCGATTTTGATTCTCAAACAAATGTGTCACAAAGTAAG<br>GATTCTGATGTGTATATCACAGACAAAACTGTGCTAGAC<br>ATGAGGTCTATGGACTTCAggctccggtgcccgtcagtgggcagagcgca<br>catcgcccacagtccccgagaagttggggggaggggtcggcaattgaaccggtgcctaga<br>gaaggtggcgcggggtaaactgggaaagtgatgtcgtgtactggctccgcctttttcccgagg<br>gtgggggagaaccgtatataagtgcagtagtcgccgtgaacgttctttttcgcaacgggtttgc<br>cgccagaacacaggtaagtgccgtgtgtggttcccgcgggcctggcctctttacgggttatgg<br>cccttgcgtgccttgaattacttccactggctgcagtacgtgattcttgatcccgagcttcgggtt<br>ggaagtgggtgggagagttcgaggccttgcgcttaaggagccccttcgcctcgtgcttgagtt<br>gaggcctggcctgggcgctggggccgccgcgtgcgaatctggtggcaccttcgcgcctgtc<br>tcgctgctttcgataagtctctagccatttaaaatttttgatgacctgctgcgacgctttttttctggc<br>aagatagtcttgtaaatgcgggccaagatctgcacactggtatttcggtttttggggccgcggg<br>cggcgacggggcccgtgcgtcccagcgcacatgttcggcgaggcggggcctgcgagcgc<br>ggccaccgagaatcggacgggggtagtctcaagctggccggcctgctctggtgcctggcct<br>cgcgccgccgtgtatcgccccgccctgggcggcaaggctggcccggtcggcaccagttgc<br>gtgagcggaaagatggccgcttcccggccctgctgcagggagctcaaaatggaggacgcg<br>gcgctcgggagagcgggcgggtgagtcacccacacaaaggaaaagggcctttccgtcctc<br>agccgtcgcttcatgtgactccacggagtaccgggcgccgtccaggcacctcgattagttctc<br>gagcttttggagtacgtcgtctttaggttggggggaggggttttatgcgatggagtttccccaca<br>ctgagtgggtggagactgaagttaggccagcttggcacttgatgtaattctccttggaatttgcc<br>ctttttgagtttggatcttggttcattctcaagcctcagacagtggttcaaagtttttttcttccatttc<br>aggtgtcgtgaCCACCATGGCGCTTCCGGTGACAGCACTGCTC<br>CTCCCCTTGGCGCTGTTGCTCCACGCAGCAAGGCCGGAT<br>GTAGTTATGACCCAGAGTCCGCTCTCTTTGCCGGTGACG | 107 |

TABLE 10-continued

| CAR Components | | |
|---|---|---|
| Name | Sequence | SEQ ID NO: |
| | CTCGGCCAACCGGCGTCTATTTCTTGCAGAAGTAGTCAA TCACTTCTGCACTCTAGCGGTAACACTTATTTGGAGTGGT ATCTCCAACGACCAGGGCAAAGCCCCAAGCCGTTGATTT ATAAGATCTCTACAAGATTCAGCGGAGTGCCCGACAGAT TTTCCGGGAGTGGGTCCGGTACTGATTTCACTTTGAAAA TTTCCCGCGTCGAGGCTGAAGATGTTGGTGTCTACTACT GCTTTCAGGGGAGCCATGTTCCATATACCTTTGGAGGTG GGACTAAGGTAGAAATTAAAGGTGGGGGTGGATCAGGG GGTGGCGGCAGCGGGGGAGGGGGCTCACAAGTGCAACT TGTGCAAAGTGGGGCCGAGGTGAAAAAACCCGGTGCAA GTGTAAAGGTCTCATGCAAAGCGTCTGGTTTGACAATTG AAGACTATTATATGCATTGGGTGAGACAGGCCCCGGGCC AAGGCTTGGAATGGATGGGATGGATAGACCCCGAAAAC GGTGACACGGAGTACGGACCTAAATTTCAAGGAAGAGT GACAATGACACGCGATACATCTATTAACACGGCTTATAT GGAACTGAGCCGACTTCGGAGTGATGACACTGCTGTATA TTATTGCGCCGTCCACAACGCACATTATGGCACCTGGTT TGCGTACTGGGGACAGGGAACTTTGGTTACAGTATCAAG CAGTGCTGCTGCCTTTGTCCCGGTATTTCTCCCAGCCAAA CCGACCACGACTCCCGCCCCGCGCCCTCCGACACCCGCT CCCACCATCGCCTCTCAACCTCTTAGTCTTCGCCCCGAGG CATGCCGACCCGCCGCCGGGGGTGCTGTTCATACGAGGG GCTTGGACTTCGCTTGTGATATTTACATTTGGGCTCCGTT GGCGGGTACGTGCGGCGTCCTTTTGTTGTCACTCGTTATT ACTTTGTATTGTAATCACAGGAATCGCAAACGGGGCAGA AAGAAACTCCTGTATATATTCAAACAACCATTTATGAGA CCAGTACAAACTACTCAAGAGGAAGATGGCTGTAGCTG CCGATTTCCAGAAGAAGAAGAAGGAGGATGTGAACTGC GAGTGAAGTTTTCCCGAAGCGCAGACGCTCCGGCATATC AGCAAGGACAGAATCAGCTGTATAACGAACTGAATTTG GGACGCCGCGAGGAGTATGACGTGCTTGATAAACGCCG GGGGAGAGACCCGGAAATGGGGGGTAAACCCCGAAGAA AGAATCCCCAAGAAGGACTCTACAATGAACTCCAGAAG GATAAGATGGCGGAGGCCTACTCAGAAATAGGTATGAA GGGCGAACGACGACGGGGAAAAGGTCACGATGGCCTCT ACCAAGGGTTGAGTACGGCAACCAAAGATACGTACGAT GCACTGCATATGCAGGCCCTGCCTCCCAGATAATAATAA AATCGCTATCCATCGAAGATGGATGTGTGTTGGTTTTTTG TGTGTGGAGCAACAAATCTGACTTTGCATGTGCAAACGC CTTCAACAACAGCATTATTCCAGAAGACACCTTCTTCCC CAGCCCAGGTAAGGGCAGCTTTGGTGCCTTCGCAGGCTG TTTCCTTGCTTCAGGAATGGCCAGGTTCTGCCCAGAGCT CTGGTCAATGATGTCTAAAACTCCTCTGATTGGTGGTCTC GGCCTTATCCATTGCCACCAAAACCCTCTTTTTACTAAGA AACAGTGAGCCTTGTTCTGGCAGTCCAGAGAATGACACG GGAAAAAAGCAGATGAAGAGAAGGTGGCAGGAGAGGG CACGTGGCCCAGCCTCAGTCTCTCCAACTGAGTTCCTGC CTGCCTGCCTTTGCTCAGACTGTTTGCCCCTTACTGCTCT TCTAGGCCTCATTCTAAGCCCCTTCTCCAAGTTGCCTCTC CTTATTTCTCCCTGTCTGCCAAAAAATCTTTCCCAGCTCA CTAAGTCAGTCTCACGCAGTCACTCATTAACCCACCAAT CACTGATTGTGCCGGCACATGAATGCACCAGGTGTTGAA GTGGAGGAATTAAAAAGTCAGATGAGGGGTGTGCCCAG AGGAAGCACCATTCTAGTTGGGGGAGCCCATCTGTCAGC TGGGAAAAGTCCAAATAACTTCAGATTGGAATGTGTTTT AACTCAGGGTTGAGAAAACAGCTACCTTCAGGACAAAA GTCAGGGAAGGGCTCTCTGAAGAAATGCTACTTGAAGAT ACCAGCCCTACCAAGGGCAGGGAGAGGACCCTATAGAG GCCTGGGACAGGAGCTCAATGAGAAAGG | |
| CTX-976 CAR 41BB co-stim (nt) | CCACCATGGCGCTTCCGGTGACAGCACTGCTCCTCCCCT TGGCGCTGTTGCTCCACGCAGCAAGGCCGCAGGTTCAAC TGGTTCAGAGTGGAGCAGAGGTAAAAAAGCCCGGAGCG TCCGTCAAAGTGTCATGTAAAGCCTCTGGACTTACTATC GAAGACTACTACATGCACTGGGTGAGGCAGGCGCCTGG CCAAGGTCTCGAGTGGATGGGTTGGATTGACCCTGAAA ATGGAGATACAGAATACGGCCCTAAGTTTCAAGGGCGA GTAACTATGACTCGAGATACGTCAATTAATACGGCATAC ATGGAGTTGTCTCGGCTCCGATCTGATGACACTGCAGTT TACTATTGTGCCGTCCACAATGCTCATTACGGGACATGG TTCGCTTACTGGGGGCAAGGGACACTCGTAACGGTTAGC TCTGGGGGAGGAGGGTCTGGTGGAGGGGGCTCAGGAGG GGGTGGTAGCGACGTAGTAATGACCCAGTCACCTCTGTC TTTGCCGGTCACGTTGGGCCAGCCTGCATCCATATCCTG CAGATCCAGCCAGAGCCTCCTGCACAGTAGTGGCAACA | 108 |

TABLE 10-continued

CAR Components

| Name | Sequence | SEQ ID NO: |
|---|---|---|
| | CGTATTTGGAATGGTACCTGCAGAGGCCGGGTCAAAGTC<br>CAAAACCGCTGATCTATAAGATATCTACGCGATTTTCAG<br>GGGTGCCGGACCGATTTAGCGGATCAGGAAGTGGAACC<br>GACTTTACGCTCAAGATCAGCCGGGTTGAAGCCGAAGA<br>TGTCGGCGTTTACTACTGTTTCCAAGGAAGCCACGTACC<br>CTATACGTTTGGTGGCGGCACGAAGGTCGAGATAAAGA<br>GTGCTGCTGCCTTTGTCCCGGTATTTCTCCCAGCCAAACC<br>GACCACGACTCCCGCCCCGCGCCCTCCGACACCCGCTCC<br>CACCATCGCCTCTCAACCTCTTAGTCTTCGCCCCGAGGC<br>ATGCCGACCCGCCGCCGGGGGTGCTGTTCATACGAGGG<br>GCTTGGACTTCGCTTGTGATATTTACATTTGGGCTCCGTT<br>GGCGGGTACGTGCGGCGTCCTTTTGTTGTCACTCGTTATT<br>ACTTTGTATTGTAATCACAGGAATCGCAAACGGGGCAG<br>AAAGAAACTCCTGTATATATTCAAACAACCATTTATGAG<br>ACCAGTACAAACTACTCAAGAGGAAGATGGCTGTAGCT<br>GCCGATTTCCAGAAGAAGAAGAAGGAGGATGTGAACTG<br>CGAGTGAAGTTTTCCCGAAGCGCAGACGCTCCGGCATAT<br>CAGCAAGGACAGAATCAGCTGTATAACGAACTGAATTT<br>GGGACGCCGCGAGGAGTATGACGTGCTTGATAAACGCC<br>GGGGGAGAGACCCGGAAATGGGGGGTAAACCCCGAAG<br>AAAGAATCCCCAAGAAGGACTCTACAATGAACTCCAGA<br>AGGATAAGATGGCGGAGGCCTACTCAGAAATAGGTATG<br>AAGGGCGAACGACGACGGGGAAAAGGTCACGATGGCCT<br>CTACCAAGGGTTGAGTACGGCAACCAAAGATACGTACG<br>ATGCACTGCATATGCAGGCCCTGCCTCCCAGATAAT | |
| CTX-976 CAR 41BB co-stim (aa) | MALPVTALLLPLALLLHAARPQVQLVQSGAEVKKPGASV<br>KVSCKASGLTIEDYYMHWVRQAPGQGLEWMGWIDPENG<br>DTEYGPKFQGRVTMTRDTSINTAYMELSRLRSDDTAVYYC<br>AVHNAHYGTWFAYWGQGTLVTVSSGGGGSGGGGSGGGG<br>SDVVMTQSPLSLPVTLGQPASISCRSSQSLLHSSGNTYLEW<br>YLQRPGQSPKPLIYKISTRFSGVPDRFSGSGSGTDFTLKISRV<br>EAEDVGVYYCFQGSHVPYTFGGGTKVEIKSAAAFVPVFLP<br>AKPTTTPAPRPPTPAPTIASQPLSLRPEACRPAAGGAVHTRG<br>LDFACDIYIWAPLAGTCGVLLLSLVITLYCNHRNRKRGRK<br>KLLYIFKQPFMRPVQTTQEEDGCSCRFPEEEEGGCELRVKF<br>SRSADAPAYQQGQNQLYNELNLGRREEYDVLDKRRGRDP<br>EMGGKPRRKNPQEGLYNELQKDKMAEAYSEIGMKGERRR<br>GKGHDGLYQGLSTATKDTYDALHMQALPPR | 109 |
| CTX-976 scFv (nt) | CAGGTTCAACTGGTTCAGAGTGGAGCAGAGGTAAAAAA<br>GCCCGGAGCGTCCGTCAAAGTGTCATGTAAAGCCTCTGG<br>ACTTACTATCGAAGACTACTACATGCACTGGGTGAGGCA<br>GGCGCCTGGCCAAGGTCTCGAGTGGATGGGTTGGATTGA<br>CCCTGAAAATGGAGATACAGAATACGGCCCTAAGTTTCA<br>AGGGCGAGTAACFATGACTCGAGATACGTCAATTAATAC<br>GGCATACATCCAGTTGTGTCGGCTCCGATCTGATGACAC<br>TGCAGTTTACTATTGTGCCGTCCACAATGCTCATTACGG<br>GACATGGTTCGCTTACTGGGGGCAAGGGACACTCGTAAC<br>GGTTAGCTCTGGGGGAGGAGGGTCTGGTGGAGGGGGCT<br>CAGGAGGGGGTGGTAGCGACGTAGTAATGACCCAGTCA<br>CCTCTGTCTTTGCCGGTCACGTTGGGCCAGCCTGCATCCA<br>TATCCTGCAGATCCAGCCAGAGCCTCCTGCACAGTAGTG<br>GCAACACGTATTTGGAATGGTACCTGCAGAGGCCGGGTC<br>AAAGTCCAAAACCGCTGATCTATAAGATATCTACGCGAT<br>TTTCAGGGGTGCCGGACCGATTTAGCGGATCAGGAAGTG<br>GAACCGACTTTACGCTCAAGATCAGCCGGGTTGAAGCCG<br>AAGATGTCGGCGTTTACTACTGTTTCCAAGGAAGCCACG<br>TACCCTATACGTTTGGTGGCGGCACGAAGGTCGAGATAA<br>AG | 110 |
| CTX-976 scFv (aa) (linker underlined) | QVQLVQSGAEVKKPGASVKVSCKASGLTIEDYYMHWVRQ<br>APGQGLEWMGWIDPENGDTEYGPKFQGRVTMTRDTSINT<br>AYMELSRLRSDDTAVYYCAVHNAHYGTWFAYWGQGTLV<br>TVSSGGGGSGGGGSGGGGSDVVMTQSPLSLPVTLGQPASIS<br>CRSSQSLLHSSGNTYLEWYLQRPGQSPKPLIYKISTRFSGVP<br>DRFSGSGSGTDFTLKISRVEAEDVGVYYCFQGSHVPYTFGG<br>GTKVEIK | 86 |
| CTX-976 scFv VH (aa) | QVQLVQSGAEVKKPGASVKVSCKASGLTIEDYYMHWVRQ<br>APGQGLEWMGWIDPENGDTEYGPKFQGRVTMTRDTSINT<br>AYMELSRLRSDDTAVYYCAVHNAHYGTWFAYWGQGTLV<br>TVSS | 90 |

TABLE 10-continued

| CAR Components | | |
|---|---|---|
| Name | Sequence | SEQ ID NO: |
| CTX-976<br>scFv VL (aa) | DVVMTQSPLSLPVTLGQPASISCRSSQSLLHSSGNTYLEWY<br>LQRPGQSPKPLIYKISTRFSGVPDRFSGSGSGTDFTLKISRVE<br>AEDVGVYYCFQGSHVPYTFGGGTKVEIK | 88 |
| CTX-976<br>Donor (nt)<br>LHA to RHA | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCA<br>ATCTCCTGGTAATGTGATAGATTTCCCAACTTAATGCCA<br>ACATACCATAAACCTCCCATTCTGCTAATGCCCAGCCTA<br>AGTTGGGGAGACCACTCCAGATTCCAAGATGTACAGTTT<br>GCTTTGCTGGGCCTTTTTCCCATGCCTGCCTTTACTCTGC<br>CAGAGTTATATTGCTGGGGTTTTGAAGAAGATCCTATTA<br>AATAAAAGAATAAGCAGTATTATTAAGTAGCCCTGCATT<br>TCAGGTTTCCTTGAGTGGCAGGCCAGGCCTGGCCGTGAA<br>CGTTCACTGAAATCATGGCCTCTTGGCCAAGATTGATAG<br>CTTGTGCCTGTCCCTGAGTCCCAGTCCATCACGAGCAGC<br>TGGTTTCTAAGATGCTATTTCCCGTATAAAGCATGAGAC<br>CGTGACTTGCCAGCCCCACAGAGCCCCGCCCTTGTCCAT<br>CACTGGCATCTGGACTCCAGCCTGGGTTGGGGCAAAGAG<br>GGAAATGAGATCATGTCCTAACCCTGATCCTCTTGTCCC<br>ACAGATATCCAGAACCCTGACCCTGCCGTGTACCAGCTG<br>AGAGACTCTAAATCCAGTGACAAGTCTGTCTGCCTATTC<br>ACCGATTTTGATTCTCAAACAAATGTGTCACAAAGTAAG<br>GATTCTGATGTGTATATCACAGACAAAACTGTGCTAGAC<br>ATGAGGTCTATGGACTTCAggctccggtgcccgtcagtgggcagagcgca<br>catcgcccacagtccccgagaagttggggggaggggtcggcaattgaaccggtgcctaga<br>gaaggtggcgcggggtaaactgggaaagtgatgtcgtgtactggctccgcctttttcccgagg<br>gtgggggagaaccgtatataagtgcagtagtcgccgtgaacgttctttttcgcaacgggtttgc<br>cgccagaacacaggtaagtgccgtgtgtggttcccgcgggcctggcctctttacgggttatgg<br>cccttgcgtgccttgaattacttccactggctgcagtacgtgattcttgatcccgagcttcgggtt<br>ggaagtgggtgggagagttcgaggccttgcgcttaaggagccccttcgcctcgtgcttgagtt<br>gaggcctggcctgggcgctggggccgccgcgtgcgaatctggtggcaccttcgcgcctgtc<br>tcgctgctttcgataagtctctagccatttaaaatttttgatgacctgctgcgacgctttttttctggc<br>aagatagtcttgtaaatgcgggccaagatctgcacactggtatttcggtttttggggccgcggg<br>cggcgacggggcccgtgcgtcccagcgcacatgttcggcgaggcggggcctgcgagcgc<br>ggccaccgagaatcggacgggggtagtctcaagctggccggcctgctctggtgcctggcct<br>cgcgccgccgtgtatcgccccgccctgggcggcaaggctggcccggtcggcaccagttgc<br>gtgagcggaaagatggccgcttcccggccctgctgcagggagctcaaaatggaggacgcg<br>gcgctcgggagagcgggcgggtgagtcacccacacaaaggaaaagggcctttccgtcctc<br>agccgtcgcttcatgtgactccacggagtaccgggcgccgtccaggcacctcgattagttctc<br>gagcttttggagtacgtcgtctttaggttggggggaggggttttatgcgatggagtttccccaca<br>ctgagtgggtggagactgaagttaggccagcttggcacttgatgtaattctccttggaatttgcc<br>ctttttgagtttggatcttggttcattctcaagcctcagacagtggttcaaagtttattcttccatttc<br>aggtgtcgtgaCCACCATGGCGCTTCCGGTGACAGCACTGCTC<br>CTCCCCTTGGCGCTGTTGCTCCACGCAGCAAGGCCGCAG<br>GTTCAACTGGTTCAGAGTGGAGCAGAGGTAAAAAAGCC<br>CGGAGCGTCCGTCAAAGTGTCATGTAAAGCCTCTGGACT<br>TACTATCGAAGACTACTACATGCACTGGGTGAGGCAGGC<br>GCCTGGCCAAGGTCTCGAGTGGATGGGTTGGATTGACCC<br>TGAAAATGGAGATACAGAATACGGCCCTAAGTTTCAAG<br>GGCGAGTAACTATGACTCGAGATACGTCAATTAATACGG<br>CATACATGGAGTTGTCTCGGCTCCGATCTGATGACACTG<br>CAGTTTACTATTGTGCCGTCCACAATGCTCATTACGGGA<br>CATGGTTCGCTTACTGGGGGCAAGGGACACTCGTAACGG<br>TTAGCTCTGGGGGAGGAGGGTCTGGTGGAGGGGGCTCA<br>GGAGGGGGTGGTAGCGACGTAGTAATGACCCAGTCACC<br>TCTGTCTTTGCCGGTCACGTTGGGCCAGCCTGCATCCATA<br>TCCTGCAGATCCAGCCAGAGCCTCCTGCACAGTAGTGGC<br>AACACGTATTTGGAATGGTACCTGCAGAGGCCGGGTCAA<br>AGTCCAAAACCGCTGATCTATAAGATATCTACGCGATTT<br>TCAGGGGTGCCGGACCGATTTAGCGGATCAGGAAGTGG<br>AACCGACTTTACGCTCAAGATCAGCCGGGTTGAAGCCGA<br>AGATGTCGGCGTTTACTACTGTTTCCAAGGAAGCCACGT<br>ACCCTATACGTTTGGTGGCGGCACGAAGGTCGAGATAAA<br>GAGTGCTGCTGCCTTTGTCCCGGTATTTCTCCCAGCCAAA<br>CCGACCACGACTCCCGCCCCGCGCCCTCCGACACCCGCT<br>CCCACCATCGCCTCTCAACCTCTTAGTCTTCGCCCCGAGG<br>CATGCCGACCCGCCGCCGGGGGTGCTGTTCATACGAGGG<br>GCTTGGACTTCGCTTGTGATATTTACATTTGGGCTCCGTT<br>GGCGGGTACGTGCGGCGTCCTTTTGTTGTCACTCGTTATT<br>ACTTTGTATTGTAATCACAGGAATCGCAAACGGGGCAGA<br>AAGAAACTCCTGTATATATTCAAACAACCATTTATGAGA<br>CCAGTACAAACTACTCAAGAGGAAGATGGCTGTAGCTG<br>CCGATTTCCAGAAGAAGAAGAAGGAGGATGTGAACTGC<br>GAGTGAAGTTTTCCCGAAGCGCAGACGCTCCGGCATATC | 111 |

TABLE 10-continued

| CAR Components | | |
|---|---|---|
| Name | Sequence | SEQ ID NO: |
| | AGCAAGGACAGAATCAGCTGTATAACGAACTGAATTTG GGACGCCGCGAGGAGTATGACGTGCTTGATAAACGCCG GGGGAGAGACCCGGAAATGGGGGGTAAACCCCGAAGAA AGAATCCCCAAGAAGGACTCTACAATGAACTCCAGAAG GATAAGATGGCGGAGGCCTACTCAGAAATAGGTATGAA GGGCGAACGACGACGGGGAAAAGGTCACGATGGCCTCT ACCAAGGGTTGAGTACGGCAACCAAAGATACGTACGAT GCACTGCATATGCAGGCCCTGCCTCCCAGATAATAATAA AATCGCTATCCATCGAAGATGGATGTGTGTTGGTTTTTTG TGTGTGGAGCAACAAATCTGACTTTGCATGTGCAAACGC CTTCAACAACAGCATTATTCCAGAAGACACCTTCTTCCC CAGCCCAGGTAAGGGCAGCTTTGGTGCCTTCGCAGGCTG TTTCCTTGCTTCAGGAATGGCCAGGTTCTGCCCAGAGCT CTGGTCAATGATGTCTAAAACTCCTCTGATTGGTGGTCTC GGCCTTATCCATTGCCACCAAAACCCTCTTTTTACTAAGA AACAGTGAGCCTTGTTCTGGCAGTCCAGAGAATGACACG GGAAAAAAGCAGATGAAGAGAAGGTGGCAGGAGAGGG CACGTGGCCCAGCCTCAGTCTCTCCAACTGAGTTCCTGC CTGCCTGCCTTTGCTCAGACTGTTTGCCCCTTACTGCTCT TCTAGGCCTCATTCTAAGCCCCTTCTCCAAGTTGCCTCTC CTTATTTCTCCCTGTCTGCCAAAAAATCTTTCCCAGCTCA CTAAGTCAGTCTCACGCAGTCACTCATTAACCCACCAAT CACTGATTGTGCCGGCACATGAATGCACCAGGTGTTGAA GTGGAGGAATTAAAAAGTCAGATGAGGGGTGTGCCCAG AGGAAGCACCATTCTAGTTGGGGGAGCCCATCTGTCAGC TGGGAAAAGTCCAAATAACTTCAGATTGGAATGTGTTTT AACTCAGGGTTGAGAAAACAGCTACCTTCAGGACAAAA GTCAGGGAAGGGCTCTCTGAAGAAATGCTACTTGAAGAT ACCAGCCCTACCAAGGGCAGGGAGAGGACCCTATAGAG GCCTGGGACAGGAGCTCAATGAGAAAGG | |
| CTX-977 CAR 41BB co-stim (nt) | CCACCATGGCGCTTCCGGTGACAGCACTGCTCCTCCCCT TGGCGCTGTTGCTCCACGCAGCAAGGCCGGACGTTGTGA TGACGCAGTCTCCTCTGAGCCTGCCAGTTACGTTGGGGC AACCCGCATCAATATCTTGTAGGTCCAGTCAGAGCCTGC TTCACAGCTCTGGCAACACTTACTTGGAATGGTACCTCC AGAGACCTGGACAGAGTCCCAAGCCATTGATTTACAAG ATTTCAACGCGATTTAGTGGAGTGCCCGATCGATTCTCT GGGAGTGGCTCTGGGACTGATTTCACACTTAAAATAAGT AGGGTGGAGGCTGAAGATGTGGGTGTATATTATTGTTTT CAAGGGTCCCATGTCCCTTACACTTTCGGCGGCGGCACC AAAGTTGAGATCAAAGGTGGTGGTGGGTCCGGCGGTGG AGGCAGTGGGGGTGGCGGGTCACAAGTTCAACTTGTCC AGTCAGGGGCTGAAGTAAAAAAGCCTGGTGCATCAGTT AAAGTTTCATGTAAGGCTTCCGGCCTTACCATTGAAGAT TACTATATGCACTGGGTTAGACAAGCTCCTGGACAAGGT CTGGAGTGGATGGGCTGGATAGACCCCGAGAATGGTGA CACAGAATACGGGCCTAAGTTCCAGGGTAGGGTAACAA TGACGCGGGATACATCCATTTCCACAGCTTACATGGAAC TGAGTAGACTCAGATCTGACGACACTGCTGTCTACTATT GTGCCGTCCATAACGCGCATTATGGCACTTGGTTCGCAT ATTGGGGGCAAGGCACTCTTGTTACAGTGTCCTCAAGTG CTGCTGCCTTTGTCCCGGTATTTCTCCCAGCCAAACCGA CCACGACTCCCGCCCCGCGCCCTCCGACACCCGCTCCCA CCATCGCCTCTCAACCTCTTAGTCTTCGCCCCGAGGCAT GCCGACCCGCCGCCGGGGGTGCTGTTCATACGAGGGGC TTGGACTTCGCTTGTGATATTTACATTTGGGCTCCGTTGG CGGGTACGTGCGGCGTCCTTTTGTTGTCACTCGTTATTAC TTTGTATTGTAATCACAGGAATCGCAAACGGGGCAGAA AGAAACTCCTGTATATATTCAAACAACCATTTATGAGAC CAGTACAAACTACTCAAGAGGAAGATGGCTGTAGCTGC CGATTTCCAGAAGAAGAAGAAGGAGGATGTGAACTGCG AGTGAAGTTTTCCCGAAGCGCAGACGCTCCGGCATATCA GCAAGGACAGAATCAGCTGTATAACGAACTGAATTTGG GACGCCGCGAGGAGTATGACGTGCTTGATAAACGCCGG GGGAGAGACCCGGAAATGGGGGGTAAACCCCGAAGAA AGAATCCCCAAGAAGGACTCTACAATGAACTCCAGAAG GATAAGATGGCGGAGGCCTACTCAGAAATAGGTATGAA GGGCGAACGACGACGGGGAAAAGGTCACGATGGCCTCT ACCAAGGGTTGAGTACGGCAACCAAAGATACGTACGAT GCACTGCATATGCAGGCCCTGCCTCCCAGATAAT | 112 |
| CTX-977 CAR 41BB co-stim (aa) | MALPVTALLLPLALLLHAARPDVVMTQSPLSLPVTLGQPA SISCRSSQSLLHSSGNTYLEWYLQRPGQSPKPLIYKISTRFSG VPDRFSGSGSGTDFTLKISRVEAEDVGVYYCFQGSHVPYTF | 113 |

TABLE 10-continued

| CAR Components | | |
|---|---|---|
| Name | Sequence | SEQ ID NO: |
| | GGGTKVEIKGGGGSGGGGSGGGGSQVQLVQSGAEVKKPG ASVKVSCKASGLTIEDYYMHWVRQAPGQGLEWMGWIDP ENGDTEYGPKFQGRVTMTRDTSISTAYMELSRLRSDDTAV YYCAVHNAHYGTWFAYWGQGTLVTVSSSAAAFVPVFLPA KPTTTPAPRPPTPAPTIASQPLSLRPEACRPAAGGAVHTRGL DFACDIYIWAPLAGTCGVLLLSLVITLYCNHRNRKRGRKK LLYIFKQPFMRPVQTTQEEDGCSCRFPEEEEGGCELRVKFS RSADAPAYQQGQNQLYNELNLGRREEYDVLDKRRGRDPE MGGKPRRKNPQEGLYNELQKDKMAEAYSEIGMKGERRRG KGHDGLYQGLSTATKDTYDALHMQALPPR | |
| CTX-977 scFv (nt) | GACGTTGTGATGACGCAGTCTCCTCTGAGCCTGCCAGTT ACGTTGGGGCAACCCGCATCAATATCTTGTAGGTCCAGT CAGAGCCTGCTTCACAGCTCTGGCAACACTTACTTGGAA TGGTACCTCCAGAGACCTGGACAGAGTCCCAAGCCATTG ATTTACAAGATTTCAACGCGATTTAGTGGAGTGCCCGAT CGATTCTCTGGGAGTGGCTCTGGGACTGATTTCACACTT AAAATAAGTAGGGTGGAGGCTGAAGATGTGGGTGTATA TTATTGTTTTCAAGGGTCCCATGTCCCTTACACTTTCGGC GGCGGCACCAAAGTTGAGATCAAAGGTGGTGGTGGGTC CGGCGGTGGAGGCAGTGGGGGTGGCGGGTCACAAGTTC AACTTGTCCAGTCAGGGGCTGAAGTAAAAAAGCCTGGT GCATCAGTTAAAGTTTCATGTAAGGCTTCCGGCCTTACC ATTGAAGATTACTATATGCACTGGGTTAGACAAGCTCCT GGACAAGGTCTGGAGTGGATGGGCTGGATAGACCCCGA GAATGGTGACACAGAATACGGGCCTAAGTTCCAGGGTA GGGTAACAATGACGCGGGATACATCCATTTCCACAGCTT ACATCGAACTGAGTAGACTCAGATCTGACGACACTGCTG TCTACTATTGTGCCGTCCATAACGCGCATTATGGCACrTG GTTCGCATATTGGGGGCAAGGCACTCTTGTTACAGTGTC CTCA | 114 |
| CTX-977 scFv (aa) (linker underlined) | DVVMTQSPLSLPVTLGQPASISCRSSQSLLHSSGNTYLEWY LQRPGQSPKPLIYKISTRFSGVPDRFSGSGSGTDFTLKISRVE AEDVGVYYCFQGSHVPYTFGGGTKVEIKGGGGSGGGGSG GGGSQVQLVQSGAEVKKPGASVKVSCKASGLTIEDYYMH WVRQAPGQGLEWMGWIDPENGDTEYGPKFQGRVTMTRD TSISTAYMELSRLRSDDTAVYYCAVHNAHYGTWFAYWGQ GTLVTVSS | 84 |
| CTX-977 scFv VH (aa) | QVQLVQSGAEVKKPGASVKVSCKASGLTIEDYYMHWVRQ APGQGLEWMGWIDPENGDTEYGPKFQGRVTMTRDTSIST AYMELSRLRSDDTAVYYCAVHNAHYGTWFAYWGQGTLV TVSS | 98 |
| CTX-977 scFv VL (aa) | DVVMTQSPLSLPVTLGQPASISCRSSQSLLHSSGNTYLEWY LQRPGQSPKPLIYKISTRFSGVPDRFSGSGSGTDFTLKISRVE AEDVGVYYCFQGSHVPYTFGGGTKVEIK | 88 |
| CTX-977 Donor (nt) LHA to RHA | GAGATGTAAGGAGCTGCTGTGACTTGCTCAAGGCCTTAT ATCGAGTAAACGGTAGTGCTGGGGCTTAGACGCAGGTGT TCTGATTTATAGTTCAAAACCTCTATCAATGAGAGAGCA ATCTCCTGGTAATGTGATAGATTTCCCAACTTAATGCCA ACATACCATAAACCTCCCATTCTGCTAATGCCCAGCCTA AGTTGGGGAGACCACTCCAGATTCCAAGATGTACAGTTT GCTTTGCTGGGCCTTTTTCCCATGCCTGCCTTTACTCTGC CAGAGTTATATTGCTGGGGTTTTGAAGAAGATCCTATTA AATAAAAGAATAAGCAGTATTATTAAGTAGCCCTGCATT TCAGGTTTCCTTGAGTGGCAGGCCAGGCCTGGCCGTGAA CGTTCACTGAAATCATGGCCTCTTGGCCAAGATTGATAG CTTGTGCCTGTCCCTGAGTCCCAGTCCATCACGAGCAGC TGGTTTCTAAGATGCTATTTCCCGTATAAAGCATGAGAC CGTGACTTGCCAGCCCCACAGAGCCCCGCCCTTGTCCAT CACTGGCATCTGGACTCCAGCCTGGGTTGGGGCAAAGAG GGAAATGAGATCATGTCCTAACCCTGATCCTCTTGTCCC ACAGATATCCAGAACCCTGACCCTGCCGTGTACCAGCTG AGAGACTCTAAATCCAGTGACAAGTCTGTCTGCCTATTC ACCGATTTTGATTCTCAAACAAATGTGTCACAAAGTAAG GATTCTGATGTGTATATCACAGACAAAACTGTGCTAGAC ATGAGGTCTATGGACTTCAggctccggtgcccgtcagtgggcagagcgca catcgcccacagtccccgagaagttggggggaggggtcggcaattgaaccggtgcctaga gaaggtggcgcggggtaaactgggaaagtgatgtcgtgtactggctccgcctttttcccgagg gtgggggagaaccgtatataagtgcagtagtcgccgtgaacgttctttttcgcaacgggtttgc cgccagaacacaggtaagtgccgtgtgtggttcccgcgggcctggcctctttacgggttatgg cccttgcgtgccttgaattacttccactggctgcagtacgtgattcttgatcccgagcttcgggtt | 115 |

TABLE 10-continued

| CAR Components | | |
|---|---|---|
| Name | Sequence | SEQ ID NO: |
| | ggaagtgggtgggagagttcgaggccttgcgcttaaggagccccttcgcctcgtgcttgagtt | |
| | gaggcctggcctgggcgctggggccgccgcgtgcgaatctggtggcaccttcgcgcctgtc | |
| | tcgctgctttcgataagtctctagccatttaaaatttttgatgacctgctgcgacgctttttttctggc | |
| | aagatagtcttgtaaatgcgggccaagatctgcacactggtatttcggtttttggggccgcggg | |
| | cggcgacggggcccgtgcgtcccagcgcacatgttcggcgaggcggggcctgcgagcgc | |
| | ggccaccgagaatcggacgggggtagtctcaagctggccggcctgctctggtgcctggcct | |
| | cgcgccgccgtgtatcgccccgccctgggcggcaaggctggcccggtcggcaccagttgc | |
| | gtgagcggaaagatggccgcttcccggccctgctgcagggagctcaaaatggaggacgcg | |
| | gcgctcgggagagcgggcgggtgagtcacccacacaaaggaaaagggcctttccgtcctc | |
| | agccgtcgcttcatgtgactccacggagtaccgggcgccgtccaggcacctcgattagttctc | |
| | gagcttttggagtacgtcgtctttaggttggggggaggggttttatgcgatggagtttccccaca | |
| | ctgagtgggtggagactgaagttaggccagcttggcacttgatgtaattctccttggaatttgcc | |
| | ctttttgagtttggatcttggttcattctcaagcctcagacagtggttcaaagtttattcttccatttc | |
| | aggtgtcgtgaCCACCATGGCGCTTCCGGTGACAGCACTGCTC | |
| | CTCCCCTTGGCGCTGTTGCTCCACGCAGCAAGGCCGGAC | |
| | GTTGTGATGACGCAGTCTCCTCTGAGCCTGCCAGTTACG | |
| | TTGGGGCAACCCGCATCAATATCTTGTAGGTCCAGTCAG | |
| | AGCCTGCTTCACAGCTCTGGCAACACTTACTTGGAATGG | |
| | TACCTCCAGAGACCTGGACAGAGTCCCAAGCCATTGATT | |
| | TACAAGATTTCAACGCGATTTAGTGGAGTGCCCGATCGA | |
| | TTCTCTGGGAGTGGCTCTGGGACTGATTTCACACTTAAA | |
| | ATAAGTAGGGTGGAGGCTGAAGATGTGGGTGTATATTAT | |
| | TGTTTTCAAGGGTCCCATGTCCCTTACACTTTCGGCGGCG | |
| | GCACCAAAGTTGAGATCAAAGGTGGTGGTGGGTCCGGC | |
| | GGTGGAGGCAGTGGGGGTGGCGGGTCACAAGTTCAACT | |
| | TGTCCAGTCAGGGGCTGAAGTAAAAAAGCCTGGTGCATC | |
| | AGTTAAAGTTTCATGTAAGGCTTCCGGCCTTACCATTGA | |
| | AGATTACTATATGCACTGGGTTAGACAAGCTCCTGGACA | |
| | AGGTCTGGAGTGGATGGGCTGGATAGACCCCGAGAATG | |
| | GTGACACAGAATACGGGCCTAAGTTCCAGGGTAGGGTA | |
| | ACAATGACGCGGGATACATCCATTTCCACAGCTTACATG | |
| | GAACTGAGTAGACTCAGATCTGACGACACTGCTGTCTAC | |
| | TATTGTGCCGTCCATAACGCGCATTATGGCACTTGGTTC | |
| | GCATATTGGGGGCAAGGCACTCTTGTTACAGTGTCCTCA | |
| | AGTGCTGCTGCCTTTGTCCCGGTATTTCTCCCAGCCAAAC | |
| | CGACCACGACTCCCGCCCCGCGCCCTCCGACACCCGCTC | |
| | CCACCATCGCCTCTCAACCTCTTAGTCTTCGCCCCGAGGC | |
| | ATGCCGACCCGCCGCCGGGGGTGCTGTTCATACGAGGGG | |
| | CTTGGACTTCGCTTGTGATATTTACATTTGGGCTCCGTTG | |
| | GCGGGTACGTGCGGCGTCCTTTTGTTGTCACTCGTTATTA | |
| | CTTTGTATTGTAATCACAGGAATCGCAAACGGGGCAGAA | |
| | AGAAACTCCTGTATATATTCAAACAACCATTTATGAGAC | |
| | CAGTACAAACTACTCAAGAGGAAGATGGCTGTAGCTGC | |
| | CGATTTCCAGAAGAAGAAGAAGGAGGATGTGAACTGCG | |
| | AGTGAAGTTTTCCCGAAGCGCAGACGCTCCGGCATATCA | |
| | GCAAGGACAGAATCAGCTGTATAACGAACTGAATTTGG | |
| | GACGCCGCGAGGAGTATGACGTGCTTGATAAACGCCGG | |
| | GGGAGAGACCCGGAAATGGGGGGTAAACCCCGAAGAAA | |
| | GAATCCCCAAGAAGGACTCTACAATGAACTCCAGAAGG | |
| | ATAAGATGGCGGAGGCCTACTCAGAAATAGGTATGAAG | |
| | GGCGAACGACGACGGGGAAAAGGTCACGATGGCCTCTA | |
| | CCAAGGGTTGAGTACGGCAACCAAAGATACGTACGATG | |
| | CACTGCATATGCAGGCCCTGCCTCCCAGATAATAATAAA | |
| | ATCGCTATCCATCGAAGATGGATGTGTGTTGGTTTTTTGT | |
| | GTGTGGAGCAACAAATCTGACTTTGCATGTGCAAACGCC | |
| | TTCAACAACAGCATTATTCCAGAAGACACCTTCTTCCCC | |
| | AGCCCAGGTAAGGGCAGCTTTGGTGCCTTCGCAGGCTGT | |
| | TTCCTTGCTTCAGGAATGGCCAGGTTCTGCCCAGAGCTC | |
| | TGGTCAATGATGTCTAAAACTCCTCTGATTGGTGGTCTC | |
| | GGCCTTATCCATTGCCACCAAAACCCTCTTTTTACTAAGA | |
| | AACAGTGAGCCTTGTTCTGGCAGTCCAGAGAATGACACG | |
| | GGAAAAAAGCAGATGAAGAGAAGGTGGCAGGAGAGGG | |
| | CACGTGGCCCAGCCTCAGTCTCTCCAACTGAGTTCCTGC | |
| | CTGCCTGCCTTTGCTCAGACTGTTTGCCCCTTACTGCTCT | |
| | TCTAGGCCTCATTCTAAGCCCCTTCTCCAAGTTGCCTCTC | |
| | CTTATTTCTCCCTGTCTGCCAAAAAATCTTTCCCAGCTCA | |
| | CTAAGTCAGTCTCACGCAGTCACTCATTAACCCACCAAT | |
| | CACTGATTGTGCCGGCACATGAATGCACCAGGTGTTGAA | |
| | GTGGAGGAATTAAAAAGTCAGATGAGGGGTGTGCCCAG | |
| | AGGAAGCACCATTCTAGTTGGGGGAGCCCATCTGTCAGC | |
| | TGGGAAAAGTCCAAATAACTTCAGATTGGAATGTGTTTT | |
| | AACTCAGGGTTGAGAAAACAGCTACCTTCAGGACAAAA | |
| | GTCAGGGAAGGGCTCTCTGAAGAAATGCTACTTGAAGAT | |
| | ACCAGCCCTACCAAGGGCAGGGAGAGGACCCTATAGAG | |
| | GCCTGGGACAGGAGCTCAATGAGAAAGG | |

TABLE 10-continued

| CAR Components | | |
|---|---|---|
| Name | Sequence | SEQ ID NO: |
| CTX-978 CAR 41BB co-stim (nt) | CCACCATGGCGCTTCCGGTGACAGCACTGCTCCTCCCCT TGGCGCTGTTGCTCCACGCAGCAAGGCCGCAGGTACAA CTCGTTCAGAGCGGTGCAGAGGTTAAGAAACCGGGCGC CAGTGTCAAAGTATCATGCAAGGCGAGTGGTCTGACCAT CGAAGATTATTATATGCATTGGGTGAGACAAGCACCGG GGCAGGGGCTCGAATGGATGGGTTGGATCGACCCCGAA AATGGTGATACGGAGTATGGCCCGAAATTTCAGGGTCG GGTCACGATGACCCGCGATACAAGCATCAGTACTGCAT ACATGGAGCTCTCTCGCTTGCGGAGTGATGATACCGCCG TTTATTATTGCGCGGTTCACAACGCTCATTATGGCACTTG GTTCGCGTATTGGGGCCAAGGAACACTGGTTACAGTGA GCAGTGGAGGGGGTGGCTCTGGTGGCGGCGGGAGCGGC GGAGGGGGCAGTGATGTTGTGATGACACAGTCACCCCT GAGTCTCCCGGTCACTCTTGGGCAACCAGCCAGCATAAG CTGTCGCAGTTCTCAGAGCTTGCTCCATAGCTCCGGGAA TACCTACCTCGAATGGTATCTCCAAAGACCCGGTCAATC TCCAAAGCCTTTGATTTACAAGATTAGTACACGATTTAG TGGGGTCCCAGATAGATTTTCAGGTAGTGGATCTGGTAC AGATTTCACATTGAAAATATCACGCGTCGAGGCGGAGG ATGTCGGGGTCTACTATTGCTTTCAAGGTAGTCACGTGC CCTACACGTTTGGTGGCGGTACGAAGGTCGAAATCAAG AGTGCTGCTGCCTTTGTCCCGGTATTTCTCCCAGCCAAA CCGACCACGACTCCCGCCCCGCGCCCTCCGACACCCGCT CCCACCATCGCCTCTCAACCTCTTAGTCTTCGCCCCGAG GCATGCCGACCCGCCGCCGGGGGTGCTGTTCATACGAG GGGCTTGGACTTCGCTTGTGATATTTACATTTGGGCTCC GTTGGCGGGTACGTGCGGCGTCCTTTTGTTGTCACTCGTT ATTACTTTGTATTGTAATCACAGGAATCGCAAACGGGGC AGAAAGAAACTCCTGTATATATTCAAACAACCATTTATG AGACCAGTACAAACTACTCAAGAGGAAGATGGCTGTAG CTGCCGATTTCCAGAAGAAGAAGAAGGAGGATGTGAAC TGCGAGTGAAGTTTTCCCGAAGCGCAGACGCTCCGGCAT ATCAGCAAGGACAGAATCAGCTGTATAACGAACTGAAT TTGGGACGCCGCGAGGAGTATGACGTGCTTGATAAACG CCGGGGGAGAGACCCGGAAATGGGGGGTAAACCCCGAA GAAAGAATCCCCAAGAAGGACTCTACAATGAACTCCAG AAGGATAAGATGGCGGAGGCCTACTCAGAAATAGGTAT GAAGGGCGAACGACGACGGGGAAAAGGTCACGATGGC CTCTACCAAGGGTTGAGTACGGCAACCAAAGATACGTA CGATGCACTGCATATGCAGGCCCTGCCTCCCAGATAAT | 116 |
| CTX-978 CAR 41BB co-stim (aa) | MALPVTALLLPLALLLHAARPQVQLVQSGAEVKKPGASV KVSCKASGLTIEDYYMHWVRQAPGQGLEWMGWIDPENG DTEYGPKFQGRVTMTRDTSISTAYMELSRLRSDDTAVYYC AVHNAHYGTWFAYWGQGTLVTVSSGGGGSGGGGSGGGG SDVVMTQSPLSLPVTLGQPASISCRSSQSLLHSSGNTYLEW YLQRPGQSPKPLIYKISTRFSGVPDRFSGSGSGTDFTLKISRV EAEDVGVYYCFQGSHVPYTFGGGTKVEIKSAAAFVPVFLP AKPTTTPAPRPPTPAPTIASQPLSLRPEACRPAAGGAVHTRG LDFACDIYIWAPLAGTCGVLLLSLVITLYCNHRNRKRGRK KLLYIFKQPFMRPVQTTQEEDGCSCRFPEEEEGGCELRVKF SRSADAPAYQQGQNQLYNELNLGRREEYDVLDKRRGRDP EMGGKPRRKNPQEGLYNELQKDKMAEAYSEIGMKGERRR GKGHDGLYQGLSTATKDTYDALHMQALPPR | 117 |
| CTX-978 scFv (nt) | CAGGTACAACTCGTTCAGAGCGGTGCAGAGGTTAAGAA ACCGGGCGCCAGTGTCAAAGTATCATGCAAGGCGAGTG GTCTGACCATCGAAGATTATTATATGCATTGGGTGAGAC AAGCACCGGGGCAGGGGCTCGAATGGATGGGTTGGATC GACCCCGAAAATGGTGATACGGAGTATGGCCCGAAATTT CAGGGTCGGGTCACGATGACCCGCGATACAAGCATCAG TACTGCATACATGGAGCTCTCTCGCTTGCGGAGTGATGA TACCGCCGTTTATTATTGCGCGGTTCACAACGCTCATTAT GGCACTTGGTTCGCGTATTGGGGCCAAGGAACACTGGTT ACAGTGAGCAGTGGAGGGGGTGGCTCTGGTGGCGGCGG GAGCGGCGGAGGGGGCAGTGATGTTGTGATGACACAGT CACCCCTGAGTCTCCCGGTCACTCTTGGGCAACCAGCCA GCATAAGCTGTCGCAGTTCTCAGAGCTTGCTCCATAGCT CCGGGAATACCTACCTCGAATGGTATCTCCAAAGACCCG GTCAATCTCCAAAGCCTTTGATTTACAAGATTAGTACAC GATTTAGTGGGGTCCCAGATAGATTTTCAGGTAGTGGAT | 118 |

TABLE 10-continued

| CAR Components | | |
|---|---|---|
| Name | Sequence | SEQ ID NO: |
| | CTGGTACAGATTTCACATTGAAAATATCACGCGTCGAGG<br>CGGAGGATGTCGGGGTCTACTATTGCTTTCAAGGTAGTC<br>ACGTGCCCTACACGTTTGGTGGCGGTACGAAGGTCGAAA<br>TCAAG | |
| CTX-978 scFv (aa) (linker underlined) | QVQLVQSGAEVKKPGASVKVSCKASGLTIEDYYMHWVRQ<br>APGQGLEWMGWIDPENGDTEYGPKFQGRVTMTRDTSISTA<br>YMELSRLRSDDTAVYYCAVHNAHYGTWFAYWGQGTLVT<br>VSSGGGGSGGGGSGGGGSDVVMTQSPLSLPVTLGQPASISC<br>RSSQSLLHSSGNTYLEWYLQRPGQSPKPLIYKISTRFSGVPD<br>RFSGSGSGTDFTLKISRVEAEDVGVYYCFQGSHVPYTFGGG<br>TKVEIK | 87 |
| CTX-978 scFv VH (aa) | QVQLVQSGAEVKKPGASVKVSCKASGLTIEDYYMHWVRQ<br>APGQGLEWMGWIDPENGDTEYGPKFQGRVTMTRDTSIST<br>AYMELSRLRSDDTAVYYCAVHNAHYGTWFAYWGQGTLV<br>TVSS | 98 |
| CTX-978 scFv VL (aa) | DVVMTQSPLSLPVTLGQPASISCRSSQSLLHSSGNTYLEWY<br>LQRPGQSPKPLIYKISTRFSGVPDRFSGSGSGTDFTLKISRVE<br>AEDVGVYYCFQGSHVPYTFGGGTKVEIK | 88 |
| CTX-978 Donor (nt) LHA to RHA | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCA<br>ATCTCCTGGTAATGTGATAGATTTCCCAACTTAATGCCA<br>ACATACCATAAACCTCCCATTCTGCTAATGCCCAGCCTA<br>AGTTGGGGAGACCACTCCAGATTCCAAGATGTACAGTTT<br>GCTTTGCTGGGCCTTTTTCCCATGCCTGCCTTTACTCTGC<br>CAGAGTTATATTGCTGGGGTTTTGAAGAAGATCCTATTA<br>AATAAAAGAATAAGCAGTATTATTAAGTAGCCCTGCATT<br>TCAGGTTTCCTTGAGTGGCAGGCCAGGCCTGGCCGTGAA<br>CGTTCACTGAAATCATGGCCTCTTGGCCAAGATTGATAG<br>CTTGTGCCTGTCCCTGAGTCCCAGTCCATCACGAGCAGC<br>TGGTTTCTAAGATGCTATTTCCCGTATAAAGCATGAGAC<br>CGTGACTTGCCAGCCCCACAGAGCCCCGCCCTTGTCCAT<br>CACTGGCATCTGGACTCCAGCCTGGGTTGGGGCAAAGAG<br>GGAAATGAGATCATGTCCTAACCCTGATCCTCTTGTCCC<br>ACAGATATCCAGAACCCTGACCCTGCCGTGTACCAGCTG<br>AGAGACTCTAAATCCAGTGACAAGTCTGTCTGCCTATTC<br>ACCGATTTTGATTCTCAAACAAATGTGTCACAAAGTAAG<br>GATTCTGATGTGTATATCACAGACAAAACTGTGCTAGAC<br>ATGAGGTCTATGGACTTCAggctccggtgcccgtcagtgggcagagcgca<br>catcgcccacagtccccgagaagttggggggaggggtcggcaattgaaccggtgcctaga<br>gaaggtggcgcggggtaaactgggaaagtgatgtcgtgtactggctccgcctttttcccgagg<br>gtgggggagaaccgtatataagtgcagtagtcgccgtgaacgttctttttcgcaacgggtttgc<br>cgccagaacacaggtaagtgccgtgtgtggttcccgcgggcctggcctctttacgggttatgg<br>cccttgcgtgccttgaattacttccactggctgcagtacgtgattcttgatcccgagcttcgggtt<br>ggaagtgggtgggagagttcgaggccttgcgcttaaggagccccttcgcctcgtgcttgagtt<br>gaggcctggcctgggcgctggggccgccgcgtgcgaatctggtggcaccttcgcgcctgtc<br>tcgctgctttcgataagtctctagccatttaaaatttttgatgacctgctgcgacgctttttttctggc<br>aagatagtcttgtaaatgcgggccaagatctgcacactggtatttcggtttttggggccgcggg<br>cggcgacggggcccgtgcgtcccagcgcacatgttcggcgaggcggggcctgcgagcgc<br>ggccaccgagaatcggacgggggtagtctcaagctggccggcctgctctggtgcctggcct<br>cgcgccgccgtgtatcgccccgccctgggcggcaaggctggcccggtcggcaccagttgc<br>gtgagcggaaagatggccgcttcccggccctgctgcagggagctcaaaatggaggacgcg<br>gcgctcgggagagcgggcgggtgagtcacccacacaaaggaaaagggcctttccgtcctc<br>agccgtcgcttcatgtgactccacggagtaccgggcgccgtccaggcacctcgattagttctc<br>gagcttttggagtacgtcgtctttaggttggggggaggggttttatgcgatggagtttccccaca<br>ctgagtgggtggagactgaagttaggccagcttggcacttgatgtaattctccttggaatttgcc<br>ctttttgagtttggatcttggttcattctcaagcctcagacagtggttcaaagtttattcttccatttc<br>aggtgtcgtgaCCACCATGGCGCTTCCGGTGACAGCACTGCTC<br>CTCCCCTTGGCGCTGTTGCTCCACGCAGCAAGGCCGCAG<br>GTACAACTCGTTCAGAGCGGTGCAGAGGTTAAGAAACC<br>GGGCGCCAGTGTCAAAGTATCATGCAAGGCGAGTGGTCT<br>GACCATCGAAGATTATTATATGCATTGGGTGAGACAAGC<br>ACCGGGGCAGGGGCTCGAATGGATGGGTTGGATCGACC<br>CCGAAAATGGTGATACGGAGTATGGCCCGAAATTTCAG<br>GGTCGGGTCACGATGACCCGCGATACAAGCATCAGTACT<br>GCATACATGGAGCTCTCTCGCTTGCGGAGTGATGATACC<br>GCCGTTTATTATTGCGCGGTTCACAACGCTCATTATGGC<br>ACTTGGTTCGCGTATTGGGGCCAAGGAACACTGGTTACA<br>GTGAGCAGTGGAGGGGGTGGCTCTGGTGGCGGCGGGAG<br>CGGCGGAGGGGGCAGTGATGTTGTGATGACACAGTCAC<br>CCCTGAGTCTCCCGGTCACTCTTGGGCAACCAGCCAGCA | 119 |

TABLE 10-continued

| CAR Components | | |
|---|---|---|
| Name | Sequence | SEQ ID NO: |
| | TAAGCTGTCGCAGTTCTCAGAGCTTGCTCCATAGCTCCG GGAATACCTACCTCGAATGGTATCTCCAAAGACCCGGTC AATCTCCAAAGCCTTTGATTTACAAGATTAGTACACGAT TTAGTGGGGTCCCAGATAGATTTTCAGGTAGTGGATCTG GTACAGATTTCACATTGAAAATATCACGCGTCGAGGCGG AGGATGTCGGGGTCTACTATTGCTTTCAAGGTAGTCACG TGCCCTACACGTTTGGTGGCGGTACGAAGGTCGAAATCA AGAGTGCTGCTGCCTTTGTCCCGGTATTTCTCCCAGCCAA ACCGACCACGACTCCCGCCCCGCGCCCTCCGACACCCGC TCCCACCATCGCCTCTCAACCTCTTAGTCTTCGCCCCGAG GCATGCCGACCCGCCGCCGGGGGTGCTGTTCATACGAGG GGCTTGGACTTCGCTTGTGATATTTACATTTGGGCTCCGT TGGCGGGTACGTGCGGCGTCCTTTTGTTGTCACTCGTTAT TACTTTGTATTGTAATCACAGGAATCGCAAACGGGGCAG AAAGAAACTCCTGTATATATTCAAACAACCATTTATGAG ACCAGTACAAACTACTCAAGAGGAAGATGGCTGTAGCT GCCGATTTCCAGAAGAAGAAGAAGGAGGATGTGAACTG CGAGTGAAGTTTTCCCGAAGCGCAGACGCTCCGGCATAT CAGCAAGGACAGAATCAGCTGTATAACGAACTGAATTT GGGACGCCGCGAGGAGTATGACGTGCTTGATAAACGCC GGGGGAGAGACCCGGAAATGGGGGGTAAACCCCGAAGA AAGAATCCCCAAGAAGGACTCTACAATGAACTCCAGAA GGATAAGATGGCGGAGGCCTACTCAGAAATAGGTATGA AGGGCGAACGACGACGGGGAAAAGGTCACGATGGCCTC TACCAAGGGTTGAGTACGGCAACCAAAGATACGTACGA TGCACTGCATATGCAGGCCCTGCCTCCCAGATAATAATA AAATCGCTATCCATCGAAGATGGATGTGTGTTGGTTTTTT GTGTGTGGAGCAACAAATCTGACTTTGCATGTGCAAACG CCTTCAACAACAGCATTATTCCAGAAGACACCTTCTTCC CCAGCCCAGGTAAGGGCAGCTTTGGTGCCTTCGCAGGCT GTTTCCTTGCTTCAGGAATGGCCAGGTTCTGCCCAGAGC TCTGGTCAATGATGTCTAAAACTCCTCTGATTGGTGGTCT CGGCCTTATCCATTGCCACCAAAACCCTCTTTTTACTAAG AAACAGTGAGCCTTGTTCTGGCAGTCCAGAGAATGACAC GGGAAAAAAGCAGATGAAGAGAAGGTGGCAGGAGAGG GCACGTGGCCCAGCCTCAGTCTCTCCAACTGAGTTCCTG CCTGCCTGCCTTTGCTCAGACTGTTTGCCCCTTACTGCTC TTCTAGGCCTCATTCTAAGCCCCTTCTCCAAGTTGCCTCT CCTTATTTCTCCCTGTCTGCCAAAAAATCTTTCCCAGCTC ACTAAGTCAGTCTCACGCAGTCACTCATTAACCCACCAA TCACTGATTGTGCCGGCACATGAATGCACCAGGTGTTGA AGTGGAGGAATTAAAAAGTCAGATGAGGGGTGTGCCCA GAGGAAGCACCATTCTAGTTGGGGGAGCCCATCTGTCAG CTGGGAAAAGTCCAAATAACTTCAGATTGGAATGTGTTT TAACTCAGGGTTGAGAAAACAGCTACCTTCAGGACAAA AGTCAGGGAAGGGCTCTCTGAAGAAATGCTACTTGAAG ATACCAGCCCTACCAAGGGCAGGGAGAGGACCCTATAG AGGCCTGGGACAGGAGCTCAATGAGAAAGG | |
| CTX-979 CAR 41BB co-stim (aa) | MALPVTALLLPLALLLHAARPQVQLVQSGAEVKKPGASV KVSCKASGLTIEDYYMHWVRQAPGQGLEWMGWIDPENG DTEYGPKFQGRVTMTRDTSINTAYMELSRLRSDDTAVYYC AVHNAHYGTWFAYWGQGTLVTVSSGGGGSGGGGSGGGG SDVVMTQSPLSLPVTLGQPASISCRSSQSLLHSSGNTYLEW YQQRPGQSPRPLIYKISTRFSGVPDRFSGSGSGTDFTLKISRV EAEDVGVYYCFQGSHVPYTFGGGTKVEIKSAAAFVPVFLP AKPTTTPAPRPPTPAPTIASQPLSLRPEACRPAAGGAVHTRG LDFACDIYIWAPLAGTCGVLLLSLVITLYCNHRNRKRGRK KLLYIFKQPFMRPVQTTQEEDGCSCRFPEEEEGGCELRVKF SRSADAPAYQQGQNQLYNELNLGRREEYDVLDKRRGRDP EMGGKPRRKNPQEGLYNELQKDKMAEAYSEIGMKGERRR GKGHDGLYQGLSTATKDTYDALHMQALPPR | 68 |
| CTX-979b CAR CD28 co-stim (aa) | MALPVTALLLPLALLLHAARPQVQLVQSGAEVKKPGASV KVSCKASGLTIEDYYMHWVRQAPGQGLEWMGWIDPENG DTEYGPKFQGRVTMTRDTSINTAYMELSRLRSDDTAVYYC AVHNAHYGTWFAYWGQGTLVTVSSGGGGSGGGGSGGGG SDVVMTQSPLSLPVTLGQPASISCRSSQSLLHSSGNTYLEW YQQRPGQSPRPLIYKISTRFSGVPDRFSGSGSGTDFTLKISRV EAEDVGVYYCFQGSHVPYTFGGGTKVEIKSAAAFVPVFLP AKPTTTPAPRPPTPAPTIASQPLSLRPEACRPAAGGAVHTRG LDFACDIYIWAPLAGTCGVLLLSLVITLYCNHRNRSKRSRL | 66 |

TABLE 10-continued

| CAR Components | | |
|---|---|---|
| Name | Sequence | SEQ ID NO: |
| | LHSDYMNMTPRRPGPTRKHYQPYAPPRDFAAYRSRVKFSR SADAPAYQQGQNQLYNELNLGRREEYDVLDKRRGRDPEM GGKPRRKNPQEGLYNELQKDKMAEAYSEIGMKGERRRGK GHDGLYQGLSTATKDTYDALHMQALPPR | |
| CTX-979 and CTX-979b scFv (aa) (linker underlined) | QVQLVQSGAEVKKPGASVKVSCKASGLTIEDYYMHWVRQ APGQGLEWMGWIDPENGDTEYGPKFQGRVTMTRDTSINT AYMELSRLRSDDTAVYYCAVHNAHYGTWFAYWGQGTLV TVSSGGGGSGGGGSGGGGSDVVMTQSPLSLPVTLGQPASIS CRSSQSLLHSSGNTYLEWYQQRPGQSPRPLIYKISTRFSGVP DRFSGSGSGTDFTLKISRVEAEDVGVYYCFQGSHVPYTFGG GTKVEIK | 70 |
| CTX-979 and CTX-979b scFv VH (aa) CDRs-in bold | QVQLVQSGAEVKKPGASVKVSCKASGLTIE**DYYMH**WVRQAPG QGLEWMG**WIDPENGDTEYGPKFQG**RVTMTRDTSINTAYMELS RLRSDDTAVYYCAV**HNAHYGTWFAY**WGQGTLVTVSS | 55 |
| CTX-979 and CTX-979b scFv VL (aa) CDRs-in bold | DVVMTQSPLSLPVTLGQPASISC**RSSQSLLHSSGNTYLE**WYQQR PGQSPRPLIY**KISTRFS**GVPDRFSGSGSGTDFTLKISRVEAEDVGV YYC**FQGSHVPYT**FGGGTKVEIK | 56 |

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The terms “about” and “substantially” preceding a numerical value mean±10% of the recited numerical value.

Where a range of values is provided, each value between the upper and lower ends of the range are specifically contemplated and described herein.

What is claimed is:

1. An engineered T cell comprising a nucleic acid encoding a chimeric antigen receptor (CAR) encoded by the nucleotide sequence of any one of SEQ ID NOs: 49, 51, 104, and 108.

2. The engineered T cell of claim 1 further comprising a disrupted T cell receptor alpha chain constant region (TRAC) gene.

3. The engineered T cell of claim 2, wherein the nucleic acid encoding the CAR is inserted into the disrupted TRAC gene.

4. The engineered T cell of claim 2, wherein the disrupted TRAC gene comprises the nucleotide sequence of any one of SEQ ID NOs: 63, 64, 107, and 111.

5. The engineered T cell of claim 2, wherein the disrupted TRAC gene comprises the nucleotide sequence of SEQ ID NO: 107.

6. The engineered T cell of claim 1 further comprising a disrupted beta-2-microglobulin (β2M) gene.

7. The engineered T cell of claim 1, wherein the CAR further comprises a CD28 co-stimulatory domain or a 41BB co-stimulatory domain.

8. The engineered T cell of claim 7, wherein the CAR further comprises a CD3 cytoplasmic signaling domain.

9. The engineered T cell of claim 1, wherein the T cell is a human T cell.

10. A population of cells comprising the engineered T cell of claim 1, wherein at least 15% or at least 50% of the engineered T cells of the population express the CAR.

11. The engineered T cell of claim 1, wherein the CAR comprises an anti-LIV1 scFv having the amino acid sequence of SEQ ID NO: 83.

12. The engineered T cell of claim 1, wherein the CAR comprises the amino acid sequence of SEQ ID NO: 105.

* * * * *

SEQUENCE LISTING

```
<160> NUMBER OF SEQ ID NOS: 130

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1

aagagcaaca aatctgact                                                   19


<210> SEQ ID NO 2
<211> LENGTH: 58
<212> TYPE: DNA
<213> ORGANISM: Artificial Sequence
<220> FEATURE:
<223> OTHER INFORMATION: Synthetic

<400> SEQUENCE: 2

aagagcaaca gtgctgtgcc tggagcaaca aatctgacta agagcaacaa atctgact       58


<210> SEQ ID NO 3
<211> LENGTH: 52
<212> TYPE: DNA
```

<213> ORGANISM: Artificial Sequence
<220> FEATURE:
<223> OTHER INFORMATION: Synthetic

<400> SEQUENCE: 3
aagagcaaca gtgctggagc aacaaatctg actaagagca acaaatctga ct 52

<210> SEQ ID NO 4
<211> LENGTH: 53
<212> TYPE: DNA
<213> ORGANISM: Artificial Sequence
<220> FEATURE:
<223> OTHER INFORMATION: Synthetic

<400> SEQUENCE: 4
aagagcaaca gtgcctggag caacaaatct gactaagagc aacaaatctg act 53

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
aagagcaaca gtgctgacta agagcaacaa atctgact 38

<210> SEQ ID NO 6
<211> LENGTH: 60
<212> TYPE: DNA
<213> ORGANISM: Artificial Sequence
<220> FEATURE:
<223> OTHER INFORMATION: Synthetic

<400> SEQUENCE: 6
aagagcaaca gtgctgtggg cctggagcaa caaatctgac taagagcaac aaatctgact 60

<210> SEQ ID NO 7
<211> LENGTH: 57
<212> TYPE: DNA
<213> ORGANISM: Artificial Sequence
<220> FEATURE:
<223> OTHER INFORMATION: Synthetic

<400> SEQUENCE: 7
aagagcaaca gtgctggcct ggagcaacaa atctgactaa gagcaacaaa tctgact 57

<210> SEQ ID NO 8
<211> LENGTH: 60
<212> TYPE: DNA
<213> ORGANISM: Artificial Sequence
<220> FEATURE:
<223> OTHER INFORMATION: Synthetic

<400> SEQUENCE: 8
aagagcaaca gtgctgtgtg cctggagcaa caaatctgac taagagcaac aaatctgact 60

<210> SEQ ID NO 9
<211> LENGTH: 79
<212> TYPE: DNA
<213> ORGANISM: Artificial Sequence
<220> FEATURE:
<223> OTHER INFORMATION: Synthetic

<400> SEQUENCE: 9
cgtggcctta gctgtgctcg cgctactctc tctttctgcc tggaggctat ccagcgtgag 60
tctctcctac cctcccgct 79

<210> SEQ ID NO 10
<211> LENGTH: 78
<212> TYPE: DNA
<213> ORGANISM: Artificial Sequence
<220> FEATURE:
<223> OTHER INFORMATION: Synthetic

<400> SEQUENCE: 10
cgtggcctta gctgtgctcg cgctactctc tctttcgcct ggaggctatc cagcgtgagt 60
ctctcctacc ctcccgct 78

<210> SEQ ID NO 11
<211> LENGTH: 75
<212> TYPE: DNA
<213> ORGANISM: Artificial Sequence
<220> FEATURE:
<223> OTHER INFORMATION: Synthetic

<400> SEQUENCE: 11
cgtggcctta gctgtgctcg cgctactctc tctttctgga ggctatccag cgtgagtctc 60
tcctaccctc ccgct 75

<210> SEQ ID NO 12
<211> LENGTH: 84
<212> TYPE: DNA
<213> ORGANISM: Artificial Sequence
<220> FEATURE:
<223> OTHER INFORMATION: Synthetic

<400> SEQUENCE: 12
cgtggcctta gctgtgctcg cgctactctc tctttctgga tagcctggag gctatccagc 60
gtgagtctct cctaccctcc cgct 84

<210> SEQ ID NO 13
<211> LENGTH: 55
<212> TYPE: DNA
<213> ORGANISM: Artificial Sequence
<220> FEATURE:
<223> OTHER INFORMATION: Synthetic

<400> SEQUENCE: 13
cgtggcctta gctgtgctcg cgctatccag cgtgagtctc tcctaccctc ccgct 55

<210> SEQ ID NO 14
<211> LENGTH: 82
<212> TYPE: DNA
<213> ORGANISM: Artificial Sequence
<220> FEATURE:
<223> OTHER INFORMATION: Synthetic

<400> SEQUENCE: 14
cgtggcctta gctgtgctcg cgctactctc tctttctgtg gcctggaggc tatccagcgt 60
gagtctctcc taccctcccg ct 82

<210> SEQ ID NO 15
<211> LENGTH: 100
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (1)..(20)
<223> OTHER INFORMATION: n is a, c, g, t or u

<400> SEQUENCE: 15

nnnnnnnnnn nnnnnnnnnn guuuuagagc uagaaauagc aaguuaaaau aaggcuaguc     60

cguuaucaac uugaaaaagu ggcaccgagu cggugcuuuu                          100


<210> SEQ ID NO 16
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, t or u

<400> SEQUENCE: 16

nnnnnnnnnn nnnnnnnnnn guuuuagagc uagaaauagc aaguuaaaau aaggcuaguc     60

cguuaucaac uugaaaaagu ggcaccgagu cggugc                               96


<210> SEQ ID NO 17
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: repeat_region
<222> LOCATION: (1)..(1)
<223> OTHER INFORMATION: Repeats 17-30 times
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: repeat_region
<222> LOCATION: (78)..(78)
<223> OTHER INFORMATION: Repeats 1-8 times

<400> SEQUENCE: 17

nguuuuagag cuagaaauag caaguuaaaa uaaggcuagu ccguuaucaa cuugaaaaag     60

uggcaccgag ucggugcu                                                   78


<210> SEQ ID NO 18
<211> LENGTH: 100
<212> TYPE: DNA
<213> ORGANISM: Artificial Sequence
<220> FEATURE:
<223> OTHER INFORMATION: Synthetic

<400> SEQUENCE: 18

agagcaacag ugcuguggcc guuuuagagc uagaaauagc aaguuaaaau aaggcuaguc     60

cguuaucaac uugaaaaagu ggcaccgagu cggugcuuuu                          100


<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19

agagcaacag ugcuguggcc                                                 20
```

<210> SEQ ID NO 20
<211> LENGTH: 100
<212> TYPE: DNA
<213> ORGANISM: Artificial Sequence
<220> FEATURE:
<223> OTHER INFORMATION: Synthetic

<400> SEQUENCE: 20
gcuacucucu cuuucuggcc guuuuagagc uagaaauagc aaguuaaaau aaggcuaguc 60
cguuaucaac uugaaaaagu ggcaccgagu cggugcuuuu 100

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gcuacucucu cuuucuggcc 20

<210> SEQ ID NO 22
<211> LENGTH: 100
<212> TYPE: DNA
<213> ORGANISM: Artificial Sequence
<220> FEATURE:
<223> OTHER INFORMATION: Synthetic

<400> SEQUENCE: 22
cugcagcuuc uccaacacau guuuuagagc uagaaauagc aaguuaaaau aaggcuaguc 60
cguuaucaac uugaaaaagu ggcaccgagu cggugcuuuu 100

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
cugcagcuuc uccaacacau 20

<210> SEQ ID NO 24
<211> LENGTH: 100
<212> TYPE: DNA
<213> ORGANISM: Artificial Sequence
<220> FEATURE:
<223> OTHER INFORMATION: Synthetic

<400> SEQUENCE: 24
gcuuugaucc cauuggucgc guuuuagagc uagaaauagc aaguuaaaau aaggcuaguc 60
cguuaucaac uugaaaaagu ggcaccgagu cggugcuuuu 100

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gcuuugaucc cauuggucgc 20

<210> SEQ ID NO 26
<211> LENGTH: 100
<212> TYPE: DNA
<213> ORGANISM: Artificial Sequence
<220> FEATURE:
<223> OTHER INFORMATION: Synthetic

<400> SEQUENCE: 26
gcccgcagga cgcacccaua guuuuagagc uagaaauagc aaguuaaaau aaggcuaguc 60
cguuaucaac uugaaaaagu ggcaccgagu cggugcuuuu 100

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gcccgcagga cgcacccaua 20

<210> SEQ ID NO 28
<211> LENGTH: 100
<212> TYPE: DNA
<213> ORGANISM: Artificial Sequence
<220> FEATURE:
<223> OTHER INFORMATION: Synthetic

<400> SEQUENCE: 28
agagcaacag ugcuguggcc guuuuagagc uagaaauagc aaguuaaaau aaggcuaguc 60
cguuaucaac uugaaaaagu ggcaccgagu cggugcuuuu 100

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
agagcaacag ugcuguggcc 20

<210> SEQ ID NO 30
<211> LENGTH: 100
<212> TYPE: DNA
<213> ORGANISM: Artificial Sequence
<220> FEATURE:
<223> OTHER INFORMATION: Synthetic

<400> SEQUENCE: 30
gcuacucucu cuuucuggcc guuuuagagc uagaaauagc aaguuaaaau aaggcuaguc 60
cguuaucaac uugaaaaagu ggcaccgagu cggugcuuuu 100

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gcuacucucu cuuucuggcc 20

```
<210> SEQ ID NO 32
<211> LENGTH: 100
<212> TYPE: DNA
<213> ORGANISM: Artificial Sequence
<220> FEATURE:
<223> OTHER INFORMATION: Synthetic

<400> SEQUENCE: 32

cugcagcuuc uccaacacau guuuuagagc uagaaauagc aaguuaaaau aaggcuaguc     60

cguuaucaac uugaaaaagu ggcaccgagu cggugcuuuu                          100


<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33

cugcagcuuc uccaacacau                                                 20


<210> SEQ ID NO 34
<211> LENGTH: 100
<212> TYPE: DNA
<213> ORGANISM: Artificial Sequence
<220> FEATURE:
<223> OTHER INFORMATION: Synthetic

<400> SEQUENCE: 34

gcuuugguce cauuggucgc guuuuagagc uagaaauagc aaguuaaaau aaggcuaguc     60

cguuaucaac uugaaaaagu ggcaccgagu cggugcuuuu                          100


<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35

gcuuugguce cauuggucgc                                                 20


<210> SEQ ID NO 36
<211> LENGTH: 100
<212> TYPE: DNA
<213> ORGANISM: Artificial Sequence
<220> FEATURE:
<223> OTHER INFORMATION: Synthetic

<400> SEQUENCE: 36

gcccgcagga cgcacccaua guuuuagagc uagaaauagc aaguuaaaau aaggcuaguc     60

cguuaucaac uugaaaaagu ggcaccgagu cggugcuuuu                          100


<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37

gcccgcagga cgcacccaua                                                 20


<210> SEQ ID NO 38
```

<211> LENGTH: 23
<212> TYPE: DNA
<213> ORGANISM: Artificial Sequence
<220> FEATURE:
<223> OTHER INFORMATION: Synthetic

<400> SEQUENCE: 38
gctttggtcc cattggtcgc ggg 23

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
gcccgcagga cgcacccata ggg 23

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
agagcaacag tgctgtggcc tgg 23

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
gctactctct ctttctggcc tgg 23

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
ctgcagcttc tccaacacat cgg 23

<210> SEQ ID NO 43
<211> LENGTH: 126
<212> TYPE: DNA
<213> ORGANISM: Artificial Sequence
<220> FEATURE:
<223> OTHER INFORMATION: Synthetic

<400> SEQUENCE: 43
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 44
<211> LENGTH: 42
<212> TYPE: PRT
<213> ORGANISM: Artificial Sequence
<220> FEATURE:
<223> OTHER INFORMATION: Synthetic

<400> SEQUENCE: 44

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 45
<211> LENGTH: 120
<212> TYPE: DNA
<213> ORGANISM: Artificial Sequence
<220> FEATURE:
<223> OTHER INFORMATION: Synthetic

<400> SEQUENCE: 45

```
tcaaagcgga gtaggttgtt gcattccgat tacatgaata tgactcctcg ccggcctggg     60

ccgacaagaa aacattacca accctatgcc cccccacgag acttcgctgc gtacaggtcc    120
```

<210> SEQ ID NO 46
<211> LENGTH: 40
<212> TYPE: PRT
<213> ORGANISM: Artificial Sequence
<220> FEATURE:
<223> OTHER INFORMATION: Synthetic

<400> SEQUENCE: 46

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

<210> SEQ ID NO 47
<211> LENGTH: 336
<212> TYPE: DNA
<213> ORGANISM: Artificial Sequence
<220> FEATURE:
<223> OTHER INFORMATION: Synthetic

<400> SEQUENCE: 47

```
cgagtgaagt tttcccgaag cgcagacgct ccggcatatc agcaaggaca gaatcagctg     60

tataacgaac tgaatttggg acgccgcgag gagtatgacg tgcttgataa acgccggggg    120

agagacccgg aaatgggggg taaaccccga agaaagaatc cccaagaagg actctacaat    180

gaactccaga aggataagat ggcggaggcc tactcagaaa taggtatgaa gggcgaacga    240

cgacggggaa aaggtcacga tggcctctac caagggttga gtacggcaac caaagatacg    300

tacgatgcac tgcatatgca ggccctgcct cccaga                              336
```

<210> SEQ ID NO 48
<211> LENGTH: 112
<212> TYPE: PRT
<213> ORGANISM: Artificial Sequence
<220> FEATURE:
<223> OTHER INFORMATION: Synthetic

<400> SEQUENCE: 48

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 49
<211> LENGTH: 1533
<212> TYPE: DNA
<213> ORGANISM: Artificial Sequence
<220> FEATURE:
<223> OTHER INFORMATION: Synthetic

<400> SEQUENCE: 49

```
ccaccatggc gcttccggtg acagcactgc tcctcccctt ggcgctgttg ctccacgcag     60

caaggccgga cgtggtcatg actcaaagcc cactttcctt gcccgtgact ctcggacaac    120

cggcttcaat atcttgccgc tcatcacagt ccctgctgca tagcagtggt aacacttatc    180

ttgagtggta ccaacagcgg cccggccaat ctcctaggcc cctgatatat aagataagta    240

ctcgcttttc cggggtcccg gaccggttca gcgggtctgg gagtggtaca gacttcacat    300

tgaagatttc acgagtagaa gccgaagacg tgggtgttta ttactgcttc caaggatctc    360

acgtgccata tacgtttggt gggggcacaa aagtcgagat taagggaggc ggaggatcag    420

gaggtggggg aagtggaggt ggtgggtcac aagtacagct cgtgcaatca ggggcggagg    480

tgaagaaacc aggggcgtct gtgaaggtaa gctgtaaggc atccggattg acaatcgagg    540

attattacat gcattgggtc cgccaggcac cagggcaggg attggagtgg atggggtgga    600

tagatcctga aaatggggat acagagtatg gccctaagtt ccagggcaga gttacgatga    660

ctcgagatac tagcattaat acggcctaca tggagcttag ccgcctgcgg tccgatgaca    720

cggccgttta ttattgcgcc gtacacaatg cgcactacgg gacatggttc gcgtattggg    780

gtcaaggaac gctcgttact gtctcaagta gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgctcaaagc   1080

ggagtaggtt gttgcattcc gattacatga atatgactcc tcgccggcct gggccgacaa   1140

gaaaacatta ccaaccctat gccccccac gagacttcgc tgcgtacagg tcccgagtga   1200

agttttcccg aagcgcagac gctccggcat atcagcaagg acagaatcag ctgtataacg   1260

aactgaattt gggacgccgc gaggagtatg acgtgcttga taaacgccgg gggagagacc   1320

cggaaatggg gggtaaaccc cgaagaaaga atccccaaga aggactctac aatgaactcc   1380

agaaggataa gatggcggag gcctactcag aaataggtat gaagggcgaa cgacgacggg   1440
```

```
gaaaaggtca cgatggcctc taccaagggt tgagtacggc aaccaaagat acgtacgatg   1500

cactgcatat gcaggccctg cctcccagat aat                                1533


<210> SEQ ID NO 50
<211> LENGTH: 508
<212> TYPE: PRT
<213> ORGANISM: Artificial Sequence
<220> FEATURE:
<223> OTHER INFORMATION: Synthetic

<400> SEQUENCE: 50

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Arg Ser Ser Gln
        35                  40                  45

Ser Leu Leu His Ser Ser Gly Asn Thr Tyr Leu Glu Trp Tyr Gln Gln
    50                  55                  60

Arg Pro Gly Gln Ser Pro Arg Pro Leu Ile Tyr Lys Ile Ser Thr Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Tyr Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

Lys Pro Gly Ala Ser Val Lys Val Ser Cys Lys Ala Ser Gly Leu Thr
                165                 170                 175

Ile Glu Asp Tyr Tyr Met His Trp Val Arg Gln Ala Pro Gly Gln Gly
            180                 185                 190

Leu Glu Trp Met Gly Trp Ile Asp Pro Glu Asn Gly Asp Thr Glu Tyr
        195                 200                 205

Gly Pro Lys Phe Gln Gly Arg Val Thr Met Thr Arg Asp Thr Ser Ile
    210                 215                 220

Asn Thr Ala Tyr Met Glu Leu Ser Arg Leu Arg Ser Asp Asp Thr Ala
225                 230                 235                 240

Val Tyr Tyr Cys Ala Val His Asn Ala His Tyr Gly Thr Trp Phe Ala
                245                 250                 255

Tyr Trp Gly Gln Gly Thr Leu Val Thr Val Ser Ser Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350
```

```
His Arg Asn Arg Ser Lys Arg Ser Arg Leu Leu His Ser Asp Tyr Met
        355                 360                 365

Asn Met Thr Pro Arg Arg Pro Gly Pro Thr Arg Lys His Tyr Gln Pro
    370                 375                 380

Tyr Ala Pro Pro Arg Asp Phe Ala Ala Tyr Arg Ser Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505
```

```
<210> SEQ ID NO 51
<211> LENGTH: 1539
<212> TYPE: DNA
<213> ORGANISM: Artificial Sequence
<220> FEATURE:
<223> OTHER INFORMATION: Synthetic

<400> SEQUENCE: 51

ccaccatggc gcttccggtg acagcactgc tcctcccctt ggcgctgttg ctccacgcag     60

caaggccgga cgtggtcatg actcaaagcc cactttcctt gcccgtgact ctcggacaac    120

cggcttcaat atcttgccgc tcatcacagt ccctgctgca tagcagtggt aacacttatc    180

ttgagtggta ccaacagcgg cccggccaat ctcctaggcc cctgatatat aagataagta    240

ctcgcttttc cggggtcccg gaccggttca gcgggtctgg gagtggtaca gacttcacat    300

tgaagatttc acgagtagaa gccgaagacg tgggtgttta ttactgcttc caaggatctc    360

acgtgccata tacgtttggt gggggcacaa aagtcgagat taagggaggc ggaggatcag    420

gaggtggggg aagtggaggt ggtgggtcac aagtacagct cgtgcaatca ggggcggagg    480

tgaagaaacc aggggcgtct gtgaaggtaa gctgtaaggc atccggattg acaatcgagg    540

attattacat gcattgggtc cgccaggcac cagggcaggg attggagtgg atggggtgga    600

tagatcctga aaatggggat acagagtatg gccctaagtt ccagggcaga gttacgatga    660

ctcgagatac tagcattaat acggcctaca tggagcttag ccgcctgcgg tccgatgaca    720

cggccgttta ttattgcgcc gtacacaatg cgcactacgg gacatggttc gcgtattggg    780

gtcaaggaac gctcgttact gtctcaagta gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140
```

```
aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccggggga   1320

gagacccgga aatgggggt aaaccccgaa gaaagaatcc ccaagaagga ctctacaatg   1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539
```

<210> SEQ ID NO 52
<211> LENGTH: 510
<212> TYPE: PRT
<213> ORGANISM: Artificial Sequence
<220> FEATURE:
<223> OTHER INFORMATION: Synthetic

<400> SEQUENCE: 52

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Arg Ser Ser Gln
        35                  40                  45

Ser Leu Leu His Ser Ser Gly Asn Thr Tyr Leu Glu Trp Tyr Gln Gln
    50                  55                  60

Arg Pro Gly Gln Ser Pro Arg Pro Leu Ile Tyr Lys Ile Ser Thr Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Tyr Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

Lys Pro Gly Ala Ser Val Lys Val Ser Cys Lys Ala Ser Gly Leu Thr
                165                 170                 175

Ile Glu Asp Tyr Tyr Met His Trp Val Arg Gln Ala Pro Gly Gln Gly
            180                 185                 190

Leu Glu Trp Met Gly Trp Ile Asp Pro Glu Asn Gly Asp Thr Glu Tyr
        195                 200                 205

Gly Pro Lys Phe Gln Gly Arg Val Thr Met Thr Arg Asp Thr Ser Ile
    210                 215                 220

Asn Thr Ala Tyr Met Glu Leu Ser Arg Leu Arg Ser Asp Asp Thr Ala
225                 230                 235                 240

Val Tyr Tyr Cys Ala Val His Asn Ala His Tyr Gly Thr Trp Phe Ala
                245                 250                 255

Tyr Trp Gly Gln Gly Thr Leu Val Thr Val Ser Ser Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
```

```
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510
```

<210> SEQ ID NO 53
<211> LENGTH: 741
<212> TYPE: DNA
<213> ORGANISM: Artificial Sequence
<220> FEATURE:
<223> OTHER INFORMATION: Synthetic

<400> SEQUENCE: 53

```
gacgtggtca tgactcaaag cccactttcc ttgcccgtga ctctcggaca accggcttca      60

atatcttgcc gctcatcaca gtccctgctg catagcagtg gtaacactta tcttgagtgg     120

taccaacagc ggcccggcca atctcctagg cccctgatat ataagataag tactcgcttt     180

tccggggtcc cggaccggtt cagcgggtct gggagtggta cagacttcac attgaagatt     240

tcacgagtag aagccgaaga cgtgggtgtt tattactgct tccaaggatc tcacgtgcca     300

tatacgtttg gtgggggcac aaaagtcgag attaagggag gcggaggatc aggaggtggg     360

ggaagtggag gtggtgggtc acaagtacag ctcgtgcaat caggggcgga ggtgaagaaa     420

ccaggggcgt ctgtgaaggt aagctgtaag gcatccggat tgacaatcga ggattattac     480

atgcattggg tccgccaggc accagggcag ggattggagt ggatggggtg gatagatcct     540

gaaaatgggg atacagagta tggccctaag ttccagggca gagttacgat gactcgagat     600

actagcatta atacggccta catggagctt agccgcctgc ggtccgatga cacggccgtt     660

tattattgcg ccgtacacaa tgcgcactac gggacatggt tcgcgtattg gggtcaagga     720

acgctcgtta ctgtctcaag t                                               741
```

<210> SEQ ID NO 54

<211> LENGTH: 247
<212> TYPE: PRT
<213> ORGANISM: Artificial Sequence
<220> FEATURE:
<223> OTHER INFORMATION: Synthetic

<400> SEQUENCE: 54

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Leu Thr Ile Glu Asp Tyr Tyr
145                 150                 155                 160

Met His Trp Val Arg Gln Ala Pro Gly Gln Gly Leu Glu Trp Met Gly
                165                 170                 175

Trp Ile Asp Pro Glu Asn Gly Asp Thr Glu Tyr Gly Pro Lys Phe Gln
            180                 185                 190

Gly Arg Val Thr Met Thr Arg Asp Thr Ser Ile Asn Thr Ala Tyr Met
        195                 200                 205

Glu Leu Ser Arg Leu Arg Ser Asp Asp Thr Ala Val Tyr Tyr Cys Ala
    210                 215                 220

Val His Asn Ala His Tyr Gly Thr Trp Phe Ala Tyr Trp Gly Gln Gly
225                 230                 235                 240

Thr Leu Val Thr Val Ser Ser
                245
```

<210> SEQ ID NO 55
<211> LENGTH: 120
<212> TYPE: PRT
<213> ORGANISM: Artificial Sequence
<220> FEATURE:
<223> OTHER INFORMATION: Synthetic

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
```

```
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 56
<211> LENGTH: 112
<212> TYPE: PRT
<213> ORGANISM: Artificial Sequence
<220> FEATURE:
<223> OTHER INFORMATION: Synthetic

<400> SEQUENCE: 56

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110


<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Asp Tyr Tyr Met His
1               5


<210> SEQ ID NO 58
<211> LENGTH: 17
<212> TYPE: PRT
<213> ORGANISM: Artificial Sequence
<220> FEATURE:
<223> OTHER INFORMATION: Synthetic

<400> SEQUENCE: 58

Trp Ile Asp Pro Glu Asn Gly Asp Thr Glu Tyr Gly Pro Lys Phe Gln
1               5                   10                  15

Gly


<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59
```

```
His Asn Ala His Tyr Gly Thr Trp Phe Ala Tyr
1               5                   10


<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Arg Ser Ser Gln Ser Leu Leu His Ser Ser Gly Asn Thr Tyr Leu Glu
1               5                   10                  15


<210> SEQ ID NO 61
<211> LENGTH: 7
<212> TYPE: PRT
<213> ORGANISM: Artificial Sequence
<220> FEATURE:
<223> OTHER INFORMATION: Synthetic

<400> SEQUENCE: 61

Lys Ile Ser Thr Arg Phe Ser
1               5


<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Phe Gln Gly Ser His Val Pro Tyr Thr
1               5


<210> SEQ ID NO 63
<211> LENGTH: 4364
<212> TYPE: DNA
<213> ORGANISM: Artificial Sequence
<220> FEATURE:
<223> OTHER INFORMATION: Synthetic

<400> SEQUENCE: 63

gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg gggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgtgtacca    660

gctgagagac tctaaatcca gtgacaagtc tgtctgccta ttcaccgatt ttgattctca    720

aacaaatgtg tcacaaagta aggattctga tgtgtatatc acagacaaaa ctgtgctaga    780
```

-continued

```
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccggacg tggtcatgac tcaaagccca ctttccttgc ccgtgactct cggacaaccg   2100
gcttcaatat cttgccgctc atcacagtcc ctgctgcata gcagtggtaa cacttatctt   2160
gagtggtacc aacagcggcc cggccaatct cctaggcccc tgatatataa gataagtact   2220
cgcttttccg gggtcccgga ccggttcagc gggtctggga gtggtacaga cttcacattg   2280
aagatttcac gagtagaagc cgaagacgtg ggtgtttatt actgcttcca aggatctcac   2340
gtgccatata cgtttggtgg gggcacaaaa gtcgagatta agggaggcgg aggatcagga   2400
ggtgggggaa gtggaggtgg tgggtcacaa gtacagctcg tgcaatcagg ggcggaggtg   2460
aagaaaccag gggcgtctgt gaaggtaagc tgtaaggcat ccggattgac aatcgaggat   2520
tattacatgc attgggtccg ccaggcacca gggcagggat tggagtggat ggggtggata   2580
gatcctgaaa atggggatac agagtatggc cctaagttcc agggcagagt tacgatgact   2640
cgagatacta gcattaatac ggcctacatg gagcttagcc gcctgcggtc cgatgacacg   2700
gccgtttatt attgcgccgt acacaatgcg cactacggga catggttcgc gtattggggt   2760
caaggaacgc tcgttactgt ctcaagtagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg ctcaaagcgg   3060
agtaggttgt tgcattccga ttacatgaat atgactcctc gccggcctgg gccgacaaga   3120
aaacattacc aaccctatgc ccccccacga gacttcgctg cgtacaggtc ccgagtgaag   3180
```

```
ttttcccgaa gcgcagacgc tccggcatat cagcaaggac agaatcagct gtataacgaa   3240
ctgaatttgg gacgccgcga ggagtatgac gtgcttgata aacgccgggg gagagacccg   3300
gaaatggggg gtaaaccccg aagaaagaat ccccaagaag gactctacaa tgaactccag   3360
aaggataaga tggcggaggc ctactcagaa ataggtatga agggcgaacg acgacgggga   3420
aaaggtcacg atggcctcta ccaagggttg agtacggcaa ccaaagatac gtacgatgca   3480
ctgcatatgc aggccctgcc tcccagataa taataaaatc gctatccatc gaagatggat   3540
gtgtgttggt tttttgtgtg tggagcaaca aatctgactt tgcatgtgca aacgccttca   3600
acaacagcat tattccagaa gacaccttct tccccagccc aggtaagggc agctttggtg   3660
ccttcgcagg ctgtttcctt gcttcaggaa tggccaggtt ctgcccagag ctctggtcaa   3720
tgatgtctaa aactcctctg attggtggtc tcggccttat ccattgccac caaaaccctc   3780
tttttactaa gaaacagtga gccttgttct ggcagtccag agaatgacac gggaaaaaag   3840
cagatgaaga gaaggtggca ggagagggca cgtggcccag cctcagtctc tccaactgag   3900
ttcctgcctg cctgcctttg ctcagactgt ttgcccctta ctgctcttct aggcctcatt   3960
ctaagcccct tctccaagtt gcctctcctt atttctccct gtctgccaaa aaatctttcc   4020
cagctcacta agtcagtctc acgcagtcac tcattaaccc accaatcact gattgtgccg   4080
gcacatgaat gcaccaggtg ttgaagtgga ggaattaaaa agtcagatga ggggtgtgcc   4140
cagaggaagc accattctag ttgggggagc ccatctgtca gctgggaaaa gtccaaataa   4200
cttcagattg gaatgtgttt taactcaggg ttgagaaaac agctaccttc aggacaaaag   4260
tcagggaagg gctctctgaa gaaatgctac ttgaagatac cagccctacc aagggcaggg   4320
agaggaccct atagaggcct gggacaggag ctcaatgaga aagg                     4364
```

<210> SEQ ID NO 64
<211> LENGTH: 4370
<212> TYPE: DNA
<213> ORGANISM: Artificial Sequence
<220> FEATURE:
<223> OTHER INFORMATION: Synthetic

<400> SEQUENCE: 64

```
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
```

```
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct tttcgcaacg ggtttgccg    1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccggacg tggtcatgac tcaaagccca ctttccttgc ccgtgactct cggacaaccg   2100
gcttcaatat cttgccgctc atcacagtcc ctgctgcata gcagtggtaa cacttatctt   2160
gagtggtacc aacagcggcc cggccaatct cctaggcccc tgatatataa gataagtact   2220
cgcttttccg ggtcccggga ccggttcagc gggtctggga gtggtacaga cttcacattg   2280
aagatttcac gagtagaagc cgaagacgtg ggtgtttatt actgcttcca aggatctcac   2340
gtgccatata cgtttggtgg gggcacaaaa gtcgagatta agggaggcgg aggatcagga   2400
ggtgggggaa gtggaggtgg tgggtcacaa gtacagctcg tgcaatcagg ggcggaggtg   2460
aagaaaccag gggcgtctgt gaaggtaagc tgtaaggcat ccggattgac aatcgaggat   2520
tattacatgc attgggtccg ccaggcacca gggcagggat tggagtggat ggggtggata   2580
gatcctgaaa atggggatac agagtatggc cctaagttcc agggcagagt tacgatgact   2640
cgagatacta gcattaatac ggcctacatg gagcttagcc gcctgcggtc cgatgacacg   2700
gccgtttatt attgcgccgt acacaatgcg cactacggga catggttcgc gtattggggt   2760
caaggaacgc tcgttactgt ctcaagtagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg caaacggggc   3060
agaaagaaac tcctgtatat attcaaacaa ccatttatga gaccagtaca aactactcaa   3120
gaggaagatg gctgtagctg ccgatttcca gaagaagaag aaggaggatg tgaactgcga   3180
gtgaagtttt cccgaagcgc agacgctccg gcatatcagc aaggacagaa tcagctgtat   3240
```

```
aacgaactga atttgggacg ccgcgaggag tatgacgtgc ttgataaacg ccgggggaga   3300

gacccggaaa tgggggggtaa accccgaaga aagaatcccc aagaaggact ctacaatgaa   3360

ctccagaagg ataagatggc ggaggcctac tcagaaatag gtatgaaggg cgaacgacga   3420

cggggaaaag gtcacgatgg cctctaccaa gggttgagta cggcaaccaa agatacgtac   3480

gatgcactgc atatgcaggc cctgcctccc agataataat aaaatcgcta tccatcgaag   3540

atggatgtgt gttggttttt tgtgtgtgga gcaacaaatc tgactttgca tgtgcaaacg   3600

ccttcaacaa cagcattatt ccagaagaca ccttcttccc cagcccaggt aagggcagct   3660

ttggtgcctt cgcaggctgt ttccttgctt caggaatggc caggttctgc ccagagctct   3720

ggtcaatgat gtctaaaact cctctgattg gtggtctcgg ccttatccat tgccaccaaa   3780

accctctttt tactaagaaa cagtgagcct tgttctggca gtccagagaa tgacacggga   3840

aaaaagcaga tgaagagaag gtggcaggag agggcacgtg gcccagcctc agtctctcca   3900

actgagttcc tgcctgcctg cctttgctca gactgtttgc cccttactgc tcttctaggc   3960

ctcattctaa gccccttctc caagttgcct ctccttattt ctccctgtct gccaaaaaat   4020

ctttcccagc tcactaagtc agtctcacgc agtcactcat taacccacca atcactgatt   4080

gtgccggcac atgaatgcac caggtgttga agtggaggaa ttaaaaagtc agatgagggg   4140

tgtgcccaga ggaagcacca ttctagttgg gggagcccat ctgtcagctg ggaaaagtcc   4200

aaataacttc agattggaat gtgttttaac tcagggttga gaaaacagct accttcagga   4260

caaaagtcag ggaagggctc tctgaagaaa tgctacttga agataccagc cctaccaagg   4320

gcagggagag gaccctatag aggcctggga caggagctca atgagaaagg              4370
```

```
<210> SEQ ID NO 65
<211> LENGTH: 1529
<212> TYPE: DNA
<213> ORGANISM: Artificial Sequence
<220> FEATURE:
<223> OTHER INFORMATION: Synthetic

<400> SEQUENCE: 65

caccatggcg cttccggtga cagcactgct cctccccttg gcgctgttgc tccacgcagc     60

aaggccgcaa gttcaactgg tccagtcagg cgctgaggtc aaaaagcccg gcgcgagcgt    120

aaaagtctcc tgcaaggcgt cagggttgac gatagaagat tattacatgc attgggtcag    180

acaggcaccc ggacagggat tggagtggat gggttggatc gacccggaaa acggtgacac    240

ggagtatggg ccgaagtttc aggggagggt cacaatgaca cgagatacgt ccataaatac    300

cgcttacatg gaactttctc ggcttcgctc tgatgataca gcagtttact actgcgctgt    360

tcataatgcc cattacggaa cctggttcgc gtactggggc caagggaccc tggttacggt    420

tagctctggt gggggtggaa gcgggggagg gggtagcgga ggtggcggaa gtgatgttgt    480

tatgacacag agtcccctgt cattgcccgt caccctcgga caaccagcta gcatttcatg    540

caggtctagt caaagcctcc ttcacagtag cggcaacacc tacctcgaat ggtatcaaca    600

acggccaggg caatctcctc gcccactcat atacaaaatc tctacacgct tctcaggtgt    660

tcccgaccgc ttcagcggtt ccggctctgg gacagacttt accttgaaaa taagcagggt    720

tgaagctgag gacgtagggg tatattattg ttttcagggc agtcacgtgc cgtacactgg    780

gggcggaacc aaagtcgaga taaagagtgc tgctgccttt gtcccggtat ttctcccagc    840

caaaccgacc acgactcccg ccccgcgccc tccgacaccc gctcccacca tcgcctctca    900
```

```
acctcttagt cttcgccccg aggcatgccg acccgccgcc gggggtgctg ttcatacgag    960

gggcttggac ttcgcttgtg atatttacat ttgggctccg ttggcgggta cgtgcggcgt   1020

ccttttgttg tcactcgtta ttactttgta ttgtaatcac aggaatcgct caaagcggag   1080

taggttgttg cattccgatt acatgaatat gactcctcgc cggcctgggc cgacaagaaa   1140

acattaccaa ccctatgccc ccccacgaga cttcgctgcg tacaggtccc gagtgaagtt   1200

ttcccgaagc gcagacgctc cggcatatca gcaaggacag aatcagctgt ataacgaact   1260

gaatttggga cgccgcgagg agtatgacgt gcttgataaa cgccgggga gagacccgga   1320

aatgggggt aaaccccgaa gaaagaatcc ccaagaagga ctctacaatg aactccagaa   1380

ggataagatg gcggaggcct actcagaaat aggtatgaag ggcgaacgac gacggggaaa   1440

aggtcacgat ggcctctacc aagggttgag tacggcaacc aaagatacgt acgatgcact   1500

gcatatgcag gccctgcctc ccagataat                                    1529
```

```
<210> SEQ ID NO 66
<211> LENGTH: 508
<212> TYPE: PRT
<213> ORGANISM: Artificial Sequence
<220> FEATURE:
<223> OTHER INFORMATION: Synthetic

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Asn Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Gln Gln Arg Pro Gly Gln Ser Pro Arg Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255
```

```
Tyr Thr Phe Gly Gly Gly Thr Lys Val Glu Ile Lys Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Ser Lys Arg Ser Arg Leu Leu His Ser Asp Tyr Met
        355                 360                 365

Asn Met Thr Pro Arg Arg Pro Gly Pro Thr Arg Lys His Tyr Gln Pro
    370                 375                 380

Tyr Ala Pro Pro Arg Asp Phe Ala Ala Tyr Arg Ser Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505
```

<210> SEQ ID NO 67
<211> LENGTH: 1536
<212> TYPE: DNA
<213> ORGANISM: Artificial Sequence
<220> FEATURE:
<223> OTHER INFORMATION: Synthetic

<400> SEQUENCE: 67

```
ccaccatggc gcttccggtg acagcactgc tcctcccctt ggcgctgttg ctccacgcag     60

caaggccgca agttcaactg gtccagtcag gcgctgaggt caaaaagccc ggcgcgagcg    120

taaaagtctc ctgcaaggcg tcagggttga cgatagaaga ttattacatg cattgggtca    180

gacaggcacc cggacaggga ttggagtgga tgggttggat cgacccggaa aacggtgaca    240

cggagtatgg gccgaagttt caggggaggg tcacaatgac acgagatacg tccataaata    300

ccgcttacat ggaactttct cggcttcgct ctgatgatac agcagtttac tactgcgctg    360

ttcataatgc ccattacgga acctggttcg cgtactgggg ccaagggacc ctggttacgg    420

ttagctctgg tgggggtgga agcgggggag gggtagcgg aggtggcgga agtgatgttg     480

ttatgacaca gagtcccctg tcattgcccg tcaccctcgg acaaccagct agcatttcat    540

gcaggtctag tcaaagcctc cttcacagta gcggcaacac ctacctcgaa tggtatcaac    600
```

```
aacggccagg gcaatctcct cgcccactca tatacaaaat ctctacacgc ttctcaggtg    660

ttcccgaccg cttcagcggt tccggctctg ggacagactt taccttgaaa ataagcaggg    720

ttgaagctga ggacgtaggg gtatattatt gttttcaggg cagtcacgtg ccgtacactg    780

ggggcggaac caaagtcgag ataaagagtg ctgctgcctt tgtcccggta tttctcccag    840

ccaaaccgac cacgactccc gccccgcgcc ctccgacacc cgctcccacc atcgcctctc    900

aacctcttag tcttcgcccc gaggcatgcc gacccgccgc cgggggtgct gttcatacga    960

ggggcttgga cttcgcttgt gatatttaca tttgggctcc gttggcgggt acgtgcggcg   1020

tccttttgtt gtcactcgtt attactttgt attgtaatca caggaatcgc aaacggggca   1080

gaaagaaact cctgtatata ttcaaacaac catttatgag accagtacaa actactcaag   1140

aggaagatgg ctgtagctgc cgatttccag aagaagaaga aggaggatgt gaactgcgag   1200

tgaagttttc ccgaagcgca gacgctccgg catatcagca aggacagaat cagctgtata   1260

acgaactgaa tttgggacgc cgcgaggagt atgacgtgct tgataaacgc cgggggagag   1320

acccggaaat gggggggtaaa ccccgaagaa agaatcccca agaaggactc tacaatgaac   1380

tccagaagga taagatggcg gaggcctact cagaaatagg tatgaagggc gaacgacgac   1440

ggggaaaagg tcacgatggc ctctaccaag ggttgagtac ggcaaccaaa gatacgtacg   1500

atgcactgca tatgcaggcc ctgcctccca gataat                             1536
```

```
<210> SEQ ID NO 68
<211> LENGTH: 510
<212> TYPE: PRT
<213> ORGANISM: Artificial Sequence
<220> FEATURE:
<223> OTHER INFORMATION: Synthetic

<400> SEQUENCE: 68

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Asn Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Gln Gln Arg Pro Gly Gln Ser Pro Arg Pro Leu
```

```
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Phe Gly Gly Gly Thr Lys Val Glu Ile Lys Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510
```

<210> SEQ ID NO 69
<211> LENGTH: 738
<212> TYPE: DNA
<213> ORGANISM: Artificial Sequence
<220> FEATURE:
<223> OTHER INFORMATION: Synthetic

<400> SEQUENCE: 69

```
caagttcaac tggtccagtc aggcgctgag gtcaaaaagc ccggcgcgag cgtaaaagtc      60

tcctgcaagg cgtcagggtt gacgatagaa gattattaca tgcattgggt cagacaggca     120

cccggacagg gattggagtg gatgggttgg atcgacccgg aaaacggtga cacggagtat     180

gggccgaagt ttcaggggag ggtcacaatg acacgagata cgtccataaa taccgcttac     240

atggaacttt ctcggcttcg ctctgatgat acagcagttt actactgcgc tgttcataat     300
```

```
gcccattacg gaacctggtt cgcgtactgg ggccaaggga ccctggttac ggttagctct    360

ggtgggggtg gaagcggggg agggggtagc ggaggtggcg gaagtgatgt tgttatgaca    420

cagagtcccc tgtcattgcc cgtcaccctc ggacaaccag ctagcatttc atgcaggtct    480

agtcaaagcc tccttcacag tagcggcaac acctacctcg aatggtatca acaacggcca    540

gggcaatctc ctcgcccact catatacaaa atctctacac gcttctcagg tgttcccgac    600

cgcttcagcg gttccggctc tgggacagac tttaccttga aaataagcag ggttgaagct    660

gaggacgtag ggtatatta ttgttttcag ggcagtcacg tgccgtacac tgggggcgga    720

accaaagtcg agataaag                                                  738
```

<210> SEQ ID NO 70
<211> LENGTH: 247
<212> TYPE: PRT
<213> ORGANISM: Artificial Sequence
<220> FEATURE:
<223> OTHER INFORMATION: Synthetic

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Leu Gly Gln Pro Ala Ser Ile Ser Cys Arg Ser
145                 150                 155                 160

Ser Gln Ser Leu Leu His Ser Ser Gly Asn Thr Tyr Leu Glu Trp Tyr
                165                 170                 175

Gln Gln Arg Pro Gly Gln Ser Pro Arg Pro Leu Ile Tyr Lys Ile Ser
            180                 185                 190

Thr Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Tyr Thr Phe Gly Gly
225                 230                 235                 240

Gly Thr Lys Val Glu Ile Lys
                245
```

<210> SEQ ID NO 71
<211> LENGTH: 4361
<212> TYPE: DNA
<213> ORGANISM: Artificial Sequence
<220> FEATURE:
<223> OTHER INFORMATION: Synthetic

<400> SEQUENCE: 71

```
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcaag ttcaactggt ccagtcaggc gctgaggtca aaaagcccgg cgcgagcgta   2100
aaagtctcct gcaaggcgtc agggttgacg atagaagatt attacatgca ttgggtcaga   2160
caggcacccg gacagggatt ggagtggatg ggttggatcg acccggaaaa cggtgacacg   2220
```

-continued

```
gagtatgggc cgaagtttca ggggagggtc acaatgacac gagatacgtc cataaatacc   2280
gcttacatgg aactttctcg gcttcgctct gatgatacag cagtttacta ctgcgctgtt   2340
cataatgccc attacggaac ctggttcgcg tactggggcc aagggaccct ggttacggtt   2400
agctctggtg gggtggaag cgggggaggg ggtagcggag gtggcggaag tgatgttgtt   2460
atgacacaga gtcccctgtc attgcccgtc accctcggac aaccagctag catttcatgc   2520
aggtctagtc aaagcctcct tcacagtagc ggcaacacct acctcgaatg gtatcaacaa   2580
cggccagggc aatctcctcg cccactcata tacaaaatct ctacacgctt ctcaggtgtt   2640
cccgaccgct tcagcggttc cggctctggg acagacttta ccttgaaaat aagcagggtt   2700
gaagctgagg acgtaggggt atattattgt tttcagggca gtcacgtgcc gtacactggg   2760
ggcggaacca aagtcgagat aaagagtgct gctgcctttg tcccggtatt tctcccagcc   2820
aaaccgacca cgactcccgc cccgcgccct ccgacacccg ctcccaccat cgcctctcaa   2880
cctcttagtc ttcgccccga ggcatgccga cccgccgccg gggtgctgt tcatacgagg   2940
ggcttggact tcgcttgtga tatttacatt tgggctccgt tggcgggtac gtgcggcgtc   3000
cttttgttgt cactcgttat tactttgtat tgtaatcaca ggaatcgctc aaagcggagt   3060
aggttgttgc attccgatta catgaatatg actcctcgcc ggcctgggcc gacaagaaaa   3120
cattaccaac cctatgcccc cccacgagac ttcgctgcgt acaggtcccg agtgaagttt   3180
tcccgaagcg cagacgctcc ggcatatcag caaggacaga atcagctgta taacgaactg   3240
aatttgggac gccgcgagga gtatgacgtg cttgataaac gccgggggag agacccggaa   3300
atgggggggta aaccccgaag aaagaatccc caagaaggac tctacaatga actccagaag   3360
gataagatgg cggaggccta ctcagaaata ggtatgaagg gcgaacgacg acggggaaaa   3420
ggtcacgatg gcctctacca agggttgagt acggcaacca aagatacgta cgatgcactg   3480
catatgcagg ccctgcctcc cagataataa taaaatcgct atccatcgaa gatggatgtg   3540
tgttggtttt ttgtgtgtgg agcaacaaat ctgactttgc atgtgcaaac gccttcaaca   3600
acagcattat tccagaagac accttcttcc ccagcccagg taagggcagc tttggtgcct   3660
tcgcaggctg tttccttgct tcaggaatgg ccaggttctg cccagagctc tggtcaatga   3720
tgtctaaaac tcctctgatt ggtggtctcg gccttatcca ttgccaccaa aaccctcttt   3780
ttactaagaa acagtgagcc ttgttctggc agtccagaga atgacacggg aaaaaagcag   3840
atgaagagaa ggtggcagga gagggcacgt ggcccagcct cagtctctcc aactgagttc   3900
ctgcctgcct gcctttgctc agactgtttg ccccttactg ctcttctagg cctcattcta   3960
agccccttct ccaagttgcc tctccttatt tctccctgtc tgccaaaaaa tctttcccag   4020
ctcactaagt cagtctcacg cagtcactca ttaacccacc aatcactgat tgtgccggca   4080
catgaatgca ccaggtgttg aagtggagga attaaaaagt cagatgaggg gtgtgcccag   4140
aggaagcacc attctagttg gggagcccca tctgtcagct gggaaaagtc caaataactt   4200
cagattggaa tgtgttttaa ctcagggttg agaaaacagc taccttcagg acaaaagtca   4260
gggaagggct ctctgaagaa atgctacttg aagataccag ccctaccaag ggcagggaga   4320
ggaccctata gaggcctggg acaggagctc aatgagaaag g                        4361
```

```
<210> SEQ ID NO 72
<211> LENGTH: 4367
<212> TYPE: DNA
<213> ORGANISM: Artificial Sequence
<220> FEATURE:
<223> OTHER INFORMATION: Synthetic
```

<400> SEQUENCE: 72

```
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct tttcgcaacg ggtttgccg    1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcaag ttcaactggt ccagtcaggc gctgaggtca aaaagcccgg cgcgagcgta   2100
aaagtctcct gcaaggcgtc agggttgacg atagaagatt attacatgca ttgggtcaga   2160
caggcacccg gacagggatt ggagtggatg ggttggatcg acccggaaaa cggtgacacg   2220
gagtatgggc cgaagtttca ggggagggtc acaatgacac gagatacgtc cataaatacc   2280
```

```
gcttacatgg aactttctcg gcttcgctct gatgatacag cagtttacta ctgcgctgtt   2340
cataatgccc attacggaac ctggttcgcg tactggggcc aagggaccct ggttacggtt   2400
agctctggtg ggggtggaag cgggggaggg ggtagcggag gtggcggaag tgatgttgtt   2460
atgacacaga gtcccctgtc attgcccgtc accctcggac aaccagctag catttcatgc   2520
aggtctagtc aaagcctcct tcacagtagc ggcaacacct acctcgaatg gtatcaacaa   2580
cggccagggc aatctcctcg cccactcata tacaaaatct ctacacgctt ctcaggtgtt   2640
cccgaccgct tcagcggttc cggctctggg acagacttta ccttgaaaat aagcagggtt   2700
gaagctgagg acgtaggggt atattattgt tttcagggca gtcacgtgcc gtacactggg   2760
ggcggaacca aagtcgagat aaagagtgct gctgcctttg tcccggtatt tctcccagcc   2820
aaaccgacca cgactcccgc cccgcgccct ccgacacccg ctcccaccat cgcctctcaa   2880
cctcttagtc ttcgccccga ggcatgccga cccgccgccg gggtgctgt tcatacgagg    2940
ggcttggact tcgcttgtga tatttacatt tgggctccgt tggcgggtac gtgcggcgtc   3000
cttttgttgt cactcgttat tactttgtat tgtaatcaca ggaatcgcaa acggggcaga   3060
aagaaactcc tgtatatatt caaacaacca tttatgagac cagtacaaac tactcaagag   3120
gaagatggct gtagctgccg atttccagaa gaagaagaag gaggatgtga actgcgagtg   3180
aagttttccc gaagcgcaga cgctccggca tatcagcaag gacagaatca gctgtataac   3240
gaactgaatt tgggacgccg cgaggagtat gacgtgcttg ataaacgccg gggagagac    3300
ccggaaatgg ggggtaaacc ccgaagaaag aatccccaag aaggactcta caatgaactc   3360
cagaaggata agatggcgga ggcctactca gaaataggta tgaagggcga acgacgacgg   3420
ggaaaaggtc acgatggcct ctaccaaggg ttgagtacgg caaccaaaga tacgtacgat   3480
gcactgcata tgcaggccct gcctcccaga taataataaa atcgctatcc atcgaagatg   3540
gatgtgtgtt ggtttttgt gtgtggagca acaaatctga ctttgcatgt gcaaacgcct    3600
tcaacaacag cattattcca gaagacacct tcttccccag cccaggtaag ggcagctttg   3660
gtgccttcgc aggctgtttc cttgcttcag gaatggccag gttctgccca gagctctggt   3720
caatgatgtc taaaactcct ctgattggtg gtctcggcct tatccattgc caccaaaacc   3780
ctctttttac taagaaacag tgagccttgt tctggcagtc cagagaatga cacgggaaaa   3840
aagcagatga agagaaggtg gcaggagagg gcacgtggcc cagcctcagt ctctccaact   3900
gagttcctgc ctgcctgcct ttgctcagac tgtttgcccc ttactgctct tctaggcctc   3960
attctaagcc ccttctccaa gttgcctctc cttatttctc cctgtctgcc aaaaaatctt   4020
tcccagctca ctaagtcagt ctcacgcagt cactcattaa cccaccaatc actgattgtg   4080
ccggcacatg aatgcaccag gtgttgaagt ggaggaatta aaaagtcaga tgaggggtgt   4140
gcccagagga agcaccattc tagttggggg agcccatctg tcagctggga aaagtccaaa   4200
taacttcaga ttggaatgtg ttttaactca gggttgagaa aacagctacc ttcaggacaa   4260
aagtcaggga agggctctct gaagaaatgc tacttgaaga taccagccct accaagggca   4320
gggagaggac cctatagagg cctgggacag gagctcaatg agaaagg                 4367
```

<210> SEQ ID NO 73
<211> LENGTH: 21
<212> TYPE: PRT
<213> ORGANISM: Artificial Sequence
<220> FEATURE:
<223> OTHER INFORMATION: Synthetic

<400> SEQUENCE: 73

```
Met Ala Leu Pro Val Thr Ala Leu Leu Leu Pro Leu Ala Leu Leu Leu
1               5                   10                  15

His Ala Ala Arg Pro
            20


<210> SEQ ID NO 74
<211> LENGTH: 261
<212> TYPE: DNA
<213> ORGANISM: Artificial Sequence
<220> FEATURE:
<223> OTHER INFORMATION: Synthetic

<400> SEQUENCE: 74

gctgctgcct ttgtcccggt atttctccca gccaaaccga ccacgactcc cgccccgcgc      60

cctccgacac ccgctcccac catcgcctct caacctctta gtcttcgccc cgaggcatgc     120

cgacccgccg ccgggggtgc tgttcatacg aggggcttgg acttcgcttg tgatatttac     180

atttgggctc cgttggcggg tacgtgcggc gtccttttgt tgtcactcgt tattactttg     240

tattgtaatc acaggaatcg c                                               261


<210> SEQ ID NO 75
<211> LENGTH: 88
<212> TYPE: PRT
<213> ORGANISM: Artificial Sequence
<220> FEATURE:
<223> OTHER INFORMATION: Synthetic

<400> SEQUENCE: 75

Ser Ala Ala Ala Phe Val Pro Val Phe Leu Pro Ala Lys Pro Thr Thr
1               5                   10                  15

Thr Pro Ala Pro Arg Pro Pro Thr Pro Ala Pro Thr Ile Ala Ser Gln
            20                  25                  30

Pro Leu Ser Leu Arg Pro Glu Ala Cys Arg Pro Ala Ala Gly Gly Ala
        35                  40                  45

Val His Thr Arg Gly Leu Asp Phe Ala Cys Asp Ile Tyr Ile Trp Ala
    50                  55                  60

Pro Leu Ala Gly Thr Cys Gly Val Leu Leu Leu Ser Leu Val Ile Thr
65                  70                  75                  80

Leu Tyr Cys Asn His Arg Asn Arg
                85


<210> SEQ ID NO 76
<211> LENGTH: 252
<212> TYPE: DNA
<213> ORGANISM: Artificial Sequence
<220> FEATURE:
<223> OTHER INFORMATION: Synthetic

<400> SEQUENCE: 76

tttgtcccgg tatttctccc agccaaaccg accacgactc ccgccccgcg ccctccgaca      60

cccgctccca ccatcgcctc tcaacctctt agtcttcgcc ccgaggcatg ccgacccgcc     120

gccgggggtg ctgttcatac gaggggcttg gacttcgctt gtgatattta catttgggct     180

ccgttggcgg gtacgtgcgg cgtccttttg ttgtcactcg ttattacttt gtattgtaat     240

cacaggaatc gc                                                         252


<210> SEQ ID NO 77
<211> LENGTH: 84
<212> TYPE: PRT
```

<213> ORGANISM: Artificial Sequence
<220> FEATURE:
<223> OTHER INFORMATION: Synthetic

<400> SEQUENCE: 77

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 78
<211> LENGTH: 800
<212> TYPE: DNA
<213> ORGANISM: Artificial Sequence
<220> FEATURE:
<223> OTHER INFORMATION: Synthetic

<400> SEQUENCE: 78

```
gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg ggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgtgtacca    660

gctgagagac tctaaatcca gtgacaagtc tgtctgccta ttcaccgatt ttgattctca    720

aacaaatgtg tcacaaagta aggattctga tgtgtatatc acagacaaaa ctgtgctaga    780

catgaggtct atggacttca                                                800
```

<210> SEQ ID NO 79
<211> LENGTH: 1178
<212> TYPE: DNA
<213> ORGANISM: Artificial Sequence
<220> FEATURE:
<223> OTHER INFORMATION: Synthetic

<400> SEQUENCE: 79

```
ggctccggtg cccgtcagtg ggcagagcgc acatcgccca cagtccccga gaagttgggg     60

ggaggggtcg gcaattgaac cggtgcctag agaaggtggc gcggggtaaa ctgggaaagt    120

gatgtcgtgt actggctccg cctttttccc gagggtgggg gagaaccgta tataagtgca    180

gtagtcgccg tgaacgttct ttttcgcaac gggtttgccg ccagaacaca ggtaagtgcc    240
```

```
gtgtgtggtt cccgcgggcc tggcctcttt acgggttatg gcccttgcgt gccttgaatt    300

acttccactg gctgcagtac gtgattcttg atcccgagct tcgggttgga agtgggtggg    360

agagttcgag gccttgcgct taaggagccc cttcgcctcg tgcttgagtt gaggcctggc    420

ctgggcgctg gggccgccgc gtgcgaatct ggtggcacct tcgcgcctgt ctcgctgctt    480

tcgataagtc tctagccatt taaaattttt gatgacctgc tgcgacgctt tttttctggc    540

aagatagtct tgtaaatgcg ggccaagatc tgcacactgg tatttcggtt tttggggccg    600

cgggcggcga cggggcccgt gcgtcccagc gcacatgttc ggcgaggcgg ggcctgcgag    660

cgcggccacc gagaatcgga cgggggtagt ctcaagctgg ccggcctgct ctggtgcctg    720

gcctcgcgcc gccgtgtatc gccccgccct gggcggcaag gctggcccgg tcggcaccag    780

ttgcgtgagc ggaaagatgg ccgcttcccg gccctgctgc agggagctca aaatggagga    840

cgcggcgctc gggagagcgg gcgggtgagt cacccacaca aaggaaaagg gcctttccgt    900

cctcagccgt cgcttcatgt gactccacgg agtaccgggc gccgtccagg cacctcgatt    960

agttctcgag cttttggagt acgtcgtctt taggttgggg ggaggggttt tatgcgatgg   1020

agtttcccca cactgagtgg gtggagactg aagttaggcc agcttggcac ttgatgtaat   1080

tctccttgga atttgccctt tttgagtttg gatcttggtt cattctcaag cctcagacag   1140

tggttcaaag tttttttctt ccatttcagg tgtcgtga                           1178


<210> SEQ ID NO 80
<211> LENGTH: 49
<212> TYPE: DNA
<213> ORGANISM: Artificial Sequence
<220> FEATURE:
<223> OTHER INFORMATION: Synthetic

<400> SEQUENCE: 80

aataaaatcg ctatccatcg aagatggatg tgtgttggtt ttttgtgtg                 49


<210> SEQ ID NO 81
<211> LENGTH: 804
<212> TYPE: DNA
<213> ORGANISM: Artificial Sequence
<220> FEATURE:
<223> OTHER INFORMATION: Synthetic

<400> SEQUENCE: 81

tggagcaaca aatctgactt tgcatgtgca aacgccttca acaacagcat tattccagaa     60

gacaccttct tccccagccc aggtaagggc agctttggtg ccttcgcagg ctgtttcctt    120

gcttcaggaa tggccaggtt ctgcccagag ctctggtcaa tgatgtctaa aactcctctg    180

attggtggtc tcggccttat ccattgccac caaaaccctc tttttactaa gaaacagtga    240

gccttgttct ggcagtccag agaatgacac gggaaaaaag cagatgaaga gaaggtggca    300

ggagagggca cgtggcccag cctcagtctc tccaactgag ttcctgcctg cctgcctttg    360

ctcagactgt ttgcccctta ctgctcttct aggcctcatt ctaagcccct tctccaagtt    420

gcctctcctt atttctccct gtctgccaaa aaatctttcc cagctcacta agtcagtctc    480

acgcagtcac tcattaaccc accaatcact gattgtgccg gcacatgaat gcaccaggtg    540

ttgaagtgga ggaattaaaa agtcagatga ggggtgtgcc cagaggaagc accattctag    600

ttgggggagc ccatctgtca gctgggaaaa gtccaaataa cttcagattg gaatgtgttt    660

taactcaggg ttgagaaaac agctaccttc aggacaaaag tcagggaagg gctctctgaa    720

gaaatgctac ttgaagatac cagccctacc aagggcaggg agaggaccct atagaggcct    780
```

gggacaggag ctcaatgaga aagg 804

<210> SEQ ID NO 82
<211> LENGTH: 247
<212> TYPE: PRT
<213> ORGANISM: Artificial Sequence
<220> FEATURE:
<223> OTHER INFORMATION: Synthetic

<400> SEQUENCE: 82

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Leu Thr Ile Glu Asp Tyr Tyr
145                 150                 155                 160

Met His Trp Val Arg Gln Ala Pro Gly Gln Gly Leu Glu Trp Met Gly
                165                 170                 175

Trp Ile Asp Pro Glu Asn Gly Asp Thr Glu Tyr Gly Pro Lys Phe Gln
            180                 185                 190

Gly Arg Val Thr Met Thr Arg Asp Thr Ser Ile Ser Thr Ala Tyr Met
        195                 200                 205

Glu Leu Ser Arg Leu Arg Ser Asp Asp Thr Ala Val Tyr Tyr Cys Ala
    210                 215                 220

Val His Asn Ala His Tyr Gly Thr Trp Phe Ala Tyr Trp Gly Gln Gly
225                 230                 235                 240

Thr Leu Val Thr Val Ser Ser
                245
```

<210> SEQ ID NO 83
<211> LENGTH: 247
<212> TYPE: PRT
<213> ORGANISM: Artificial Sequence
<220> FEATURE:
<223> OTHER INFORMATION: Synthetic

<400> SEQUENCE: 83

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Leu Gln Arg Pro Gly Gln Ser
        35                  40                  45
```

```
Pro Lys Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Leu Thr Ile Glu Asp Tyr Tyr
145                 150                 155                 160

Met His Trp Val Arg Gln Ala Pro Gly Gln Gly Leu Glu Trp Met Gly
                165                 170                 175

Trp Ile Asp Pro Glu Asn Gly Asp Thr Glu Tyr Gly Pro Lys Phe Gln
            180                 185                 190

Gly Arg Val Thr Met Thr Arg Asp Thr Ser Ile Asn Thr Ala Tyr Met
        195                 200                 205

Glu Leu Ser Arg Leu Arg Ser Asp Asp Thr Ala Val Tyr Tyr Cys Ala
    210                 215                 220

Val His Asn Ala His Tyr Gly Thr Trp Phe Ala Tyr Trp Gly Gln Gly
225                 230                 235                 240

Thr Leu Val Thr Val Ser Ser
                245
```

<210> SEQ ID NO 84
<211> LENGTH: 247
<212> TYPE: PRT
<213> ORGANISM: Artificial Sequence
<220> FEATURE:
<223> OTHER INFORMATION: Synthetic

<400> SEQUENCE: 84

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Leu Gln Arg Pro Gly Gln Ser
        35                  40                  45

Pro Lys Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Leu Thr Ile Glu Asp Tyr Tyr
145                 150                 155                 160
```

```
Met His Trp Val Arg Gln Ala Pro Gly Gln Gly Leu Glu Trp Met Gly
                165                 170                 175

Trp Ile Asp Pro Glu Asn Gly Asp Thr Glu Tyr Gly Pro Lys Phe Gln
            180                 185                 190

Gly Arg Val Thr Met Thr Arg Asp Thr Ser Ile Ser Thr Ala Tyr Met
        195                 200                 205

Glu Leu Ser Arg Leu Arg Ser Asp Asp Thr Ala Val Tyr Tyr Cys Ala
    210                 215                 220

Val His Asn Ala His Tyr Gly Thr Trp Phe Ala Tyr Trp Gly Gln Gly
225                 230                 235                 240

Thr Leu Val Thr Val Ser Ser
                245
```

```
<210> SEQ ID NO 85
<211> LENGTH: 247
<212> TYPE: PRT
<213> ORGANISM: Artificial Sequence
<220> FEATURE:
<223> OTHER INFORMATION: Synthetic

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Leu Gly Gln Pro Ala Ser Ile Ser Cys Arg Ser
145                 150                 155                 160

Ser Gln Ser Leu Leu His Ser Ser Gly Asn Thr Tyr Leu Glu Trp Tyr
                165                 170                 175

Gln Gln Arg Pro Gly Gln Ser Pro Arg Pro Leu Ile Tyr Lys Ile Ser
            180                 185                 190

Thr Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Tyr Thr Phe Gly Gly
225                 230                 235                 240

Gly Thr Lys Val Glu Ile Lys
                245
```

```
<210> SEQ ID NO 86
```

```
<211> LENGTH: 247
<212> TYPE: PRT
<213> ORGANISM: Artificial Sequence
<220> FEATURE:
<223> OTHER INFORMATION: Synthetic

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Leu Gly Gln Pro Ala Ser Ile Ser Cys Arg Ser
145                 150                 155                 160

Ser Gln Ser Leu Leu His Ser Ser Gly Asn Thr Tyr Leu Glu Trp Tyr
                165                 170                 175

Leu Gln Arg Pro Gly Gln Ser Pro Lys Pro Leu Ile Tyr Lys Ile Ser
            180                 185                 190

Thr Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Tyr Thr Phe Gly Gly
225                 230                 235                 240

Gly Thr Lys Val Glu Ile Lys
                245


<210> SEQ ID NO 87
<211> LENGTH: 247
<212> TYPE: PRT
<213> ORGANISM: Artificial Sequence
<220> FEATURE:
<223> OTHER INFORMATION: Synthetic

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Ser Thr Ala Tyr
```

```
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Leu Gly Gln Pro Ala Ser Ile Ser Cys Arg Ser
145                 150                 155                 160

Ser Gln Ser Leu Leu His Ser Ser Gly Asn Thr Tyr Leu Glu Trp Tyr
                165                 170                 175

Leu Gln Arg Pro Gly Gln Ser Pro Lys Pro Leu Ile Tyr Lys Ile Ser
            180                 185                 190

Thr Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Tyr Thr Phe Gly Gly
225                 230                 235                 240

Gly Thr Lys Val Glu Ile Lys
                245


<210> SEQ ID NO 88
<211> LENGTH: 112
<212> TYPE: PRT
<213> ORGANISM: Artificial Sequence
<220> FEATURE:
<223> OTHER INFORMATION: Synthetic

<400> SEQUENCE: 88

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Leu Gln Arg Pro Gly Gln Ser
        35                  40                  45

Pro Lys Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110


<210> SEQ ID NO 89

<400> SEQUENCE: 89

000


<210> SEQ ID NO 90
<211> LENGTH: 120
<212> TYPE: PRT
<213> ORGANISM: Artificial Sequence
<220> FEATURE:
```

<223> OTHER INFORMATION: Synthetic

<400> SEQUENCE: 90

```
Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120
```

<210> SEQ ID NO 91

<400> SEQUENCE: 91

000

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
agagcaacag tgctgtggcc 20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
agagcaacag ugcuguggcc 20

<210> SEQ ID NO 94
<211> LENGTH: 22
<212> TYPE: PRT
<213> ORGANISM: Artificial Sequence
<220> FEATURE:
<223> OTHER INFORMATION: Synthetic

<400> SEQUENCE: 94

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 95
<211> LENGTH: 1539
<212> TYPE: DNA

```
<213> ORGANISM: Artificial Sequence
<220> FEATURE:
<223> OTHER INFORMATION: Synthetic

<400> SEQUENCE: 95

ccaccatggc gcttccggtg acagcactgc tcctcccctt ggcgctgttg ctccacgcag     60

caaggccgga tgtcgttatg acacaatctc ccttgagttt gccggttacc ttgggacaac    120

ctgctagtat ttcatgtagg agttctcaaa gtctcttgca ctcctcaggg aacacctacc    180

tcgaatggta ccaacaacgc cctggccaaa gcccgcggcc cttgatatac aaaatatcaa    240

caagatttag cggggtaccc gatagattca gcggctctgg cagcgggacg gattttaccc    300

tgaaaattag tcgcgtagaa gctgaagacg ttggtgtgta ttactgcttt caagggagcc    360

atgtgcctta cacatttgga ggaggcacca aggtcgagat taagggaggg ggtggatcag    420

gtgggggtgg gtccggaggc ggcggcagtc aagtgcagtt ggttcaatca ggagctgaag    480

ttaaaaagcc aggagcttca gtcaaggttt catgcaaggc gtccggtctc actatagagg    540

attactacat gcactgggtg cggcaagctc caggccaggg gctggagtgg atgggatgga    600

ttgatccgga aaacggggac acagagtatg ggcccaaatt ccaaggccgg gtgacaatga    660

ccagagatac tagtatttca acagcataca tggagctgtc acggctgagg tcagacgata    720

cggcagtcta ctattgtgca gtacataacg cacattatgg tacgtggttc gcttattggg    780

gtcaaggtac cctggtcacg gtaagttcaa gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140

aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccggggga   1320

gagacccgga aatggggggt aaaccccgaa gaaagaatcc ccaagaagga ctctacaatg   1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539


<210> SEQ ID NO 96
<211> LENGTH: 509
<212> TYPE: PRT
<213> ORGANISM: Artificial Sequence
<220> FEATURE:
<223> OTHER INFORMATION: Synthetic

<400> SEQUENCE: 96

Ala Leu Pro Val Thr Ala Leu Leu Leu Pro Leu Ala Leu Leu Leu His
1               5                   10                  15

Ala Ala Arg Pro Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Leu His Ser Ser Gly Asn Thr Tyr Leu Glu Trp Tyr Gln Gln Arg
    50                  55                  60
```

```
Pro Gly Gln Ser Pro Arg Pro Leu Ile Tyr Lys Ile Ser Thr Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser His Val Pro Tyr Thr Phe Gly Gly Gly Thr Lys
        115                 120                 125

Val Glu Ile Lys Gly Gly Gly Gly Ser Gly Gly Gly Gly Ser Gly Gly
    130                 135                 140

Gly Gly Ser Gln Val Gln Leu Val Gln Ser Gly Ala Glu Val Lys Lys
145                 150                 155                 160

Pro Gly Ala Ser Val Lys Val Ser Cys Lys Ala Ser Gly Leu Thr Ile
                165                 170                 175

Glu Asp Tyr Tyr Met His Trp Val Arg Gln Ala Pro Gly Gln Gly Leu
            180                 185                 190

Glu Trp Met Gly Trp Ile Asp Pro Glu Asn Gly Asp Thr Glu Tyr Gly
        195                 200                 205

Pro Lys Phe Gln Gly Arg Val Thr Met Thr Arg Asp Thr Ser Ile Ser
    210                 215                 220

Thr Ala Tyr Met Glu Leu Ser Arg Leu Arg Ser Asp Asp Thr Ala Val
225                 230                 235                 240

Tyr Tyr Cys Ala Val His Asn Ala His Tyr Gly Thr Trp Phe Ala Tyr
                245                 250                 255

Trp Gly Gln Gly Thr Leu Val Thr Val Ser Ser Ser Ala Ala Ala Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
            340                 345                 350

Arg Asn Arg Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480
```

```
Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 97
<211> LENGTH: 741
<212> TYPE: DNA
<213> ORGANISM: Artificial Sequence
<220> FEATURE:
<223> OTHER INFORMATION: Synthetic

<400> SEQUENCE: 97

gatgtcgtta tgacacaatc tcccttgagt ttgccggtta ccttgggaca acctgctagt      60

atttcatgta ggagttctca aagtctcttg cactcctcag ggaacaccta cctcgaatgg     120

taccaacaac gccctggcca aagcccgcgg cccttgatat acaaaatatc aacaagattt     180

agcggggtac ccgatagatt cagcggctct ggcagcggga cggattttac cctgaaaatt     240

agtcgcgtag aagctgaaga cgttggtgtg tattactgct ttcaagggag ccatgtgcct     300

tacacatttg gaggaggcac caaggtcgag attaagggag ggggtggatc aggtgggggt     360

gggtccggag gcggcggcag tcaagtgcag ttggttcaat caggagctga agttaaaaag     420

ccaggagctt cagtcaaggt ttcatgcaag gcgtccggtc tcactataga ggattactac     480

atgcactggg tgcggcaagc tccaggccag gggctggagt ggatgggatg gattgatccg     540

gaaaacgggg acacagagta tggcccaaa ttccaaggcc gggtgacaat gaccagagat     600

actagtattt caacagcata catggagctg tcacggctga ggtcagacga tacggcagtc     660

tactattgtg cagtacataa cgcacattat ggtacgtggt tcgcttattg gggtcaaggt     720

accctggtca cggtaagttc a                                               741


<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 99
<211> LENGTH: 4370
```

```
<212> TYPE: DNA
<213> ORGANISM: Artificial Sequence
<220> FEATURE:
<223> OTHER INFORMATION: Synthetic

<400> SEQUENCE: 99

gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg gggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccggatg tcgttatgac acaatctccc ttgagtttgc cggttacctt gggacaacct   2100
gctagtattt catgtaggag ttctcaaagt ctcttgcact cctcagggaa cacctacctc   2160
```

gaatggtacc aacaacgccc tggccaaagc ccgcggccct tgatatacaa aatatcaaca 2220
agatttagcg gggtacccga tagattcagc ggctctggca gcgggacgga ttttaccctg 2280
aaaattagtc gcgtagaagc tgaagacgtt ggtgtgtatt actgctttca agggagccat 2340
gtgccttaca catttggagg aggcaccaag gtcgagatta agggaggggg tggatcaggt 2400
gggggtgggt ccggaggcgg cggcagtcaa gtgcagttgg ttcaatcagg agctgaagtt 2460
aaaaagccag gagcttcagt caaggtttca tgcaaggcgt ccggtctcac tatagaggat 2520
tactacatgc actgggtgcg gcaagctcca ggccaggggc tggagtggat gggatggatt 2580
gatccggaaa acggggacac agagtatggg cccaaattcc aaggccgggt gacaatgacc 2640
agagatacta gtatttcaac agcatacatg gagctgtcac ggctgaggtc agacgatacg 2700
gcagtctact attgtgcagt acataacgca cattatggta cgtggttcgc ttattggggt 2760
caaggtaccc tggtcacggt aagttcaagt gctgctgcct ttgtcccggt atttctccca 2820
gccaaaccga ccacgactcc cgccccgcgc cctccgacac ccgctcccac catcgcctct 2880
caacctctta gtcttcgccc cgaggcatgc cgacccgccg ccgggggtgc tgttcatacg 2940
aggggcttgg acttcgcttg tgatatttac atttgggctc cgttggcggg tacgtgcggc 3000
gtccttttgt tgtcactcgt tattactttg tattgtaatc acaggaatcg caaacggggc 3060
agaaagaaac tcctgtatat attcaaacaa ccatttatga gaccagtaca aactactcaa 3120
gaggaagatg gctgtagctg ccgatttcca gaagaagaag aaggaggatg tgaactgcga 3180
gtgaagtttt cccgaagcgc agacgctccg gcatatcagc aaggacagaa tcagctgtat 3240
aacgaactga atttgggacg ccgcgaggag tatgacgtgc ttgataaacg ccgggggaga 3300
gacccggaaa tggggggtaa accccgaaga aagaatcccc aagaaggact ctacaatgaa 3360
ctccagaagg ataagatggc ggaggcctac tcagaaatag gtatgaaggg cgaacgacga 3420
cggggaaaag gtcacgatgg cctctaccaa gggttgagta cggcaaccaa agatacgtac 3480
gatgcactgc atatgcaggc cctgcctccc agataataat aaaatcgcta tccatcgaag 3540
atggatgtgt gttggttttt tgtgtgtgga gcaacaaatc tgactttgca tgtgcaaacg 3600
ccttcaacaa cagcattatt ccagaagaca ccttcttccc cagcccaggt aagggcagct 3660
ttggtgcctt cgcaggctgt ttccttgctt caggaatggc caggttctgc ccagagctct 3720
ggtcaatgat gtctaaaact cctctgattg gtggtctcgg ccttatccat tgccaccaaa 3780
accctctttt tactaagaaa cagtgagcct tgttctggca gtccagagaa tgacacggga 3840
aaaaagcaga tgaagagaag gtggcaggag agggcacgtg gcccagcctc agtctctcca 3900
actgagttcc tgcctgcctg cctttgctca gactgtttgc cccttactgc tcttctaggc 3960
ctcattctaa gccccttctc caagttgcct ctccttattt ctccctgtct gccaaaaaat 4020
ctttcccagc tcactaagtc agtctcacgc agtcactcat taacccacca atcactgatt 4080
gtgccggcac atgaatgcac caggtgttga agtggaggaa ttaaaaagtc agatgagggg 4140
tgtgcccaga ggaagcacca ttctagttgg gggagcccat ctgtcagctg ggaaaagtcc 4200
aaataacttc agattggaat gtgttttaac tcagggttga gaaaacagct accttcagga 4260
caaaagtcag ggaagggctc tctgaagaaa tgctacttga agataccagc cctaccaagg 4320
gcagggagag gaccctatag aggcctggga caggagctca atgagaaagg 4370

<210> SEQ ID NO 100
<211> LENGTH: 1539
<212> TYPE: DNA
<213> ORGANISM: Artificial Sequence
<220> FEATURE:
<223> OTHER INFORMATION: Synthetic

<400> SEQUENCE: 100

```
ccaccatggc gcttccggtg acagcactgc tcctcccctt ggcgctgttg ctccacgcag     60
caaggccgca ggtgcagctg gtccaaagcg gcgccgaggt taagaaacca ggcgcatccg    120
tcaaggtttc atgtaaagca agtggcttga ctatagaaga ctactacatg cattgggtac    180
ggcaagcccc tgggcagggg ctggaatgga tggggtggat cgacccggag aatggtgata    240
cagagtacgg acctaagttc cagggacgag ttaccatgac gcgagataca tccatctcca    300
cggcatacat ggagctgagt cgactgcgga gcgatgatac agctgtctat tattgtgctg    360
tccacaatgc gcactacggc acctggttcg cttattgggg acaaggtacc ctggtcacag    420
tcagctctgg ggtggcggc agtggagggg gtggttctgg tggcgggggt tccgatgttg    480
taatgactca aagccctctt tctttgccag tcactctcgg acaacccgcg agcatatctt    540
gcaggtcttc acaatcactc cttcacagta gcgggaatac ttacttggag tggtatcagc    600
agcggcctgg tcagtcccct agaccgctta tatataagat ctccactagg ttcagtggag    660
tgccggaccg cttttcaggc tcaggttccg ggacggactt tacattgaaa atatccaggg    720
tggaggcgga ggacgtcgga gtctactatt gcttccaagg ctcccacgtc ccatacactt    780
tcggtggcgg tacaaaagtg gaaataaaaa gtgctgctgc ctttgtcccg gtatttctcc    840
cagccaaacc gaccacgact cccgccccgc gccctccgac acccgctccc accatcgcct    900
ctcaacctct tagtcttcgc cccgaggcat gccgacccgc cgccgggggt gctgttcata    960
cgaggggctt ggacttcgct tgtgatattt acatttgggc tccgttggcg ggtacgtgcg   1020
gcgtcctttt gttgtcactc gttattactt tgtattgtaa tcacaggaat cgcaaacggg   1080
gcagaaagaa actcctgtat atattcaaac aaccatttat gagaccagta caaactactc   1140
aagaggaaga tggctgtagc tgccgatttc cagaagaaga agaaggagga tgtgaactgc   1200
gagtgaagtt ttcccgaagc gcagacgctc cggcatatca gcaaggacag aatcagctgt   1260
ataacgaact gaatttggga cgccgcgagg agtatgacgt gcttgataaa cgccgggggga   1320
gagacccgga aatgggggt aaaccccgaa gaaagaatcc ccaagaagga ctctacaatg   1380
aactccagaa ggataagatg gcggaggcct actcagaaat aggtatgaag ggcgaacgac   1440
gacggggaaa aggtcacgat ggcctctacc aagggttgag tacggcaacc aaagatacgt   1500
acgatgcact gcatatgcag gccctgcctc ccagataat                           1539
```

<210> SEQ ID NO 101
<211> LENGTH: 510
<212> TYPE: PRT
<213> ORGANISM: Artificial Sequence
<220> FEATURE:
<223> OTHER INFORMATION: Synthetic

<400> SEQUENCE: 101

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60
```

```
Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Gln Gln Arg Pro Gly Gln Ser Pro Arg Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Phe Gly Gly Gly Thr Lys Val Glu Ile Lys Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
```

485 490 495

Asp Thr Tyr Asp Ala Leu His Met Gln Ala Leu Pro Pro Arg
500 505 510

<210> SEQ ID NO 102
<211> LENGTH: 741
<212> TYPE: DNA
<213> ORGANISM: Artificial Sequence
<220> FEATURE:
<223> OTHER INFORMATION: Synthetic

<400> SEQUENCE: 102
caggtgcagc tggtccaaag cggcgccgag gttaagaaac caggcgcatc cgtcaaggtt 60
tcatgtaaag caagtggctt gactatagaa gactactaca tgcattgggt acggcaagcc 120
cctgggcagg ggctggaatg gatggggtgg atcgacccgg agaatggtga tacagagtac 180
ggacctaagt tccagggacg agttaccatg acgcgagata catccatctc cacggcatac 240
atggagctga gtcgactgcg gagcgatgat acagctgtct attattgtgc tgtccacaat 300
gcgcactacg gcacctggtt cgcttattgg ggacaaggta ccctggtcac agtcagctct 360
gggggtggcg gcagtggagg gggtggttct ggtggcgggg gttccgatgt tgtaatgact 420
caaagccctc tttctttgcc agtcactctc ggacaacccg cgagcatatc ttgcaggtct 480
tcacaatcac tccttcacag tagcgggaat acttacttgg agtggtatca gcagcggcct 540
ggtcagtccc ctagaccgct tatatataag atctccacta ggttcagtgg agtgccggac 600
cgcttttcag gctcaggttc cgggacggac tttacattga aaatatccag ggtggaggcg 660
gaggacgtcg gagtctacta ttgcttccaa ggctcccacg tcccatacac tttcggtggc 720
ggtacaaaag tggaaataaa a 741

<210> SEQ ID NO 103
<211> LENGTH: 4370
<212> TYPE: DNA
<213> ORGANISM: Artificial Sequence
<220> FEATURE:
<223> OTHER INFORMATION: Synthetic

<400> SEQUENCE: 103
gagatgtaag gagctgctgt gacttgctca aggccttata tcgagtaaac ggtagtgctg 60
gggcttagac gcaggtgttc tgatttatag ttcaaaacct ctatcaatga gagagcaatc 120
tcctggtaat gtgatagatt tcccaactta atgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg ggttttgaa 300 gaagatccta ttaaataaaa gaataagcag tattattaag tagccctgca tttcaggttt 360
ccttgagtgg caggccaggc ctggccgtga acgttcactg aaatcatggc ctcttggcca 420
agattgatag cttgtgcctg tccctgagtc ccagtccatc acgagcagct ggtttctaag 480
atgctatttc ccgtataaag catgagaccg tgacttgcca gccccacaga gccccgccct 540
tgtccatcac tggcatctgg actccagcct gggttggggc aaagagggaa atgagatcat 600
gtcctaaccc tgatcctctt gtcccacaga tatccagaac cctgaccctg ccgtgtacca 660
gctgagagac tctaaatcca gtgacaagtc tgtctgccta ttcaccgatt ttgattctca 720
aacaaatgtg tcacaaagta aggattctga tgtgtatatc acagacaaaa ctgtgctaga 780
catgaggtct atggacttca ggctccggtg cccgtcagtg ggcagagcgc acatcgccca 840

-continued

```
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcagg tgcagctggt ccaaagcggc gccgaggtta agaaaccagg cgcatccgtc   2100
aaggtttcat gtaaagcaag tggcttgact atagaagact actacatgca ttgggtacgg   2160
caagcccctg ggcaggggct ggaatggatg gggtggatcg acccggagaa tggtgataca   2220
gagtacggac ctaagttcca gggacgagtt accatgacgc gagatacatc catctccacg   2280
gcatacatgg agctgagtcg actgcggagc gatgatacag ctgtctatta ttgtgctgtc   2340
cacaatgcgc actacggcac ctggttcgct tattggggac aaggtaccct ggtcacagtc   2400
agctctgggg gtggcggcag tggagggggt ggttctggtg gcgggggttc cgatgttgta   2460
atgactcaaa gccctctttc tttgccagtc actctcggac aacccgcgag catatcttgc   2520
aggtcttcac aatcactcct tcacagtagc gggaatactt acttggagtg gtatcagcag   2580
cggcctggtc agtcccctag accgcttata tataagatct ccactaggtt cagtggagtg   2640
ccggaccgct tttcaggctc aggttccggg acggacttta cattgaaaat atccagggtg   2700
gaggcggagg acgtcggagt ctactattgc ttccaaggct cccacgtccc atacactttc   2760
ggtggcggta caaaagtgga aataaaaagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg caaacggggc   3060
agaaagaaac tcctgtatat attcaaacaa ccatttatga gaccagtaca aactactcaa   3120
gaggaagatg gctgtagctg ccgatttcca gaagaagaag aaggaggatg tgaactgcga   3180
gtgaagtttt cccgaagcgc agacgctccg gcatatcagc aaggacagaa tcagctgtat   3240
```

```
aacgaactga atttgggacg ccgcgaggag tatgacgtgc ttgataaacg ccgggggaga   3300
gacccggaaa tggggggtaa accccgaaga aagaatcccc aagaaggact ctacaatgaa   3360
ctccagaagg ataagatggc ggaggcctac tcagaaatag gtatgaaggg cgaacgacga   3420
cggggaaaag gtcacgatgg cctctaccaa gggttgagta cggcaaccaa agatacgtac   3480
gatgcactgc atatgcaggc cctgcctccc agataataat aaaatcgcta tccatcgaag   3540
atggatgtgt gttggttttt tgtgtgtgga gcaacaaatc tgactttgca tgtgcaaacg   3600
ccttcaacaa cagcattatt ccagaagaca ccttcttccc cagcccaggt aagggcagct   3660
ttggtgcctt cgcaggctgt ttccttgctt caggaatggc caggttctgc ccagagctct   3720
ggtcaatgat gtctaaaact cctctgattg gtggtctcgg ccttatccat tgccaccaaa   3780
accctctttt tactaagaaa cagtgagcct tgttctggca gtccagagaa tgacacggga   3840
aaaaagcaga tgaagagaag gtggcaggag agggcacgtg gcccagcctc agtctctcca   3900
actgagttcc tgcctgcctg cctttgctca gactgtttgc cccttactgc tcttctaggc   3960
ctcattctaa gccccttctc caagttgcct ctccttattt ctccctgtct gccaaaaaat   4020
ctttcccagc tcactaagtc agtctcacgc agtcactcat taacccacca atcactgatt   4080
gtgccggcac atgaatgcac caggtgttga agtggaggaa ttaaaaagtc agatgagggg   4140
tgtgcccaga ggaagcacca ttctagttgg gggagcccat ctgtcagctg ggaaaagtcc   4200
aaataacttc agattggaat gtgttttaac tcagggttga gaaaacagct accttcagga   4260
caaaagtcag ggaagggctc tctgaagaaa tgctacttga agataccagc cctaccaagg   4320
gcagggagag gaccctatag aggcctggga caggagctca atgagaaagg              4370
```

<210> SEQ ID NO 104
<211> LENGTH: 1539
<212> TYPE: DNA
<213> ORGANISM: Artificial Sequence
<220> FEATURE:
<223> OTHER INFORMATION: Synthetic

<400> SEQUENCE: 104

```
ccaccatggc gcttccggtg acagcactgc tcctcccctt ggcgctgttg ctccacgcag     60
caaggccgga tgtagttatg acccagagtc cgctctcttt gccggtgacg ctcggccaac    120
cggcgtctat ttcttgcaga agtagtcaat cacttctgca ctctagcggt aacacttatt    180
tggagtggta tctccaacga ccagggcaaa gccccaagcc gttgatttat aagatctcta    240
caagattcag cggagtgccc gacagatttt ccgggagtgg gtccggtact gatttcactt    300
tgaaaatttc ccgcgtcgag gctgaagatg ttggtgtcta ctactgcttt caggggagcc    360
atgttccata tacctttgga ggtgggacta aggtagaaat taaaggtggg ggtggatcag    420
gggtggcgg cagcgggggga gggggctcac aagtgcaact tgtgcaaagt ggggccgagg    480
tgaaaaaacc cggtgcaagt gtaaaggtct catgcaaagc gtctggtttg acaattgaag    540
actattatat gcattgggtg agacaggccc cgggccaagg cttggaatgg atgggatgga    600
tagaccccga aaacggtgac acggagtacg gacctaaatt tcaaggaaga gtgacaatga    660
cacgcgatac atctattaac acggcttata tggaactgag ccgacttcgg agtgatgaca    720
ctgctgtata ttattgcgcc gtccacaacg cacattatgg cacctggttt gcgtactggg    780
gacagggaac tttggttaca gtatcaagca gtgctgctgc ctttgtcccg gtatttctcc    840
cagccaaacc gaccacgact cccgccccgc gccctccgac acccgctccc accatcgcct    900
```

```
ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140

aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccggggga   1320

gagacccgga aatggggggt aaaccccgaa gaaagaatcc ccaagaagga ctctacaatg   1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539
```

```
<210> SEQ ID NO 105
<211> LENGTH: 510
<212> TYPE: PRT
<213> ORGANISM: Artificial Sequence
<220> FEATURE:
<223> OTHER INFORMATION: Synthetic

<400> SEQUENCE: 105

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Arg Ser Ser Gln
        35                  40                  45

Ser Leu Leu His Ser Ser Gly Asn Thr Tyr Leu Glu Trp Tyr Leu Gln
    50                  55                  60

Arg Pro Gly Gln Ser Pro Lys Pro Leu Ile Tyr Lys Ile Ser Thr Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Tyr Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

Lys Pro Gly Ala Ser Val Lys Val Ser Cys Lys Ala Ser Gly Leu Thr
                165                 170                 175

Ile Glu Asp Tyr Tyr Met His Trp Val Arg Gln Ala Pro Gly Gln Gly
            180                 185                 190

Leu Glu Trp Met Gly Trp Ile Asp Pro Glu Asn Gly Asp Thr Glu Tyr
        195                 200                 205

Gly Pro Lys Phe Gln Gly Arg Val Thr Met Thr Arg Asp Thr Ser Ile
    210                 215                 220

Asn Thr Ala Tyr Met Glu Leu Ser Arg Leu Arg Ser Asp Asp Thr Ala
225                 230                 235                 240

Val Tyr Tyr Cys Ala Val His Asn Ala His Tyr Gly Thr Trp Phe Ala
                245                 250                 255
```

```
Tyr Trp Gly Gln Gly Thr Leu Val Thr Val Ser Ser Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510
```

<210> SEQ ID NO 106
<211> LENGTH: 741
<212> TYPE: DNA
<213> ORGANISM: Artificial Sequence
<220> FEATURE:
<223> OTHER INFORMATION: Synthetic

<400> SEQUENCE: 106

```
gatgtagtta tgacccagag tccgctctct ttgccggtga cgctcggcca accggcgtct      60

atttcttgca gaagtagtca atcacttctg cactctagcg gtaacactta tttggagtgg     120

tatctccaac gaccagggca aagccccaag ccgttgattt ataagatctc tacaagattc     180

agcggagtgc ccgacagatt ttccgggagt gggtccggta ctgatttcac tttgaaaatt     240

tcccgcgtcg aggctgaaga tgttggtgtc tactactgct ttcaggggag ccatgttcca     300

tatacctttg gaggtgggac taaggtagaa attaaaggtg gggtggatc agggggtggc     360

ggcagcgggg gagggggctc acaagtgcaa cttgtgcaaa gtggggccga ggtgaaaaaa     420

cccggtgcaa gtgtaaaggt ctcatgcaaa gcgtctggtt tgacaattga agactattat     480

atgcattggg tgagacaggc ccgggccaa ggcttggaat ggatgggatg gatagacccc     540

gaaaacggtg acacggagta cggacctaaa tttcaaggaa gagtgacaat gacacgcgat     600
```

```
acatctatta acacggctta tatggaactg agccgacttc ggagtgatga cactgctgta    660

tattattgcg ccgtccacaa cgcacattat ggcacctggt ttgcgtactg ggacagggga    720

actttggtta cagtatcaag c                                              741
```

<210> SEQ ID NO 107
<211> LENGTH: 4370
<212> TYPE: DNA
<213> ORGANISM: Artificial Sequence
<220> FEATURE:
<223> OTHER INFORMATION: Synthetic

<400> SEQUENCE: 107

```
gagatgtaag gagctgctgt gacttgctca aggccttata tcgagtaaac ggtagtgctg      60

gggcttagac gcaggtgttc tgatttatag ttcaaaacct ctatcaatga gagagcaatc     120

tcctggtaat gtgatagatt tcccaactta atgccaacat accataaacc tcccattctg     180

ctaatgccca gcctaagttg ggagaccac tccagattcc aagatgtaca gtttgctttg     240

ctgggccttt ttcccatgcc tgcctttact ctgccagagt tatattgctg gggttttgaa     300

gaagatccta ttaaataaaa gaataagcag tattattaag tagccctgca tttcaggttt     360

ccttgagtgg caggccaggc ctggccgtga acgttcactg aaatcatggc ctcttggcca     420

agattgatag cttgtgcctg tccctgagtc ccagtccatc acgagcagct ggtttctaag     480

atgctatttc ccgtataaag catgagaccg tgacttgcca gccccacaga gccccgccct     540

tgtccatcac tggcatctgg actccagcct gggttggggc aaagagggaa atgagatcat     600

gtcctaaccc tgatcctctt gtcccacaga tatccagaac cctgaccctg ccgtgtacca     660

gctgagagac tctaaatcca gtgacaagtc tgtctgccta ttcaccgatt ttgattctca     720

aacaaatgtg tcacaaagta aggattctga tgtgtatatc acagacaaaa ctgtgctaga     780

catgaggtct atggacttca ggctccggtg cccgtcagtg ggcagagcgc acatcgccca     840

cagtccccga gaagttgggg ggaggggtcg gcaattgaac cggtgcctag agaaggtggc     900

gcggggtaaa ctgggaaagt gatgtcgtgt actggctccg cctttttccc gagggtgggg     960

gagaaccgta tataagtgca gtagtcgccg tgaacgttct ttttcgcaac gggtttgccg    1020

ccagaacaca ggtaagtgcc gtgtgtggtt cccgcgggcc tggcctcttt acgggttatg    1080

gcccttgcgt gccttgaatt acttccactg gctgcagtac gtgattcttg atcccgagct    1140

tcgggttgga agtgggtggg agagttcgag gccttgcgct taaggagccc cttcgcctcg    1200

tgcttgagtt gaggcctggc ctgggcgctg gggccgccgc gtgcgaatct ggtggcacct    1260

tcgcgcctgt ctcgctgctt tcgataagtc tctagccatt taaaattttt gatgacctgc    1320

tgcgacgctt tttttctggc aagatagtct tgtaaatgcg ggccaagatc tgcacactgg    1380

tatttcggtt tttggggccg cgggcggcga cggggcccgt gcgtcccagc gcacatgttc    1440

ggcgaggcgg ggcctgcgag cgcggccacc gagaatcgga cgggggtagt ctcaagctgg    1500

ccggcctgct ctggtgcctg gcctcgcgcc gccgtgtatc gccccgccct gggcggcaag    1560

gctggcccgg tcggcaccag ttgcgtgagc ggaaagatgg ccgcttcccg gccctgctgc    1620

agggagctca aaatggagga cgcggcgctc gggagagcgg gcgggtgagt cacccacaca    1680

aaggaaaagg gcctttccgt cctcagccgt cgcttcatgt gactccacgg agtaccgggc    1740

gccgtccagg cacctcgatt agttctcgag cttttggagt acgtcgtctt taggttgggg    1800

ggaggggttt tatgcgatgg agtttcccca cactgagtgg gtggagactg aagttaggcc    1860

agcttggcac ttgatgtaat tctccttgga atttgccctt tttgagtttg gatcttggtt    1920
```

```
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccggatg tagttatgac ccagagtccg ctctctttgc cggtgacgct cggccaaccg   2100
gcgtctattt cttgcagaag tagtcaatca cttctgcact ctagcggtaa cacttatttg   2160
gagtggtatc tccaacgacc agggcaaagc cccaagccgt tgatttataa gatctctaca   2220
agattcagcg gagtgcccga cagattttcc gggagtgggt ccggtactga tttcactttg   2280
aaaatttccc gcgtcgaggc tgaagatgtt ggtgtctact actgctttca ggggagccat   2340
gttccatata cctttggagg tgggactaag gtagaaatta aaggtggggg tggatcaggg   2400
ggtggcggca gcgggggagg gggctcacaa gtgcaacttg tgcaaagtgg ggccgaggtg   2460
aaaaaacccg gtgcaagtgt aaaggtctca tgcaaagcgt ctggtttgac aattgaagac   2520
tattatatgc attgggtgag acaggccccg ggccaaggct tggaatggat gggatggata   2580
gaccccgaaa acggtgacac ggagtacgga cctaaatttc aaggaagagt gacaatgaca   2640
cgcgatacat ctattaacac ggcttatatg gaactgagcc gacttcggag tgatgacact   2700
gctgtatatt attgcgccgt ccacaacgca cattatggca cctggtttgc gtactgggga   2760
cagggaactt tggttacagt atcaagcagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg caaacggggc   3060
agaaagaaac tcctgtatat attcaaacaa ccatttatga gaccagtaca aactactcaa   3120
gaggaagatg gctgtagctg ccgatttcca gaagaagaag aaggaggatg tgaactgcga   3180
gtgaagtttt cccgaagcgc agacgctccg gcatatcagc aaggacagaa tcagctgtat   3240
aacgaactga atttgggacg ccgcgaggag tatgacgtgc ttgataaacg ccgggggaga   3300
gacccggaaa tgggggggtaa accccgaaga aagaatcccc aagaaggact ctacaatgaa   3360
ctccagaagg ataagatggc ggaggcctac tcagaaatag gtatgaaggg cgaacgacga   3420
cggggaaaag gtcacgatgg cctctaccaa gggttgagta cggcaaccaa agatacgtac   3480
gatgcactgc atatgcaggc cctgcctccc agataataat aaaatcgcta tccatcgaag   3540
atggatgtgt gttggttttt tgtgtgtgga gcaacaaatc tgactttgca tgtgcaaacg   3600
ccttcaacaa cagcattatt ccagaagaca ccttcttccc cagcccaggt aagggcagct   3660
ttggtgcctt cgcaggctgt ttccttgctt caggaatggc caggttctgc ccagagctct   3720
ggtcaatgat gtctaaaact cctctgattg gtggtctcgg ccttatccat tgccaccaaa   3780
accctctttt tactaagaaa cagtgagcct tgttctggca gtccagagaa tgacacggga   3840
aaaaagcaga tgaagagaag gtggcaggag agggcacgtg gcccagcctc agtctctcca   3900
actgagttcc tgcctgcctg cctttgctca gactgtttgc cccttactgc tcttctaggc   3960
ctcattctaa gccccttctc caagttgcct ctccttattt ctccctgtct gccaaaaaat   4020
ctttcccagc tcactaagtc agtctcacgc agtcactcat taacccacca atcactgatt   4080
gtgccggcac atgaatgcac caggtgttga agtggaggaa ttaaaaagtc agatgagggg   4140
tgtgcccaga ggaagcacca ttctagttgg gggagcccat ctgtcagctg ggaaaagtcc   4200
aaataacttc agattggaat gtgttttaac tcagggttga gaaaacagct accttcagga   4260
```

```
caaaagtcag ggaagggctc tctgaagaaa tgctacttga agataccagc cctaccaagg   4320

gcagggagag gaccctatag aggcctggga caggagctca atgagaaagg              4370


<210> SEQ ID NO 108
<211> LENGTH: 1539
<212> TYPE: DNA
<213> ORGANISM: Artificial Sequence
<220> FEATURE:
<223> OTHER INFORMATION: Synthetic

<400> SEQUENCE: 108

ccaccatggc gcttccggtg acagcactgc tcctcccctt ggcgctgttg ctccacgcag     60

caaggccgca ggttcaactg gttcagagtg gagcagaggt aaaaaagccc ggagcgtccg    120

tcaaagtgtc atgtaaagcc tctggactta ctatcgaaga ctactacatg cactgggtga    180

ggcaggcgcc tggccaaggt ctcgagtgga tgggttggat tgaccctgaa aatggagata    240

cagaatacgg ccctaagttt caagggcgag taactatgac tcgagatacg tcaattaata    300

cggcatacat ggagttgtct cggctccgat ctgatgacac tgcagtttac tattgtgccg    360

tccacaatgc tcattacggg acatggttcg cttactgggg gcaagggaca ctcgtaacgg    420

ttagctctgg gggaggaggg tctggtggag gggctcagg agggggtggt agcgacgtag    480

taatgaccca gtcacctctg tctttgccgg tcacgttggg ccagcctgca tccatatcct    540

gcagatccag ccagagcctc ctgcacagta gtggcaacac gtatttggaa tggtacctgc    600

agaggccggg tcaaagtcca aaaccgctga tctataagat atctacgcga ttttcagggg    660

tgccggaccg atttagcgga tcaggaagtg gaaccgactt tacgctcaag atcagccggg    720

ttgaagccga agatgtcggc gtttactact gtttccaagg aagccacgta ccctatacgt    780

ttggtggcgg cacgaaggtc gagataaaga gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140

aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccgggga   1320

gagacccgga aatgggggt aaaccccgaa gaaagaatcc ccaagaagga ctctacaatg   1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539


<210> SEQ ID NO 109
<211> LENGTH: 510
<212> TYPE: PRT
<213> ORGANISM: Artificial Sequence
<220> FEATURE:
<223> OTHER INFORMATION: Synthetic

<400> SEQUENCE: 109

Met Ala Leu Pro Val Thr Ala Leu Leu Leu Pro Leu Ala Leu Leu Leu
1               5                   10                  15
```

```
His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Asn Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Leu Gln Arg Pro Gly Gln Ser Pro Lys Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Phe Gly Gly Gly Thr Lys Val Glu Ile Lys Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
```

```
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510


<210> SEQ ID NO 110
<211> LENGTH: 741
<212> TYPE: DNA
<213> ORGANISM: Artificial Sequence
<220> FEATURE:
<223> OTHER INFORMATION: Synthetic

<400> SEQUENCE: 110

caggttcaac tggttcagag tggagcagag gtaaaaaagc ccggagcgtc cgtcaaagtg     60

tcatgtaaag cctctggact tactatcgaa gactactaca tgcactgggt gaggcaggcg    120

cctggccaag gtctcgagtg gatgggttgg attgaccctg aaaatggaga tacagaatac    180

ggccctaagt ttcaagggcg agtaactatg actcgagata cgtcaattaa tacggcatac    240

atggagttgt ctcggctccg atctgatgac actgcagttt actattgtgc cgtccacaat    300

gctcattacg ggacatggtt cgcttactgg gggcaaggga cactcgtaac ggttagctct    360

gggggaggag ggtctggtgg agggggctca ggagggggtg gtagcgacgt agtaatgacc    420

cagtcacctc tgtctttgcc ggtcacgttg ggccagcctg catccatatc ctgcagatcc    480

agccagagcc tcctgcacag tagtggcaac acgtatttgg aatggtacct gcagaggccg    540

ggtcaaagtc caaaaccgct gatctataag atatctacgc gattttcagg ggtgccggac    600

cgatttagcg gatcaggaag tggaaccgac tttacgctca agatcagccg ggttgaagcc    660

gaagatgtcg gcgtttacta ctgtttccaa ggaagccacg taccctatac gtttggtggc    720

ggcacgaagg tcgagataaa g                                              741


<210> SEQ ID NO 111
<211> LENGTH: 4370
<212> TYPE: DNA
<213> ORGANISM: Artificial Sequence
<220> FEATURE:
<223> OTHER INFORMATION: Synthetic

<400> SEQUENCE: 111

gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg ggttttgaa     300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600
```

```
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcagg ttcaactggt tcagagtgga gcagaggtaa aaaagcccgg agcgtccgtc   2100
aaagtgtcat gtaaagcctc tggacttact atcgaagact actacatgca ctgggtgagg   2160
caggcgcctg gccaaggtct cgagtggatg ggttggattg accctgaaaa tggagataca   2220
gaatacggcc ctaagtttca agggcgagta actatgactc gagatacgtc aattaatacg   2280
gcatacatgg agttgtctcg gctccgatct gatgacactg cagtttacta ttgtgccgtc   2340
cacaatgctc attacgggac atggttcgct tactgggggc aagggacact cgtaacggtt   2400
agctctgggg gaggagggtc tggtggaggg ggctcaggag ggggtggtag cgacgtagta   2460
atgacccagt cacctctgtc tttgccggtc acgttgggcc agcctgcatc catatcctgc   2520
agatccagcc agagcctcct gcacagtagt ggcaacacgt atttggaatg gtacctgcag   2580
aggccgggtc aaagtccaaa accgctgatc tataagatat ctacgcgatt ttcaggggtg   2640
ccggaccgat ttagcggatc aggaagtgga accgacttta cgctcaagat cagccgggtt   2700
gaagccgaag atgtcggcgt ttactactgt ttccaaggaa gccacgtacc ctatacgttt   2760
ggtggcggca cgaaggtcga gataaagagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
```

aggggcttgg acttcgcttg tgatatttac atttgggctc cgttggcggg tacgtgcggc 3000
gtccttttgt tgtcactcgt tattactttg tattgtaatc acaggaatcg caaacggggc 3060
agaaagaaac tcctgtatat attcaaacaa ccatttatga gaccagtaca aactactcaa 3120
gaggaagatg gctgtagctg ccgatttcca gaagaagaag aaggaggatg tgaactgcga 3180
gtgaagtttt cccgaagcgc agacgctccg gcatatcagc aaggacagaa tcagctgtat 3240
aacgaactga atttgggacg ccgcgaggag tatgacgtgc ttgataaacg ccgggggaga 3300
gacccggaaa tgggggtaa accccgaaga aagaatcccc aagaaggact ctacaatgaa 3360
ctccagaagg ataagatggc ggaggcctac tcagaaatag gtatgaaggg cgaacgacga 3420
cggggaaaag gtcacgatgg cctctaccaa gggttgagta cggcaaccaa agatacgtac 3480
gatgcactgc atatgcaggc cctgcctccc agataataat aaaatcgcta tccatcgaag 3540
atggatgtgt gttggttttt tgtgtgtgga gcaacaaatc tgactttgca tgtgcaaacg 3600
ccttcaacaa cagcattatt ccagaagaca ccttcttccc cagcccaggt aagggcagct 3660
ttggtgcctt cgcaggctgt ttccttgctt caggaatggc caggttctgc ccagagctct 3720
ggtcaatgat gtctaaaact cctctgattg gtggtctcgg ccttatccat tgccaccaaa 3780
accctctttt tactaagaaa cagtgagcct tgttctggca gtccagagaa tgacacggga 3840
aaaaagcaga tgaagagaag gtggcaggag agggcacgtg gcccagcctc agtctctcca 3900
actgagttcc tgcctgcctg cctttgctca gactgtttgc cccttactgc tcttctaggc 3960
ctcattctaa gccccttctc caagttgcct ctccttattt ctccctgtct gccaaaaaat 4020
ctttcccagc tcactaagtc agtctcacgc agtcactcat taacccacca atcactgatt 4080
gtgccggcac atgaatgcac caggtgttga agtggaggaa ttaaaaagtc agatgagggg 4140
tgtgcccaga ggaagcacca ttctagttgg gggagcccat ctgtcagctg ggaaaagtcc 4200
aaataacttc agattggaat gtgttttaac tcagggttga gaaaacagct accttcagga 4260
caaaagtcag ggaagggctc tctgaagaaa tgctacttga agataccagc cctaccaagg 4320
gcagggagag gaccctatag aggcctggga caggagctca atgagaaagg 4370

<210> SEQ ID NO 112
<211> LENGTH: 1539
<212> TYPE: DNA
<213> ORGANISM: Artificial Sequence
<220> FEATURE:
<223> OTHER INFORMATION: Synthetic

<400> SEQUENCE: 112
ccaccatggc gcttccggtg acagcactgc tcctcccctt ggcgctgttg ctccacgcag 60
caaggccgga cgttgtgatg acgcagtctc ctctgagcct gccagttacg ttggggcaac 120
ccgcatcaat atcttgtagg tccagtcaga gcctgcttca cagctctggc aacacttact 180
tggaatggta cctccagaga cctggacaga gtcccaagcc attgatttac aagatttcaa 240
cgcgatttag tggagtgccc gatcgattct ctgggagtgg ctctgggact gatttcacac 300
ttaaaataag tagggtggag gctgaagatg tgggtgtata ttattgtttt caagggtccc 360
atgtccctta cactttcggc ggcggcacca aagttgagat caaaggtggt ggtgggtccg 420
gcggtggagg cagtgggggt ggcgggtcac aagttcaact tgtccagtca ggggctgaag 480
taaaaaagcc tggtgcatca gttaaagttt catgtaaggc ttccggcctt accattgaag 540
attactatat gcactgggtt agacaagctc ctggacaagg tctggagtgg atgggctgga 600
tagaccccga gaatggtgac acagaatacg ggcctaagtt ccagggtagg gtaacaatga 660

```
cgcgggatac atccatttcc acagcttaca tggaactgag tagactcaga tctgacgaca    720

ctgctgtcta ctattgtgcc gtccataacg cgcattatgg cacttggttc gcatattggg    780

ggcaaggcac tcttgttaca gtgtcctcaa gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgagggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140

aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccggggga   1320

gagacccgga aatgggggt aaaccccgaa gaaagaatcc ccaagaagga ctctacaatg   1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539
```

<210> SEQ ID NO 113
<211> LENGTH: 510
<212> TYPE: PRT
<213> ORGANISM: Artificial Sequence
<220> FEATURE:
<223> OTHER INFORMATION: Synthetic

<400> SEQUENCE: 113

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Arg Ser Ser Gln
        35                  40                  45

Ser Leu Leu His Ser Ser Gly Asn Thr Tyr Leu Glu Trp Tyr Leu Gln
    50                  55                  60

Arg Pro Gly Gln Ser Pro Lys Pro Leu Ile Tyr Lys Ile Ser Thr Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Phe Gln Gly Ser His Val Pro Tyr Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

Lys Pro Gly Ala Ser Val Lys Val Ser Cys Lys Ala Ser Gly Leu Thr
                165                 170                 175

Ile Glu Asp Tyr Tyr Met His Trp Val Arg Gln Ala Pro Gly Gln Gly
            180                 185                 190

Leu Glu Trp Met Gly Trp Ile Asp Pro Glu Asn Gly Asp Thr Glu Tyr
        195                 200                 205
```

```
Gly Pro Lys Phe Gln Gly Arg Val Thr Met Thr Arg Asp Thr Ser Ile
    210                 215                 220

Ser Thr Ala Tyr Met Glu Leu Ser Arg Leu Arg Ser Asp Asp Thr Ala
225                 230                 235                 240

Val Tyr Tyr Cys Ala Val His Asn Ala His Tyr Gly Thr Trp Phe Ala
                245                 250                 255

Tyr Trp Gly Gln Gly Thr Leu Val Thr Val Ser Ser Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510
```

<210> SEQ ID NO 114
<211> LENGTH: 741
<212> TYPE: DNA
<213> ORGANISM: Artificial Sequence
<220> FEATURE:
<223> OTHER INFORMATION: Synthetic

<400> SEQUENCE: 114

```
gacgttgtga tgacgcagtc tcctctgagc ctgccagtta cgttggggca acccgcatca      60

atatcttgta ggtccagtca gagcctgctt cacagctctg gcaacactta cttggaatgg     120

tacctccaga gacctggaca gagtcccaag ccattgattt acaagatttc aacgcgattt     180

agtggagtgc ccgatcgatt ctctgggagt ggctctggga ctgatttcac acttaaaata     240

agtagggtgg aggctgaaga tgtgggtgta tattattgtt ttcaagggtc ccatgtccct     300

tacactttcg gcggcggcac caaagttgag atcaaaggtg gtggtgggtc cggcggtgga     360
```

```
ggcagtgggg gtggcgggtc acaagttcaa cttgtccagt caggggctga agtaaaaaag    420

cctggtgcat cagttaaagt ttcatgtaag gcttccggcc ttaccattga agattactat    480

atgcactggg ttagacaagc tcctggacaa ggtctggagt ggatgggctg gatagacccc    540

gagaatggtg acacagaata cgggcctaag ttccagggta gggtaacaat gacgcgggat    600

acatccattt ccacagctta catggaactg agtagactca gatctgacga cactgctgtc    660

tactattgtg ccgtccataa cgcgcattat ggcacttggt tcgcatattg gggcaaggc     720

actcttgtta cagtgtcctc a                                             741
```

<210> SEQ ID NO 115
<211> LENGTH: 4370
<212> TYPE: DNA
<213> ORGANISM: Artificial Sequence
<220> FEATURE:
<223> OTHER INFORMATION: Synthetic

<400> SEQUENCE: 115

```
gagatgtaag gagctgctgt gacttgctca aggccttata tcgagtaaac ggtagtgctg     60

gggcttagac gcaggtgttc tgatttatag ttcaaaacct ctatcaatga gagagcaatc    120

tcctggtaat gtgatagatt tcccaactta atgccaacat accataaacc tcccattctg    180

ctaatgccca gcctaagttg ggagaccac tccagattcc aagatgtaca gtttgctttg    240

ctgggccttt ttcccatgcc tgcctttact ctgccagagt tatattgctg gggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgtgtacca    660

gctgagagac tctaaatcca gtgacaagtc tgtctgccta ttcaccgatt ttgattctca    720

aacaaatgtg tcacaaagta aggattctga tgtgtatatc acagacaaaa ctgtgctaga    780

catgaggtct atggacttca ggctccggtg cccgtcagtg ggcagagcgc acatcgccca    840

cagtccccga gaagttgggg ggaggggtcg gcaattgaac cggtgcctag agaaggtggc    900

gcggggtaaa ctgggaaagt gatgtcgtgt actggctccg cctttttccc gagggtgggg    960

gagaaccgta tataagtgca gtagtcgccg tgaacgttct ttttcgcaac gggtttgccg   1020

ccagaacaca ggtaagtgcc gtgtgtggtt cccgcgggcc tggcctcttt acgggttatg   1080

gcccttgcgt gccttgaatt acttccactg gctgcagtac gtgattcttg atcccgagct   1140

tcgggttgga agtgggtggg agagttcgag gccttgcgct taaggagccc cttcgcctcg   1200

tgcttgagtt gaggcctggc ctgggcgctg gggccgccgc gtgcgaatct ggtggcacct   1260

tcgcgcctgt ctcgctgctt tcgataagtc tctagccatt taaaattttt gatgacctgc   1320

tgcgacgctt tttttctggc aagatagtct tgtaaatgcg ggccaagatc tgcacactgg   1380

tatttcggtt tttggggccg cgggcggcga cggggcccgt gcgtcccagc gcacatgttc   1440

ggcgaggcgg ggcctgcgag cgcggccacc gagaatcgga cgggggtagt ctcaagctgg   1500

ccggcctgct ctggtgcctg gcctcgcgcc gccgtgtatc gccccgccct gggcggcaag   1560

gctggcccgg tcggcaccag ttgcgtgagc ggaaagatgg ccgcttcccg gccctgctgc   1620
```

```
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccggacg ttgtgatgac gcagtctcct ctgagcctgc cagttacgtt ggggcaaccc   2100
gcatcaatat cttgtaggtc cagtcagagc ctgcttcaca gctctggcaa cacttacttg   2160
gaatggtacc tccagagacc tggacagagt cccaagccat tgatttacaa gatttcaacg   2220
cgatttagtg gagtgcccga tcgattctct gggagtggct ctgggactga tttcacactt   2280
aaaataagta gggtggaggc tgaagatgtg ggtgtatatt attgttttca agggtcccat   2340
gtcccttaca ctttcggcgg cggcaccaaa gttgagatca aaggtggtgg tgggtccggc   2400
ggtggaggca gtgggggtgg cgggtcacaa gttcaacttg tccagtcagg ggctgaagta   2460
aaaaagcctg gtgcatcagt taaagtttca tgtaaggctt ccggccttac cattgaagat   2520
tactatatgc actgggttag acaagctcct ggacaaggtc tggagtggat gggctggata   2580
gaccccgaga atggtgacac agaatacggg cctaagttcc agggtagggt aacaatgacg   2640
cgggatacat ccatttccac agcttacatg gaactgagta gactcagatc tgacgacact   2700
gctgtctact attgtgccgt ccataacgcg cattatggca cttggttcgc atattggggg   2760
caaggcactc ttgttacagt gtcctcaagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg caaacggggc   3060
agaaagaaac tcctgtatat attcaaacaa ccatttatga gaccagtaca aactactcaa   3120
gaggaagatg gctgtagctg ccgatttcca gaagaagaag aaggaggatg tgaactgcga   3180
gtgaagtttt cccgaagcgc agacgctccg gcatatcagc aaggacagaa tcagctgtat   3240
aacgaactga atttgggacg ccgcgaggag tatgacgtgc ttgataaacg ccgggggaga   3300
gacccggaaa tggggggtaa accccgaaga aagaatcccc aagaaggact ctacaatgaa   3360
ctccagaagg ataagatggc ggaggcctac tcagaaatag gtatgaaggg cgaacgacga   3420
cggggaaaag gtcacgatgg cctctaccaa gggttgagta cggcaaccaa agatacgtac   3480
gatgcactgc atatgcaggc cctgcctccc agataataat aaaatcgcta tccatcgaag   3540
atggatgtgt gttggttttt tgtgtgtgga gcaacaaatc tgactttgca tgtgcaaacg   3600
ccttcaacaa cagcattatt ccagaagaca ccttcttccc cagcccaggt aagggcagct   3660
ttggtgcctt cgcaggctgt ttccttgctt caggaatggc caggttctgc ccagagctct   3720
ggtcaatgat gtctaaaact cctctgattg gtggtctcgg ccttatccat tgccaccaaa   3780
accctctttt tactaagaaa cagtgagcct tgttctggca gtccagagaa tgacacggga   3840
aaaaagcaga tgaagagaag gtggcaggag agggcacgtg gcccagcctc agtctctcca   3900
actgagttcc tgcctgcctg cctttgctca gactgtttgc cccttactgc tcttctaggc   3960
ctcattctaa gccccttctc caagttgcct ctccttattt ctccctgtct gccaaaaaat   4020
```

```
ctttcccagc tcactaagtc agtctcacgc agtcactcat taacccacca atcactgatt   4080

gtgccggcac atgaatgcac caggtgttga agtggaggaa ttaaaaagtc agatgagggg   4140

tgtgcccaga ggaagcacca ttctagttgg gggagcccat ctgtcagctg ggaaaagtcc   4200

aaataacttc agattggaat gtgttttaac tcagggttga gaaaacagct accttcagga   4260

caaaagtcag ggaagggctc tctgaagaaa tgctacttga agataccagc cctaccaagg   4320

gcagggagag gaccctatag aggcctggga caggagctca atgagaaagg              4370
```

<210> SEQ ID NO 116
<211> LENGTH: 1539
<212> TYPE: DNA
<213> ORGANISM: Artificial Sequence
<220> FEATURE:
<223> OTHER INFORMATION: Synthetic

<400> SEQUENCE: 116

```
ccaccatggc gcttccggtg acagcactgc tcctcccctt ggcgctgttg ctccacgcag     60

caaggccgca ggtacaactc gttcagagcg gtgcagaggt taagaaaccg ggcgccagtg    120

tcaaagtatc atgcaaggcg agtggtctga ccatcgaaga ttattatatg cattgggtga    180

gacaagcacc ggggcagggg ctcgaatgga tgggttggat cgaccccgaa aatggtgata    240

cggagtatgg cccgaaattt cagggtcggg tcacgatgac ccgcgataca agcatcagta    300

ctgcatacat ggagctctct cgcttgcgga gtgatgatac cgccgtttat tattgcgcgg    360

ttcacaacgc tcattatggc acttggttcg cgtattgggg ccaaggaaca ctggttacag    420

tgagcagtgg agggggtggc tctggtggcg gcgggagcgg cggagggggc agtgatgttg    480

tgatgacaca gtcacccctg agtctcccgg tcactcttgg gcaaccagcc agcataagct    540

gtcgcagttc tcagagcttg ctccatagct ccgggaatac ctacctcgaa tggtatctcc    600

aaagacccgg tcaatctcca aagcctttga tttacaagat tagtacacga tttagtgggg    660

tcccagatag attttcaggt agtggatctg gtacagattt cacattgaaa atatcacgcg    720

tcgaggcgga ggatgtcggg gtctactatt gctttcaagg tagtcacgtg ccctacacgt    780

ttggtggcgg tacgaaggtc gaaatcaaga gtgctgctgc ctttgtcccg gtatttctcc    840

cagccaaacc gaccacgact cccgccccgc gccctccgac acccgctccc accatcgcct    900

ctcaacctct tagtcttcgc cccgaggcat gccgacccgc cgccgggggt gctgttcata    960

cgaggggctt ggacttcgct tgtgatattt acatttgggc tccgttggcg ggtacgtgcg   1020

gcgtcctttt gttgtcactc gttattactt tgtattgtaa tcacaggaat cgcaaacggg   1080

gcagaaagaa actcctgtat atattcaaac aaccatttat gagaccagta caaactactc   1140

aagaggaaga tggctgtagc tgccgatttc cagaagaaga agaaggagga tgtgaactgc   1200

gagtgaagtt ttcccgaagc gcagacgctc cggcatatca gcaaggacag aatcagctgt   1260

ataacgaact gaatttggga cgccgcgagg agtatgacgt gcttgataaa cgccggggga   1320

gagacccgga aatgggggt aaaccccgaa gaaagaatcc ccaagaagga ctctacaatg    1380

aactccagaa ggataagatg gcggaggcct actcagaaat aggtatgaag ggcgaacgac   1440

gacggggaaa aggtcacgat ggcctctacc aagggttgag tacggcaacc aaagatacgt   1500

acgatgcact gcatatgcag gccctgcctc ccagataat                          1539
```

<210> SEQ ID NO 117
<211> LENGTH: 510
<212> TYPE: PRT

<213> ORGANISM: Artificial Sequence
<220> FEATURE:
<223> OTHER INFORMATION: Synthetic

<400> SEQUENCE: 117

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Leu Gln Arg Pro Gly Gln Ser Pro Lys Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Phe Gly Gly Gly Thr Lys Val Glu Ile Lys Ser Ala Ala Ala
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Asn
            340                 345                 350

His Arg Asn Arg Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
```

```
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510


<210> SEQ ID NO 118
<211> LENGTH: 741
<212> TYPE: DNA
<213> ORGANISM: Artificial Sequence
<220> FEATURE:
<223> OTHER INFORMATION: Synthetic

<400> SEQUENCE: 118

caggtacaac tcgttcagag cggtgcagag gttaagaaac cgggcgccag tgtcaaagta      60

tcatgcaagg cgagtggtct gaccatcgaa gattattata tgcattgggt gagacaagca     120

ccggggcagg ggctcgaatg gatgggttgg atcgaccccg aaaatggtga tacggagtat     180

ggcccgaaat ttcagggtcg ggtcacgatg acccgcgata caagcatcag tactgcatac     240

atggagctct ctcgcttgcg gagtgatgat accgccgttt attattgcgc ggttcacaac     300

gctcattatg gcacttggtt cgcgtattgg ggccaaggaa cactggttac agtgagcagt     360

ggaggggggtg gctctggtgg cggcgggagc ggcggagggg gcagtgatgt tgtgatgaca     420

cagtcacccc tgagtctccc ggtcactctt gggcaaccag ccagcataag ctgtcgcagt     480

tctcagagct tgctccatag ctccgggaat acctacctcg aatggtatct ccaaagaccc     540

ggtcaatctc caaagccttt gatttacaag attagtacac gatttagtgg ggtcccagat     600

agattttcag gtagtggatc tggtacagat ttcacattga aaatatcacg cgtcgaggcg     660

gaggatgtcg ggtctacta ttgctttcaa ggtagtcacg tgccctacac gtttggtggc     720

ggtacgaagg tcgaaatcaa g                                               741


<210> SEQ ID NO 119
<211> LENGTH: 4370
<212> TYPE: DNA
<213> ORGANISM: Artificial Sequence
<220> FEATURE:
<223> OTHER INFORMATION: Synthetic

<400> SEQUENCE: 119

gagatgtaag gagctgctgt gacttgctca aggccttata tcgagtaaac ggtagtgctg      60

gggcttagac gcaggtgttc tgatttatag ttcaaaacct ctatcaatga gagagcaatc     120

tcctggtaat gtgatagatt tcccaactta atgccaacat accataaacc tcccattctg     180

ctaatgccca gcctaagttg gggagaccac tccagattcc aagatgtaca gtttgctttg     240

ctgggccttt ttcccatgcc tgcctttact ctgccagagt tatattgctg ggttttgaa      300
```

```
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cgggggtagt ctcaagctgg   1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg gatcttggtt   1920
cattctcaag cctcagacag tggttcaaag tttttttctt ccatttcagg tgtcgtgacc   1980
accatggcgc ttccggtgac agcactgctc ctccccttgg cgctgttgct ccacgcagca   2040
aggccgcagg tacaactcgt tcagagcggt gcagaggtta agaaaccggg cgccagtgtc   2100
aaagtatcat gcaaggcgag tggtctgacc atcgaagatt attatatgca ttgggtgaga   2160
caagcaccgg ggcaggggct cgaatggatg ggttggatcg accccgaaaa tggtgatacg   2220
gagtatggcc cgaaatttca gggtcgggtc acgatgaccc gcgatacaag catcagtact   2280
gcatacatgg agctctctcg cttgcggagt gatgataccg ccgtttatta ttgcgcggtt   2340
cacaacgctc attatggcac ttggttcgcg tattggggcc aaggaacact ggttacagtg   2400
agcagtggag ggggtggctc tggtggcggc gggagcggcg gagggggcag tgatgttgtg   2460
atgacacagt cacccctgag tctcccggtc actcttgggc aaccagccag cataagctgt   2520
cgcagttctc agagcttgct ccatagctcc gggaatacct acctcgaatg gtatctccaa   2580
agacccggtc aatctccaaa gcctttgatt tacaagatta gtacacgatt tagtggggtc   2640
ccagatagat tttcaggtag tggatctggt acagatttca cattgaaaat atcacgcgtc   2700
```

```
gaggcggagg atgtcggggt ctactattgc tttcaaggta gtcacgtgcc ctacacgttt   2760
ggtggcggta cgaaggtcga aatcaagagt gctgctgcct ttgtcccggt atttctccca   2820
gccaaaccga ccacgactcc cgccccgcgc cctccgacac ccgctcccac catcgcctct   2880
caacctctta gtcttcgccc cgaggcatgc cgacccgccg ccgggggtgc tgttcatacg   2940
aggggcttgg acttcgcttg tgatatttac atttgggctc cgttggcggg tacgtgcggc   3000
gtccttttgt tgtcactcgt tattactttg tattgtaatc acaggaatcg caaacggggc   3060
agaaagaaac tcctgtatat attcaaacaa ccatttatga gaccagtaca aactactcaa   3120
gaggaagatg gctgtagctg ccgatttcca gaagaagaag aaggaggatg tgaactgcga   3180
gtgaagtttt cccgaagcgc agacgctccg gcatatcagc aaggacagaa tcagctgtat   3240
aacgaactga atttgggacg ccgcgaggag tatgacgtgc ttgataaacg ccgggggaga   3300
gacccggaaa tgggggggtaa accccgaaga aagaatcccc aagaaggact ctacaatgaa   3360
ctccagaagg ataagatggc ggaggcctac tcagaaatag gtatgaaggg cgaacgacga   3420
cggggaaaag gtcacgatgg cctctaccaa gggttgagta cggcaaccaa agatacgtac   3480
gatgcactgc atatgcaggc cctgcctccc agataataat aaaatcgcta tccatcgaag   3540
atggatgtgt gttggttttt tgtgtgtgga gcaacaaatc tgactttgca tgtgcaaacg   3600
ccttcaacaa cagcattatt ccagaagaca ccttcttccc cagcccaggt aagggcagct   3660
ttggtgcctt cgcaggctgt ttccttgctt caggaatggc caggttctgc ccagagctct   3720
ggtcaatgat gtctaaaact cctctgattg gtggtctcgg ccttatccat tgccaccaaa   3780
accctctttt tactaagaaa cagtgagcct tgttctggca gtccagagaa tgacacggga   3840
aaaaagcaga tgaagagaag gtggcaggag agggcacgtg gcccagcctc agtctctcca   3900
actgagttcc tgcctgcctg cctttgctca gactgtttgc cccttactgc tcttctaggc   3960
ctcattctaa gccccttctc caagttgcct ctccttattt ctccctgtct gccaaaaaat   4020
ctttcccagc tcactaagtc agtctcacgc agtcactcat taacccacca atcactgatt   4080
gtgccggcac atgaatgcac caggtgttga agtggaggaa ttaaaaagtc agatgagggg   4140
tgtgcccaga ggaagcacca ttctagttgg gggagcccat ctgtcagctg ggaaaagtcc   4200
aaataacttc agattggaat gtgttttaac tcagggttga gaaaacagct accttcagga   4260
caaaagtcag ggaagggctc tctgaagaaa tgctacttga agataccagc cctaccaagg   4320
gcagggagag gaccctatag aggcctggga caggagctca atgagaaagg               4370
```

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

```
<210> SEQ ID NO 123

<400> SEQUENCE: 123

000


<210> SEQ ID NO 124

<400> SEQUENCE: 124

000


<210> SEQ ID NO 125
<211> LENGTH: 507
<212> TYPE: PRT
<213> ORGANISM: Artificial Sequence
<220> FEATURE:
<223> OTHER INFORMATION: Synthetic

<400> SEQUENCE: 125

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Asn Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160

Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Gln Gln Arg Pro Gly Gln Ser Pro Arg Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Gly Gly Gly Thr Lys Val Glu Ile Lys Ser Ala Ala Ala Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300
```

```
Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
            340                 345                 350

Arg Asn Arg Ser Lys Arg Ser Arg Leu Leu His Ser Asp Tyr Met Asn
        355                 360                 365

Met Thr Pro Arg Arg Pro Gly Pro Thr Arg Lys His Tyr Gln Pro Tyr
    370                 375                 380

Ala Pro Pro Arg Asp Phe Ala Ala Tyr Arg Ser Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
            500                 505
```

<210> SEQ ID NO 126
<211> LENGTH: 509
<212> TYPE: PRT
<213> ORGANISM: Artificial Sequence
<220> FEATURE:
<223> OTHER INFORMATION: Synthetic

<400> SEQUENCE: 126

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Leu
        35                  40                  45

Thr Ile Glu Asp Tyr Tyr Met His Trp Val Arg Gln Ala Pro Gly Gln
    50                  55                  60

Gly Leu Glu Trp Met Gly Trp Ile Asp Pro Glu Asn Gly Asp Thr Glu
65                  70                  75                  80

Tyr Gly Pro Lys Phe Gln Gly Arg Val Thr Met Thr Arg Asp Thr Ser
                85                  90                  95

Ile Asn Thr Ala Tyr Met Glu Leu Ser Arg Leu Arg Ser Asp Asp Thr
            100                 105                 110

Ala Val Tyr Tyr Cys Ala Val His Asn Ala His Tyr Gly Thr Trp Phe
        115                 120                 125

Ala Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Val Val Met
145                 150                 155                 160
```

```
Thr Gln Ser Pro Leu Ser Leu Pro Val Thr Leu Gly Gln Pro Ala Ser
                165                 170                 175

Ile Ser Cys Arg Ser Ser Gln Ser Leu Leu His Ser Ser Gly Asn Thr
            180                 185                 190

Tyr Leu Glu Trp Tyr Gln Gln Arg Pro Gly Gln Ser Pro Arg Pro Leu
        195                 200                 205

Ile Tyr Lys Ile Ser Thr Arg Phe Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Phe Gln Gly Ser His Val Pro
                245                 250                 255

Tyr Thr Gly Gly Gly Thr Lys Val Glu Ile Lys Ser Ala Ala Ala Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
            340                 345                 350

Arg Asn Arg Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 127
<211> LENGTH: 246
<212> TYPE: PRT
<213> ORGANISM: Artificial Sequence
<220> FEATURE:
<223> OTHER INFORMATION: Synthetic

<400> SEQUENCE: 127

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Leu Gly Gln Pro Ala Ser Ile Ser Cys Arg Ser
145                 150                 155                 160

Ser Gln Ser Leu Leu His Ser Ser Gly Asn Thr Tyr Leu Glu Trp Tyr
                165                 170                 175

Gln Gln Arg Pro Gly Gln Ser Pro Arg Pro Leu Ile Tyr Lys Ile Ser
            180                 185                 190

Thr Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Tyr Thr Gly Gly Gly
225                 230                 235                 240

Thr Lys Val Glu Ile Lys
                245
```

<210> SEQ ID NO 128
<211> LENGTH: 111
<212> TYPE: PRT
<213> ORGANISM: Artificial Sequence
<220> FEATURE:
<223> OTHER INFORMATION: Synthetic

<400> SEQUENCE: 128

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Gly Gly Gly Thr Lys Val Glu Ile Lys
            100                 105                 110
```

<210> SEQ ID NO 129

-continued

```
<211> LENGTH: 84
<212> TYPE: PRT
<213> ORGANISM: Artificial Sequence
<220> FEATURE:
<223> OTHER INFORMATION: Synthetic

<400> SEQUENCE: 129

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg


<210> SEQ ID NO 130
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n is a, c, g, t or u

<400> SEQUENCE: 130

nnnnnnnnnn nnnnnnnnnn nrg                                            23
```